(12) United States Patent
Suzuki et al.

(10) Patent No.: US 11,442,066 B2
(45) Date of Patent: Sep. 13, 2022

(54) METHOD FOR IDENTIFYING DRUG-DISCOVERY TARGET PROTEIN FOR DEVELOPMENT OF ANTIBODY DRUG, AND METHOD FOR PRODUCING ANTIBODY AGAINST TARGET PROTEIN

(71) Applicants: MITSUI CHEMICALS, INC., Tokyo (JP); NATIONAL INSTITUTES OF BIOMEDICAL INNOVATION, HEALTH AND NUTRITION, Ibaraki (JP); SAVID THERAPEUTICS INC., Tokyo (JP)

(72) Inventors: Tsuneji Suzuki, Sodegaura (JP); Yoshiyuki Totani, Sodegaura (JP); Kosuke Mano, Sodegaura (JP); Shinichi Banba, Sodegaura (JP); Haruhiko Kamada, Ibaraki (JP); Taisuke Nakayama, Ibaraki (JP); Hiroki Akiba, Ibaraki (JP); Kouhei Tsumoto, Ibaraki (JP); Tsuyoshi Inoue, Ibaraki (JP)

(73) Assignees: MITSUI CHEMICALS, INC, Tokyo (JP); NATIONAL INSTITUTES OF BIOMEDICAL INNOVATION HEALTH AND NUTRITION, Ibaraki (JP); SAVID THERAPEUTICS INC., Tokyo (JP)

( * ) Notice: Subject to any disclaimer, the term of this patent is extended or adjusted under 35 U.S.C. 154(b) by 238 days.

(21) Appl. No.: 16/486,723

(22) PCT Filed: Feb. 19, 2018

(86) PCT No.: PCT/JP2018/005814
§ 371 (c)(1),
(2) Date: Aug. 16, 2019

(87) PCT Pub. No.: WO2018/151301
PCT Pub. Date: Aug. 23, 2018

(65) Prior Publication Data
US 2019/0383821 A1 Dec. 19, 2019

(30) Foreign Application Priority Data
Feb. 17, 2017 (JP) .............................. JP2017-028520

(51) Int. Cl.
| | |
|---|---|
| *G01N 33/58* | (2006.01) |
| *G01N 33/68* | (2006.01) |
| *C07K 16/28* | (2006.01) |
| *C07K 14/36* | (2006.01) |
| *C07D 495/04* | (2006.01) |
| *C07D 519/00* | (2006.01) |

(52) U.S. Cl.
CPC ........... *G01N 33/58* (2013.01); *C07D 495/04* (2013.01); *C07D 519/00* (2013.01); *C07K 14/36* (2013.01); *C07K 16/2878* (2013.01); *G01N 33/68* (2013.01)

(58) Field of Classification Search
CPC .. C07D 207/40; C07D 233/20; C07D 487/04; C07D 495/04; C07D 519/00; C07K 14/36; C07K 16/00; C07K 16/28; C07K 16/2878; C07K 2317/10; G01N 33/54353; G01N 33/58; G01N 33/68
See application file for complete search history.

(56) References Cited

U.S. PATENT DOCUMENTS

| | | | |
|---|---|---|---|
| 6,153,442 A | 11/2000 | Pirio et al. | |
| 2017/0145063 A1* | 5/2017 | Sugiyama | .......... C07K 16/2887 |

FOREIGN PATENT DOCUMENTS

| | | |
|---|---|---|
| JP | H1028589 A | 2/1998 |
| JP | H11501008 A | 1/1999 |
| JP | 2001514524 A | 9/2001 |
| JP | 2002516252 A | 6/2002 |
| JP | 2004503299 A | 2/2004 |
| JP | 2005502030 A | 1/2005 |
| JP | 2011122957 A | 6/2011 |
| JP | 2012-167987 A | 9/2012 |
| JP | 2016027006 A | 2/2016 |

(Continued)

OTHER PUBLICATIONS

European Search Opinion issued for the European counterpart EP20180754223 dated Feb. 5, 2021.*

(Continued)

*Primary Examiner* — Galina M. Yakovleva
(74) *Attorney, Agent, or Firm* — Buchanan Ingersoll & Rooney PC

(57) ABSTRACT

Finding a protein of a minute amount present on a cell membrane to provide a method for producing an antibody against the protein. Producing an antibody using a protein identified by an identification method including: a labeling step of using a labeling agent comprising at least one selected from bis-iminobiotin compounds and bis-biotin compounds to obtain cells having a labeled protein; a degradation step of preparing a degradation product for an immobilization treatment, the degradation product containing the labeled protein; an immobilization step of immobilizing the labeled protein contained in the degradation product for an immobilization treatment on a stationary phase via a streptavidin mutant; a cleavage step of releasing an analysis sample from the stationary phase on which the labeled protein is immobilized; and an analysis step of analyzing the analysis sample to identify the labeled protein.

3 Claims, No Drawings
Specification includes a Sequence Listing.

(56) References Cited

FOREIGN PATENT DOCUMENTS

| WO | 9960400 | A1 | 11/1999 |
|---|---|---|---|
| WO | 2001095857 | A2 | 12/2001 |
| WO | 02100892 | A1 | 12/2002 |
| WO | 2009088694 | A1 | 7/2009 |
| WO | 2009089262 | A1 | 7/2009 |
| WO | 2013084526 | A1 | 6/2013 |
| WO | 2015125820 | A1 | 8/2015 |

OTHER PUBLICATIONS

Mobley et al., Binding of Small-Molecule Ligands to Proteins: "What You See" Is Not Always "What You Get," Structure, 2009, vol. 17, issue 4, pp. 489-498.*

Thermo Scientific "Crosslinking Reagents Technical Handbook," 2012, pp. 1-56.*

Partial Supplementary European Search Report dated Oct. 30, 2020, by the European Patent Office in corresponding European Patent Application No. 18754223.8. (56 pages).

Hamblett et al., "A Streptavidin-Biotin Binding System That Minimizes Blocking by Endogenous Biotin," Bioconjugate Chemistry, 2002, vol. 13, No. 3, pp. 588-598.

Wilbur et al., "Design and Synthesis of Bis-Biotin-Containing Reagents for Applications Utilizing Monoclonal Antibody-Based Pretargeting Systems with Streptavidin Mutants," Bioconjugate Chemistry, 2010, vol. 21, No. 7, pp. 1225-1238.

Bausch-Fluck, D., et al., "A Mass Spectrometric-Derived Cell Surface Protein Atlas," PLOS|ONE, 10(4), doi:10.1371/journal.pone.0121314 (Apr. 20, 2015).

Giuliano, E., "Biotinylation reagents for the study of cell surface proteins," Proteomics Journal, InterScience, Wiley-VCH Verlag GmbH & Co. KGaA, Weinheim, 8, pp. 4012-4024, (2008).

International Search Report (with English translation) and Written Opinion issued in corresponding International Patent Application No. PCT/JP2018/005814, 18 pages (May 22, 2018).

Kawato, T., et al., "Structure-based design and synthesis of a bivalent iminobiotin analog showing strong affinity toward a low immunogenic streptavidin mutant," https://doi.org/10.1080/09168451.2014.991692, Bioscience, Biotechnology, and Biochemistry, 79:4, pp. 640-642, (2015).

Melkko, S., et al., "On the Magnitude of the Chelate Effect for the Recognition of Proteins by Pharmacophores Scaffolded by Self-Assembling Oligonucleotides," Elsevier Ltd, Chemistry & Biology 13, 225-231, (Feb. 2006).

"Avidin-Biotin Technical Handbook," (Selection Guide, p. 3), Thermo Fisher Scientific Inc., pp. 1-48 (2009).

* cited by examiner

METHOD FOR IDENTIFYING DRUG-DISCOVERY TARGET PROTEIN FOR DEVELOPMENT OF ANTIBODY DRUG, AND METHOD FOR PRODUCING ANTIBODY AGAINST TARGET PROTEIN

SEQUENCE LISTING

Incorporated by reference herein in its entirety is a computer-readable sequence listing submitted via EFS-Web and identified as follows: One (8,484 byte ASCII (Text)) file named "Sequence listing.txt" created on Feb. 19, 2018.

TECHNICAL FIELD

The present invention relates to a method, useful in a variety of fields of not only pharmaceuticals and agricultural chemicals but also biological studies, for identifying a cell surface protein of a minute amount present on a cell membrane, or an interstitial protein present in a blood vessel or interstitium of a tissue, and an antibody production method for producing an antibody against the identified protein.

BACKGROUND ART

In recent years, antibody drugs have been exhibiting remarkable effects in treatment of diseases. Such effects have resulted from accumulation of its production and modification techniques practically employable, in addition to the therapeutic effect with high selectivity and low toxicity inherent in an antibody. Although treatment of a disease for which a target protein of an antibody has been found has progressed, there still remain a large number of diseases for which a target protein has not been found.

It is regarded that cell surface proteins include those playing a significant role in biological functions such as cell recognition, protein interaction in signal transduction pathway, and response to a pharmaceutical. If a surface protein peculiar to a disease-related cell can be newly identified to obtain an antibody against it, an antibody can be provided, which is useful for, for example, specifying a disease-related cell; analyzing the function of the cell; making study on response of the cell to a pharmaceutical; developing a pharmaceutical, etc.

Besides, it becomes clear that an interstitial protein such as an extracellular matrix included in the interstitium of a tissue/organ has a significant role for keeping a function of a parenchyma cell that is a principal component cell of a tissue. It is expected that information significant for clarification of pathological condition or development of an epoch-making pharmaceutical can be provided by efficiently purifying/identifying such an interstitial protein. Basic technology for easily and efficiently purifying such a protein present in the interstitium has not been established yet, and it should be said that qualitative/quantitative detailed analysis of an interstitial protein present in a minute amount in pathological condition is extremely difficult.

With respect to a drug-discovery target useful for development of an antibody drug present in a minute amount, an attempt has been made to obtain a novel target protein for antibody production. However, a method for finding a protein of a minute amount useful as a target to produce an antibody against it has not been sufficiently established until now.

Examples of conventional methods for finding a target protein include a method comprising a step of labeling a protein with biotin, capturing the labeled protein using a column in which streptavidin (SA) strongly binding to biotin has been immobilized, and separating the labeled protein thus captured from the column for analysis and identification.

Biotinylated proteins are present, however, in a large amount in a living body, the background of the analysis is so high that a protein of a minute amount cannot be sufficiently analyzed in some cases.

Non Patent Literature 1 discloses a method for analyzing a cell surface protein and an interstitial protein contained in a tissue/organ. Non Patent Literature 2 discloses analysis of a cell surface protein and an interstitial protein contained in a tissue/organ using a biotin compound.

On the other hand, with regard to a biotin compound, Patent Literature 1 discloses a bis-biotin compound for antibody analysis. Patent Literature 1 discloses, regarding the bis-biotin compound for antibody analysis, Compound 17 having the following molecular structure:

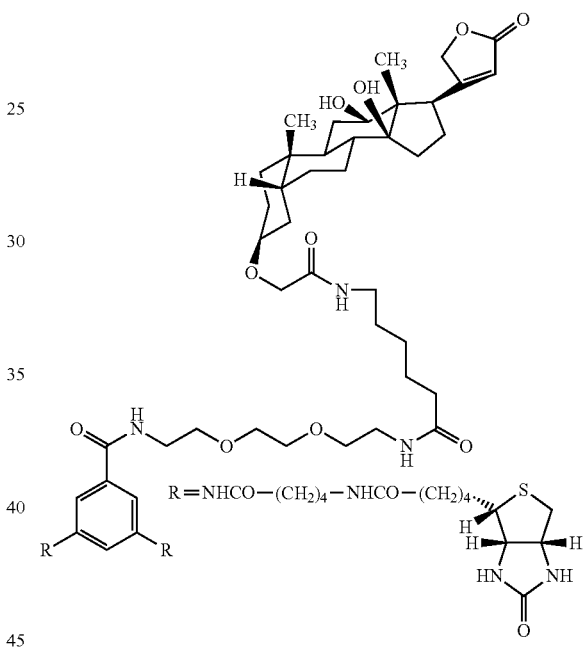

Besides, Patent Literature 2, Non Patent Literature 3 and Non Patent Literature 4 disclose bis-iminobiotin compounds. Furthermore, Patent Literature 3, Patent Literature 4 and Patent Literature 5 disclose bis-biotin compounds. These literatures, however, neither disclose nor suggest use of a bis-biotin compound or an bis-iminobiotin compound as a protein labeling agent, and further identification of a labeled protein for producing an antibody against the protein.

CITATION LIST

Patent Literature

Patent Literature 1: U.S. Pat. No. 6,153,442
Patent Literature 2: International Publication No. WO2015/125820
Patent Literature 3: International Publication No. WO2009/089262
Patent Literature 4: International Publication No. WO2009/088694

Patent Literature 5: International Publication No. WO1999/60400

Non Patent Literature

Non Patent Literature 1: Bausch-Fluck D, Hofmann A, Bock T, Frei A P, Cerciello F, et al. (2015), A Mass Spectrometric-Derived Cell Surface Protein Atlas. PLoS One 10: e0121314.
Non Patent Literature 2: Elia G1., Biotinylation reagents for the study of cell surface proteins. Proteomics. 2008 October; 8 (19):4012-24.
Non Patent Literature 3: Bioscience, Biotechnology, and Biochemistry (2015), 79 (4), 640-642
Non Patent Literature 4: Chemistry & Biology (2006), 13 (2), 225-231

SUMMARY OF INVENTION

Technical Problem

Known cell surface proteins (also designated as membrane proteins) present in a minute amount in cell membranes are as follows:
(a) a cell surface protein containing a marker molecule significant for finding the type and the property of a cell;
(b) a cell surface protein corresponding to a node (inlet) for information transmission from outside to inside of a cell, such as a receptor, and significant for clarification of the function of the information transmission; and
(c) a cell surface protein corresponding to a target of an antibody drug.

It is very useful to provide antibodies against the cell surface proteins (a) to (c) for clarification of the type and the property of cells, clarification of the information transmission function from outside to inside of cells, and provision of antibody drugs. In particular, it is currently difficult to target a protein present inside of a cell kept in a cell shape, and hence, it is very significant in the field of antibody drugs to specify a cell surface protein for pharmaceutical antibody production.

It is known that not only cell surface proteins but also interstitial proteins containing a blood vessel, etc., of a pathological tissue play a significant role in maintenance of a function of a parenchyma cell of the tissue and pathogenesis, and, therefore, it is regarded that such a protein can be a target molecule in drug discovery, and attention is being paid to effective detection/identification techniques. In general, however, means for efficiently recovering such interstitial tissues (including blood vessels) to purify/identify a useful protein therefrom has not been substantially established, and such a technique needs to be urgently developed.

An object of the present invention is, regarding production of an antibody useful in the pharmaceutical and agricultural fields, to find a protein of a minute amount present on a cell membrane or in a blood vessel or interstitium in a tissue, and to provide a method for producing an antibody against the protein.

Solution to Problem

A method for identifying a protein according to the present invention is characterized in comprising the following steps (1) to (5):
(1) a step of providing a cell and/or a tissue having a labeled protein;
(2) a degradation step of degrading the cell and/or the tissue having a labeled protein to prepare a degradation product containing the labeled protein;
(3) an immobilization step of contacting the degradation product with a streptavidin mutant immobilized on a stationary phase to immobilize the labeled protein contained in the degradation product on the stationary phase via the streptavidin mutant;
(4) a cleavage step of releasing an analysis sample from the stationary phase on which the labeled protein is immobilized; and
(5) an analysis step of analyzing the analysis sample to identify the labeled protein.

A method for producing an antibody against a target protein according to the present invention is characterized in comprising:
a step of providing a target protein for antibody production; and
a step of producing, from the target protein, an antibody against the target protein,
in which a protein identified by the above-described identification method is used as the target protein for antibody production.

A bis-biotin compound or a bis-iminobiotin compound according to the present invention usable in the above-described identification method is characterized in that they are represented by the following general formula (1):

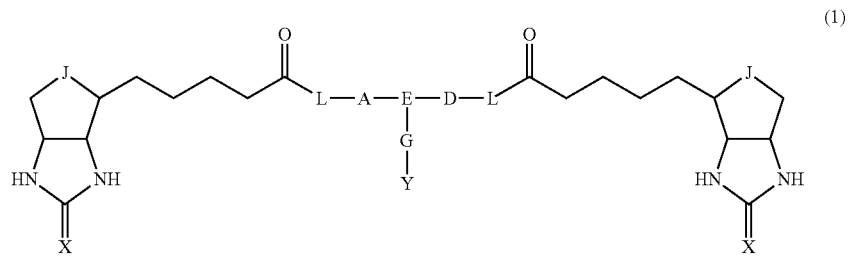

(1)

wherein A, D and E each independently represent a spacer connecting two bicyclo rings to each other, and E represents a structure capable of forming a branch. J represents a sulfur atom $S^+$—$O^-$ or $SO_2$, L represents NH, an oxygen atom or methylene, X represents NH or an oxygen atom, Y represents a structure for forming a bond to a protein, and G represents a spacer connecting E and Y.

A protein labeling compound according to the present invention is characterized in being at least one selected from compounds represented by the above-described general formula (1).

A streptavidin mutant for identifying a labeled protein according to the present invention is characterized in that the labeled protein is labeled with at least one selected from the compounds represented by the above-described general formula (1), and that the streptavidin mutant has an enhanced affinity for the above-described labeling compound, and a weakened affinity for biotin as compared with natural streptavidin, through modification of an amino acid sequence.

Use of a labeling compound for labeling a protein according to the present invention is characterized in that the labeling compound is at least one selected from the compounds represented by the above-described general formula (1).

Use of a streptavidin mutant for identifying a labeled protein according to the present invention is characterized in that the labeled protein is labeled with at least one selected from the compounds represented by the above-described general formula (1), and that the streptavidin mutant has an enhanced affinity for the above-described labeling compound, and a weakened affinity for biotin as compared with natural streptavidin, through modification of an amino acid sequence.

A kit for identifying a protein according to the present invention is characterized in comprising a labeling compound for labeling a protein in a sample, and a streptavidin mutant having an enhanced affinity for the labeling compound, and a weakened affinity for biotin as compared with natural streptavidin, through modification of an amino acid sequence, wherein the labeling compound is at least one selected from compounds represented by the above-described general formula (1).

Advantageous Effects of Invention

According to the present invention, various proteins of a minute amount present on a cell surface and in interstitium can be obtained, and a novel antibody can be efficiently produced from such a protein. An antibody obtained by a production method of the present invention can not only be used in a pharmaceutical and an agricultural chemical but also make contribution to biological studies.

DESCRIPTION OF EMBODIMENTS

A method for identifying a protein according to the present invention is that for identifying a cell surface protein and an interstitial protein of a tissue/organ, and comprises the following steps (1) to (5):

(1) a step of providing a cell and/or a tissue having a labeled protein;

(2) a degradation step of degrading the cell and/or the tissue having a labeled protein to prepare a degradation product containing the labeled protein;

(3) an immobilization step of contacting the degradation product with a streptavidin mutant immobilized on a stationary phase to immobilize the labeled protein contained in the degradation product on the stationary phase via the streptavidin mutant;

(4) a cleavage step of releasing an analysis sample from the stationary phase on which the labeled protein is immobilized; and (5) an analysis step of analyzing the analysis sample to identify the labeled protein.

The step (1) can be carried out through the following step (1A):

(1A) a labeling step of labeling a protein present on a cell membrane of a cell and/or an extracellular protein present in a tissue with a labeling agent comprising at least one selected from a bis-iminobiotin compound and a bis-biotin compound, to obtain the labeled protein.

The cell and/or tissue having a labeled protein in the step (1) can be provided in the form of a sample for a treatment employed in the step (2) and can be used in the step (2).

The aforementioned respective steps are described below.

[Step (1A)] (Labeling Step)

The cell and/or the tissue having a labeled protein used in the step (1) can be prepared by the step (1A).

The labeling step is described below.

In the labeling step, a protein is labeled with a labeling agent comprising at least one of the bis-iminobiotin compounds and the bis-biotin compounds.

In order to produce an antibody for purpose of treatment of a disease, it is necessary to first find a cell surface protein (membrane protein) specific to a cause of pathological condition. A surface protein is a protein in a state buried in a lipid bilayer of a cell membrane or bound to a lipid itself. It is known that a cell surface protein is characteristically inherent to each type of a cell. It is also known that when a given type of cell surface protein excessively expresses or an abnormal cell surface protein having mutation in the type of amino acid is present, the cell itself becomes abnormal to cause a disease.

Therefore, when a protein present in a cell and in a tissue/organ is labeled to comparatively analyze a difference from a normal cell/tissue/organ, a protein peculiar to the pathological condition can be found.

In order to clarify the action mechanism of a drug, it is necessary to identify a target protein, etc., to which the drug binds. Therefore, for identifying a target protein present in a cell, etc., having pharmacological activity, a derivative, to which a drug (a drug conjugate to bis-iminobiotin/bis-biotin, etc.) is bound, is caused to act on an organ/tissue/cell or a lysate thereof, and thus, a protein strongly binding to the drug can be found by means of proteome analysis, etc.

In the present invention, the term "labeling" means causing a labeling agent to strongly bind to a protein, and they can be bound through a covalent bond or a noncovalent bond, and are bound more preferably through a covalent bond.

In the present invention, a bis-iminobiotin compound refers to two iminobiotins bound to each other through a spacer structure, which may comprise a structure in which sulfur included in a ring is oxidized.

In the present invention, a bis-biotin compound refers to two biotins bound to each other through a spacer structure, which may comprise a structure in which sulfur included in a ring is oxidized.

Any bis-iminobiotin compound and bis-biotin compound can be used without any limitation as long as it has a function as the labeling agent required in the present invention.

The bis-iminobiotin compound or the bis-biotin compound is preferably a compound represented by the following general formula (1):

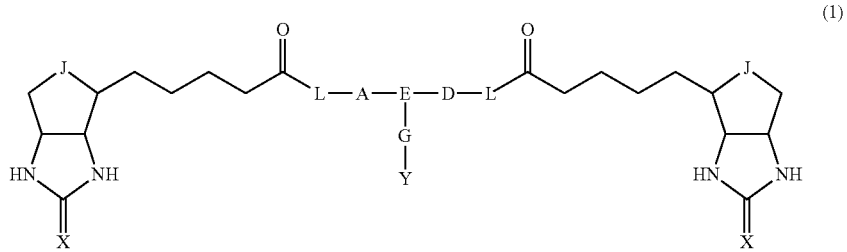

(1)

In the general formula (1), A, D and E each independently represent a spacer connecting two bicyclo rings to each other, and E represents a structure capable of forming a branch. J represents a sulfur atom, $S^+$—$O^-$ or $SO_2$, L represents NH, an oxygen atom or methylene, X represents NH or an oxygen atom, Y represents a structure for forming a bond to a protein, and G represents a spacer connecting E and Y.

L is a group for binding A and D as the spacers to an iminobiotin portion or a biotin portion through an amide bond, an ester bond or a C—C bond. Two Ls may be different groups or the same group, and are preferably the same group.

A and D may be the same, or may be different from each other for adjusting the lengths of the spacers.

When J is a sulfur atom, the compound of the general formula (1) is iminobiotin or biotin. A compound in which the sulfur atom represented by J is oxidized into $S^+$—$O^-$ or $SO_2$ can be also used.

When X is NH, the compound of the general formula (1) is an iminobiotin compound, and when X is an oxygen atom, it is a biotin compound, and these compounds may be also used.

In the general formula (1), two Js are the same group, and two Xs are the same group.

When there is asymmetric carbon in the molecular structure of the compound represented by the general formula (1), the compound may have a structure of any of stereoisomers.

The spacer structures represented by A, E and D in the bis-iminobiotin compounds and the bis-biotin compounds according to the present invention can be any one of various structures, and an appropriate length of A-E-D can be calculated based on X-ray structure data of a streptavidin tetramer. Specifically, X-ray structure data of streptavidin, a streptavidin mutant and iminobiotin or biotin complexes thereof was obtained from Protein Data Bank (PDB). 100 or more such structures are known under PDB IDs of 1DF8, 1MEP, 3WYP, 3WYQ, 3WZO, 3WZP, 3WZN, 3WZQ, 3X00, etc. These structures were used for performing docking analysis. First, bis-iminobiotins or bis-biotins were individually bound to a streptavidin mutant, in which two Ls are connected through carbon chains of different lengths for docking on a computer. Thus, it was found that the number of bonds between the two Ls is preferably 13 or more for simultaneously binding two bicyclo rings. It was found that the two bicyclo rings can be more efficiently simultaneously bound to a streptavidin mutant when the number of bonds is 21 or less. Therefore, it is preferred that the minimum bond number of the spacer structure binding the two Ls is preferably 13 to 21 because thus, the desired purpose of obtaining a rigid bond to a streptavidin mutant can be more effectively attained.

The minimum bond number means the smallest number of bonds counted as the number of bonds present between the two Ls when there can be a variety of kinds of bond number due to a cyclic structure, etc.

The spacer structure can be partially a cyclic structure, such as an alicyclic structure, an aromatic ring, a heterocycle or a condensed ring, but is not limited to such a structure.

Preferably, A represents a1-a2-a3-a4, and a1, a2, a3 and a4 each independently represent a nitrogen atom, an oxygen atom, a carbonyl group, —NH—, —$(CH_2)$n- (wherein n represents an integer of 0 to 9), —CH(COOH)—, —CH(COOMe)- (wherein Me represents a methyl group), —$(CF_2)$n- (wherein n represents an integer of 0 to 9), a benzene ring, a heterocycle or a bond.

Preferably, D represents d1-d2-d3-d4, and d1, d2, d3 and d4 each independently represent a nitrogen atom, an oxygen atom, a carbonyl group, —NH—, —$(CH_2)$n- (wherein n represents an integer of 0 to 9), —CH(COOH)—, —CH(COOMe)- (wherein Me represents a methyl group), —$(CF_2)$n- (wherein n represents an integer of 0 to 9), a benzene ring, a heterocycle or a bond.

G is a spacer connecting E and Y and is not especially limited, but needs to have an appropriate length as a spacer for avoiding steric bump between a labeled surface protein and immobilized streptavidin. The number of bonds included in the spacer of G is preferably 10 or more, and more preferably 14 or more. The number of bonds is preferably 113 or less, and more preferably 50 or less. This number of bonds, which is defined in the same manner as the number of bonds present between the two Ls, means the minimum bond number corresponding to the smallest bond number because there may be a variety of kinds of bond number when G has a cyclic structure, etc.

Since water solubility to some extent is required in labeling, G preferably has a hydrophilic structure.

The spacer of G can have a structure that is cut by reduction, oxidation, irradiation, an enzyme, a nucleophile, an electrophile or an organometallic reagent. Such a cuttable structure is not especially limited as long as a desired effect of cutting can be obtained. A cuttable structure is described in detail in Bioorganic & Medicinal Chemistry 20 (2012) 571, and a cuttable structure selected from those described in this literature can be incorporated into the spacer of G. A disulfide bond is well known as a structure cut by reduction, and a nitrobenzyl structure is known as a structure cut by irradiation. Such a bond can be used in the structure of G.

G can have any of various structures as long as these requirements are satisfied.

Preferably, G represents g1-g2-g3-g4-g5-g6-g7, and g1, g2, g3, g4, g5, g6 and g7 each independently represent a nitrogen atom, an oxygen atom, a carbonyl group, a nitrobenzyl group, a disulfide bond, —NH—, —$(CH_2)$n- (wherein n represents an integer of 0 to 9), —$(CH_2CH_2O)$n- (wherein n represents an integer of 0 to 9), a benzene ring, a heterocycle or a bond.

Preferable examples of the heterocycle of A, D and G include a pyridine ring, a pyrimidine ring, a triazine ring, a thiophen ring, a furan ring, a pyrrole ring, a pyrrolidine ring, a piperidine ring, an imidazole ring, a pyrazole ring, an oxazole ring, a triazole ring structure, and a heterocycle represented by the following structural formula (2):

Structural Formula 2

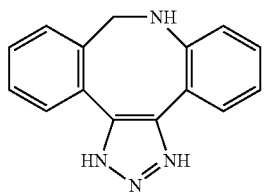

8,9-dihydro-1H-dibenzo[b,f][1,2,3]triazolo[4,5-d]azocine

When a benzene ring or a heterocycle is selected independently as A, D and G, two groups connected to the selected ring structure can be substituted in a chemically acceptable arbitrary position in the ring.

E is not especially limited as long as it has a structure that can branch a side chain. The structure of E capable of forming a branch means that E can bind to G in addition to the structures A and D.

E is preferably a group containing a nitrogen atom, a carbon atom, a benzene ring or a heterocycle as a binding portion to A, D and G.

When E is a group having a benzene ring or a heterocycle, at least one of A, D and G may bind to such a ring structure.

When a benzene ring or a heterocycle itself is selected as E, each of A, D and G may be substituted in a chemically acceptable arbitrary position in the selected ring structure. Substitution positions are preferably highly symmetric. More specifically, substitution positions for a benzene ring are the 1-, 3- and 5-positions, and substitution positions for a pyridine ring are the 2-, 4- and 6-positions.

Preferable examples of the heterocycle of E include a pyridine ring, a pyrimidine ring, a triazine ring, a thiophen ring, a furan ring, a pyrrole ring, a pyrrolidine ring, a piperidine ring, an imidazole ring, a pyrazole ring, an oxazole ring, a triazole ring structure, and a heterocycle represented by the above-described structural formula (2).

More preferably, A-E-D is represented by a1-a2-a3-a4-E-d4-d3-d2-d1, and a1 to a4, E and d1 to d4 are each independently selected from Table A1 below.

TABLE A1

| A | | | | | D | | | |
|---|---|---|---|---|---|---|---|---|
| a1 | a2 | a3 | a4 | E | d4 | d3 | d2 | d1 |
| $(CH_2)_1$ | NH | NH | NH | Ph | NH | NH | NH | $(CH_2)_1$ |
| $(CH_2)_2$ | CO | CO | N | CO | CO | CO | $(CH_2)_2$ |
| $(CH_2)_3$ | O | $(CH_2)_2$ | NHCO | CH | NHCO | $(CH_2)_2$ | O | $(CH_2)_3$ |
| $(CH_2)_4$ | $(CH_2)_1$ | Bond | $(CH_2)_1$ | Heterocycle | $(CH_2)_1$ | Bond | $(CH_2)_1$ | $(CH_2)_4$ |
| $(CH_2)_5$ | $(CH_2)_2$ | | $(CH_2)_2$ | | $(CH_2)_2$ | | $(CH_2)_2$ | $(CH_2)_5$ |
| $(CH_2)_6$ | $(CH_2)_3$ | | $(CH_2)_3$ | | $(CH_2)_3$ | | $(CH_2)_3$ | $(CH_2)_6$ |
| $(CH_2)_7$ | $(CH_2)_4$ | | $(CH_2)_4$ | | $(CH_2)_4$ | | $(CH_2)_4$ | $(CH_2)_7$ |
| $(CH_2)_8$ | $(CH_2)_5$ | | $(CH_2)_5$ | | $(CH_2)_5$ | | $(CH_2)_5$ | $(CH_2)_8$ |
| CH(COOH) | CH(COOH) | | Bond | | Bond | | CH(COOH) | CH(COOH) |
| CH(COOMe) | CH(COOMe) | | Bond | | Bond | | CH(COOMe) | CH(COOMe) |
| $(CF_2)_1$ | $(CF_2)_1$ | | | | | | $(CF_2)_1$ | $(CF_2)_1$ |
| $(CF_2)_2$ | $(CF_2)_2$ | | | | | | $(CF_2)_2$ | $(CF_2)_2$ |
| $(CF_2)_3$ | $(CF_2)_3$ | | | | | | $(CF_2)_3$ | $(CF_2)_3$ |
| Bond | Bond | | | | | | Bond | Bond |

More preferably, G is represented by g1-g2-g3-g4-g5-g6-g7, and g1 to g7 are each independently selected from Table G1 below.

TABLE G1

| g1 | g2 | g3 | g4 | g5 | g6 | g7 |
|---|---|---|---|---|---|---|
| NH | (structure) | NH | (structure) | $(CH_2CH_2O)_1$ | $(CH_2)_1$ | CO |
| O | CO | O | (structure) | $(CH_2CH_2O)_2$ | $(CH_2)_2$ | Bond |

TABLE G1-continued

| g1 | g2 | g3 | g4 | g5 | g6 | g7 |
|---|---|---|---|---|---|---|
| CO | $(CH_2)_1$ | CO | [structure: N-C(=O)-CH(CH_3)-S-S-CH(CH_3)-C(=O)-N] | $(CH_2CH_2O)_3$ | $(CH_2)_3$ | |
| CONH | $(CH_2)_2$ | CONH | $(CH_2)_1$ | $(CH_2CH_2O)_4$ | $(CH_2)_4$ | |
| $(CH_2)_1$ | $(CH_2)_3$ | $(CH_2)_1$ | $(CH_2)_2$ | $(CH_2CH_2O)_5$ | $(CH_2)_5$ | |
| $(CH_2)_2$ | $(CH_2)_4$ | $(CH_2)_2$ | $(CH_2)_3$ | $(CH_2CH_2O)_6$ | $(CH_2)_6$ | |
| $(CH_2)_3$ | $(CH_2)_5$ | $(CH_2)_3$ | $(CH_2)_4$ | $(CH_2CH_2O)_7$ | Bond | |
| $(CH_2)_4$ | $(CH_2)_6$ | $(CH_2)_4$ | $(CH_2)_5$ | $(CH_2CH_2O)_8$ | | |
| $(CH_2)_5$ | $(CH_2CH_2O)_1$ | $(CH_2)_5$ | $(CH_2)_6$ | $(CH_2CH_2O)_9$ | | |
| $(CH_2)_6$ | $(CH_2CH_2O)_2$ | $(CH_2)_6$ | Ph | Bond | | |
| Ph | $(CH_2CH_2O)_3$ | Ph | Heterocycle | | | |
| Heterocycle | $(CH_2CH_2O)_4$ | $OCH_2$ | CONH | | | |
| Bond | $(CH_2CH_2O)_5$ | $(CH_2CH_2O)_1$ | $(CH_2CH_2O)_1$ | | | |
| | $(CH_2CH_2O)_6$ | $(CH_2CH_2O)_2$ | $(CH_2CH_2O)_2$ | | | |
| | $(CH_2CH_2O)_7$ | $(CH_2CH_2O)_3$ | $(CH_2CH_2O)_3$ | | | |
| | $(CH_2CH_2O)_8$ | $(CH_2CH_2O)_4$ | $(CH_2CH_2O)_4$ | | | |
| | $(CH_2CH_2O)_9$ | $(CH_2CH_2O)_5$ | $(CH_2CH_2O)_5$ | | | |
| | Bond | $(CH_2CH_2O)_6$ | $(CH_2CH_2O)_6$ | | | |
| | | $(CH_2CH_2O)_7$ | $(CH_2CH_2O)_7$ | | | |
| | | $(CH_2CH_2O)_8$ | $(CH_2CH_2O)_8$ | | | |
| | | $(CH_2CH_2O)_9$ | $(CH_2CH_2O)_9$ | | | |
| | | Bond | Bond | | | |

More preferably, A-E-D is represented by a1-a2-a3-a4-E-d4-d3-d2-d1, a1 to a4, E, and d1 to d4 are each independently selected from Table A1 above, G is represented by g1-g2-g3-g4-g5-g6-g7, and g1 to g7 are each independently selected from Table G1 above.

More preferably, A-E-D is represented by a1-a2-a3-a4-E-d4-d3-d2-d1, and is one selected from combinations 1 to 114 shown in Table A2 below, G is represented by g1-g2-g3-g4-g5-g6-g7, and g1 to g7 are each independently selected from Table G1 above.

TABLE A2

| | A | | | | | D | | | |
|---|---|---|---|---|---|---|---|---|---|
| | a1 | a2 | a3 | a4 | E | d4 | d3 | d2 | d1 |
| 1 | $(CH_2)_5$ | Bond | Bond | Bond | N | Bond | Bond | Bond | $(CH_2)_5$ |
| 2 | $(CH_2)_5$ | Bond | Bond | Bond | N | Bond | Bond | Bond | $(CH_2)_6$ |
| 3 | $(CH_2)_6$ | Bond | Bond | Bond | N | Bond | Bond | Bond | $(CH_2)_6$ |
| 4 | $(CH_2)_6$ | Bond | Bond | Bond | N | Bond | Bond | Bond | $(CH_2)_7$ |
| 5 | $(CH_2)_7$ | Bond | Bond | Bond | N | Bond | Bond | Bond | $(CH_2)_7$ |
| 6 | $(CH_2)_7$ | Bond | Bond | Bond | N | Bond | Bond | Bond | $(CH_2)_8$ |
| 7 | $(CH_2)_8$ | Bond | Bond | Bond | N | Bond | Bond | Bond | $(CH_2)_8$ |
| 8 | $(CH_2)_8$ | Bond | Bond | Bond | N | Bond | Bond | $(CH_2)_1$ | $(CH_2)_8$ |
| 9 | $(CH_2)_8$ | $(CH_2)_1$ | Bond | Bond | N | Bond | Bond | $(CH_2)_1$ | $(CH_2)_8$ |
| 10 | $(CH_2)_8$ | $(CH_2)_1$ | Bond | Bond | N | Bond | Bond | $(CH_2)_2$ | $(CH_2)_8$ |
| 11 | $(CH_2)_8$ | $(CH_2)_2$ | Bond | Bond | N | Bond | Bond | $(CH_2)_2$ | $(CH_2)_8$ |
| 12 | $(CH_2)_7$ | CO | NH | Bond | Ph | Bond | NH | CO | $(CH_2)_7$ |
| 13 | $(CH_2)_6$ | CO | NH | Bond | Ph | Bond | NH | CO | $(CH_2)_6$ |
| 14 | $(CH_2)_5$ | CO | NH | Bond | Ph | Bond | NH | CO | $(CH_2)_6$ |
| 15 | $(CH_2)_5$ | CO | NH | Bond | Ph | Bond | NH | CO | $(CH_2)_5$ |
| 16 | $(CH_2)_4$ | CO | NH | Bond | Ph | Bond | NH | CO | $(CH_2)_5$ |
| 17 | $(CH_2)_4$ | CO | NH | Bond | Ph | Bond | NH | CO | $(CH_2)_4$ |
| 18 | $(CH_2)_3$ | CO | NH | Bond | Ph | Bond | NH | CO | $(CH_2)_4$ |
| 19 | $(CH_2)_3$ | CO | NH | Bond | Ph | Bond | NH | CO | $(CH_2)_3$ |
| 20 | $(CH_2)_7$ | NH | CO | Bond | Ph | Bond | CO | NH | $(CH_2)_7$ |
| 21 | $(CH_2)_6$ | NH | CO | Bond | Ph | Bond | CO | NH | $(CH_2)_6$ |
| 22 | $(CH_2)_5$ | NH | CO | Bond | Ph | Bond | CO | NH | $(CH_2)_5$ |
| 23 | $(CH_2)_4$ | NH | CO | Bond | Ph | Bond | CO | NH | $(CH_2)_5$ |
| 24 | $(CH_2)_4$ | NH | CO | Bond | Ph | Bond | CO | NH | $(CH_2)_4$ |
| 25 | $(CH_2)_3$ | NH | CO | Bond | Ph | Bond | CO | NH | $(CH_2)_4$ |
| 26 | $(CH_2)_3$ | NH | CO | Bond | Ph | Bond | CO | NH | $(CH_2)_3$ |
| 27 | CH(COOH) | $(CH_2)_2$ | CO | NH | Ph | NH | CO | $(CH_2)_2$ | CH(COOH) |
| 28 | CH(COOH) | $(CH_2)_2$ | CO | NH | Ph | NH | CO | $(CH_2)_3$ | CH(COOH) |
| 29 | CH(COOH) | $(CH_2)_3$ | CO | NH | Ph | NH | CO | $(CH_2)_3$ | CH(COOH) |
| 30 | CH(COOH) | $(CH_2)_3$ | CO | NH | Ph | NH | CO | $(CH_2)_4$ | CH(COOH) |
| 31 | CH(COOH) | $(CH_2)_4$ | CO | NH | Ph | NH | CO | $(CH_2)_4$ | CH(COOH) |
| 32 | CH(COOH) | $(CH_2)_4$ | CO | NH | Ph | NH | CO | $(CH_2)_5$ | CH(COOH) |
| 33 | $(CH_2)_2$ | CH(COOH) | CO | NH | Ph | NH | CO | CH(COOH) | $(CH_2)_2$ |
| 34 | $(CH_2)_2$ | CH(COOH) | CO | NH | Ph | NH | CO | CH(COOH) | $(CH_2)_3$ |
| 35 | $(CH_2)_3$ | CH(COOH) | CO | NH | Ph | NH | CO | CH(COOH) | $(CH_2)_3$ |
| 36 | $(CH_2)_3$ | CH(COOH) | CO | NH | Ph | NH | CO | CH(COOH) | $(CH_2)_4$ |

TABLE A2-continued

| | A | | | | E | D | | | |
| | a1 | a2 | a3 | a4 | | d4 | d3 | d2 | d1 |
|---|---|---|---|---|---|---|---|---|---|
| 37 | (CH$_2$)$_4$ | CH(COOH) | CO | NH | Ph | NH | CO | CH(COOH) | (CH$_2$)$_4$ |
| 38 | (CH$_2$)$_4$ | CH(COOH) | CO | NH | Ph | NH | CO | CH(COOH) | (CH$_2$)$_5$ |
| 39 | (CH$_2$)$_2$ | CH(COOH) | NH | CO | Ph | CO | NH | CH(COOH) | (CH$_2$)$_2$ |
| 40 | (CH$_2$)$_2$ | CH(COOH) | NH | CO | Ph | CO | NH | CH(COOH) | (CH$_2$)$_3$ |
| 41 | (CH$_2$)$_3$ | CH(COOH) | NH | CO | Ph | CO | NH | CH(COOH) | (CH$_2$)$_3$ |
| 42 | (CH$_2$)$_3$ | CH(COOH) | NH | CO | Ph | CO | NH | CH(COOH) | (CH$_2$)$_4$ |
| 43 | (CH$_2$)$_4$ | CH(COOH) | NH | CO | Ph | CO | NH | CH(COOH) | (CH$_2$)$_4$ |
| 44 | (CH$_2$)$_4$ | CH(COOH) | NH | CO | Ph | CO | NH | CH(COOH) | (CH$_2$)$_5$ |
| 45 | CH(COOH) | (CH$_2$)$_2$ | NH | CO | Ph | CO | NH | (CH$_2$)$_2$ | CH(COOH) |
| 46 | CH(COOH) | (CH$_2$)$_2$ | NH | CO | Ph | CO | NH | (CH$_2$)$_3$ | CH(COOH) |
| 47 | CH(COOH) | (CH$_2$)$_3$ | NH | CO | Ph | CO | NH | (CH$_2$)$_3$ | CH(COOH) |
| 48 | CH(COOH) | (CH$_2$)$_3$ | NH | CO | Ph | CO | NH | (CH$_2$)$_4$ | CH(COOH) |
| 49 | CH(COOH) | (CH$_2$)$_4$ | NH | CO | Ph | CO | NH | (CH$_2$)$_4$ | CH(COOH) |
| 50 | CH(COOH) | (CH$_2$)$_4$ | NH | CO | Ph | CO | NH | (CH$_2$)$_5$ | CH(COOH) |
| 51 | CH(COOMe) | (CH$_2$)$_2$ | CO | NH | Ph | NH | CO | (CH$_2$)$_2$ | CH(COOMe) |
| 52 | CH(COOMe) | (CH$_2$)$_2$ | CO | NH | Ph | NH | CO | (CH$_2$)$_3$ | CH(COOMe) |
| 53 | CH(COOMe) | (CH$_2$)$_3$ | CO | NH | Ph | NH | CO | (CH$_2$)$_3$ | CH(COOMe) |
| 54 | CH(COOMe) | (CH$_2$)$_3$ | CO | NH | Ph | NH | CO | (CH$_2$)$_4$ | CH(COOMe) |
| 55 | CH(COOMe) | (CH$_2$)$_4$ | CO | NH | Ph | NH | CO | (CH$_2$)$_4$ | CH(COOMe) |
| 56 | CH(COOMe) | (CH$_2$)$_4$ | CO | NH | Ph | NH | CO | (CH$_2$)$_5$ | CH(COOMe) |
| 57 | (CH$_2$)$_2$ | CH(COOMe) | CO | NH | Ph | NH | CO | CH(COOMe) | (CH$_2$)$_2$ |
| 58 | (CH$_2$)$_2$ | CH(COOMe) | CO | NH | Ph | NH | CO | CH(COOMe) | (CH$_2$)$_3$ |
| 59 | (CH$_2$)$_3$ | CH(COOMe) | CO | NH | Ph | NH | CO | CH(COOMe) | (CH$_2$)$_3$ |
| 60 | (CH$_2$)$_3$ | CH(COOMe) | CO | NH | Ph | NH | CO | CH(COOMe) | (CH$_2$)$_4$ |
| 61 | (CH$_2$)$_4$ | CH(COOMe) | CO | NH | Ph | NH | CO | CH(COOMe) | (CH$_2$)$_4$ |
| 62 | (CH$_2$)$_4$ | CH(COOMe) | CO | NH | Ph | NH | CO | CH(COOMe) | (CH$_2$)$_5$ |
| 63 | (CH$_2$)$_2$ | CH(COOMe) | NH | CO | Ph | CO | NH | CH(COOMe) | (CH$_2$)$_2$ |
| 64 | (CH$_2$)$_2$ | CH(COOMe) | NH | CO | Ph | CO | NH | CH(COOMe) | (CH$_2$)$_3$ |
| 65 | (CH$_2$)$_3$ | CH(COOMe) | NH | CO | Ph | CO | NH | CH(COOMe) | (CH$_2$)$_3$ |
| 66 | (CH$_2$)$_3$ | CH(COOMe) | NH | CO | Ph | CO | NH | CH(COOMe) | (CH$_2$)$_4$ |
| 67 | (CH$_2$)$_4$ | CH(COOMe) | NH | CO | Ph | CO | NH | CH(COOMe) | (CH$_2$)$_4$ |
| 68 | (CH$_2$)$_4$ | CH(COOMe) | NH | CO | Ph | CO | NH | CH(COOMe) | (CH$_2$)$_5$ |
| 69 | CH(COOMe) | (CH$_2$)$_2$ | NH | CO | Ph | CO | NH | (CH$_2$)$_2$ | CH(COOMe) |
| 70 | CH(COOMe) | (CH$_2$)$_2$ | NH | CO | Ph | CO | NH | (CH$_2$)$_3$ | CH(COOMe) |
| 71 | CH(COOMe) | (CH$_2$)$_3$ | NH | CO | Ph | CO | NH | (CH$_2$)$_3$ | CH(COOMe) |
| 72 | CH(COOMe) | (CH$_2$)$_3$ | NH | CO | Ph | CO | NH | (CH$_2$)$_4$ | CH(COOMe) |
| 73 | CH(COOMe) | (CH$_2$)$_4$ | NH | CO | Ph | CO | NH | (CH$_2$)$_4$ | CH(COOMe) |
| 74 | CH(COOMe) | (CH$_2$)$_4$ | NH | CO | Ph | CO | NH | (CH$_2$)$_5$ | CH(COOMe) |
| 75 | (CH$_2$)$_3$ | NH | CO | (CH$_2$) | N | (CH$_2$) | CO | NH | (CH$_2$)$_3$ |
| 76 | (CH$_2$)$_3$ | NH | CO | (CH$_2$) | N | (CH$_2$) | CO | NH | (CH$_2$)$_4$ |
| 77 | (CH$_2$)$_4$ | NH | CO | (CH$_2$) | N | (CH$_2$) | CO | NH | (CH$_2$)$_4$ |
| 78 | (CH$_2$)$_4$ | NH | CO | (CH$_2$) | N | (CH$_2$) | CO | NH | (CH$_2$)$_5$ |
| 79 | (CH$_2$)$_5$ | NH | CO | (CH$_2$) | N | (CH$_2$) | CO | NH | (CH$_2$)$_5$ |
| 80 | (CH$_2$)$_5$ | NH | CO | (CH$_2$) | N | (CH$_2$) | CO | NH | (CH$_2$)$_6$ |
| 81 | (CH$_2$)$_2$ | NH | CO | (CH$_2$)$_2$ | N | (CH$_2$)$_2$ | CO | NH | (CH$_2$)$_2$ |
| 82 | (CH$_2$)$_2$ | NH | CO | (CH$_2$)$_2$ | N | (CH$_2$)$_2$ | CO | NH | (CH$_2$)$_3$ |
| 83 | (CH$_2$)$_3$ | NH | CO | (CH$_2$)$_2$ | N | (CH$_2$)$_2$ | CO | NH | (CH$_2$)$_3$ |
| 84 | (CH$_2$)$_3$ | NH | CO | (CH$_2$)$_2$ | N | (CH$_2$)$_2$ | CO | NH | (CH$_2$)$_4$ |
| 85 | (CH$_2$)$_4$ | NH | CO | (CH$_2$)$_2$ | N | (CH$_2$)$_2$ | CO | NH | (CH$_2$)$_4$ |
| 86 | (CH$_2$)$_4$ | NH | CO | (CH$_2$)$_2$ | N | (CH$_2$)$_2$ | CO | NH | (CH$_2$)$_5$ |
| 87 | (CH$_2$)$_3$ | CO | NH | Bond | CH | (CH$_2$) | NH | CO | (CH$_2$)$_3$ |
| 88 | (CH$_2$)$_3$ | CO | NH | Bond | CH | (CH$_2$) | NH | CO | (CH$_2$)$_4$ |
| 89 | (CH$_2$)$_4$ | CO | NH | Bond | CH | (CH$_2$) | NH | CO | (CH$_2$)$_4$ |
| 90 | (CH$_2$)$_4$ | CO | NH | Bond | CH | (CH$_2$) | NH | CO | (CH$_2$)$_5$ |
| 91 | (CH$_2$)$_5$ | CO | NH | Bond | CH | (CH$_2$) | NH | CO | (CH$_2$)$_5$ |
| 92 | (CH$_2$)$_5$ | CO | NH | Bond | CH | (CH$_2$) | NH | CO | (CH$_2$)$_6$ |
| 93 | (CH$_2$)$_6$ | CO | NH | Bond | CH | (CH$_2$) | NH | CO | (CH$_2$)$_6$ |
| 94 | (CH$_2$)$_3$ | CO | NH | (CH$_2$) | CH | (CH$_2$) | NH | CO | (CH$_2$)$_3$ |
| 95 | (CH$_2$)$_3$ | CO | NH | (CH$_2$) | CH | (CH$_2$) | NH | CO | (CH$_2$)$_4$ |
| 96 | (CH$_2$)$_4$ | CO | NH | (CH$_2$) | CH | (CH$_2$) | NH | CO | (CH$_2$)$_4$ |
| 97 | (CH$_2$)$_4$ | CO | NH | (CH$_2$) | CH | (CH$_2$) | NH | CO | (CH$_2$)$_5$ |
| 98 | (CH$_2$)$_5$ | CO | NH | (CH$_2$) | CH | (CH$_2$) | NH | CO | (CH$_2$)$_5$ |
| 99 | (CH$_2$)$_5$ | CO | NH | (CH$_2$) | CH | (CH$_2$) | NH | CO | (CH$_2$)$_6$ |
| 100 | (CH$_2$)$_4$ | NH | CO | Bond | CH | Bond | CO | NH | (CH$_2$)$_4$ |
| 101 | (CH$_2$)$_4$ | NH | CO | Bond | CH | Bond | CO | NH | (CH$_2$)$_5$ |
| 102 | (CH$_2$)$_5$ | NH | CO | Bond | CH | Bond | CO | NH | (CH$_2$)$_5$ |
| 103 | (CH$_2$)$_5$ | NH | CO | Bond | CH | Bond | CO | NH | (CH$_2$)$_6$ |
| 104 | (CH$_2$)$_6$ | NH | CO | Bond | CH | Bond | CO | NH | (CH$_2$)$_6$ |
| 105 | (CH$_2$)$_6$ | NH | CO | Bond | CH | Bond | CO | NH | (CH$_2$)$_7$ |
| 106 | (CH$_2$)$_2$ | O | (CH$_2$)$_2$ | NHCO | Ph | NHCO | (CH$_2$)$_2$ | O | (CH$_2$)$_2$ |
| 107 | (CH$_2$)$_7$ | CO | NH | Bond | Pyridyl | Bond | NH | CO | (CH$_2$)$_7$ |
| 108 | (CH$_2$)$_6$ | CO | NH | Bond | Pyridyl | Bond | NH | CO | (CH$_2$)$_6$ |
| 109 | (CH$_2$)$_6$ | CO | NH | Bond | Pyridyl | Bond | NH | CO | (CH$_2$)$_5$ |
| 110 | (CH$_2$)$_5$ | CO | NH | Bond | Pyridyl | Bond | NH | CO | (CH$_2$)$_5$ |
| 111 | (CH$_2$)$_4$ | CO | NH | Bond | Pyridyl | Bond | NH | CO | (CH$_2$)$_5$ |
| 112 | (CH$_2$)$_4$ | CO | NH | Bond | Pyridyl | Bond | NH | CO | (CH$_2$)$_4$ |

| | A | | | | | D | | | |
|---|---|---|---|---|---|---|---|---|---|
| | a1 | a2 | a3 | a4 | E | d4 | d3 | d2 | d1 |
| 113 | (CH$_2$)$_3$ | CO | NH | Bond | Pyridyl | Bond | NH | CO | (CH$_2$)$_4$ |
| 114 | (CH$_2$)$_3$ | CO | NH | Bond | Pyridyl | Bond | NH | CO | (CH$_2$)$_3$ |
Preferable specific compounds usable as the compound of the general formula (1) are shown in Tables A3 to A10 below. In each of Tables A3 to 10, L, J, X and Y are defined in the same manner as in the general formula (1).
TABLE A3
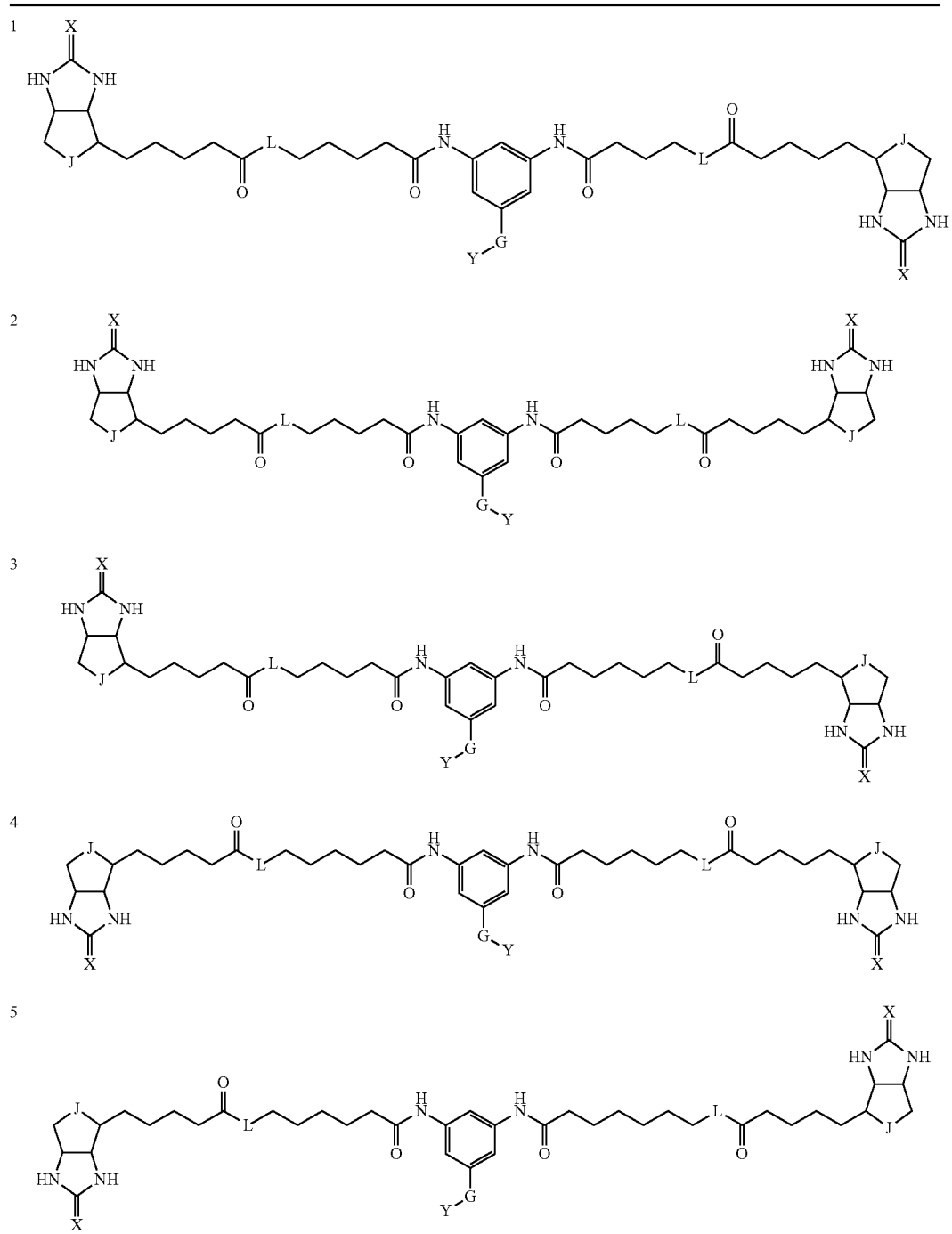

TABLE A3-continued
6 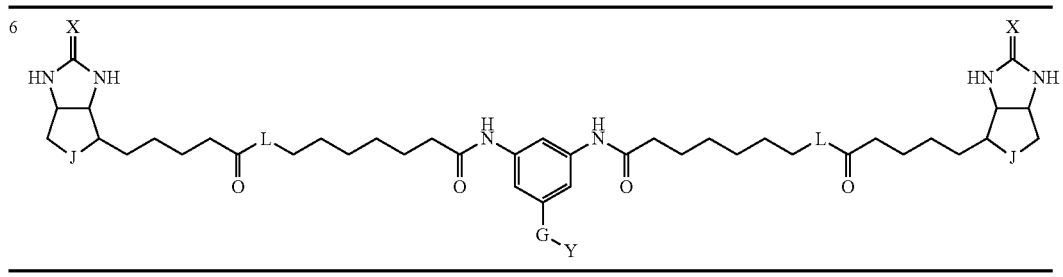
TABLE A4
1 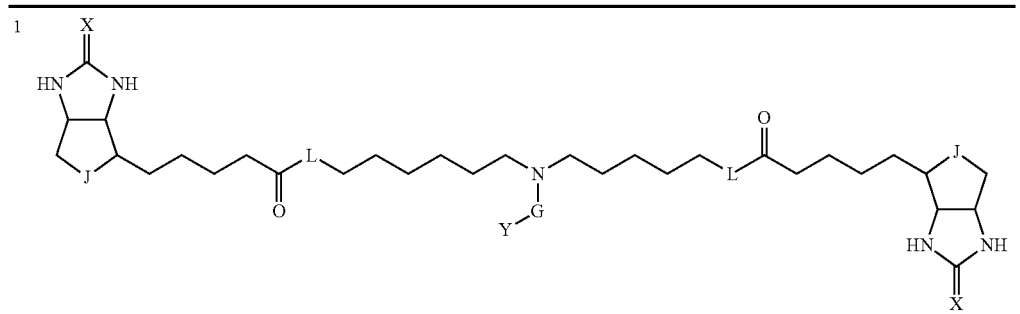
2 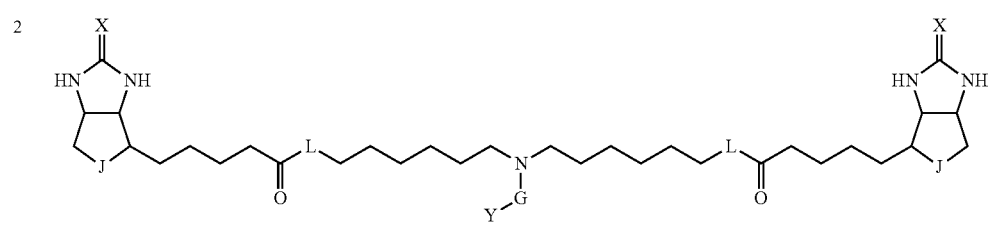
3 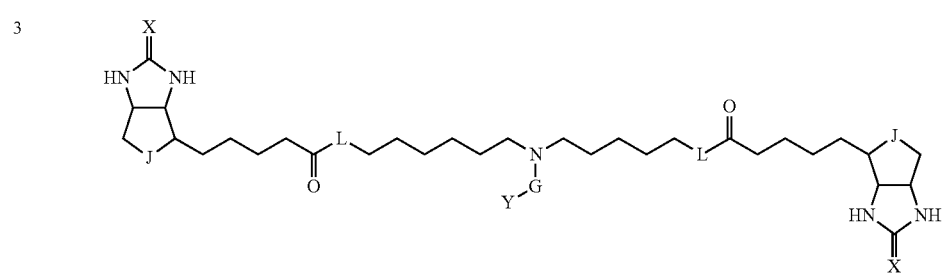
4 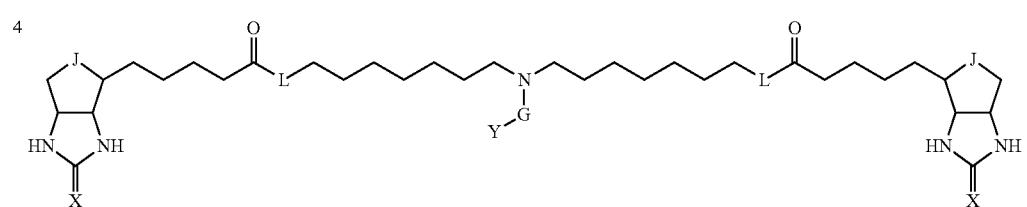
5 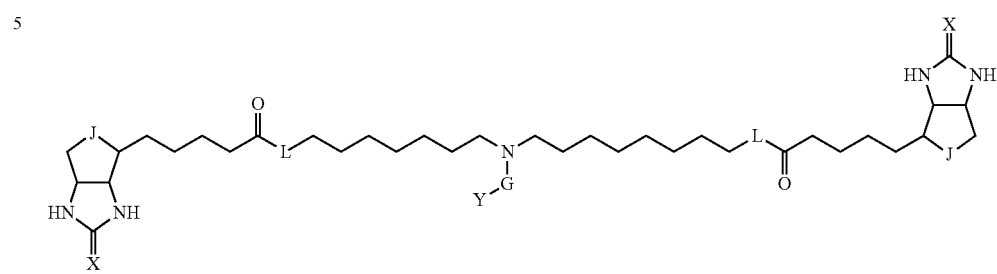

TABLE A4-continued
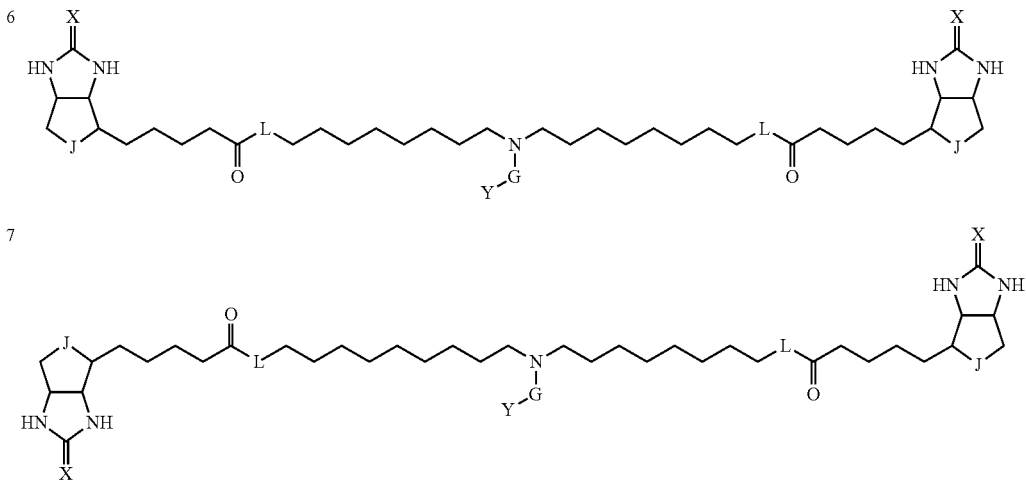
TABLE A5
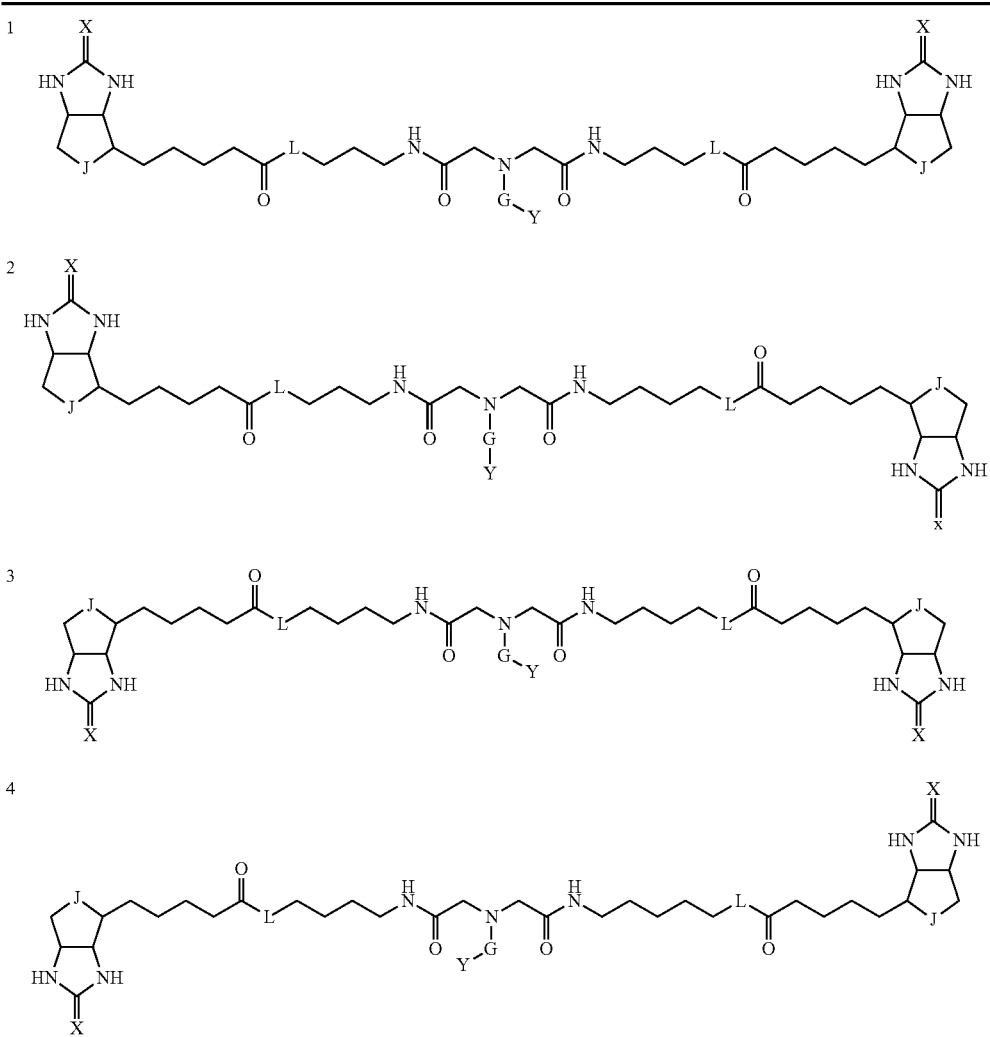

TABLE A5-continued
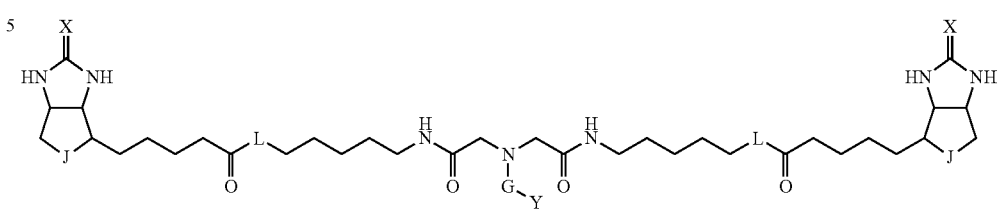
TABLE A6
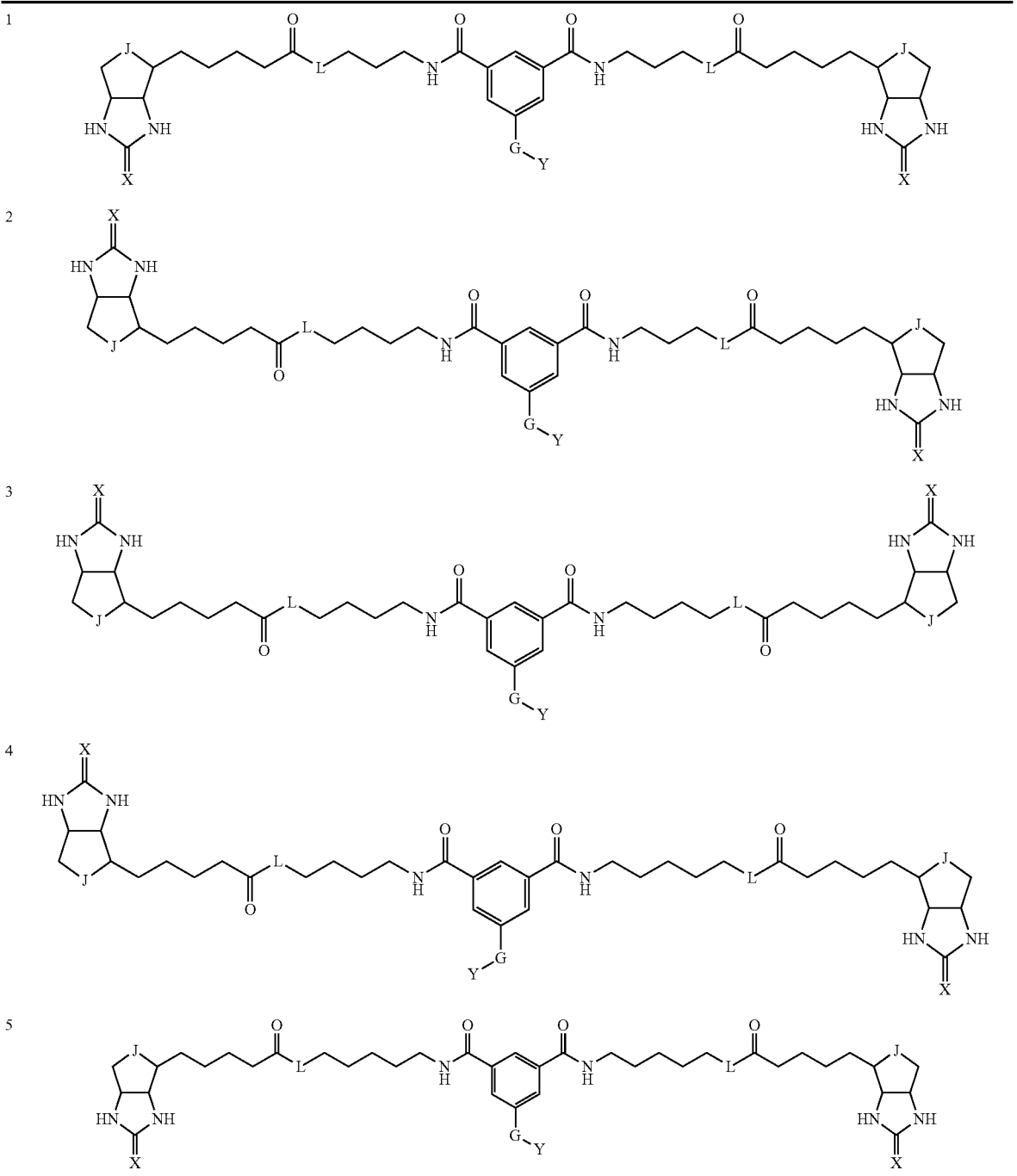

TABLE A7
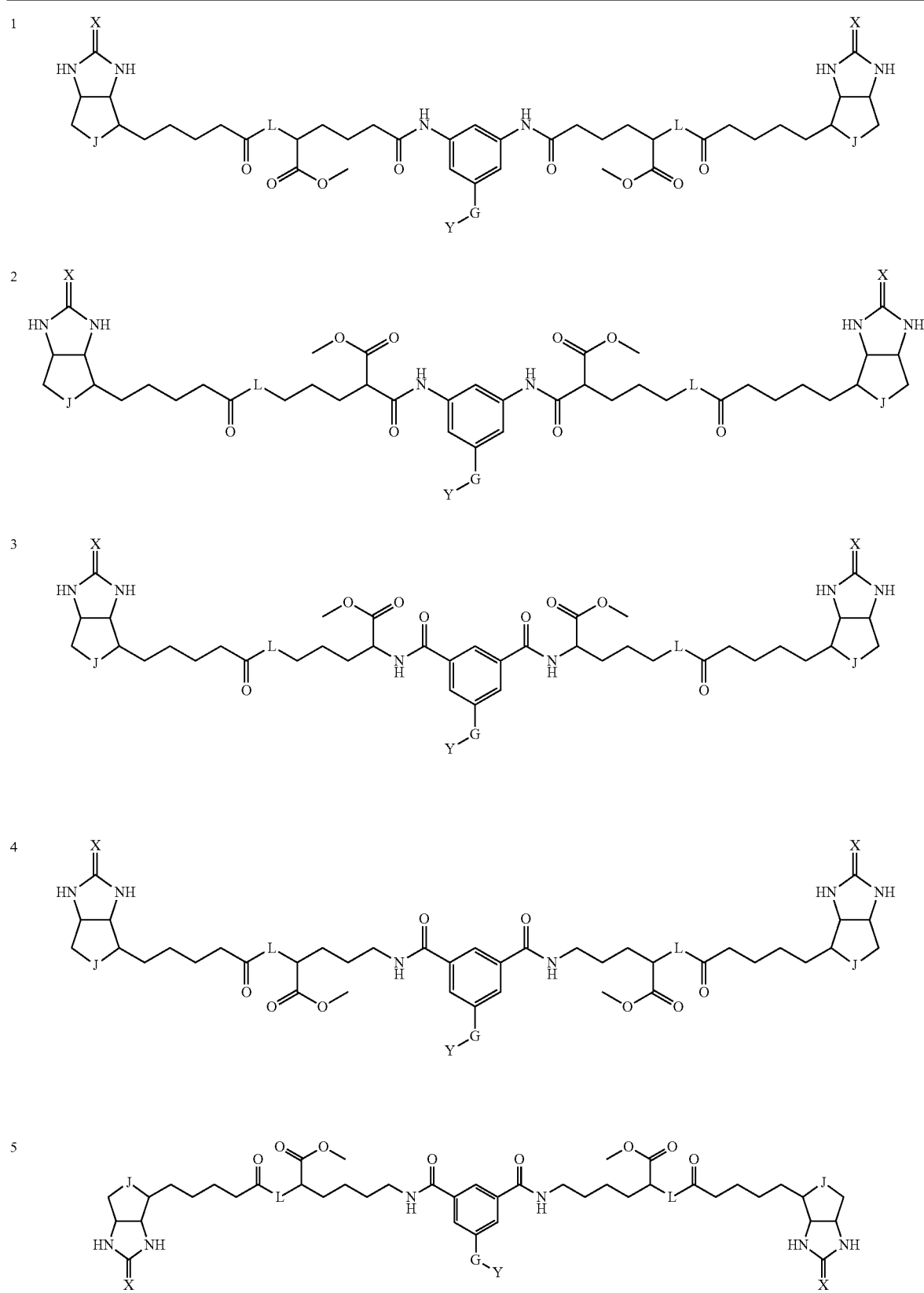

TABLE A8
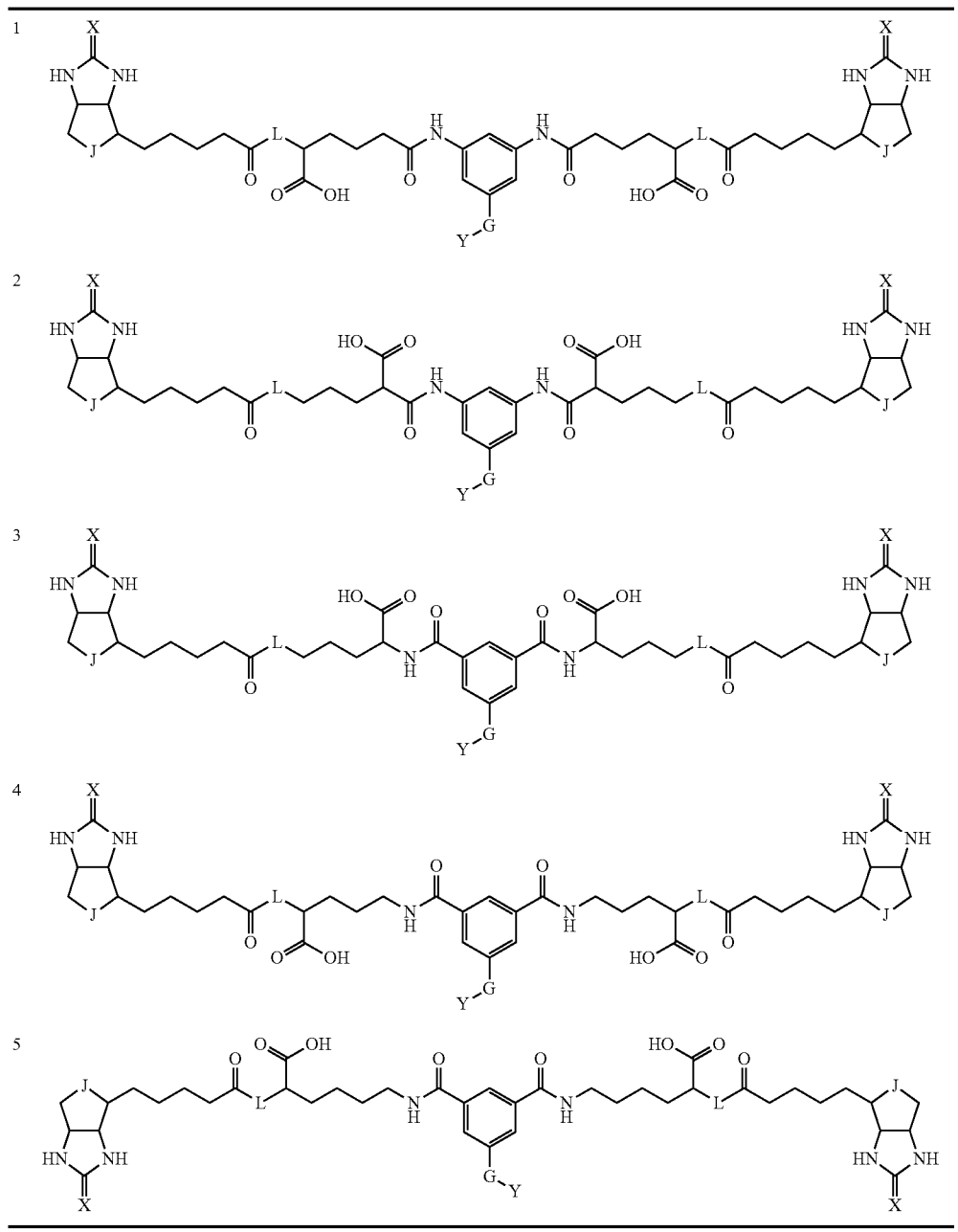
TABLE A9
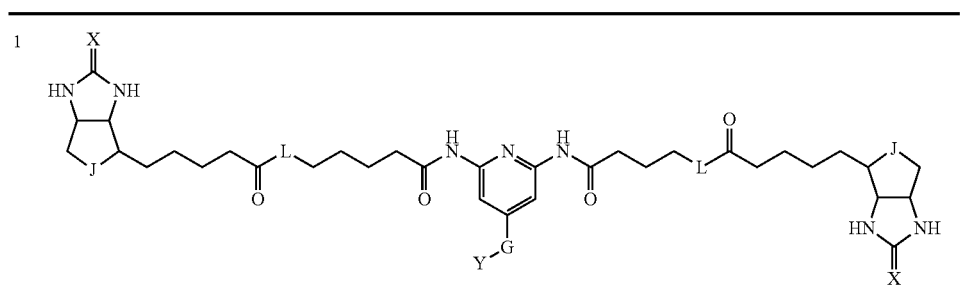

TABLE A9-continued
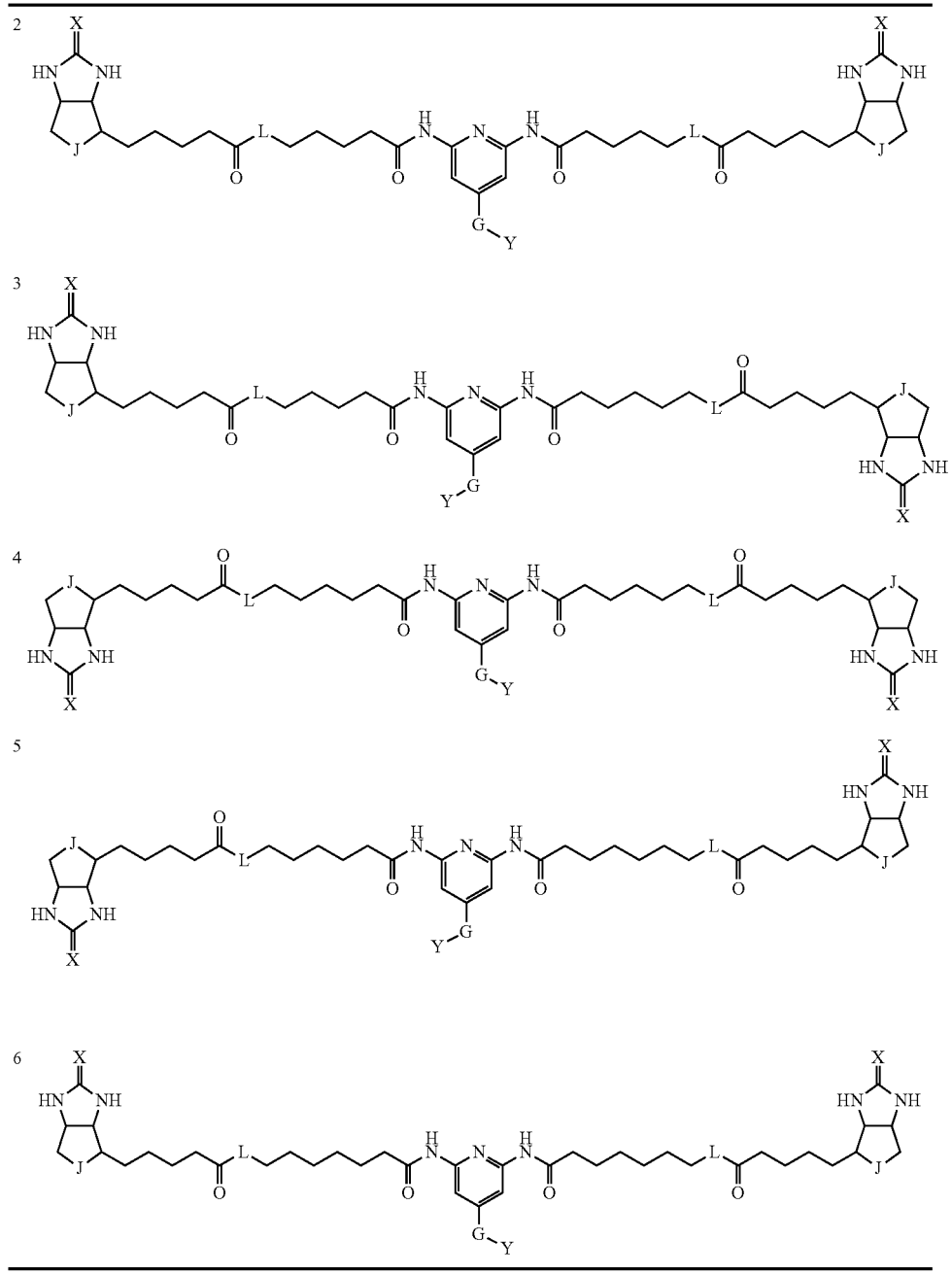
TABLE A10
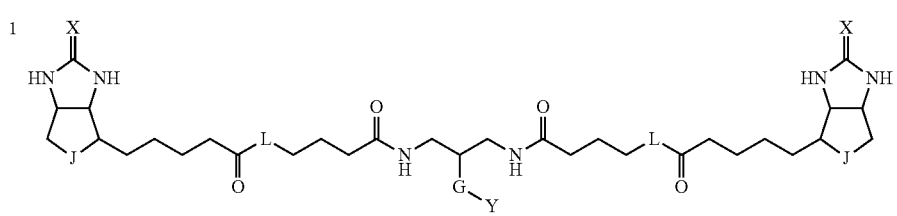

TABLE A10-continued

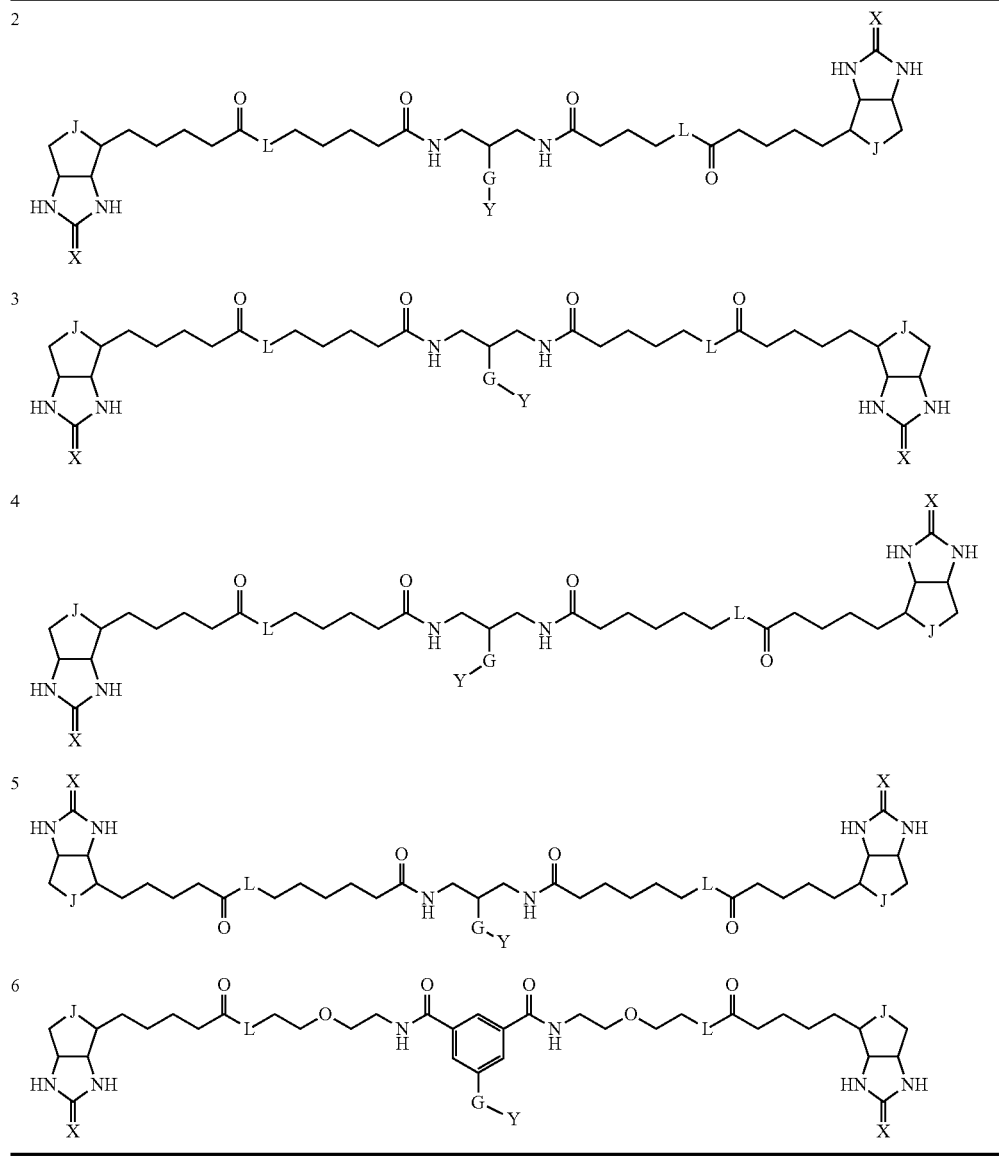

Further preferably, G of each compound shown in Tables A3 to A10 above is independently represented by g1-g2-g3-g4-g5-g6-g7, and g1 to g7 are each independently selected from Table G1.

Further preferably, independently in each compound shown in Tables A3 to A10 above, J is a sulfur atom, L is a nitrogen atom, Y is an active ester, maleinimide or hydrazide, and G is one group selected from Table G2 below (E in Table G2 means a bond to E in the general formula (1)).

TABLE G2

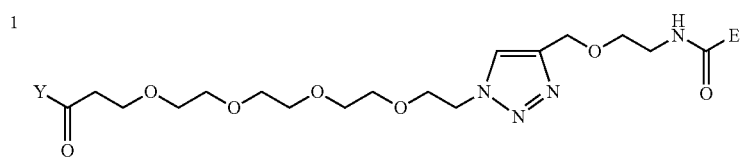

TABLE G2-continued
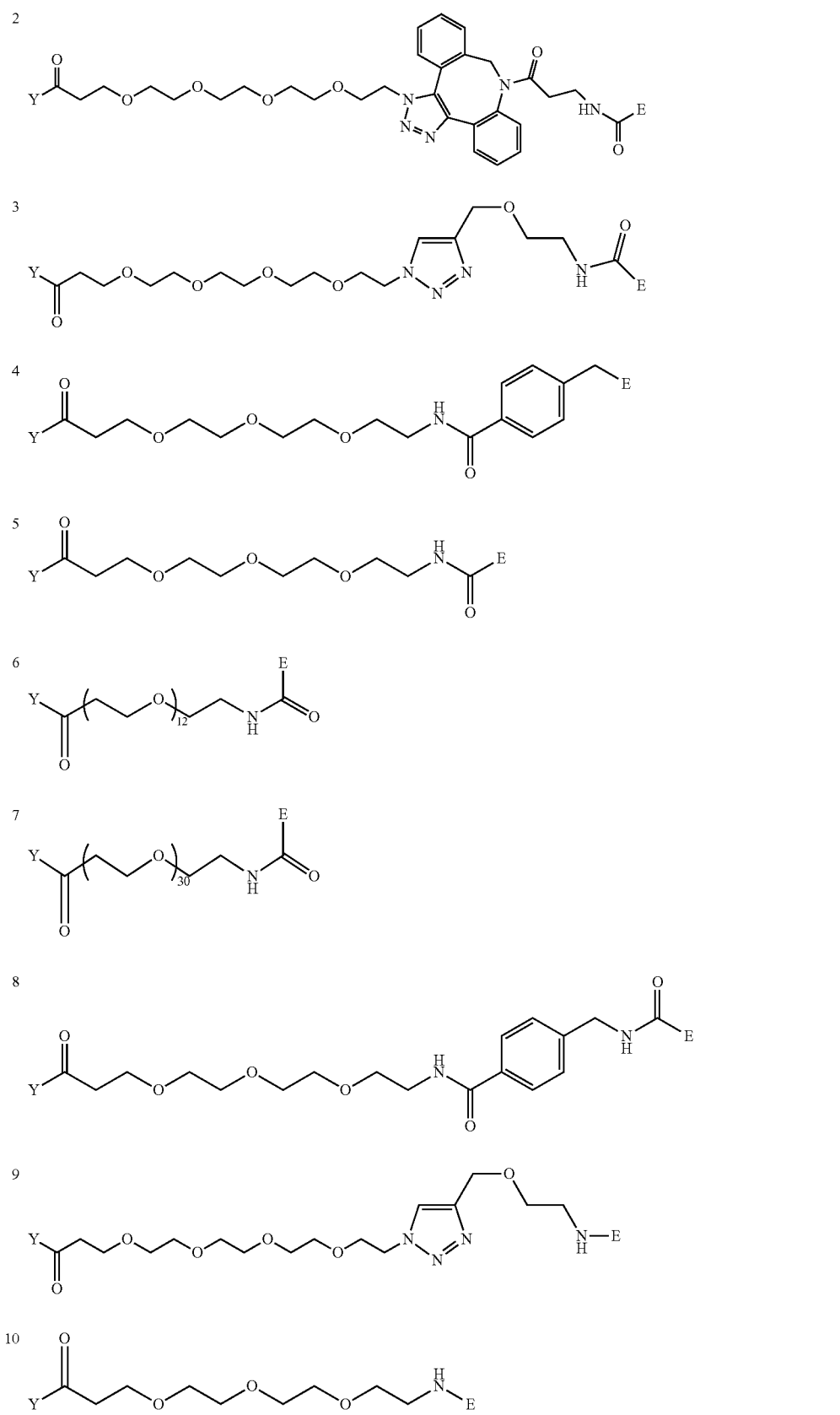

TABLE G2-continued

11

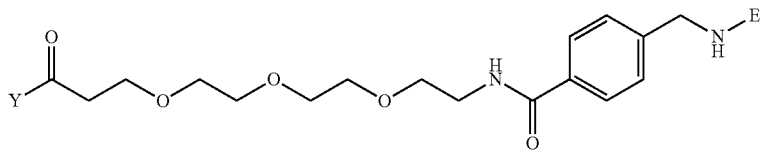

The structure for forming a bond to a protein represented by Y means a structure capable binding through a covalent bond or a noncovalent bond. A structure for forming a bond to a protein through a covalent bond may be a structure in which an amino group or a SH group of a protein can form a covalent bond through addition or substitution. Besides, an example of a structure for forming a bond to a protein through a noncovalent bond includes a pharmaceutical structure having strong affinity for a specific protein receptor. The pharmaceutical structure may be selected in accordance with a receptor corresponding to a target, and is not especially limited.

Preferable specific examples of the structure for forming a covalent bond to a protein include, but are not limited to, active ester, acid chloride, maleinimide, hydrazide, halogenated alkyl, isothiocyanate, isocyanate, aldehyde, glyoxal, epoxide, imide ester, carbodiimide, anhydride, and fluoro ester.

More specifically, examples of the active ester include, but are not limited to, carboxylic acid whose ester portion is a phenol compound, hydroxypyridine, hydroxyquinoline, N-hydroxysuccinimide, N-hydroxysulfosuccinimide, N-hydroxy-maleimide, 2-hydroxybenzoxazole, 2-hydroxybenzothiazole, 1-hydroxybenzotriazole, and mercapto compounds of these.

The compound represented by the general formula (1) can be synthesized by a method described in each of the examples disclosing the synthesis examples described below, or a method easily obtained based on the method described in each of the examples.

At least one of the bis-biotin compounds and the bis-iminobiotin compounds according to the present invention can be formulated by using at least one of various pharmaceutically acceptable carriers, excipients and diluents. In this formulation, a known formulation method using at least one of known carriers, excipients and diluents can be employed. In other words, at least one of the bis-biotin compounds and the bis-iminobiotin compounds according to the present invention can be used as an active ingredient in production of a labeling formulation.

The cell or tissue having a protein to be labeled with the labeling agent may be selected in accordance with desired use of antibody production, etc. The tissue to be subjected to a labeling treatment may constitute an organ.

As the cell to be subjected to the labeling treatment, a cell separated from a living body and cultured (an immobilized cell or a floating cell), an ES cell, an iPS cell, a cell differentiated from any of these, a cell present within a living body, etc., can be used. Alternatively, a cell, a tissue, an organ, etc., collected from, namely, taken out of a living body of, an animal including a mammal can be used as a sample to be subjected to the labeling treatment. A sample to be labeled by labeling may be prepared by administering a labeling agent to a site of a subject to be labeled such as pharmacological model animals, etc., including a mammal, optionally through a circulatory system such as the heart to label the target site of a cell, a tissue and an organ, etc., and taking out the labeled site from the animal. Alternatively, a surgically resected organ or a blood cell used in diagnosis, etc., can be subjected to the labeling treatment after being taken out of a living body. For this treatment, a mammal excluding a human can be suitably used. For example, as in an example described later, a similar treatment can be performed on an animal individual excluding a human so that an extracellular matrix, etc., present in a basement membrane of a blood vessel or interstitial tissue can be used.

For labeling a cultured cell, a method in which the labeling agent is added to a culture fluid containing the cultured cell, a method in which a culture fluid containing the cultured cell is replaced with a solution containing the labeling agent, etc., can be employed. Alternatively, labeling of a cell in a living body (of, for example, an animal excluding a human) can be performed by a method in which the labeling agent is administered into the living body and the thus labeled cell or interstitial protein is taken out. As described in the examples later, a method can be also employed, in which the labeling agent is administered into a blood vessel of an animal, a protein contained in a blood vessel cell is caused to reach a tissue of liver, etc., through blood flow in the circulatory organ, and the thus labeled protein or extracellular matrix is taken out from the whole tissue.

[Step (2)] (Degradation Step for Cell and/or Tissue)

Next, the degradation step for the cell and/or the tissue is described below. In the step (2), the cell and/or the tissue having a labeled protein is degraded to obtain a degradation product for an immobilization treatment. The degradation product for an immobilization treatment is contacted with a streptavidin mutant immobilized on a stationary phase, so as to cause the labeled protein contained in the degradation product to bind to the immobilized streptavidin mutant.

As a method for degrading the cell and/or the tissue, any of various methods can be employed. Examples include an osmotic shock method, a freezing and thawing method, use of a surfactant, an enzyme digestion method, ultrasonic treatment, French pressing, pulverization using a mortar, pulverization using a homogenizer, and pulverization using glass beads, but the method is not especially limited. One of these methods can be singly employed, or two or more of these can be employed in combination.

[Step (3)] (Immobilization Step)

Next, the immobilization step is described below.

The "stationary phase" used in the immobilization step comprises a structure not dissolved in a solvent to be used, and comprises preferably a structure slightly soluble in water.

As the stationary phase, a carrier used in ordinary protein immobilization can be used. Specific examples include, but are not limited to, hydroxyapatite, alumina, silica gel, celite, zirconia, zeolite, montmorillonite clay, titania, zinc hydroxide, agarose, dextran, polyacrylic acid, polyimine, vinyl polymers, polyacrylamide, polysaccharides, cellulose, polystyrene modified with divinylbenzene, an acrylate/ethylene glycol copolymer and aluminum oxide. The stationary phase can be used in any of various shapes including a bead, a film or a membrane, a monolith, etc.

A method for immobilizing the streptavidin mutant on the stationary phase comprises causing a reaction with a reactive group of the stationary phase. The stationary phase can be imparted with a reactive group capable of binding to the streptavidin mutant, so as to form a strong bond to the streptavidin mutant in a solvent through a covalent bond, etc.

Examples of the reactive group include active ester, acid chloride, maleinimide, hydrazide, halogenated alkyl, isothiocyanate, isocyanate, aldehyde, glyoxal, epoxide, imide ester, carbodiimide, anhydride, and fluoro ester. A covalent bond can be formed through addition or substitution of such a reactive group and an amino group or a SH group of a protein. Alternatively, the bond can be formed using a condensing agent such as a carbodiimide or CDI. Further alternatively, the bond can be formed by light or radiation, or using a silane coupling agent.

The labeled protein contained in the degradation product for an immobilization treatment forms a complex with the streptavidin mutant immobilized on the stationary phase, and is immobilized on the stationary phase via the immobilized streptavidin mutant.

Streptavidin is a protein produced by *Streptomyces avidinii*, that is, a kind of *Streptomyces*, and has characteristics to form a tetramer having a molecular weight of 53,000 Daltons, and to strongly bind to one molecule of biotin per subunit. Avidin is a basic glycoprotein having a sugar chain derived from albumen similarly strongly binding to biotin. These are used for immobilization, etc., of a protein labeled with biotin.

In the present invention, streptavidin and avidin are not used, but a streptavidin mutant having a biotin binding force, i.e., a binding strength or affinity to biotin, weakened by varying natural streptavidin is used.

Examples of the amino acid sequence of natural streptavidin includes a wild type amino acid sequence set forth in SEQ ID NO: 1 excluding signal peptide disclosed in Carlos E. Argarahal, etc., Nucleic Acids Research, Vol. 14, No. 4, 1986, and an amino acid sequence of natural core streptavidin (127 amino acid residues, 13.3 kDa) set forth in SEQ ID NO: 2 below consisting of the 13th to 139th regions of the amino acid sequence of the wild type streptavidin disclosed in International Publication No. WO2015/125820, and Takeshi Sano, etc., The Journal of Biological Chemistry, Vol. 270, No. 47, Issue of November 24, pp. 28204-28209, 1995.

```
SEQ ID NO: 1:
Asp Pro Ser Lys Asp Ser Lys Ala Gln Val Ser Ala Ala
Glu Ala Gly Ile Thr Gly Thr Trp Tyr Asn Gln Leu Gly
Ser Thr Phe Ile Val Thr Ala Gly Ala Asp Gly Ala Leu
Thr Gly Thr Tyr Glu Ser Ala Val Gly Asn Ala Glu Ser
Arg Tyr Val Leu Thr Gly Arg Tyr Asp Ser Ala Pro Ala
Thr Asp Gly Ser Gly Thr Ala Leu Gly Trp Thr Val Ala
Trp Lys Asn Asn Tyr Arg Asn Ala His Ser Ala Thr Thr
Trp Ser Gly Gln Tyr Val Gly Gly Ala Glu Ala Arg Ile
Asn Thr Gln Trp Leu Leu Thr Ser Gly Thr Thr Glu Ala
Asn Ala Trp Lys Ser Thr Leu Val Gly His Asp Thr Phe
Thr Lys Val Lys Pro Ser Ala Ala Ser Ile Asp Ala Ala
Lys Lys Ala Gly Val Asn Asn Gly Asn Pro Leu Asp Ala
Val Gln Gln

SEQ ID NO: 2:
Ala Glu Ala Gly Ile Thr Gly Thr Trp Tyr Asn Gln Leu
Gly Ser Thr Phe Ile Val Thr Ala Gly Ala Asp Gly Ala
Leu Thr Gly Thr Tyr Glu Ser Ala Val Gly Asn Ala Glu
Ser Arg Tyr Val Leu Thr Gly Arg Tyr Asp Ser Ala Pro
Ala Thr Asp Gly Ser Gly Thr Ala Leu Gly Trp Thr Val
Ala Trp Lys Asn Asn Tyr Arg Asn Ala His Ser Ala Thr
Thr Trp Ser Gly Gln Tyr Val Gly Gly Ala Glu Ala Arg
Ile Asn Thr Gln Trp Leu Leu Thr Ser Gly Thr Thr Glu
Ala Asn Ala Trp Lys Ser Thr Leu Val Gly His Asp Thr
Phe Thr Lys Val Lys Pro Ser Ala Ala Ser
```

Introduction of mutation into natural streptavidin and production of a mutant can be performed by any of known methods including a method described in International Publication No. WO2015/125820.

Weakened binding force means that binding between a streptavidin mutant and natural biotin or biocytin is lowered as compared with binding between streptavidin and natural biotin or biocytin. The affinity/binding between a streptavidin mutant and natural biotin or biocytin can be measured by any of known methods including a method described in Bioscience, Biotechnology, and Biochemistry, 79:4, 640-642 (2015), Biochemical journal (1963), 89, 585. It can be evaluated by isothermal titration calorimetry (ITC), surface plasmon resonance (SPR analysis), etc.

Accordingly, when a mutation position and amino acid to be introduced for mutation are selected, a mutant of natural streptavidin can be produced by a known method, and characteristics of the thus obtained mutant can be checked by known methods.

The mutation position for natural streptavidin is not especially limited as long as mutation for weakening the binding force to biotin can be obtained. For the mutation, amino acid substitution in at least one mutation position can be employed. The number of mutation positions can be selected from preferably 1 to 15, more preferably 1 to 10, and further preferably 3 to 10.

Preferable mutation positions in natural streptavidin can be the following mutation position group A in the amino acid sequence set forth in SEQ ID NO: 2:

Mutation Position Group A:

In terms of mutation positions represented by the number of amino acids from the N-terminal amino acid (Ala) of the amino acid sequence of natural streptavidin set forth in SEQ ID NO: 2, and by known one letter codes of amino acids, Y at position 10, N at position 11, S at position 15, S at position 33, N at position 37, Y at position 71, R at position 72, E at position 89, R at position 91, and E at position 104.

At least one of these mutation positions can be used.

Examples of a preferable combination of the mutation positions of the mutation position group A include the following combinations A and B:

Mutation Position Combination A:
Y10S/N11D/S15D/S33N/Y71S/R72K/E89D/R91K/E104N

Mutation Position Combination B:
Y10S/N11D/S15D/S33N/N37GN71S/R72K/E89D/R91K/E104N More preferable mutation positions in natural streptavidin can be the following mutation position group B in the amino acid sequence set forth in SEQ ID NO: 2:

Mutation Position Group B:

In terms of mutation positions represented by the number of amino acids from the N-terminal amino acid (Ala) of the amino acid sequence of natural streptavidin set forth in SEQ ID NO: 2, and by known one letter codes of amino acids, N at position 11, S at position 15, Y at position 31, E at position 32, S at position 33, A at position 34, V at position 35, G at position 36, N at position 37, G at position 38, E at position 39, S at position 40, R at position 41, Y at position 42, W at position 67, A at position 74, S at position 76, T at position 78, W at position 80, W at position 96, L at position 98, S at position 100, E at position 104, W at position 108, K at position 109, L at position 112, and D at position 116.

At least one of these mutation positions can be used.

Among the mutation positions belonging to the mutation position group B, the mutation positions excluding N at position 11, S at position 15, S at position 33, N at position 37 and E at position 104 are novel mutation positions not disclosed in International Publication No. WO2015/125820. Not only a mutant, which has at least one mutation position selected from these novel mutation positions, but also a mutant, which has at least one mutation position selected from these novel mutation positions and at least one of the mutation positions disclosed in International Publication No. WO2015/125820, are novel.

Preferable examples of amino acid substitution in the mutation group B include the following amino acid substitutions:

N11D, N11A, N11S, N11C, S15D, S15A, S15G, S15C, S15T, S15N, Y31F, Y31W, Y31H, S33N, S33A, S33G, S33H, 533T, A34G, A34S, V35A, V35T, V35N, V35L, V35I, G36A, G36P, G36S, N37G, N37A, N37S, N37D, N37E, N37T, A38G, A38S, W67F, W67Y, A74G, A74S, S76R, S76A, S76G, T78S, T78C, T78V, Y71S, R72K, T78A, W80M, W80L, E89D, R91K, W96F, W96L, L98V, L98F, S100R, S100I, S100M, S100L, S100C, S100K, S100V, E104N, W108F, W108M, W108L, K109R, K109E, K109M, L112N, L112Q, D116N, D116S and D116H.

Specific examples of preferable combinations of the mutation positions selected from the group B and the amino acid substitutions include the following mutation combinations (1) to (42):

(1) N11D/S15A/S33A,
(2) N11D/S15A/S33H,
(3) N11D/S15A/S33N,
(4) N11D/S15A/S33Q,
(5) N11D/S15A/S33T,
(6) N11D/S15A/S33A/N37G,
(7) N11D/S15A/S33H/N37G,
(8) N11D/S15A/S33N/N37G,
(9) N11D/S15A/S33Q/N37G,
(10) N11D/S15A/S33T/N37G,
(11) N11D/S15A/S33N/N37G/S76G,
(12) N11D/S15A/S33A/N37G/S76G,
(13) N11D/S15A/S33N/N37G/S76R,
(14) N11D/S15A/S33A/N37G/S76R,
(15) N11D/S15A/S33N/N37G/S100L,
(16) N11D/S15A/S33A/N37G/S100L,
(17) N11D/S15A/S33A/N37G/S100I,
(18) N11D/S15A/S33A/N37G/S100M,
(19) N11D/S15A/S33A/N37G/S100V,
(20) N11D/S15A/S33N/N37G/S100R,
(21) N11D/S15A/S33A/N37G/S100R,
(22) N11D/S15A/S33A/N37G/S100K,
(23) N11D/S15A/S33N/N37G/K109M,
(24) N11D/S15A/S33A/N37G/K109M,
(25) N11D/S15A/S33N/N37G/K109R,
(26) N11D/S15A/S33A/N37G/K109R,
(27) N11D/S15A/S33A/N37G/K109E,
(28) N11D/S15A/S33A/N37G/L112N,
(29) N11D/S15A/S33A/N37G/L112Q,
(30) Y10S/N11D/S15A/S33A/Y71S/R72K/E89D/R91K/E104N,
(31) Y10S/N11D/S15A/S33H/Y71S/R72K/E89D/R91K/E104N,
(32) Y10S/N11D/S15A/S33N/Y71S/R72K/E89D/R91K/E104N,
(33) Y10S/N11D/S15A/S33Q/Y71S/R72K/E89D/R91K/E104N,
(34) Y10S/N11D/S15A/S33T/Y71S/R72K/E89D/R91K/E104N,
(35) Y10S/N11D/S15A/S33A/N37G/Y71S/R72K/E89D/R91K/E104N,
(36) Y10S/N11D/S15A/S33H/N37G/Y71S/R72K/E89D/R91K/E104N,
(37) Y10S/N11D/S15A/S33N/N37G/Y71S/R72K/E89D/R91K/E104N,
(38) Y10S/N11D/S15A/S33Q/N37G/Y71S/R72K/E89D/R91K/E104N,
(39) Y10S/N11D/S15A/S33T/N37G/Y71S/R72K/E89D/R91K/E104N,
(40) Y10S/N11D/S15D/Y71S/R72K/E89D/R91K/E104N,
(41) Y10S/N11D/S15D/S33A/Y71S/R72K/E89D/R91K/E104N, and
(42) Y10S/N11D/S15D/S33T/Y71S/R72K/E89D/R91K/E104N.

Among the mutation positions belonging to the mutation position group B, the positions excluding N at position 11, S at position 15, S at position 33, N at position 37 and E at position 104 are novel mutation positions not disclosed in International Publication No. WO2015/125820. A mutant, which has at least one mutation position selected from these novel mutation positions, and a mutant, which has not only at least one mutation position selected from these novel mutation positions, but also at least one of the mutation positions disclosed in International Publication No. WO2015/125820, are novel.

Accordingly, a first aspect of the streptavidin mutant according to the present invention is a streptavidin mutant having a weakened affinity for biotin as compared with natural streptavidin, by causing mutation in the amino acid sequence set forth in SEQ ID NO: 2 of natural streptavidin at at least one position selected from the group consisting of N at position 11, S at position 15, Y at position 31, E at position 32, S at position 33, A at position 34, V at position 35, G at position 36, N at position 37, G at position 38, E at position 39, S at position 40, R at position 41, Y at position 42, W at position 67, A at position 74, S at position 76, T at position 78, W at position 80, W at position 96, L at position 98, S at position 100, E at position 104, W at position 108, K at position 109, L at position 112, and D at position 116, provided that a mutant having mutation of Y10S/N11D/S15D/S33N/Y71S/R72K/E89D/R91K/E104N and a mutant having mutation of Y10S/N11D/S15D/S33N/N37G/Y71S/

R72K/E89D/R91K/E104N in the amino acid sequence set forth in SEQ ID NO: 2 of natural streptavidin are excluded.

A second aspect of the streptavidin mutant according to the present invention is a streptavidin mutant having a weakened affinity for biotin as compared with natural streptavidin, by causing mutation in the amino acid sequence set forth in SEQ ID NO: 2 of natural streptavidin at at least one position selected from the group consisting of Y at position 31, E at position 32, A at position 34, V at position 35, G at position 36, G at position 38, E at position 39, S at position 40, R at position 41, Y at position 42, W at position 67, A at position 74, S at position 76, T at position 78, W at position 80, W at position 96, L at position 98, S at position 100, W at position 108, K at position 109, L at position 112 and D at position 116.

The second aspect of the streptavidin mutant according to the present invention may further have mutation in the amino acid sequence set forth in SEQ ID NO: 2 of natural streptavidin at at least one position selected from the group consisting of N at position 11, S at position 15, S at position 33, N at position 37 and E at position 104.

A third aspect of the streptavidin mutant according to the present invention is a streptavidin mutant having a weakened affinity for biotin as compared with natural streptavidin, by causing, in the amino acid sequence set forth in SEQ ID NO: 2 of natural streptavidin, at least one mutation selected from the group consisting of Y10S, N11D, N11A, N11S, N11C, S15D, S15A, S15G, S15C, S15T, S15N, Y31F, Y31W, Y31H, S33N, S33A, S33G, S33H, S33T, A34G, A34S, V35A, V35T, V35N, V35L, V35I, G36A, G36P, G36S, N37G, N37A, N37S, N37D, N37E, N37T, A38G, A38S, W67F, W67Y, A74G, A74S, S76R, S76A, S76G, T78S, T78C, T78V, Y71S, R72K, T78A, W80M, W80L, E89D, R91K, W96F, W96L, L98V, L98F, S100R, S100I, S100M, S100L, S100C, S100K, S100V, E104N, W108F, W108M, W108L, K109R, K109E, K109M, L112N, L112Q, D116N, D116S and D116H, provided that a mutant having mutation of Y10S/N11D/S15D/S33N/Y71S/R72K/E89D/R91K/E104N and a mutant having mutation of Y10S/N11D/S15D/S33N/N37G/Y71S/R72K/E89D/R91K/E104N are excluded.

A fourth aspect of the streptavidin mutant according to the present invention is a streptavidin mutant having a weakened affinity for biotin as compared with natural streptavidin, by causing, in the amino acid sequence set forth in SEQ ID NO: 2 of natural streptavidin, at least one mutation selected from the group consisting of N11A, N11S, N11C, S15A, S15G, S15C, S15T, S15N, Y31F, Y31W, Y31H, S33A, S33G, S33H, S33T, A34G, A34S, V35A, V35T, V35N, V35L, V35I, G36A, G36P, G36S, N37A, N37S, N37D, N37E, N37T, A38G, A38S, W67F, W67Y, A74G, A74S, S76R, S76A, S76G, T78S, T78C, T78V, T78A, W80M, W80L, W96F, W96L, L98V, L98F, S100R, S100I, S100M, S100L, S100C, S100K, S100V, W108F, W108M, W108L, K109R, K109E, K109M, L112N, L112Q, D116N, D116S and D116H.

The fourth aspect of the streptavidin mutant according to the present invention may further have, in the amino acid sequence set forth in SEQ ID NO: 2 of natural streptavidin, at least one mutation selected from the group consisting of Y10S, N11D, S15D, S33N, N37G, Y71S, R72K, E89D, R91K and E104N.

A fifth aspect of the streptavidin mutant according to the present invention is a streptavidin mutant having, in the amino acid sequence set forth in SEQ ID NO: 2 of natural streptavidin, one selected from the group consisting of the above-described mutation combinations (1) to (42) and having a weakened affinity for biotin as compared with natural streptavidin.

The mutation in the streptavidin having the natural amino acid sequence set forth in SEQ ID NO: 2 can be also used for introducing mutation into a corresponding position in streptavidin having the natural amino acid sequence set forth in SEQ ID NO: 1 or streptavidin having a part of the natural amino acid sequence set forth in SEQ ID NO: 1. For example, N at position 11 in SEQ ID NO: 2 corresponds to N at position 23 in SEQ ID NO: 1, and mutation can be introduced into the streptavidin having the amino acid sequence set forth in SEQ ID NO: 1 by causing amino acid substitution in N at position 23 of SEQ ID NO: 1.

In the expression of mutation caused by amino acid substitution, a numeral corresponds to the mutation position in the amino acid sequence, a letter preceding the numeral corresponds to an amino acid in the natural sequence, and a letter following the numeral corresponds to an amino acid to be introduced for causing mutation. Each letter corresponds to a well-known one letter code of amino acid. For example, N23D refers to that amino acid N (asparagine) at position 23 from the N-terminal amino acid sequence of natural streptavidin is substituted with D (aspartic acid).

As a result of weakening the binding force to biotin, binding of endogenous biotinylated protein to the immobilized streptavidin mutant is effectively reduced, or binding therebetween is prevented, so that the protein labeled with a bis-iminobiotin compound or a bis-biotin compound can be selectively bound, and as a result, the protein of a minute amount can be identified.

When an endogenous biotinylated intracellular protein is present in a large amount in cells, an artificially labeled protein, etc., and the endogenous biotinylated intracellular protein are mixed in the degradation product for an immobilization treatment. When streptavidin having a strong binding force to biotin is caused to bind to the stationary phase to be used for capturing the artificially labeled protein, etc., in the degradation product, the endogenous biotinylated intracellular protein is simultaneously captured in the stationary phase. The endogenous biotinylated intracellular protein is also purified together by purifying the artificially labeled protein, etc., from the stationary phase. As a result, the endogenous biotinylated intracellular protein purified together is mixed in an analysis sample, and becomes background in the protein analysis/identification. When the amount of the endogenous biotinylated intracellular protein thus mixed is large, the background is increased, which can be a factor to inhibit highly accurate analysis and identification of the artificially labeled protein of interest.

On the contrary, in the present invention, the streptavidin mutant having a weakened binding force to biotin is used for capturing the artificially labeled protein, and thus, the endogenous biotinylated intracellular protein is inhibited from being taken into the stationary phase, and therefore, the background in the analysis/identification is reduced so that a protein present in a minute amount can be highly accurately analyzed/identified.

The degradation product for an immobilization treatment can be subjected, if necessary, to a pretreatment of the treatment with the streptavidin mutant, such as dilution, removal of components other than the protein, and addition of an additive.

The degradation product applied to an immobilization treatment can be contacted with the streptavidin mutant immobilized on the stationary phase, by a known method, in accordance with the form of the stationary phase. For example, usable methods include
- a method, in which the stationary phase in the form of beads, on which the streptavidin mutant is immobilized, is mixed with the degradation product for an immobilization treatment in a reaction vessel for causing a reaction therebetween for a prescribed period of time, and
- a method in which the stationary phase on which the streptavidin mutant is immobilized is filled in a column, and the degradation product for an immobilization treatment is caused to pass therethrough, so as to contact the degradation product for an immobilization treatment with the streptavidin mutant immobilized on the stationary phase filled in the column, etc.

When the stationary phase having the immobilized streptavidin mutant thereon and the artificially labeled protein contained in the degradation product for the immobilization treatment are contacted with each other, a strong bond through a noncovalent bond is formed. As a result, a complex of the streptavidin mutant and the labeled protein is formed, i. e., the labeled protein binds to the stationary phase. Various components such as a protein not labeled with the bis-iminobiotin compound or the bis-biotin compound and other components contained in cells or tissues can be easily removed by washing the stationary phase.

[Step (4)] (Cleavage Step)

Next, the cleavage step of releasing an analysis sample from the stationary phase on which the labeled protein has been immobilized is described below.

The cleavage step comprises a step of releasing, by various cleaving methods, an analysis sample from the stationary phase on which the labeled protein has been immobilized. For the cleavage, any of physical, chemical and enzyme reactive methods can be employed. Specifically, a cleavage treatment or a degradation treatment using at least one selected from reduction, oxidation, irradiation, an enzyme, a nucleophile, an electrophile, an organometallic reagent, etc., can be employed.

For example, a method in which the protein immobilized on the stationary phase is degraded with a protease, a method in which the sample is physically cleavage by a ultrasonic treatment, a method in which a binding site between the protein and the labeling agent immobilized on the stationary phase is cut or the protein is degraded by reduction, oxidation, irradiation, etc., can be employed. The methods are not especially limited. When the protein is released from the labeling agent immobilized on the stationary phase, a cuttable structure may be imparted to G so as to use the cuttable structure as described above.

A method for cutting a binding site between the protein and the labeling agent immobilized on the stationary phase may be selected from ordinary methods depending on a form of the bond, namely, whether the bond is a covalent bond or a noncovalent bond. When a receptor is labeled with a drug having affinity for the receptor, a cutting method for these can be selected from ordinary methods depending on the types of the receptor and the drug.

A composition of the analysis sample is varied depending on the method employed for the cleavage.

For example, when the method for cleaving a bond between the labeling agent and the protein is employed, samples containing different proteins can be obtained.

Alternatively, when a protease for randomly degrading the protein is used, a degradation product containing various oligonucleotides generated through random degradation of the protein and the streptavidin can be obtained as the analysis sample.

[Step (5)] (Analysis Step)

Next, the step of analyzing the protein for analysis released from the stationary phase to identify the protein is described below.

The analysis sample released from the stationary phase is analyzed by an analysis method according to the form of the analysis sample, and thus, the protein labeled in the step (1A) can be identified based on a result of the analysis. In this analysis step, any of known analysis methods can be employed. The analysis method can be selected in accordance with the type of a substance to be analyzed contained in the sample. The method can be selected from, for example, a method in which a molecular weight of oligopeptide is measured by mass spectrometry as the released protein and/or the degradation product thereof, a method in which an amino acid sequence of oligopeptide is checked as the released protein and/or the degradation product thereof, etc. The analysis sample may be subjected to, if necessary, a pretreatment necessary for the analysis such as dilution, purification or mixture with an analysis reagent.

The labeled protein can be identified based on the analysis result, such as the molecular weight obtained by mass spectrometry or the amino acid sequence obtained by the amino acid analysis. Specifically, the identification of the protein refers to determination of the type of the labeled protein based on the data of the molecular weight or the amino acid sequence thus obtained. For the determination of the type of the protein, known database can be utilized.

For example, when a protease such as trypsin is used for fragmenting the protein binding to the stationary phase to cleave it into the form of random oligopeptide fragments, a mass spectrum of ions derived from fragment peptides are measured by tandem mass spectrometry (MS/MS). The thus obtained mass spectral data is used for searching the protein in known sequence database, and thus, the labeled protein can be identified.

Examples of usable database include the following publicly accessible database:

Website database: http://wlab.ethz.ch/cspa/#abstract

Literature: Bausch-Fluck D, Hofmann A, Bock T, Frei A P, Cerciello F, et al., (2015), A Mass Spectrometric-Derived Cell Surface Protein Atlas. PLoS One 10: e0121314

Alternatively, database of the following domains can be used for searching a protein having a cell membrane domain:

http://phobius.sbc.su.se/ http://www.cbs.dtu.dk/services/TMHMM/

The database to be used for identifying the protein is not limited to those described above, but any database can be used without limitation as long as it is publicly accessible.

Amino acid sequences of various proteins have been already registered in database. There is data that which portion of each of these amino acid sequences is produced as a parent peptide ion by an enzyme specifically cutting the amino acid sequence (for example, trypsin cleaves an amino acid sequence at lysine or arginine), and that how the parent peptide ion is fragmented by the MS/MS. Results of such search are matched to identify a possible peptide, based on which the protein can be identified.

A method for producing an antibody according to the present invention comprises: a step of providing a target protein for antibody production; and a step of producing, from the target protein, an antibody against the target protein.

As the target protein for antibody production, a protein identified by the above-described identification method is used.

The method for producing an antibody of the present invention may comprise the above-described identification method, and may comprise the following steps (1) to (6):

(1) a step of providing a cell and/or a tissue having a labeled protein;

(2) a degradation step of degrading the cell and/or the tissue having a labeled protein to prepare a degradation product containing the labeled protein;

(3) an immobilization step of contacting the degradation product with a streptavidin mutant immobilized on a stationary phase to immobilize the labeled protein contained in the degradation product on the stationary phase via the streptavidin mutant;

(4) a cleavage step of releasing an analysis sample from the stationary phase on which the labeled protein is immobilized;

(5) an analysis step of analyzing the analysis sample to identify the labeled protein; and (6) a step of producing an antibody against the target protein identified in the analysis step, as a drug-discovery target protein.

The step (1) can be carried out through the following step (1A):

(1A) a labeling step of labeling a protein present on a cell membrane of a cell and/or an extracellular protein present in a tissue with a labeling agent containing at least one selected from a bis-iminobiotin compound and a bis-biotin compound, to obtain the labeled protein.

The protein identified in the analysis step can be used as an antigen in producing an antibody against the identified protein.

The production of an antibody is carried out by either a method, in which an antibody is prepared by immunizing an animal with an antigen (immunogen), or a method, in which an antibody is obtained without immunization of an animal. The former method is further divided into methods producing a polyclonal antibody and a monoclonal antibody. As the latter method, for example, a method designated as phage display is known.

A polyclonal antibody is obtained as follows: An antigen (immunogen) is repeatedly injected into any of various mammals and birds, including not only a mouse and a rabbit but also a rat, a hamster, a guinea pig, a fowl, a goat, a sheep and a donkey, to produce an antibody in a large amount in blood, and, then, the blood (plasma and serum) is collected. The collected blood is purified by an ordinary method using a column in which an enzyme capturing the antibody is immobilized.

A monoclonal antibody is obtained as follows: An immortalized cancer cell (myeloma) and a B cell producing an antibody are artificially fused to produce fused cells (hybridomas) capable of semi-permanently surviving with keeping a specific antibody gene. Then, the cells producing a useful monoclonal antibody excellent in binding affinity and specificity are selected from the hybridomas to cause the cells to produce the antibody.

The phage display is a technique, for example, using libraries, displayed on phage, of variable regions of H chain and L chain determining the binding ability of an antibody linked through a short amino acid sequence, to select an antibody having affinity for a target molecule. The phage is then infected with *E. coli* so that the antibody can be produced. Proteins to be displayed on the phage are not limited to amino acid sequences derived from antibodies produced in the above-described animals. For example, a phage that displays an antibody specific to the protein identified by the identification method according to the present invention, or an antibody specific to an antigen obtained from the protein (for example, a combination of H chain and L chain) is prepared by the phage display. The thus obtained phage is infected with a bacterial host such as *E. coli*, and, thus, an antibody of interest can be obtained.

Each step employed in the method for producing an antibody of the present invention is not especially limited. The steps can be selected from known methods in accordance with the type and antigenicity (or immunogenicity) of the identified protein.

The thus obtained antibody can be used for various desired uses. For example, an antibody against CD30 identified in an example described below is expected to be used for cancer treatment (as an anticancer drug), and as antibody drugs for rheumatism, allergic disease, asthma, atopic dermatitis, primary biliary cirrhosis, scleroderma, Sjogren's syndrome, lupus erythematosus, etc.

At least one compound represented by the general formula (1) can be used as a labeling compound for a protein. A protein labeled with the compound represented by the general formula (1) can be suitably used in an identification method for a protein, preferably the identification method for a protein including the above-described steps (1) to (5).

The streptavidin mutant described above can be used as a streptavidin mutant for identifying the labeled protein, and is suitably used in the identification method for a protein including the above-described steps (1) to (5).

At least one labeling compound for a protein and at least one streptavidin mutant described above are used together to prepare a kit for identifying a protein.

EXAMPLES

Examples of the present invention is described below, and it is noted that the present invention is not limited to these examples. "%" used herein is on mass basis unless otherwise stated.

NMR analysis values were measured using EX-270 (270 MHz) manufactured by JEOL Ltd.

HPLC analysis was performed under either of the following two conditions:

Analysis Conditions A:
Column: YMC-Pack ODS-AM 150×6 mm
Flow Rate: 1 mL/min.
Column Temperature: 40° C.
Detection Wavelength: 254 nm
Mobile Phase: 0.1% trifluoroacetic acid aqueous solution/ $CH_3CN$ Analysis Conditions B:
Column: YMC Triart C18 75×2 mm
Flow Rate: 0.3 mL/min.
Column Temperature: 35° C.
Detection Wavelength: 254 nm
Mobile Phase: 0.1% trifluoroacetic acid aqueous solution/ $CH_3CN$ A gradient condition is described as, for example, "0.1% trifluoroacetic acid aqueous solution/$CH_3CN$=85/15 (12 min) 35/65", which means a condition that a 0.1% trifluoroacetic acid aqueous solution is reduced from 85% to 35% over 12 minutes, and then returns to 85%.

Example 1-1

Synthesis of N-Boc Protected Iminobiotin 11 mL of methanol and 0.6 mL of trifluoroacetic acid were added to 115 mg of iminobiotin, followed by heating to reflux for 7.5 hours. The resultant was concentrated under reduced pressure to obtain 192 mg of a target reaction product of iminobiotin methyl ester in the form of a solid. The product was not purified but directly used in the following reaction.

(Analysis Values of Target Reaction Product)
$^1$H-NMR (CDCl$_3$): 7.8 (1H, br.s), 7.2 (1H, br.s), 4.7-4.8 (1H, m), 4.5-4.6 (1H, m), 3.7 (3H, s), 3.2-3.3 (1H, m), 2.8-3.0 (2H, m), 2.3-2.4 (2H, t), 1.4-1.8 (6H, m)

To the iminobiotin methyl ester synthesized as above, 2 mL of chloroform, 0.3 mL of triethylamine and 413 mg of a Boc anhydride were added, followed by stirring at room temperature overnight. To the resultant, 4 mL of chloroform was added, and the resultant was washed with 3 mL of water. The resultant was dried over magnesium sulfate, and concentrated to obtain a residue.

To the residue, 99 mg (5 equivalents) of a lithium hydroxide hydrate, 0.7 mL of water and 2.5 mL of methanol were added, followed by stirring at room temperature overnight. The resultant was concentrated under reduced pressure, and 5 mL of a 5% citric acid aqueous solution was added thereto to adjust to pH 5. The resultant was extracted with 10 mL of chloroform, dried over magnesium sulfate, and concentrated to obtain 102 mg (63%) of a target reaction product of N-Boc protected iminobiotin.

(Analysis Values of Target Reaction Product)
$^1$H-NMR (CDCl$_3$): 4.6-4.7 (1H, m), 4.4-4.5 (1H, m), 3.2-3.3 (1H, q), 2.9-3.0 (1H, dd), 2.8-2.9 (1H, d), 2.2-2.4 (2H, t), 1.4-1.8 (6H, m), 1.49 (9H, s)

Example 1-2

Synthesis of Bis(Boc-iminobiotin)-COOMe 1

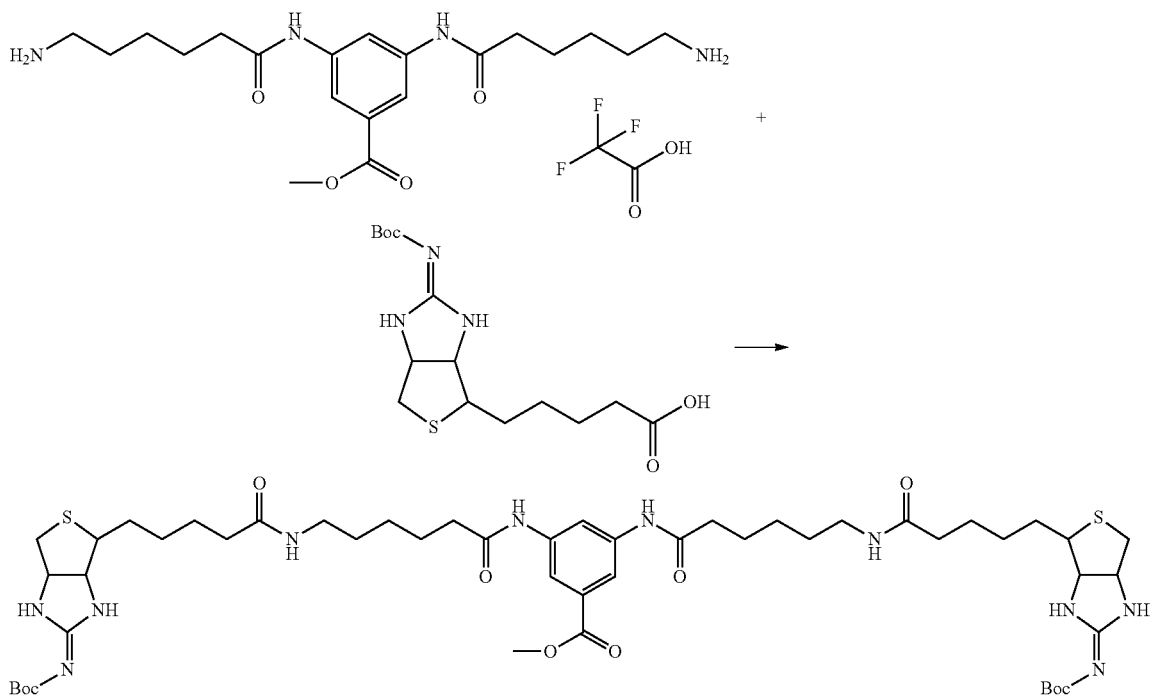

To 367 mg (2.1 equivalents) of the N-Boc iminobiotin synthesized in Example 1-1, 6 mL of dehydrated DMF was added, and a condensing agent of CDI (182 mg, 2.2 equivalents) and 0.55 mL (4 equivalents) of triethylamine were further added thereto. The resultant was stirred at room temperature for 2 hours, and 3 mL of a dehydrated DMF solution of 316 mg (0.51 mmol) of methyl 3,5-bis(6-aminohexanamide) benzoate/di-trifluoroacetate was added thereto, followed by stirring under heating at 50° C. to 60° C. for 3 hours. The resultant was concentrated under reduced pressure, and 20 mL of chloroform and 10 mL of 5% citric acid were added thereto. Since an insoluble matter was separated, water and chloroform were removed, and the resultant was dissolved in methanol. The resultant was combined with chloroform, dried over magnesium sulfate, and concentrated to obtain a residue. The residue was purified by a silica gel column (CHCl$_3$/MeOH=10/1 to 3/1) to obtain 383 mg of a target reaction product of bis(Boc-iminobiotin)-COOMe 1 (Me=methyl group) (yield: 72%).

(Analysis Values of Target Reaction Product)
$^1$H-NMR (DMSO-d6): 10.0 (2H, s), 8.2 (1H, s), 8.0 (2H, s), 7.95 (2H, d), 7.90 (2H, br.s), 7.6 (1H, br.s), 4.5-4.6 (2H, m), 4.2-4.3 (2H, m), 3.84 (3H, s), 3.1-3.3 (2H, m), 2.95-3.1 (4H, m), 2.8-2.9 (4H, m), 2.25-2.35 (4H, t), 2.0-2.1 (4H, t), 1.2-1.7 (24H, m), 1.35 (18H, s)

Retention Time under HPLC Analysis Conditions A: 15.3 min (0.1% trifluoroacetic acid aqueous solution/CH$_3$CN=90/10 (18 min) 30/70)

Example 1-3

Synthesis of Bis(Boc-iminobiotin)-COOH 2

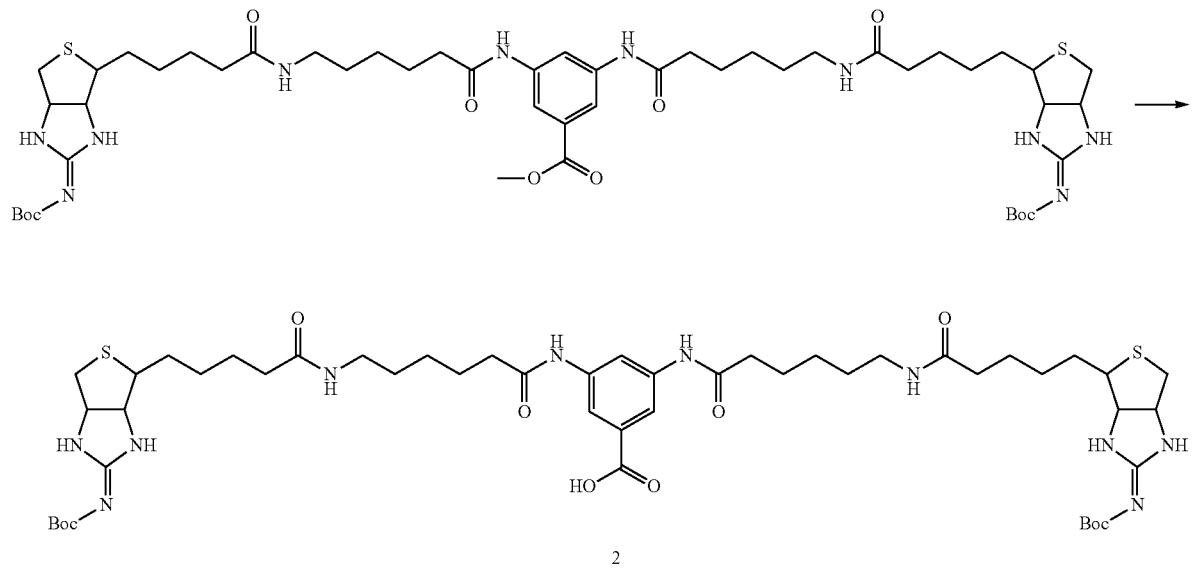 [SMILES: COC(=O)c1cc(NC(=O)CCCCCNC(=O)CCCCC2SCC3N/C(=N/C(=O)OC(C)(C)C)NC32)cc(NC(=O)CCCCCNC(=O)CCCCC2SCC3N/C(=N\C(=O)OC(C)(C)C)NC32)c1 ; CC(C)(C)OC(=O)/N=C1/NC2CSC(CCCCC(=O)NCCCCCC(=O)Nc3cc(NC(=O)CCCCCNC(=O)CCCCC4SCC5N/C(=N\C(=O)OC(C)(C)C)NC54)cc(C(=O)O)c3)C2N1]

180 mg (0.226 mmol) of the bis(Boc-iminobiotin)-COOMe 1 synthesized in Example 1-2 was dissolved in 1 mL of methanol, 35 mg (4.8 equivalents) of a lithium hydroxide hydrate and 0.3 mL of water were added thereto, followed by stirring under heating at 40° C. for 2 hours. The resultant was concentrated under reduced pressure, and adjusted to pH 5 by 0.5 N hydrochloric acid. The thus precipitated solid was filtered off, and washed with 2 mL of water. The solid was dried at 60° C. under reduced pressure to obtain 137 mg of a target reaction product of bis(Boc-iminobiotin)-COOH 2 (yield: 77%).

(Analysis Values of Target Reaction Product)

$^1$H-NMR (DMSO-d6): 9.9 (2H, s), 8.2 (1H, s), 8.0 (2H, s), 7.8 (2H, br.s), 7.7 (2H, m), 4.5-4.6 (2H, m), 4.35-4.45 (2H, m), 3.15-3.3 (2H, m), 3.0-3.1 (4H, m), 2.8-2.9 (4H, m), 2.25-2.35 (4H, t), 2.0-2.1 (4H, t), 1.2-1.7 (24H, m), 1.37 (18H, s)

Retention Time under HPLC Analysis Conditions A: 14.3 min (0.1% trifluoroacetic acid aqueous solution/ CH$_3$CN=90/10 (18 min) 30/70)

Retention Time under HPLC Analysis Conditions A: 12.6 min (0.1% trifluoroacetic acid aqueous solution/ CH$_3$CN=85/15 (18 min) 5/95)

Example 1-4

Synthesis of Bis(Boc-iminobiotin) 3

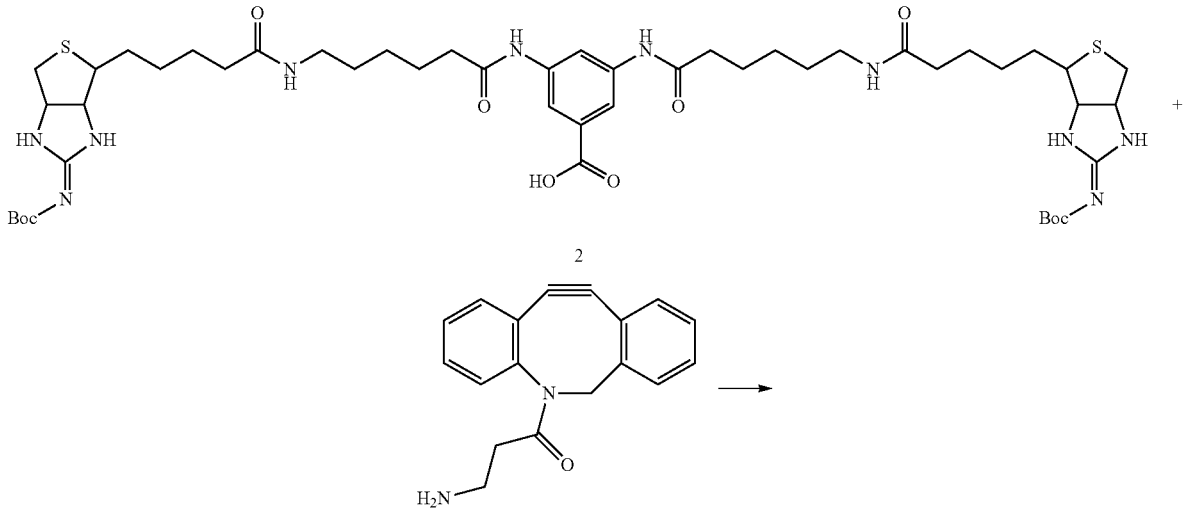

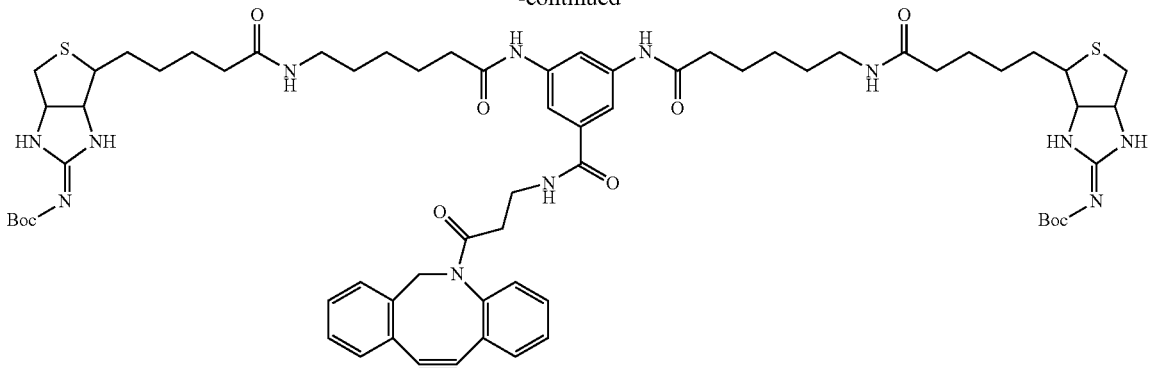

3

To 135 mg (0.13 mmol) of the bis(Boc-iminobiotin)-COOH 2 synthesized in Example 1-3, 1 mL of dehydrated DMF was added, and a condensing agent of CDI (22.3 mg, 1.05 equivalents) was further added thereto. The resultant was stirred at 40° C. for 1 hour, and 0.7 mL of a dehydrated chloroform solution of 36 mg (1 equivalent) of Dibenzocyclooctyne-amine (Sigma-Aldrich, CAS NO: 1255942-06-3) was added thereto, followed by stirring at room temperature for 5 hours. The resultant was concentrated under reduced pressure, 10 mL of chloroform was added thereto, and the resultant was adjusted to pH 5 by 0.1 N hydrochloric acid. Since an insoluble matter was separated, water and chloroform were removed, and the resultant was dissolved in methanol. The resultant was combined with chloroform, dried over magnesium sulfate, and concentrated to obtain a residue. The residue was purified by a silica gel column (CHCl$_3$/MeOH=20/1 to 5/1) to obtain 128 mg of a target reaction product of bis(Boc-iminobiotin)-DBCO 3 (yield: 75%).

(Analysis Values of Target Reaction Product)
$^1$H-NMR (DMSO-d6): 8.2 (1H, br.t), 8.0 (1H, s), 7.95 (1H, s), 7.75 (2H, t), 7.3-7.7 (12H, m), 5.05 (1H, d), 4.55-4.65 (2H, m), 4.3-4.4 (3H, m), 4.1 (1H, m), 3.64 (1H, d), 3.4-3.5 (4H, m), 3.2-3.3 (2H, m), 3.16 (4H, d), 2.95-3.1 (4H, br.t), 2.8-2.9 (4H, m), 2.5-2.6 (1H, m), 2.2-2.35 (4H, t), 2.0-2.1 (4H, t), 1.8-2.0 (1H, m), 1.2-1.7 (24H, m), 1.4 (18H, s)

Retention Time under HPLC Analysis Conditions A: 14.7 min (0.1% trifluoroacetic acid aqueous solution/CH$_3$CN=85/15 (18 min) 5/95)

Example 1-5

Synthesis of 1-[(1-Azido-15-oxo-3,6,9,12-tetraoxapentadecan-15-yl)oxy]-2,5-pyrrolidinedione

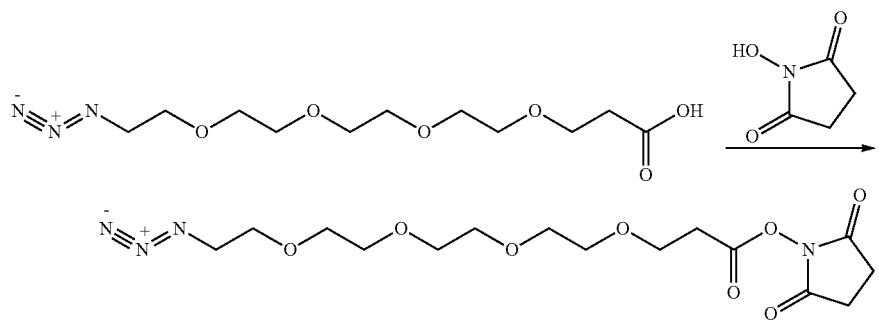

To 100 mg (0.34 mol) of 15-Azido-4,7,10,13-tetraoxapentadecanoic acid and 47 mg (1.2 equivalents) of N-hydroxysuccinimide, 5 mL of dehydrated chloroform was added. 100 mg (1.5 equivalents) of a condensing agent of EDC hydrochloride was further added thereto, and the resultant was stirred at room temperature for 3 hours to synthesize a target reaction product of 1-[(1-Azido-15-oxo-3,6,9,12-tetraoxapentadecan-15-yl)oxy]-2,5-pyrrolidinedione. The resultant solution was not purified but directly used in the following reaction.

(Analysis Values of Target Reaction Product)
$^1$H-NMR (DMSO); 3.71 (2H, t), 3.60 (2H, t), 3.6-3.5 (12H, m), 2.92 (2H, t), 2.81 (4H, s)

Example 1-6

Synthesis of 1-[(1-Azido-15-oxo-3,6,9,12-tetraoxa-pentadecan-15-yl)oxy]-3-sulfonyl-2,5-pyrrolidinedione

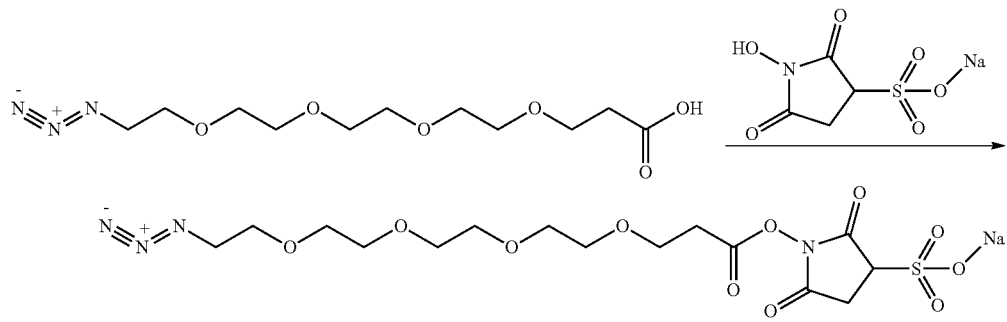

To 310 mg (1.07 mol) of 15-azido-4,7,10,13-tetraoxapentadecanoic acid and 266 mg (1.15 equivalents) of N-hydroxysulfosuccinimide sodium salt, 6.2 mL of dehydrated DMF was added. 296 mg (1.45 equivalents) of a condensing agent of EDC hydrochloride was further added thereto, and the resultant was stirred at room temperature for 5 hours to synthesize a target reaction product of 1-[(1-azido-15-oxo-3,6,9,12-tetraoxapentadecan-15-yl)oxy]-3-sulfonyl-2,5-pyrrolidinedione. The resultant solution was not purified but directly used in the following reaction.

(Analysis Values of Target Reaction Product)
$^1$H-NMR (DMSO); 4.0-3.9 (1H, br.d), 3.71 (2H, t), 3.60 (2H, t), 3.6-3.5 (12H, m), 3.1-3.3 (2H, br.), 2.92 (2H, t)

Example 1-7

Synthesis of Bis-iminobiotin-DBCO-NHS 5

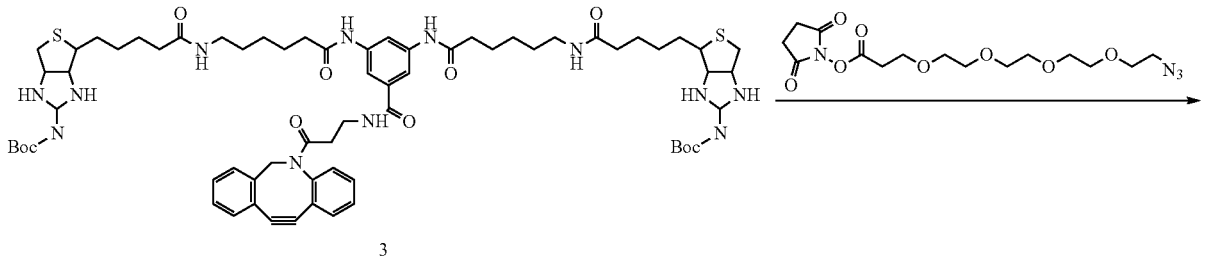

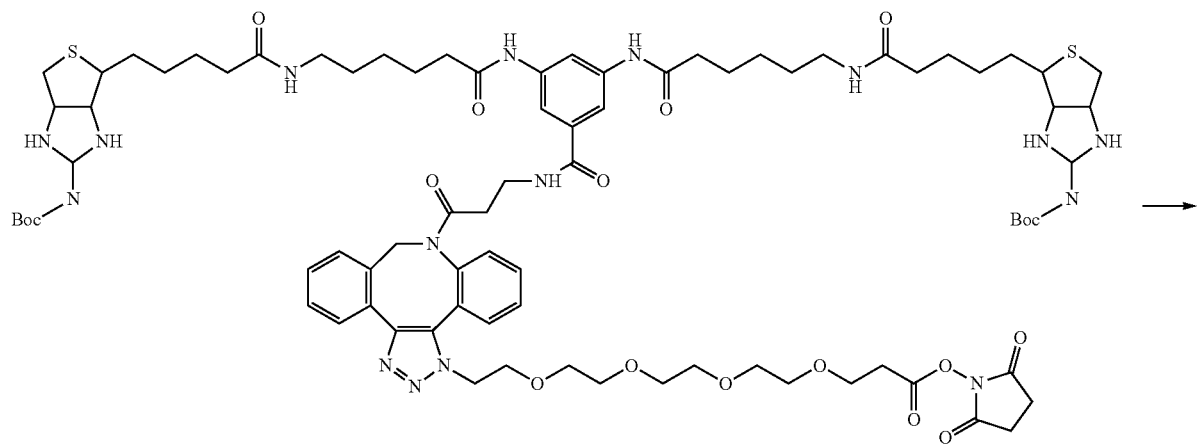

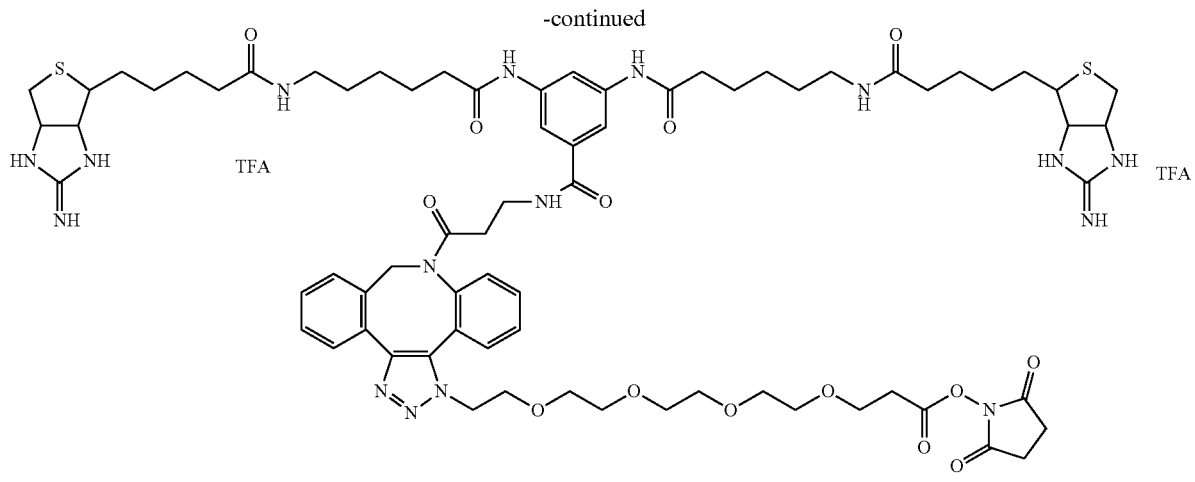

5

The bis(Boc-iminobiotin)-DBCO 3 (33 mg, 0.03 mmol) synthesized in Example 1-4 was dissolved in 1 mL of dehydrated DMF, and 0.72 mL of a 5% trifluoroacetic acid/chloroform solution was added thereto. A chloroform solution of the 1-[(1-azido-15-oxo-3,6,9,12-tetraoxapentadecan-15-yl)oxy]-2,5-pyrrolidinedione (18 mg, 2 equivalents) synthesized in Example 1-5 was further added thereto. The resultant was stirred at room temperature overnight to obtain a condensate of bis(Boc-iminobiotin)-DBCO-NHS 4.

Retention Time under HPLC Analysis Conditions A: 14.5 min (0.1% trifluoroacetic acid aqueous solution/ $CH_3CN$=75/25 (18 min) 30/70)

When the product was reacted with N-methylbutylamine and the HPLC was performed to check the product, the retention time was changed to 15.3 minutes and the product was confirmed to be an active ester.

The resultant reaction solution was concentrated with dry nitrogen, the thus obtained residue was not purified but dissolved in 0.4 mL of trifluoroacetic acid, and the resultant was allowed to stand still at room temperature for 1.5 hours. The resultant reaction solution was concentrated under reduced pressure to obtain 40 mg of a target product of bis-iminobiotin-DBCO-NHS 5.

(Analysis Values of Target Reaction Product)

$^1$H-NMR (DMSO-d6); 10.0 (2H, br.), 8.3-8.0 (5H, m), 7.9-7.2 (16H, m), 6.0-5.8 (1H, m), 4.7-4.6 (2H, m), 4.6-4.4 (4H, m), 4.1-4.0 (1H, m), 3.8-3.4 (18H, m), 3.3-3.2 (2H, m), 3.1-3.0 (4H, br.q), 3.0-2.85 (4H, m), 2.9-2.8 (4H, m), 2.80 (4H, s), 2.35-2.2 (4H, br.t), 2.1-2.0 (4H, t), 1.8-1.2 (24H, m)

Retention Time under HPLC Analysis Conditions A: 11.0 min (0.1% trifluoroacetic acid aqueous solution/ $CH_3CN$=75/25 (18 min) 30/70)

When the product was reacted with N-methylbutylamine and the HPLC was performed to check the product, the retention time was changed to 12.1 minutes and the product was confirmed to be an active ester.

Example 1-8

Synthesis of Bis(Boc-iminobiotin)-DBCO-sulfo-NHS 6

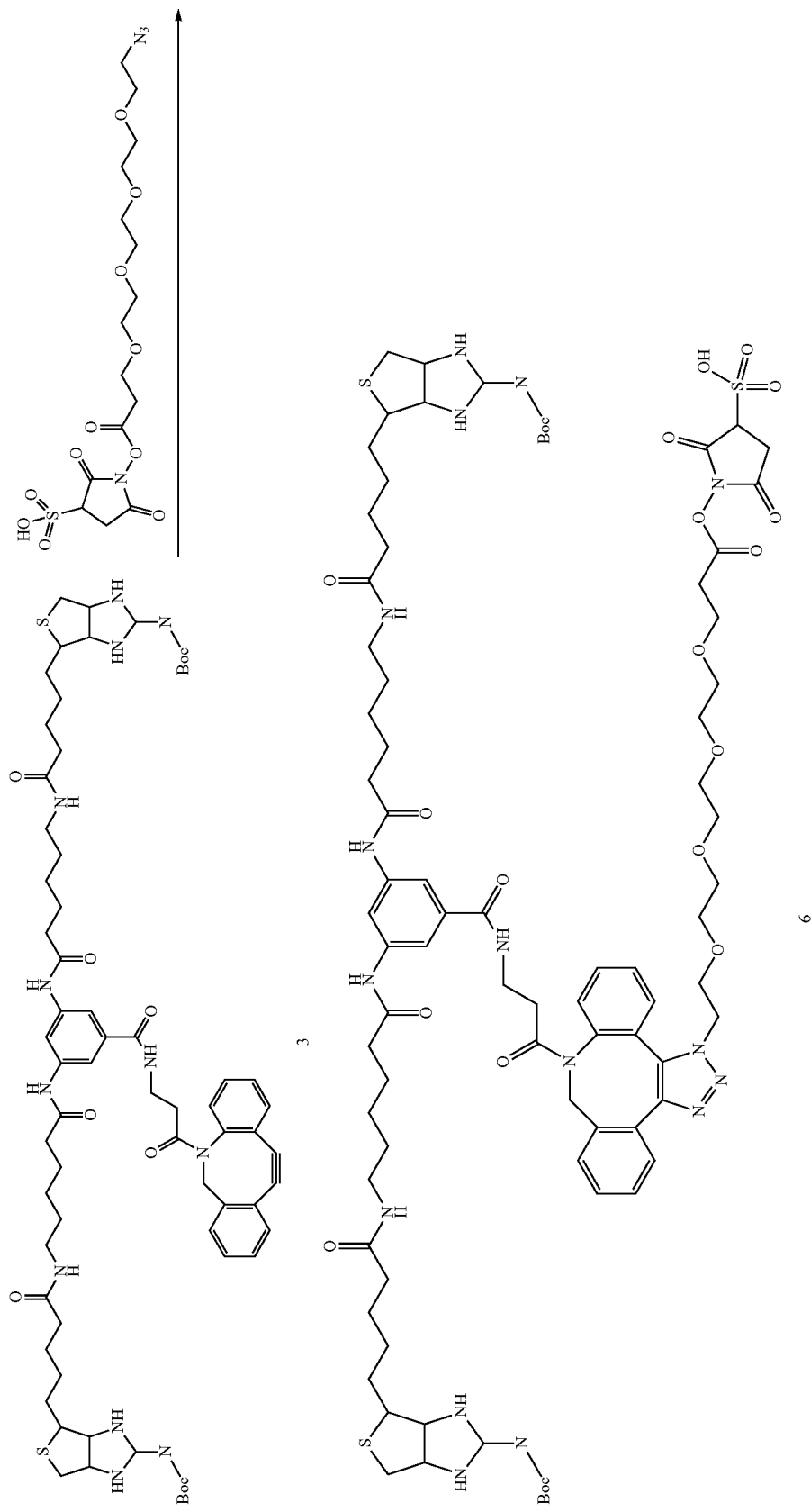

40 mg (0.03 mmol) of the bis(Boc-iminobiotin)-DBCO 3 synthesized in Example 1-4 was dissolved in 0.4 mL of dehydrated DMF, and 0.65 mL of a 5% trifluoroacetic acid/chloroform solution was added thereto.

To the resultant, a DMF solution of 22 mg (1.5 equivalents) of the 1-[(1-azido-15-oxo-3,6,9,12-tetraoxapentadecan-15-yl)oxy]-3-sulfonyl-2,5-pyrrolidinedione synthesized in Example 1-6 was added. The resultant was stirred at room temperature for 30 minutes, and the resultant reaction solution was concentrated with dry nitrogen. The thus obtained residue was washed with 2 mL and 0.5 mL of a 1N hydrochloric acid aqueous solution, and the resultant was When the product was reacted with N-methylbutylamine and the HPLC was performed to check the product, the retention time was changed to 15.3 minutes and the product was confirmed to be an active ester.

Example 1-9

Synthesis of Bis-iminobiotin-DBCO-sulfo-NHS 7

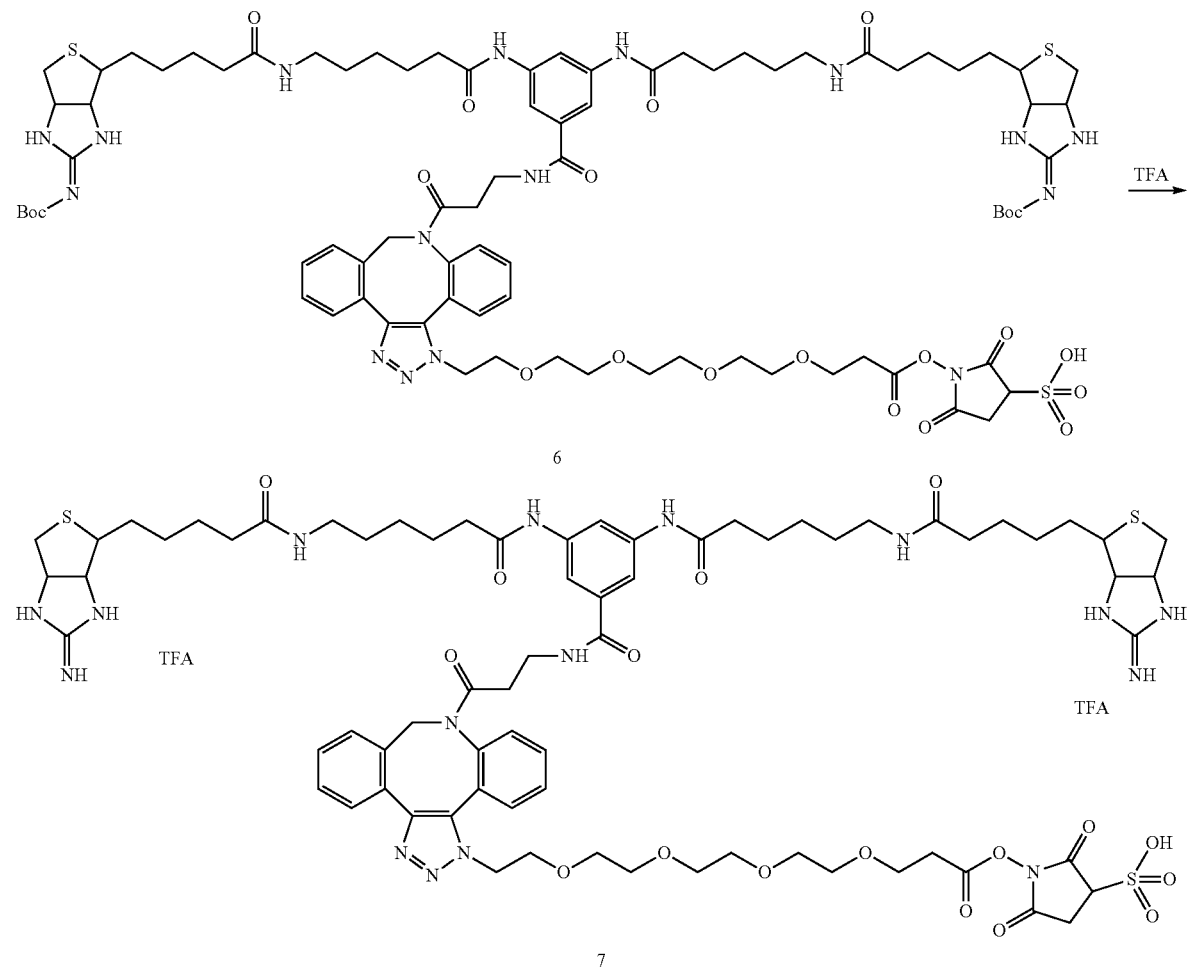

dried under reduced pressure to obtain 59 mg of a target reaction product of bis(Boc-iminobiotin)-sulfo-NHS 6 in an amorphous form.

(Analysis Values of Target Reaction Product)

$^1$H-NMR (DMSO-d6); 11.8 (1H, br.s), 10.0 (2H, br.), 9.1 (2H, br.s), 8.8 (1H, br.s), 8.2-7.2 (18H, m), 6.0-5.8 (1H, m), 4.85-4.75 (2H, m), 4.6-4.4 (4H, m), 4.1-3.8 (2H, m), 3.8-3.4 (18H, m), 3.25-3.35 (2H, m), 3.3-3.0 (2H, m), 3.1-2.9 (8H, m), 2.9-2.8 (4H, m), 2.75 (2H, d), 2.6-2.4 (1H, m), 2.4-2.2 (4H, br.t), 2.1-2.0 (4H, t), 2.0-1.9 (1H, m), 1.9-1.2 (24H, m), 1.49 (18H, s)

Retention Time under HPLC Analysis Conditions A: 13.8 min (0.1% trifluoroacetic acid aqueous solution/ $CH_3CN$=75/25 (18 min) 30/70)

The bis(Boc-iminobiotin)-sulfo-NHS 6 (44 mg, 0.025 mmol) synthesized in Example 1-8 was dissolved in 0.38 mL of trifluoroacetic acid, and the resultant was allowed to stand still at room temperature for 1 hour. The resultant reaction solution was concentrated under reduced pressure to obtain 58 mg of a target of bis-iminobiotin-sulfo-NHS 7.

(Analysis Values of Target Reaction Product)

$^1$H-NMR (DMSO-d6); 10.0 (2H, br.), 8.3-8.0 (5H, m), 7.9-7.2 (16H, m), 6.0-5.8 (1H, m), 4.7-4.6 (2H, m), 4.6-4.4 (4H, m), 4.1-4.0 (1H, m), 4.0-3.9 (1H, m), 3.8-3.4 (18H, m), 3.3-3.2 (2H, m), 3.2-3.0 (2H, br.), 3.1-3.0 (4H, br.q), 3.0-2.85 (4H, m), 2.9-2.8 (4H, m), 2.35-2.2 (4H, br.t), 2.1-2.0 (4H, t), 1.8-1.2 (24H, m)

Retention Time under HPLC Analysis Conditions A: 10.3 min (0.1% trifluoroacetic acid aqueous solution/ CH$_3$CN=75/25 (18 min) 30/70)

When the product was reacted with N-methylbutylamine and the HPLC was performed to check the product, the retention time was changed to 12.1 minutes and the product was confirmed to be an active ester.

Example 1-10

Synthesis of Bis(Boc-iminobiotin)-acetylene 8

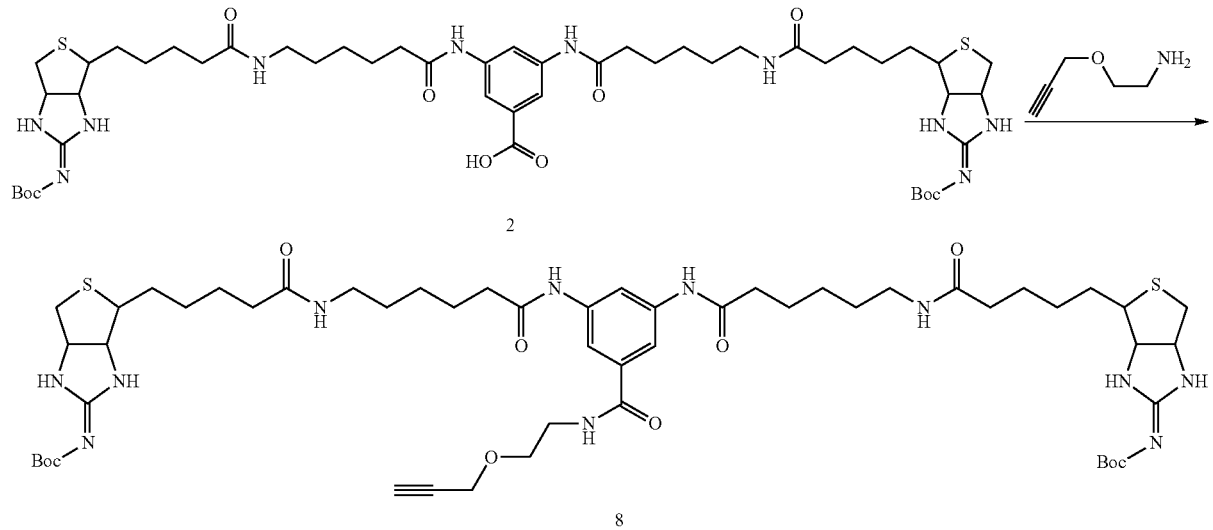

To the bis(Boc-iminobiotin)-COOH 2 (500 mg, 0.49 mmol) synthesized in Example 1-3, 5 mL of dehydrated DMF was added, and a condensing agent of CDI (100 mg, 1.27 equivalents) was further added thereto. The resultant was stirred under heating at 45° C. for 1 hour, and 0.2 mL of a dehydrated chloroform solution of 36 mg (1.2 equivalents) of 2-(prop-2-yn-1-yloxy)ethan-1-amine was added thereto, followed by stirring at room temperature overnight. The resultant was concentrated under reduced pressure, and was adjusted to pH 4 by 0.1 N hydrochloric acid. Since an insoluble matter was separated, an aqueous layer was removed, the resultant was washed with 5 mL of water, and the thus obtained residue was dried under reduced pressure. The resultant was purified by a silica gel column (CHCl$_3$/MeOH=20/1 to 5/1) to obtain 128 mg of a target reaction product of bis(Boc-iminobiotin)-acetylene 8 (yield: 49%).

(Analysis Values of Target Reaction Product)

$^1$H-NMR (DMSO-d6): 9.97 (2H, s), 8.4 (1H, br.t), 8.0 (1H, s), 7.95 (1H, s), 7.74 (2H, t), 7.65 (3H, d), 4.6-4.5 (2H, m), 4.35-4.25 (2H, m), 4.16 (2H, d), 4.1 (1H, m), 3.56 (2H, t), 3.45-3.35 (3H, m), 3.25-3.15 (1H, m), 2.95-3.1 (4H, br.q), 2.9-2.75 (4H, m), 2.45-2.2 (4H, t), 2.1-2.0 (4H, t), 1.2-1.7 (24H, m), 1.4 (18H, s)

Example 1-11

Synthesis of Bis-iminobiotin-triazole-sulfo-NHS 10

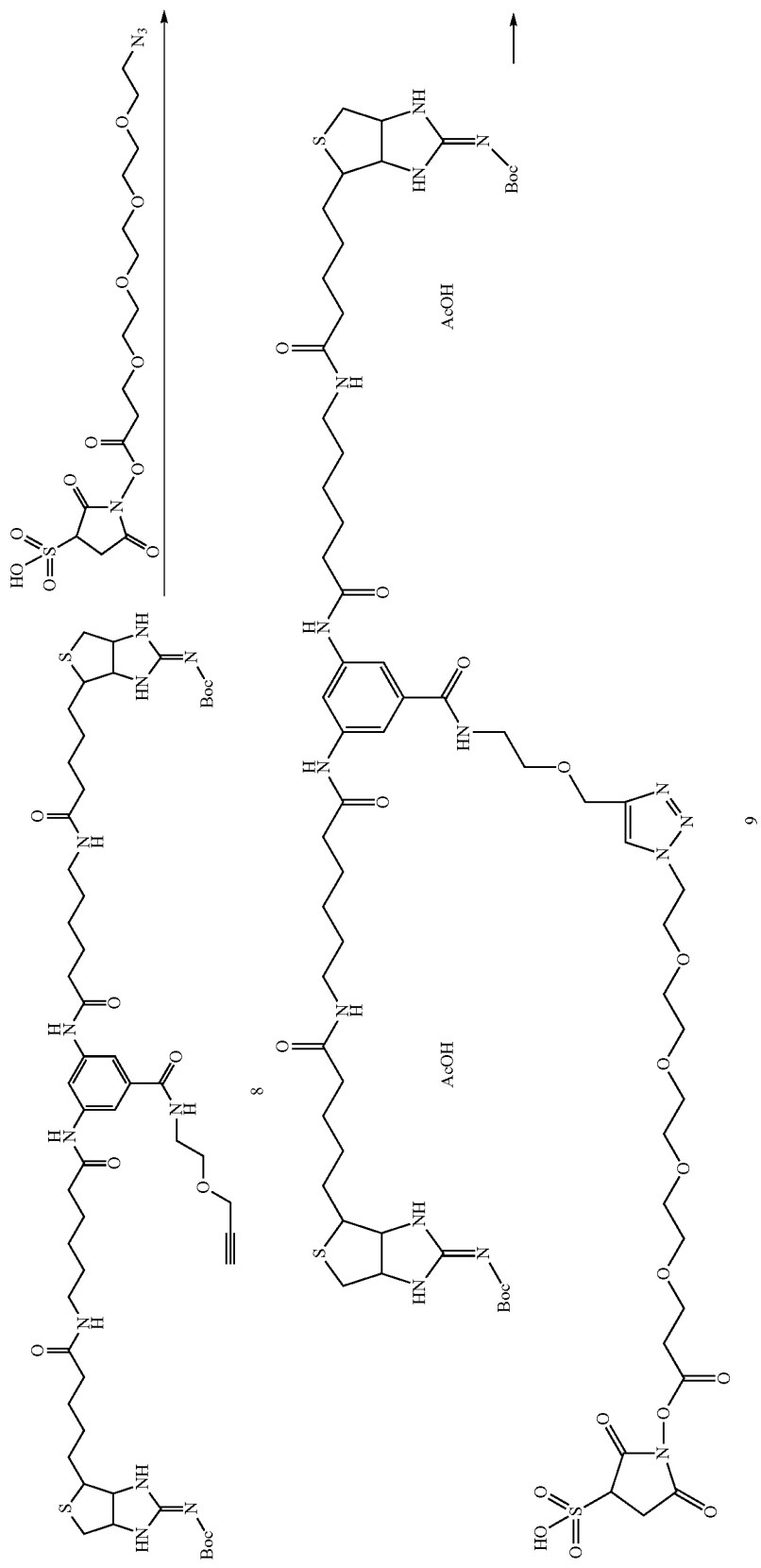

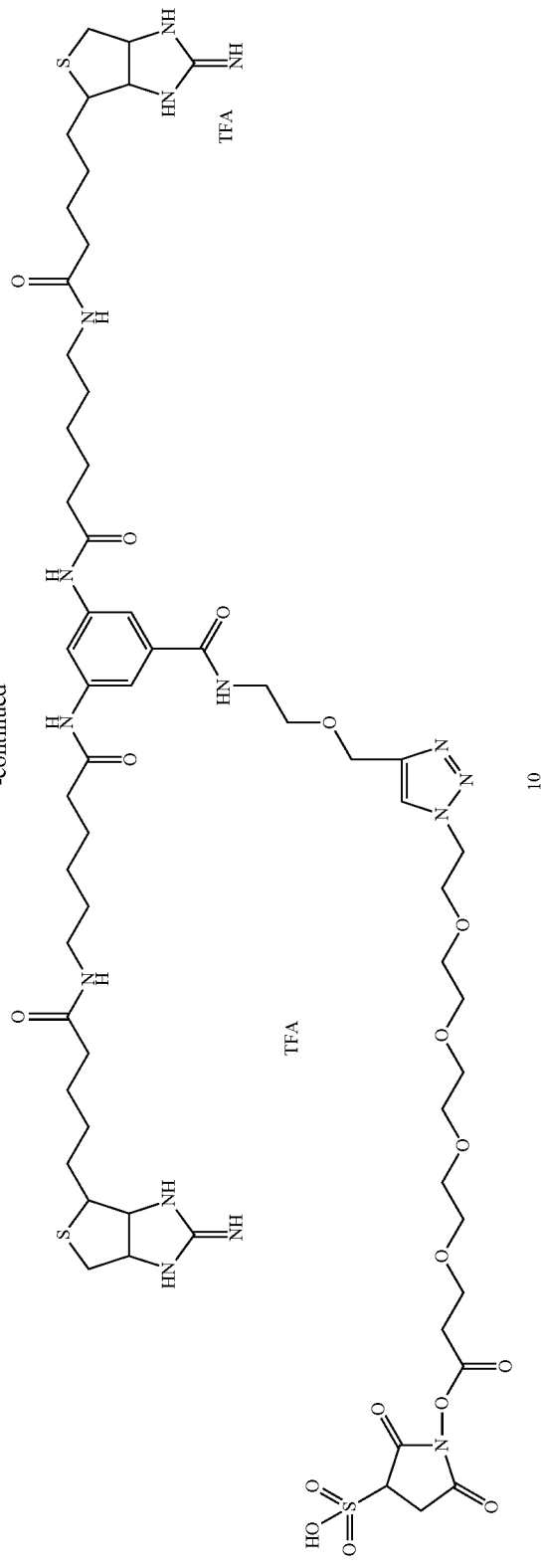

The bis(Boc-iminobiotin)-acetylene 8 (20 mg, 0.18 mmol) synthesized in Example 1-10 was dissolved in dehydrated DMF, and acetic acid, copper acetate and a DMF solution of 13 mg (1.5 equivalents) of 1-[(1-azido-15-oxo-3,6,9,12-tetraoxapentadecan-15-yl)oxy]-3-sulfonyl-2,5-pyrrolidinedione synthesized in Example 1-6 were added thereto. The resultant was stirred at room temperature for 1 hour, and the resultant reaction solution was concentrated with dry nitrogen. The thus obtained residue was washed with 2 mL and 0.66 mL of a 1N hydrochloric acid aqueous solution, and dried under reduced pressure to obtain bis(Boc-iminobiotin)-triazole-sulfo-NHS 9 in an amorphous form.

HPLC Retention Time: 9.9 minutes (0.1% trifluoroacetic acid aqueous solution/CH$_3$CN=70/30 (12 min) 55/45)

When the product was reacted with butylamine and the HPLC was performed to check the product, the retention time was changed to 12.4 minutes and the product was confirmed to be an active ester.

(Analysis Values of Target Reaction Product)

$^1$H-NMR (DMSO-d6); 10.0 (2H, br.s.), 8.4 (1H, br.t), 8.3 (2H, br.s), 8.2-8.05 (4H, m), 7.8 (2H, br.t), 7.7-7.6 (6H, br), 4.7-4.6 (2H, m), 4.6-4.4 (6H, m), 4.0-3.9 (1H, br), 3.80 (2H, t), 3.7 (2H, t), 3.6-3.4 (20H, m), 3.3-3.2 (2H, m), 3.2-3.1 (1H, br), 3.02 (4H, q), 2.95-2.85 (6H, m), 2.79 (2H, d), 2.30 (4H, t), 2.06 (4H, t), 1.8-1.2 (24H, m)

Retention Time under HPLC Analysis Conditions A: 9.1 minutes (0.1% trifluoroacetic acid aqueous solution/CH$_3$CN=80/20 (12 min) 55/45)

When the product was reacted with amylamine and the HPLC was performed to check the product, the retention time was changed to 12.4 minutes and the product was confirmed to be an active ester.

Example 1-12

Synthesis of Bis-iminobiotin-triazole-NHS 12

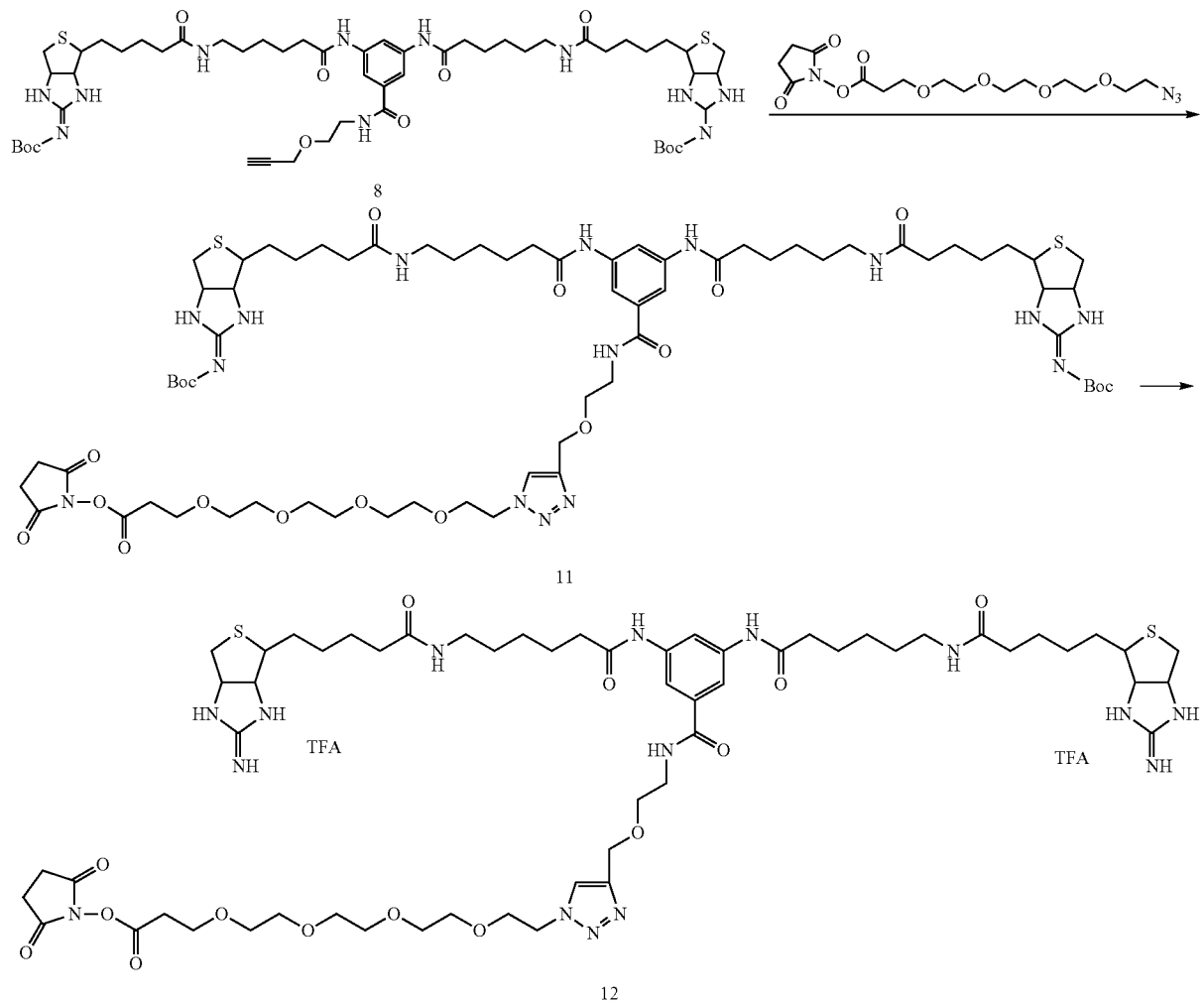

Subsequently, 0.55 mL of trifluoroacetic acid was added thereto without purification, the resultant was allowed to stand still at room temperature for 1 hour, and concentrated under reduced pressure to obtain 33 mg of a target reaction product of bis-iminobiotin-triazole-sulfo-NHS 10.

The bis(Boc-iminobiotin)-acetylene 8 (20 mg, 0.18 mmol) synthesized in Example 1-10 was dissolved in dehydrated DMF, and acetic acid, copper acetate, sodium ascorbate and a chloroform solution of 13 mg (2.0 equivalents) of 1-[(1-azido-15-oxo-3,6,9,12-tetraoxapentadecan-15-yl)oxy]-2,5-pyrrolidinedione synthesized in Example 1-5 were added thereto. The resultant was stirred at room temperature for 2 hours, and the resultant reaction solution was concentrated with dry nitrogen. The thus obtained residue was washed with 0.3 mL of ethyl acetate and 0.3 mL and 0.1 mL of a 1N hydrochloric acid aqueous solution, and then dried under reduced pressure to obtain bis(Boc-iminobiotin)-triazole-NHS 11 in an amorphous form.

HPLC Retention Time: 11.8 minutes (0.1% trifluoroacetic acid aqueous solution/CH$_3$CN=70/30 (12 min) 55/45)

When the product was reacted with N-butylamine and the HPLC was performed to check the product, the retention time was changed to 12.4 minutes and the product was confirmed to be an active ester.

Subsequently, 0.2 mL of trifluoroacetic acid was added thereto, the resultant was allowed to stand still at room temperature for 1 hour, and concentrated under reduced pressure to obtain 33 mg of a target reaction product of bis-iminobiotin-triazole-NHS 12.

(Analysis Values of Target Reaction Product)
$^1$H-NMR (DMSO-d6); 10.0 (2H, br.s.), 8.38 (1H, br.t), 8.23 (2H, br.s), 8.07 (4H, s), 7.75 (2H, br.t), 7.7-7.6 (6H, br), 4.7-4.6 (2H, m), 4.6-4.4 (6H, m), 3.80 (2H, t), 3.73 (2H, t), 3.6-3.35 (18H, m), 3.3-3.2 (2H, m), 3.02 (4H, br.q), 2.95-2.85 (4H, m), 2.80 (4H, s), 2.78 (2H, d), 2.30 (4H, t), 2.05 (4H, t), 1.8-1.2 (24H, m)

Retention Time under HPLC Analysis Conditions A: 9.8 minutes (0.1% trifluoroacetic acid aqueous solution/CH$_3$CN=80/20 (12 min) 55/45)

When the product was reacted with amylamine and the HPLC was performed to check the product, the retention time was changed to 12.6 minutes and the product was confirmed to be an active ester.

Example 1-13

Synthesis of Bis(Boc-iminobiotin)-COOH 13

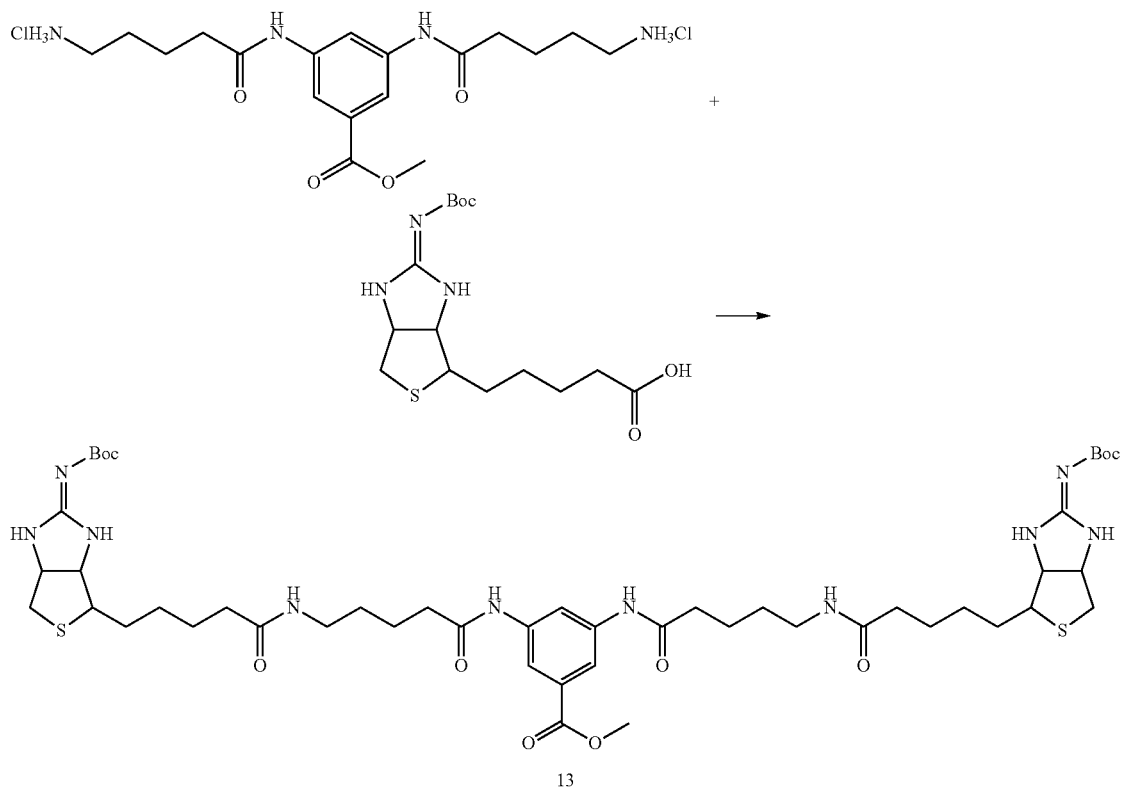

13

A reaction was performed in the same manner as in Example 1-2 by using 1.447 g (3.31 mmol) of methyl 3,5-bis(5-aminopentanamido)benzoate hydrochloride and 2.5 g (7.28 mmol) of the N-Boc iminobiotin synthesized in Example 1-1 to obtain 1.281 g (38%) of a target reaction product of bis(Boc-iminobiotin)-COOMe 13.

(Analysis Values of Target Reaction Product)
$^1$H-NMR (DMSO-d6): 10.1 (2H, s), 8.2 (1H, s), 8.0 (2H, s), 7.95 (2H, d), 7.92 (2H, br.s), 7.62 (1H, br.s), 4.5-4.6 (2H, m), 4.2-4.3 (2H, m), 3.83 (3H, s), 3.1-3.3 (2H, m), 2.95-3.1 (4H, m), 2.8-2.9 (4H, m), 2.25-2.35 (4H, t), 2.0-2.1 (4H, t), 1.2-1.7 (20H, m), 1.35 (18H, s)

HPLC Retention Time (analysis conditions B): 5.03 min (0.1% trifluoroacetic acid aqueous solution/CH$_3$CN=85/15 (7 min) 5/95)

Example 1-14

Synthesis of Bis(Boc-iminobiotin)-COOH 14

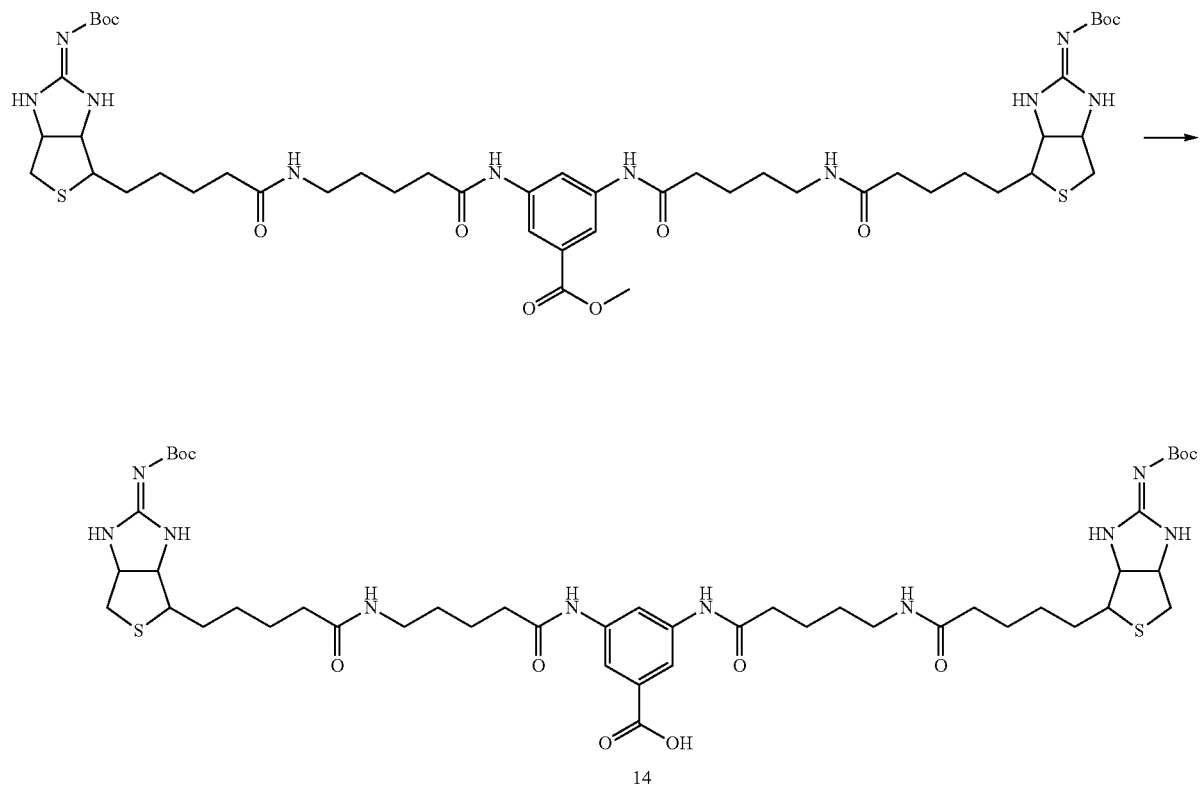

A reaction was performed in the same manner as in Example 1-3 by using 886.3 mg (0.873 mmol) of the bis(Boc-iminobiotin)-COOMe 13 synthesized in Example 1-13 to obtain 707.8 mg (65%) of a target reaction product of bis(Boc-iminobiotin)-COOH 14.

(Analysis Values of Target Reaction Product)

$^1$H-NMR (DMSO-d6): 9.92 (2H, s), 8.21 (1H, s), 8.0 (2H, s), 7.79 (2H, br.s), 7.7 (2H, m), 4.5-4.6 (2H, m), 4.35-4.45 (2H, m), 3.15-3.3 (2H, m), 3.0-3.1 (4H, m), 2.8-2.9 (4H, m), 2.25-2.35 (4H, t), 2.0-2.1 (4H, t), 1.2-1.7 (20H, m), 1.37 (18H, s)

HPLC Retention Time (Analysis Conditions B): 4.71 min (0.1% trifluoroacetic acid aqueous solution/CH$_3$CN=85/15 (7 min) 5/95)

Example 1-15

Synthesis of Bis(Boc-iminobiotin)-acetylene 15

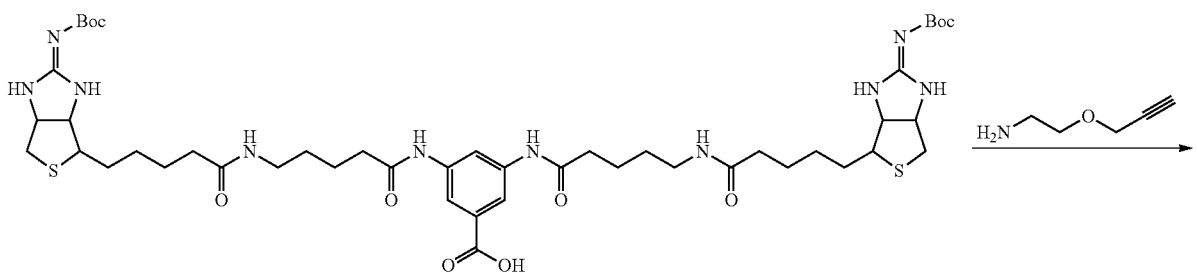

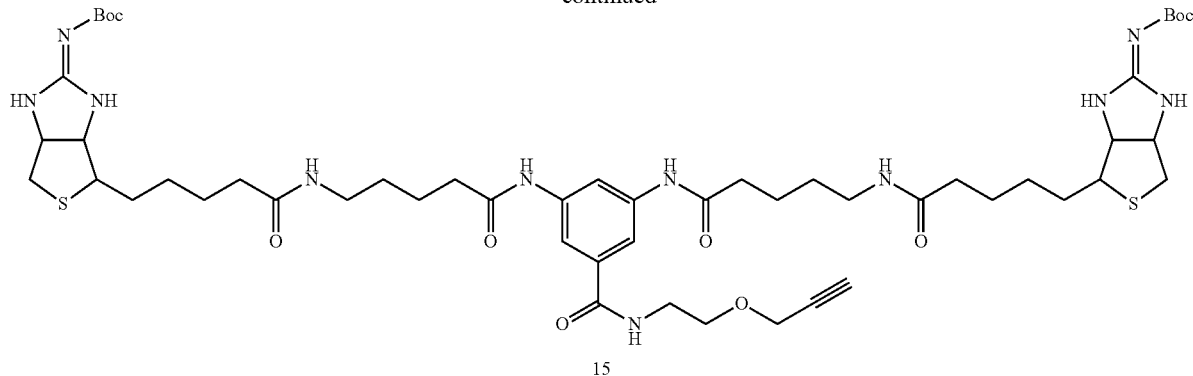

15

A reaction was performed in the same manner as in Example 1-10 by using 355.3 mg (0.355 mmol) of the bis(Boc-iminobiotin)-COOH 14 synthesized in Example 1-14 to obtain 55.6 mg (14%) of a target reaction product of bis(Boc-iminobiotin)-acetylene 15.

(Analysis Values of Target Reaction Product)
$^1$H-NMR (DMSO-d6): 9.91 (2H, s), 8.2 (1H, s), 8.0 (2H, s), 7.8 (2H, br.s), 7.72 (2H, m), 4.5-4.6 (2H, m), 4.35-4.45 (2H, m), 3.15-3.3 (2H, m), 3.0-3.1 (4H, m), 2.8-2.9 (4H, m), 2.25-2.35 (4H, t), 2.0-2.1 (4H, t), 1.2-1.7 (20H, m), 1.37 (18H, s)

HPLC Retention Time (Analysis Conditions B): 4.91 min (0.1% trifluoroacetic acid aqueous solution/CH$_3$CN=85/15 (7 min) 5/95)

Example 1-16

Synthesis of Bis-iminobiotin-triazole-sulfo-NHS 17

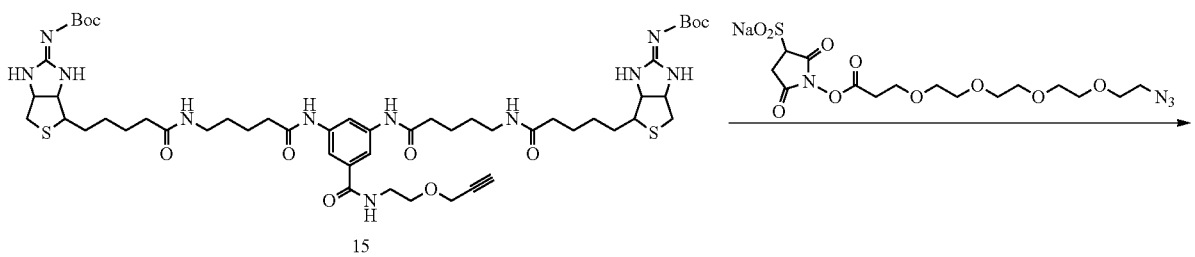

15

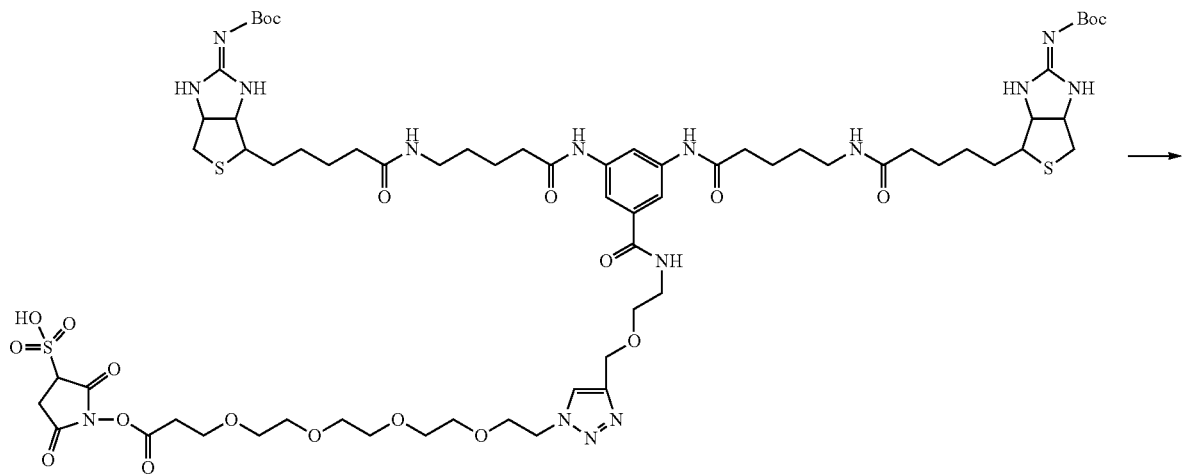

16

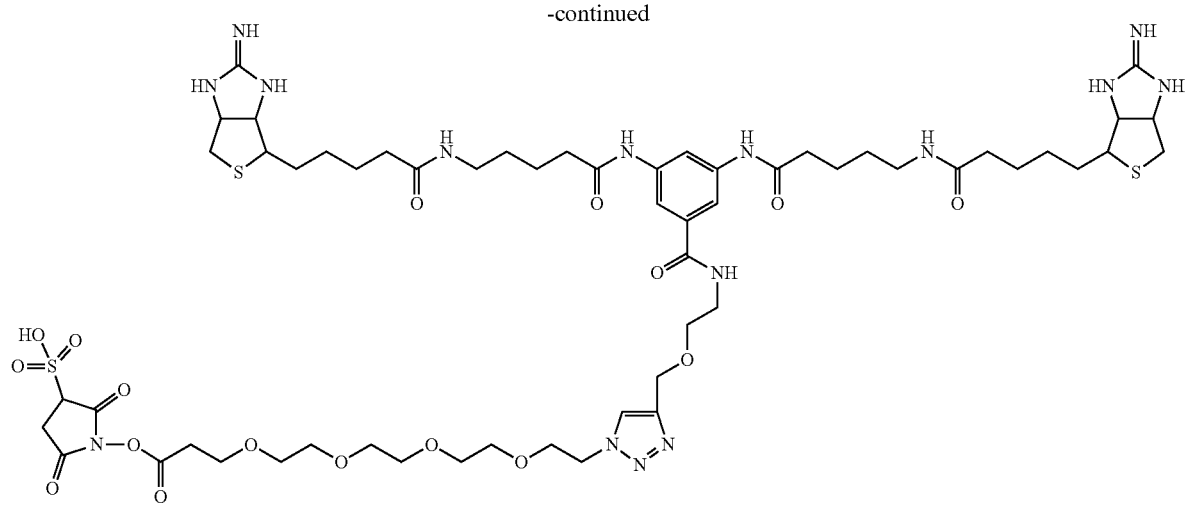

17

A reaction was performed in the same manner as in Example 1-11 by using 51.8 mg (0.048 mmol) of the bis(Boc-iminobiotin)-acetylene 15 synthesized in Example 1-15 and a DMF solution of 35.2 mg (0.072 mmol, 1.5 equivalents) of the 1-[(1-azido-15-oxo-3,6,9,12-tetraoxa-pentadecan-15-yl)oxy]-3-sulfonyl-2,5-pyrrolidinedione synthesized in Example 1-6 to obtain bis(Boc-iminobiotin)-triazole-sulfo-NHS 16.

HPLC Retention Time (Analysis Conditions B): 4.68 min (0.1% trifluoroacetic acid aqueous solution/CH$_3$CN=85/15 (7 min) 5/95)

When the product was reacted with a small amount of butylamine and the HPLC was performed to check the product, the retention time was changed to 5.01 and the product was confirmed to be an active ester.

Subsequently, the resultant was reacted with trifluoroacetic acid without purification to obtain 30 mg of a target reaction product of bis-iminobiotin-triazole-sulfo-NHS 17.

(Analysis Values of Target Reaction Product)

$^1$H-NMR (DMSO-d6); 10.1 (2H, br.s.), 8.4 (1H, br.t), 8.3 (2H, br.s), 8.2-8.05 (4H, m), 7.82 (2H, br.t), 7.7-7.6 (6H, br), 4.7-4.6 (2H, m), 4.6-4.4 (6H, m), 4.0-3.9 (1H, br), 3.80 (2H, t), 3.7 (2H, t), 3.6-3.4 (20H, m), 3.3-3.2 (2H, m), 3.2-3.1 (1H, br), 3.02 (4H, q), 2.95-2.85 (6H, m), 2.79 (2H, d), 2.30 (4H, t), 2.06 (4H, t), 1.8-1.2 (20H, m)

HPLC Retention Time (Analysis Conditions B): compound reacted with butylamine: 4.03 min (0.1% trifluoroacetic acid aqueous solution/CH$_3$CN=85/15 (7 min) 5/95)

Example 2-1

Synthesis of N,N-Bis[(ethoxycarbonyl)methyl]-3-(tert-butoxycarbonylamino) propionylamide

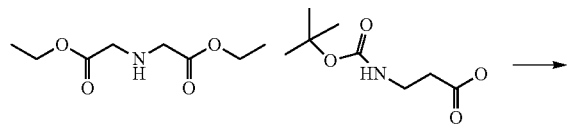

-continued 2.5 g (13.3 mmol) of 3-(tert-butoxycarbonylamino)propanoic acid was dissolved in dehydrated THF, and 2.6 g (1.2 equivalents) of a condensing agent of CDI was added thereto, followed by stirring at room temperature for 3.5 hours. To the resultant, 2.73 g (1.08 equivalents) of bis[(ethoxycarbonyl)methyl]amine was added, followed by stirring at room temperature overnight. The solvent was concentrated under reduced pressure, 15 mL of ethyl acetate was added thereto, and the resultant was washed with 20 mL and 5 mL of a 5% citric acid aqueous solution. The resultant was further washed with 5 mL of water and 5 mL of saturated brine, and dried over magnesium sulfate. After distilling off the solvent, the resultant was crystallized with 100 mL of diisopropyl ether and filtered off. The resultant was dried under reduced pressure to obtain 1.26 g (26%) of a target product of N,N-bis[(ethoxycarbonyl)methyl]-3-(tert-butoxycarbonylamino)propionylamide.

(Analysis Values of Target Reaction Product)

$^1$H-NMR (CDCl$_3$); 4.3-4.1 (8H, m), 3.43 (2H, q), 2.51 (2H, t), 1.43 (9H, s), 1.35-1.25 (6H, m)

Example 2-2

Synthesis of N-(3-(tert-Butoxycarbonylamino)propiony)iminodiacetic Acid

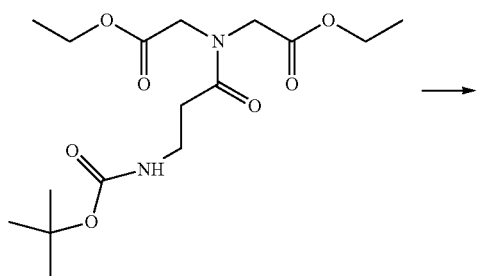

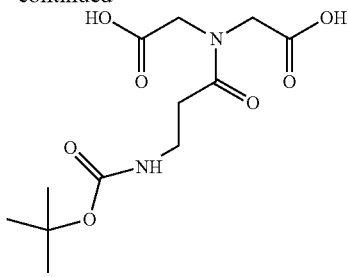

The N, N-bis[(ethoxycarbonyl)methyl]-3-(tert-butoxycarbonylamino) propionylamide (1.2 g, 3.3 mmol) synthesized in Example 2-1 was dissolved in 8.4 mL of methanol, 420 mg (3 equivalents) of lithium hydroxide hydrate and 1.7 mL of water were added thereto, followed by stirring under heating at 60° C. for 4.5 hours. The resultant was concentrated under reduced pressure, and dried under reduced pressure at 60° C. for 5 hours to obtain 1.3 g of N-(3-(tert-butoxycarbonylamino)propiony)iminodiacetic acid. This compound was not purified but directly used in the following reaction.

Example 2-3

Synthesis of Bis-biotin-NH-Boc 13

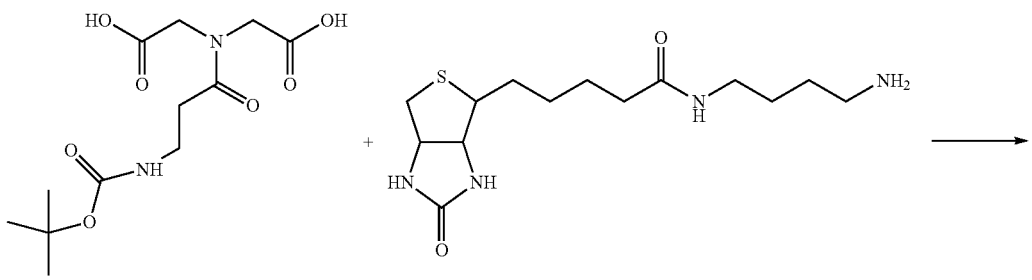

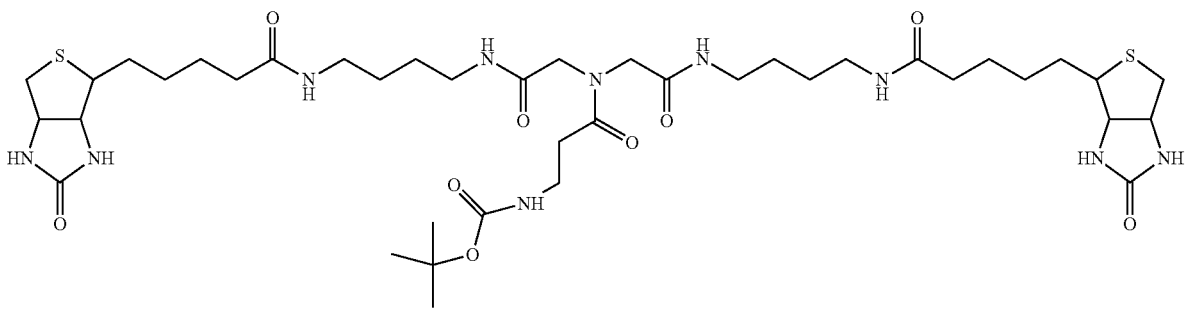

325 mg of N-(3-(tert-butoxycarbonylamino)propiony) iminodiacetic acid synthesized in Example 2-2, 773 mg (2.1 equivalents) of N-(4-aminobutyl)biotinamide, 6.5 mL of dry DMF, 0.6 mL of triethylamine and a condensing agent of DMT-MM (784 mg, 2.65 equivalents) were mixed, followed by stirring at room temperature overnight. The solvent was concentrated under reduced pressure, and 14 mL of a 5% citric acid aqueous solution and NaCl were added thereto, followed by stirring. The thus precipitated insoluble matter was dried under reduced pressure, and purified by a silica gel column (CHCl$_3$/MeOH) to obtain 157 mg of a target product of bis-biotin-NH-Boc 13. Yield: 16%.

(Analysis Values of Target Reaction Product)
$^1$H-NMR (DMSO-d6): 8.7-8.6 (1H, br.t), 8.25-8.15 (1H, br.t), 6.7-6.6 (1H, br.t), 6.38 (4H, d), 4.35-4.25 (2H, m), 4.2-4.1 (2H, m), 4.00 (2H, s), 3.86 (2H, s), 3.2-2.9 (12H, m), 2.82 (2H, dd), 2.58 (2H, d), 2.35 (2H, t), 2.05 (4H, t), 1.2-1.7 (20H, m), 1.37 (9H, s)

Example 2-4

Synthesis of Bis-biotin-NH2-TFA Salt 14

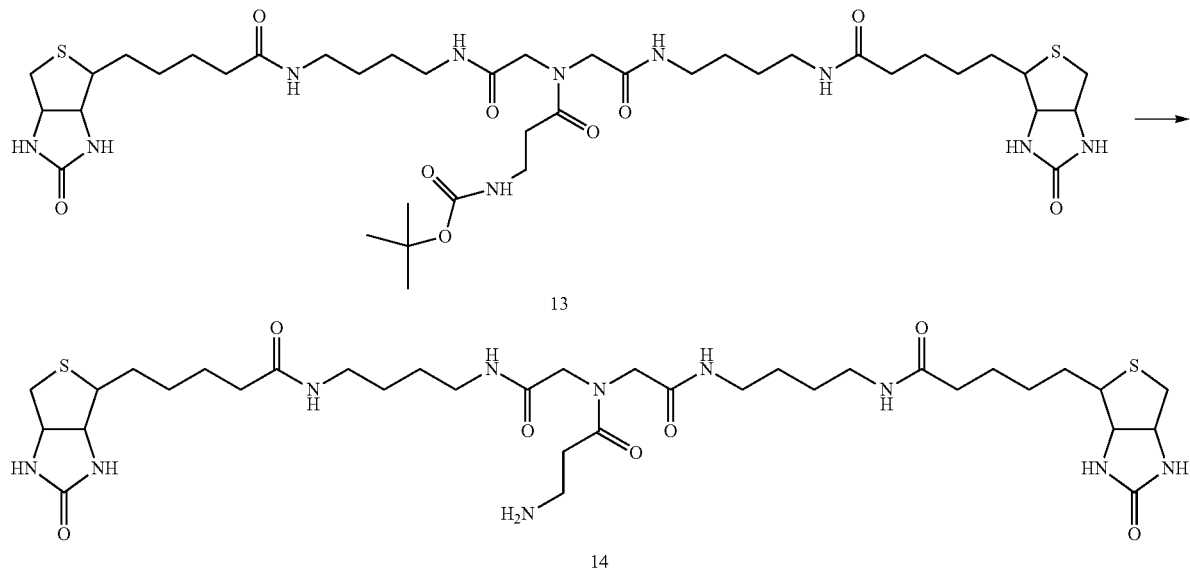

The bis-biotin-NH-Boc 13 (80 mg, 0.89 mmol) synthesized in Example 2-3 was dissolved in 0.4 mL of trifluoroacetic acid, followed by stirring at room temperature for 2.5 hours. The trifluoroacetic acid was concentrated under reduced pressure to obtain 75 mg of a target product of bis-biotin-NH$_2$-TFA salt 14.

(Analysis Values of Target Reaction Product)
$^1$H-NMR (DMSO-d6): 8.69 (1H, t), 8.20 (1H, t), 7.8-7.6 (5H, br.m), 4.31 (2H, dd), 4.13 (2H, dd), 4.04 (2H, s), 3.90 (2H, s), 3.2-2.9 (12H, m), 2.82 (2H, dd), 2.65-2.55 (4H, m), 2.05 (4H, t), 1.2-1.7 (20H, m)

Example 2-5

Synthesis of Bis-biotin-DBCO 15

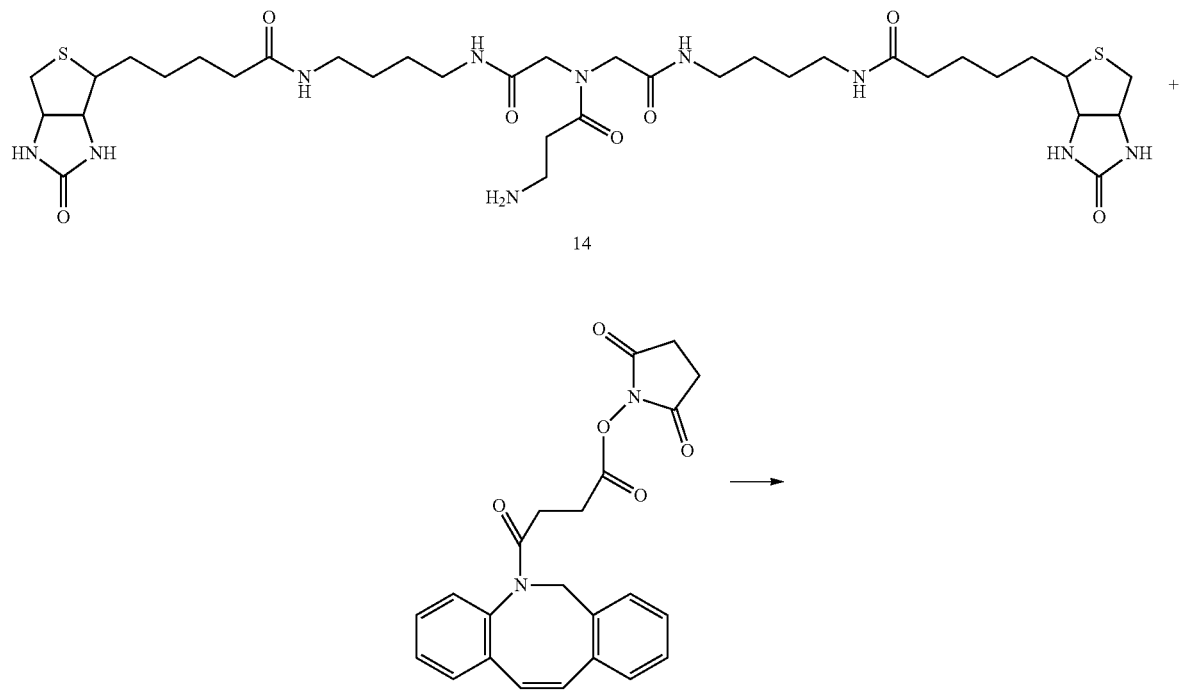

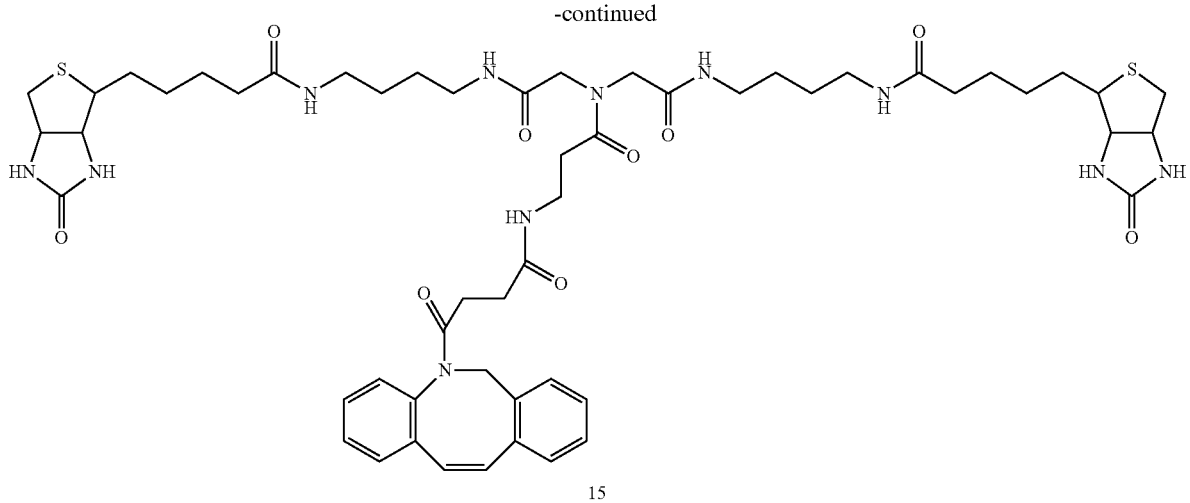

15

The bis-biotin-NH$_2$-TFA salt 14 (115 mg, 0.126 mmol) synthesized in Example 2-4 was dissolved in 2.3 mL of dehydrated DMF, and 50 mg (1 equivalent) of dibenzocyclooctyne-N-hydroxysuccinimidyl ester (Sigma-Aldrich) and 0.05 mL of triethylamine were added thereto, followed by stirring at room temperature overnight. A condensing agent of HBTU (48 mg, 1 equivalent) was further added thereto, followed by stirring for 2 hours. The solvent was concentrated with dry nitrogen, and 12 mL of a 5% citric acid aqueous solution was added thereto to obtain an insoluble matter. The thus obtained aqueous layer was discarded, and the resultant was washed with 1 mL of water. The insoluble matter was dried under reduced pressure, and purified by a silica gel column (CHCl$_3$/MeOH=10/1 to 3/1) to obtain 27 mg of a target reaction product of bis-biotin-DBCO 15 (yield: 20%).

(Analysis Values of Target Reaction Product)
$^1$H-NMR (DMSO-d6): 8.68 (1H, br.t), 8.16 (1H, br.t), 7.8-7.2 (10H, m), 6.48 (4H, d), 5.03 (1H, d), 4.35-4.25 (2H, m), 4.2-4.1 (2H, m), 3.96 (2H, s), 3.83 (2H, s), 3.5-3.3 (2H, m), 3.17 (2H, d), 3.2-2.9 (10H, m), 2.82 (2H, dd), 2.57 (2H, d), 2.25 (2H, t), 2.25-2.1 (1H, m), 2.04 (4H, t), 2.0-1.85 (1H, m), 1.8-1.2 (20H, m)

Retention Time under HPLC Analysis Conditions A: 11.2 min (0.1% trifluoroacetic acid aqueous solution/CH$_3$CN=85/15 (12 min) 5/95)

Retention Time under HPLC Analysis Conditions A: 13.7 min (0.1% trifluoroacetic acid aqueous solution/CH$_3$CN=85/15 (12 min) 35/65)

Example 2-6

Synthesis of Bis-biotin-DBCO-sulfo-NHS 16

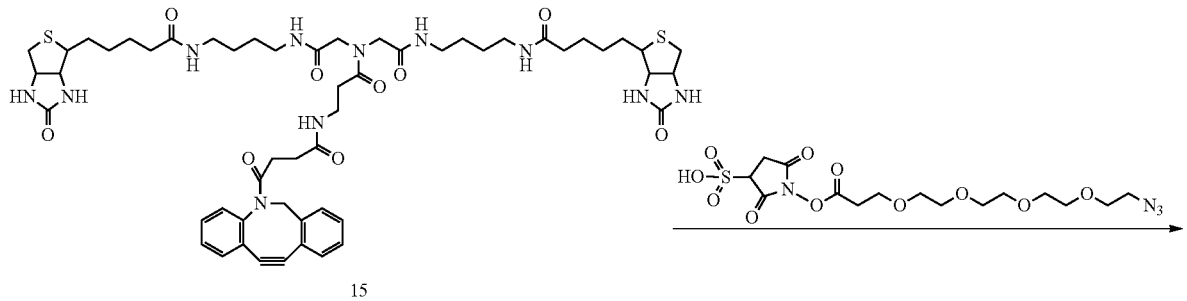

15

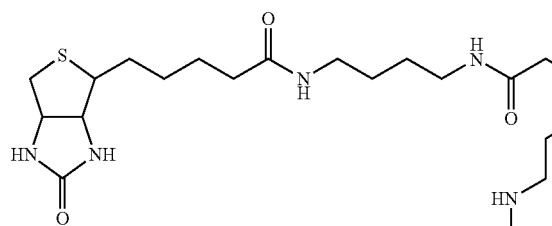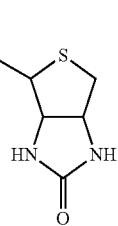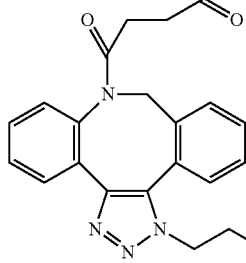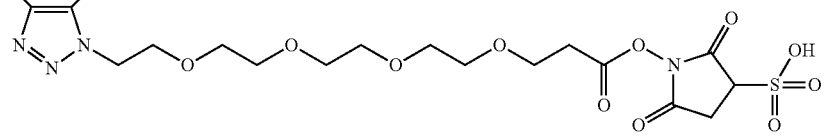

The bis-biotin-DBCO 15 (20 mg, 0.018 mmol) synthesized in Example 2-5 was dissolved in 0.2 mL of dehydrated DMF, and 0.03 mL of trifluoroacetic acid was added thereto. A DMF solution of 9 mg (1.1 equivalents) of the 1-[(1-azido-15-oxo-3,6,9,12-tetraoxapentadecan-15-yl)oxy]-3-sulfonyl-2,5-pyrrolidinedione synthesized in Example 1-6 was further added thereto. The resultant was stirred at room temperature for 30 minutes, and the resultant reaction solution was concentrated with dry nitrogen. The thus obtained residue was washed with 1 mL of dry chloroform twice, and dried under reduced pressure to obtain 30 mg of a target reaction product of bis-biotin-DBCO-sulfo-NHS 16 in an amorphous form.

(Analysis Values of Target Reaction Product)
$^1$H-NMR (DMSO-d6); 8.0 (1H, br.t), 8.3 (1H, s), 8.18 (1H, br.t), 8.0-7.2 (13H, m), 6.4 (2H, br), 5.87 (1H, dd), 4.46 (1H, dd), 4.35-4.25 (2H, m), 4.2-4.1 (2H, m), 3.99 (2H, s), 4.0-3.9 (1H, br), 3.85 (2H, s), 3.75-3.35 (21H, m), 3.25-2.95 (12H, m), 2.95-2.75 (4H, m), 2.56 (2H, d), 2.34 (2H, t), 2.04 (4H, t), 1.95-1.8 (2H, m), 2.4-2.2 (4H, br.t), 1.7-1.1 (20H, m)

Retention Time under HPLC Analysis Conditions A: 11.8 min (0.1% trifluoroacetic acid aqueous solution/CH$_3$CN=85/15 (12 min) 35/65)

When the product was reacted with butylamine and the HPLC was performed to check the product, the retention time was changed to 13.2 minutes and the product was confirmed to be an active ester.

Example 3-1

Synthesis of 6-((tert-Butoxycarbonyl)amino)hexyl Methanesulfonate

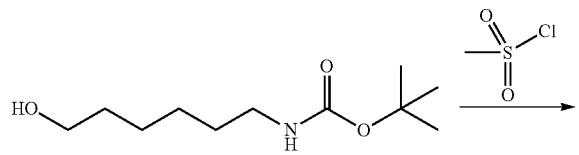

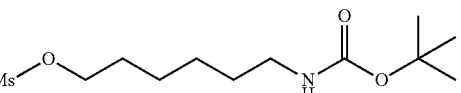

5.3 g (24.4 mmol) of 6-Boc-aminohexanol was dissolved in 53 mL of chloroform, and 4.93 g (48.8 mmol) of triethylamine was added thereto. 3.63 g (31.7 mmol) of MsCl was added thereto in a dropwise manner under ice cooling, followed by stirring at room temperature for 1 day. The resultant was washed with 30 mL of a 5% citric acid aqueous solution twice, and further washed with 20 mL of water and 20 mL of saturated brine. The resultant was dried over magnesium sulfate, and concentrated to obtain 8.7 g of a crude product of 6-((tert-butoxycarbonyl)amino)hexyl methanesulfonate. This compound was not purified but directly used in the following reaction.

(Analysis Values of Target Reaction Product)
1H-NMR (CDCl3): 4.22 (2H, t), 3.1 (2H, q), 3.01 (3H, s), 1.8-1.3 (8H, m), 1.44 (9H, s)

Example 3-2

Synthesis of Bis(6-tert-butoxycarbonylaminohexyl)amine

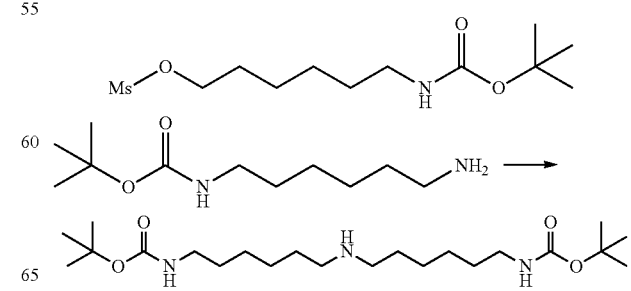

0.8 g (2.7 mmol) of 6-((tert-butoxycarbonyl)amino)hexyl methanesulfonate synthesized as above was dissolved in 8 mL of chloroform, 2.35 g (10.8 mmol) of 6-((tert-butoxycarbonyl)amino)hexylamine and 0.55 g (5.4 mmol) of triethylamine were added thereto, followed by heating to reflux for 16 hours. The resultant reaction solution was cooled, washed with 15 mL of a 5% citric acid aqueous solution twice, dried over sodium sulfate and concentrated. The thus obtained residue was purified by a silica gel column to obtain 0.59 g (53%) of a target product of bis(6-tert-butoxycarbonylaminohexyl)amine.

(Analysis Values of Target Reaction Product)
$^1$H-NMR (CDCl3): 3.2-3.0 (4H, br), 2.9-2.7 (4H, br), 1.8-1.3 (16H, m), 1.43 (18H, s)

Example 3-3

Synthesis of Methyl 4-((Bis(6-(tert-butoxycarbonylamino)hexyl)amino)methyl) benzoate

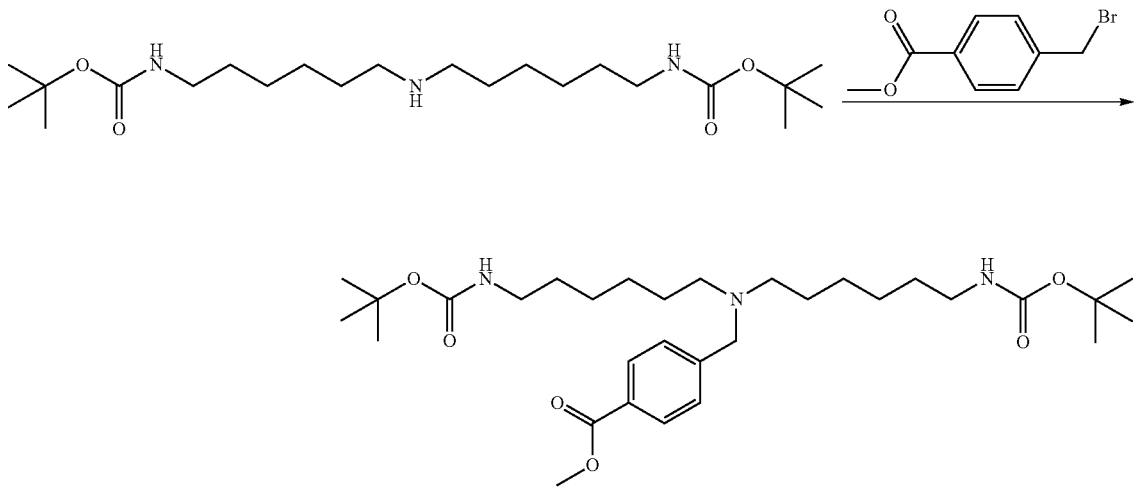

0.59 g (1.4 mmol) of the bis(6-tert-butoxycarbonylaminohexyl)amine synthesized as above was dissolved in 15 mL of chloroform, 0.49 g (2.1 mmol) of 4-bromomethyl benzoic acid and 0.29 g (2.8 mmol) of triethylamine were added thereto, followed by heating to reflux for 7 hours. The resultant reaction solution was cooled, and concentrated, and the thus obtained residue was purified by a silica gel column to obtain 0.496 g (62%) of a target product of methyl 4-((bis(6-(tert-butoxycarbonylamino)hexyl)amino)methyl) benzoate.

(Analysis Values of Target Reaction Product)
$^1$H-NMR (CDCl$_3$): 7.97 (2H, d), 7.39 (2H, d), 3.91 (3H, s), 3.56 (2H, s), 3.1 (4H, br, q), 2.37 (4H, t), 1.8-1.3 (16H, m), 1.44 (18H, s)

Example 3-4

Synthesis of Methyl 4-((Bis(6-amino)hexyl)amino)methylbenzoate

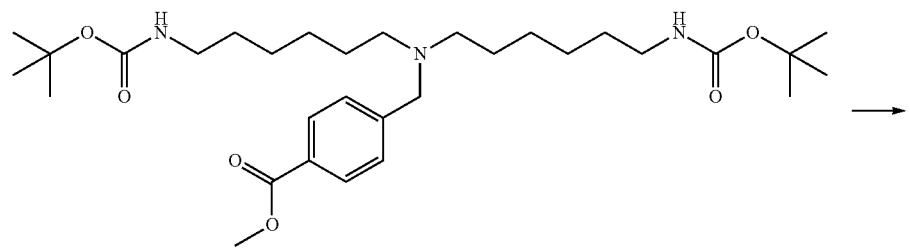

-continued

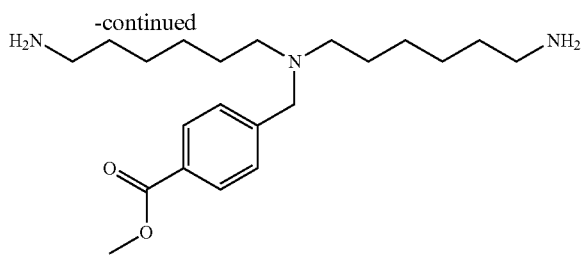

0.76 g (1.35 mmol) of the methyl 4-((bis(6-(tert-butoxycarbonylamino)hexyl) amino)methyl)benzoate synthesized as above was dissolved in 2 mL of trifluoroacetic acid, and the resultant was allowed to stand still at room temperature for 1 hour. The resultant was concentrated under reduced pressure to obtain, as a residue, 1.74 g of a crude product of methyl 4-((bis(6-amino)hexyl)amino)methylbenzoate trifluoroacetate. This product was not purified but directly used in the following reaction.

(Analysis Values of Target Reaction Product)
$^1$H-NMR (CDCl$_3$): 8.08 (2H, d), 7.66 (2H, d), 4.34 (2H, s), 3.93 (3H, s), 3.2-3.0 (4H, br), 3.0-2.8 (4H, br), 1.9-1.6 (8H, m), 1.6-1.3 (8H, m)

Example 3-5

Synthesis of Methyl 4-((Bis(6-(biotinylamino)hexyl)amino)methyl)benzoate

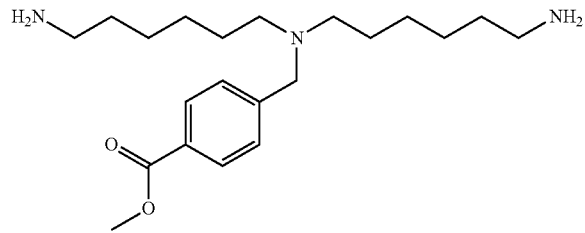

1.74 g (1.35 mmol) of the crude product of the methyl 4-((bis(6-amino)hexyl)amino)methylbenzoate trifluoroacetate synthesized as above was dissolved in 20 mL of DMF, and 0.82 g (3.4 mmol) of biotin and 1.64 g (16 mmol) of triethylamine were added thereto. 1.53 g (4 mmol) of HBTU was further added thereto, followed by stirring at room temperature overnight. The DMF was concentrated under reduced pressure, and the thus obtained residue was washed with 30 mL of dilute sodium bicarbonate water, and dried under reduced pressure. The resultant was further purified by a silica gel column to obtain 556 mg (60% through two steps) of a target product of methyl 4-((bis(6-(biotinylamino)hexyl)amino)methyl)benzoate.

(Analysis Values of Target Reaction Product)
$^1$H-NMR (DMSO-d6): 8.06 (2H, d), 7.8-7.6 (4H, m), 6.41 (2H, s), 6.38 (2H, s), 4.35-4.25 (2H, m), 4.15-4.1 (2H, m), 3.88 (3H, s), 3.5 (2H, s), 3.2-3.0 (2H, m), 3.0-2.9 (4H, m), 2.81 (2H, dd), 2.57 (2H, d), 2.33 (4H, br.t), 2.04 (4H, t), 1.7-1.1 (28H, m)

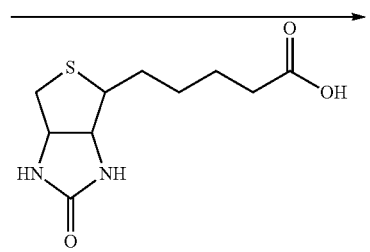

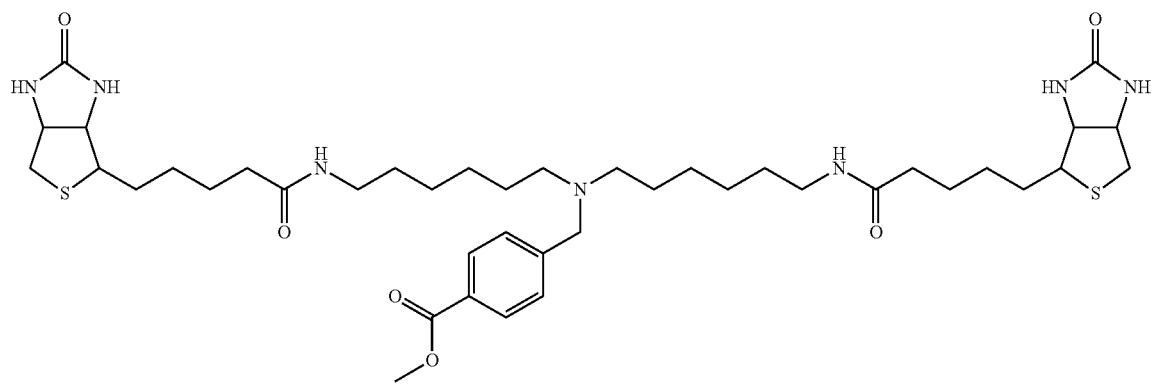

Example 3-6

Synthesis of 4-((Bis(6-(biotinylamino)hexyl)amino)methyl)benzoic Acid

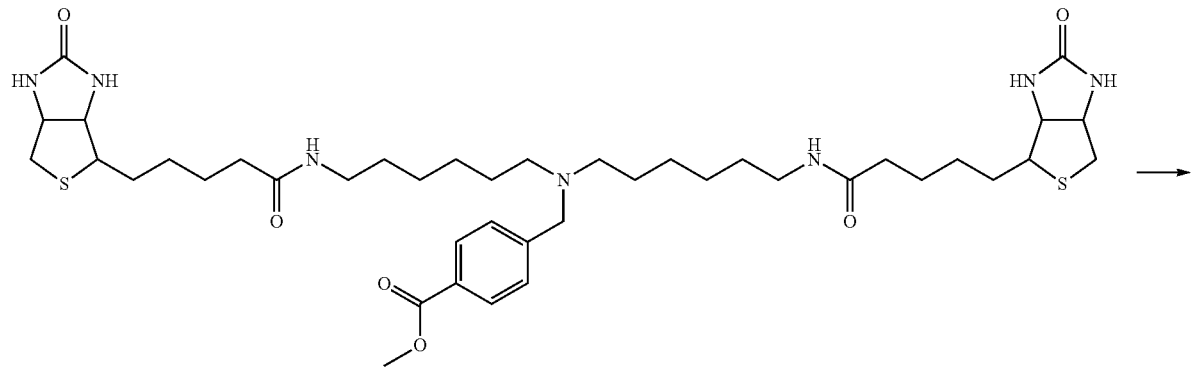

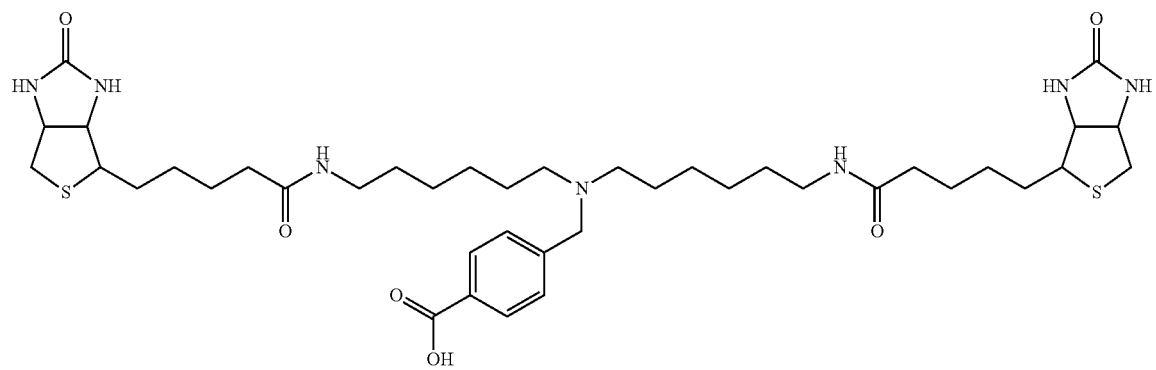

0.55 g (0.67 mmol) of the methyl 4-((bis(6-(biotinylamino)hexyl)amino)methyl) benzoate synthesized as above was dissolved in 3 mL of MeOH, and 177 mg (4.2 mmol) of a lithium hydroxide hydrate and 0.8 mL of water were added thereto, followed by stirring under heating at 40° C. for 8 hours. The solvent was concentrated under reduced pressure, and dilute hydrochloric acid was added to the thus obtained residue to adjust to pH 7. Then, 3 mL of chloroform was added to the resultant, and the thus precipitated solid was filtered off and washed with 2 mL of water. The resultant solid was dried under reduced pressure to obtain 380 mg (70%) of a target product of 4-((bis(6-(biotinylamino)hexyl)amino)methyl)benzoic acid.

(Analysis Values of Target Reaction Product)
$^1$H-NMR (DMSO-d6): 7.83 (2H, d), 7.74 (2H, t), 7.29 (2H, d), 6.51 (2H, s), 6.37 (2H, s), 4.35-4.25 (2H, m), 4.15-4.1 (2H, m), 3.51 (2H, s), 3.2-3.0 (2H, m), 3.0-2.9 (4H, m), 2.81 (2H, dd), 2.57 (2H, d), 2.33 (4H, br.t), 2.04 (4H, t), 1.7-1.1 (28H, m)

Example 3-7

Synthesis of tert-Butyl 1-(4-((Bis(6-(biotinylamino)hexyl)amino)methyl)phenyl)-1-oxo-5,8,11-trioxa-2-azatetradecan-14-oate

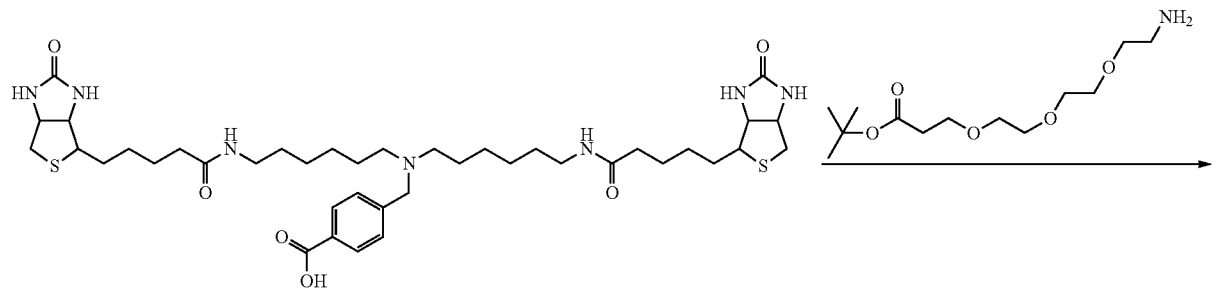

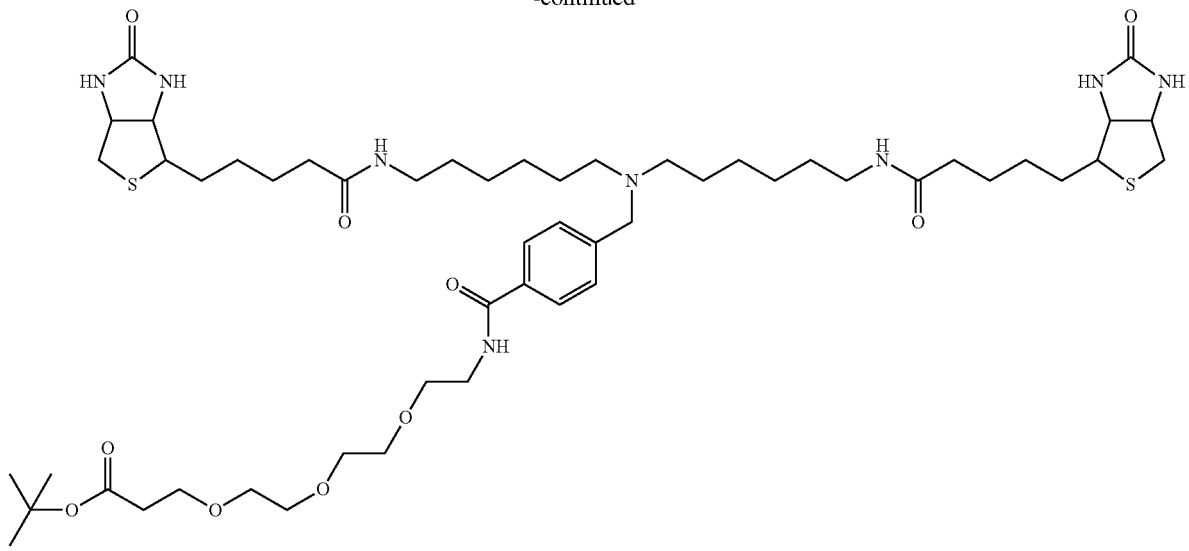

40 mL of DMF was added to 0.33 g (0.41 mmol) of the 4-((bis(6-(biotinylamino) hexyl)amino)methyl)benzoic acid synthesized as above, and 171 mg (0.6 mmol) of tert-butyl 3-(2-(2-(2-aminoethoxy)ethoxy)ethoxy)propanoate and 166 mg (1.65 mmol) of triethylamine were added thereto. 234 mg (0.62 mmol) of HBTU was further added thereto, followed by stirring at room temperature overnight. The DMF was concentrated under reduced pressure, and the thus obtained residue was washed with 20 mL of 5% citric acid water and 20 mL of water, and the resultant residue was dried under reduced pressure. The resultant was further purified by a silica gel column to obtain 316 mg (72%) of a target product of tert-butyl 1-(4-((bis(6-(biotinylamino) hexyl)amino)methyl) phenyl)-1-oxo-5,8,11-trioxa-2-azatetradecan-14-oate.

(Analysis Values of Target Reaction Product)
$^1$H-NMR (DMSO-d6): 7.9 (2H, br.d), 7.74 (2H, t), 7.65 (2H, br.d), 6.42 (2H, s), 6.37 (2H, s), 4.35-4.25 (2H, m), 4.15-4.1 (2H, m), 3.6-3.4 (12H, m), 3.2-2.9 (8H, m), 2.79 (2H, dd), 2.58 (2H, d), 2.40 (2H, t), 2.04 (4H, t), 1.8-1.2 (28H, m), 1.39 (9H, s)
HPLC Retention Time (Analysis Conditions B): 4.66 min (0.1% trifluoroacetic acid aqueous solution/CH$_3$CN=85/15 (7 min) 5/95)

Example 3-8

Synthesis of 1-(4-((Bis(6-(biotinylamino)hexyl) amino)methyl)phenyl)-1-oxo-5,8,11-trioxa-2-azatetradecan-14-oic Acid

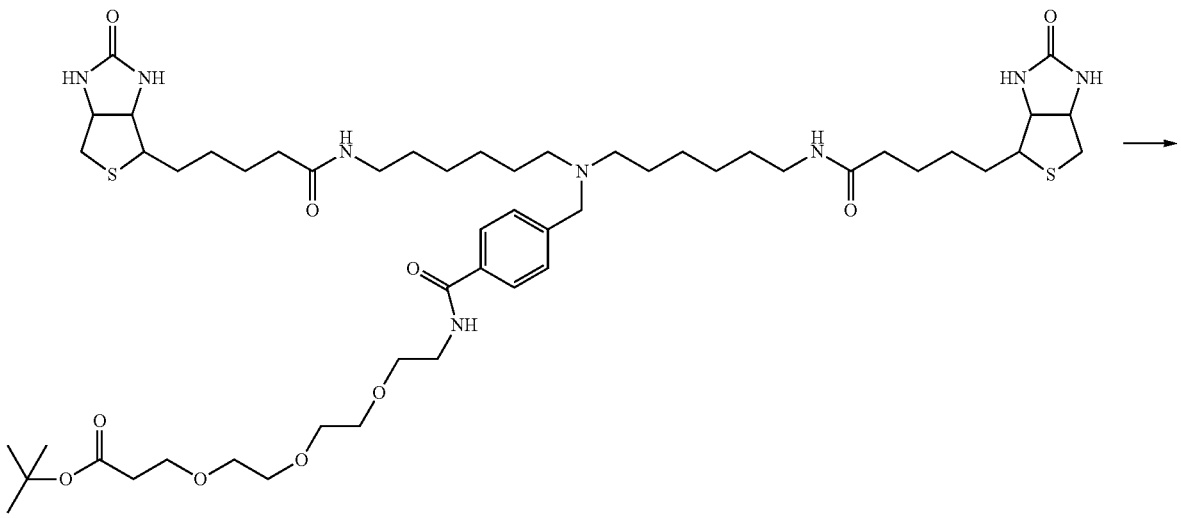

-continued

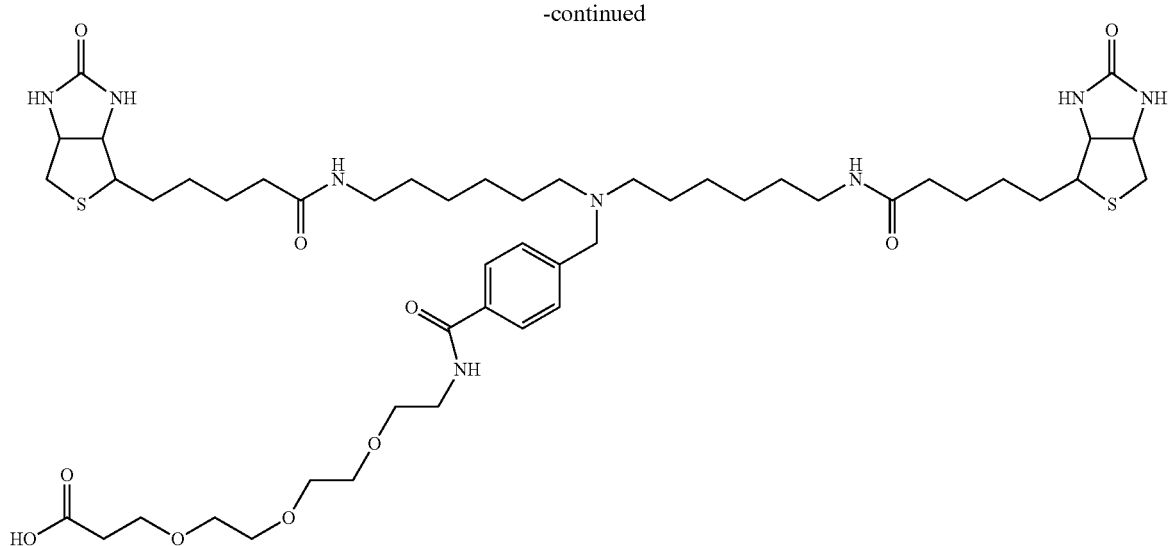

80 mg (0.075 mmol) of the tert-butyl 1-(4-((bis(6-(biotinylamino)hexyl)amino) methyl)phenyl)-1-oxo-5,8,11-trioxa-2-azatetradecan-14-oate synthesized as above was dissolved in 0.3 mL of trifluoroacetic acid, and the resultant was allowed to stand still at room temperature for 1 hour. The resultant was concentrated under reduced pressure to obtain, as a residue, a crude product of 1-(4-((bis(6-(biotinylamino)hexyl)amino)methyl) phenyl)-1-oxo-5,8,11-trioxa-2-azatetradecan-14-oic acid trifluoroacetate. This product was not purified but directly used in the following reaction.

(Analysis Values of Target Reaction Product)
HPLC Retention Time (Analysis Conditions B): 3.83 min (0.1% trifluoroacetic acid aqueous solution/CH$_3$CN=85/15 (7 min) 5/95)

Example 3-9

Synthesis of 1-(4-((Bis(6-(biotinylamino)hexyl)amino)methyl)phenyl)-1-oxo-5,8,11-trioxa-2-azatetradecan-14-oic Acid Sulfo-NHS Ester

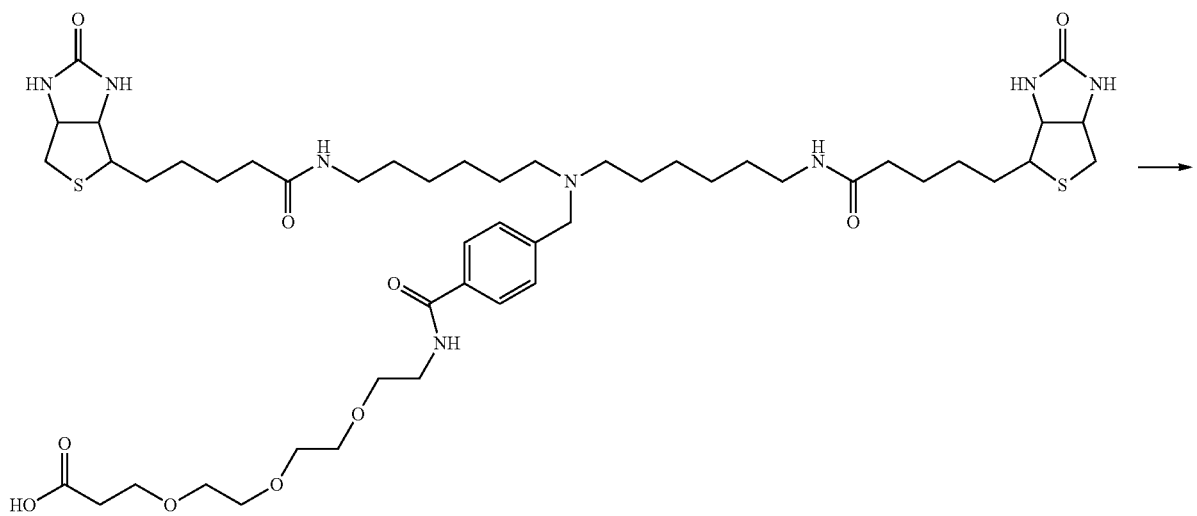

-continued

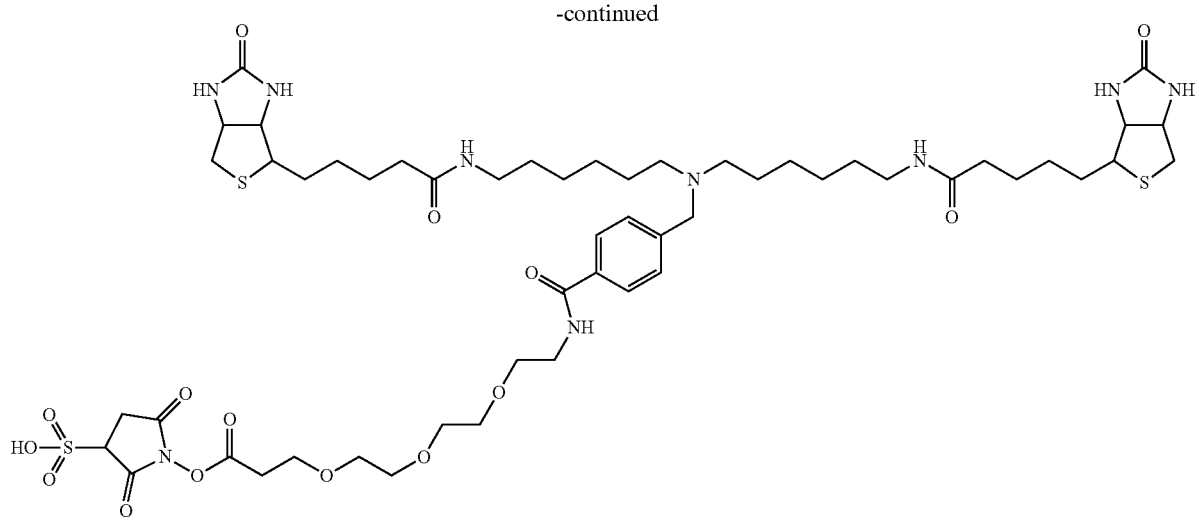

The crude product of 1-(4-((bis(6-(biotinylamino)hexyl)amino)methyl)phenyl)-1-oxo-5,8,11-trioxa-2-azatetradecan-14-oic acid trifluoroacetate synthesized as above was dissolved in 3 mL of DMF, and 24 mg (0.11 mmol) of sulfo-NHS sodium salt was added thereto. 285 mg (2.2 mmol) of DIC was further added thereto, followed by stirring at room temperature for 3 hours. 2 mL of hexane and 0.5 mL of chloroform were added thereto to precipitate gum, followed by standing still for 30 minutes. The solvent was removed, and the resultant was washed with 2 mL of chloroform twice and dried under reduced pressure to obtain 74 mg of 1-(4-((bis(6-(biotinylamino)hexyl)amino)methyl)phenyl)-1-oxo-5,8,11-trioxa-2-azatetradecan-14-oic acid sulfo-NHS ester in an amorphous form.

(Analysis Values of Target Reaction Product)

$^1$H-NMR (DMSO-d6): 8.0-7.9 (4H, m), 7.8-7.6 (4H, m), 6.4 (2H, s), 6.36 (2H, s), 4.4-4.25 (4H, m), 4.15-4.1 (2H, m), 4.0-3.9 (1H, br.d), 3.69 (2H, t), 3.6-3.3 (14H, m), 3.2-2.9 (8H, m), 2.79 (2H, dd), 2.58 (2H, d), 2.05 (4H, t), 1.8-1.1 (28H, m)

For the HPLC analysis, N-butylamine was reacted to be analyzed as butylamide.

HPLC Retention Time (Analysis Conditions B): 4.21 min (0.1% trifluoroacetic acid aqueous solution/CH$_3$CN=85/15 (7 min) 5/95)

Example 4-1

Synthesis of Methyl 4-(((7-((tert-Butoxycarbonyl)amino)heptyl)-(6-((tert-butoxycarbonyl)amino)hexyl)amino)methyl)benzoate

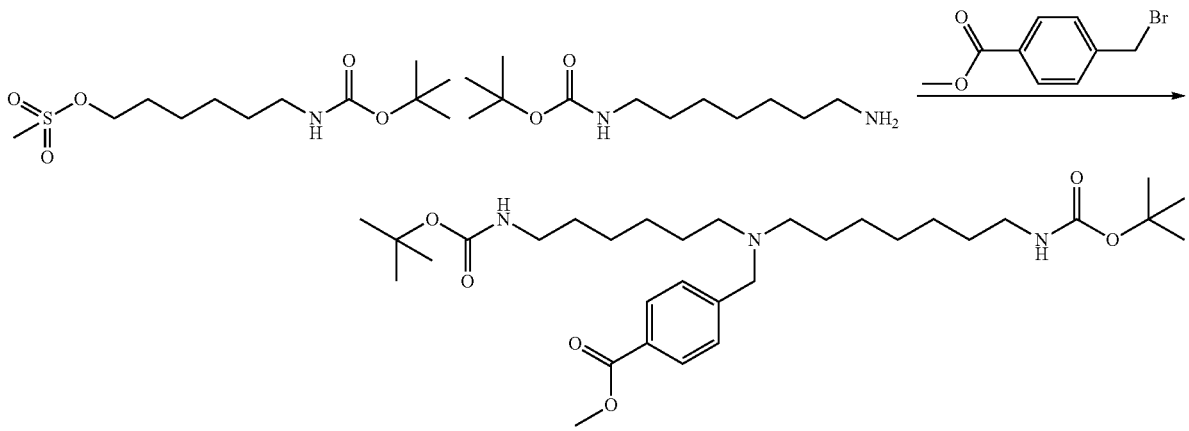

2.0 g (6.77 mmol) of the 6-((tert-butoxycarbonyl)amino)hexyl methanesulfonate synthesized in Example 3-1 was dissolved in 20 mL of chloroform, and 2.73 g (11.8 mmol) of tert-butyl (7-aminoheptyl)carbamate and 1.85 g (18.3 mmol) of triethylamine were added thereto, followed by heating to reflux for 22 hours. The resultant reaction solution was cooled, washed with 15 mL of a 5% citric acid aqueous solution twice, and dried over sodium sulfate to obtain a chloroform solution of tert-butyl (6-((7-((tert-butoxycarbonyl)amino)heptyl)amino)hexyl)carbamate. To the solution, 2.64 g (11.5 mmol) of 4-bromomethylbenzoic acid and 1.37 g (13.5 mmol) of triethylamine were added, followed by heating to reflux for 3 hours. After cooling, 10 mL of chloroform was added thereto, and the resultant was washed with 25 mL of 0.1 N NaOH water twice, and washed with 20 mL of saturated NaCl water. The resultant was dried over sodium sulfate and concentrated, and the thus obtained residue was purified by a silica gel column to obtain 855 mg (22%) of a target product of methyl 4-(((7-((tert-butoxycarbonyl)amino)heptyl)-(6-((tert-butoxycarbonyl)amino) hexyl)amino)methyl)benzoate.

(Analysis Values of Target Reaction Product)
$^1$H-NMR (CDCl$_3$): 7.97 (2H, d), 7.39 (2H, d), 3.91 (3H, s), 3.56 (2H, s), 3.2-3.0 (4H, m), 2.37 (4H, t), 1.8-1.3 (18H, m), 1.44 (18H, s)

Example 4-2

Synthesis of Methyl 4-(((7-(Biotinylamino)heptyl)-(6-(biotinylamino)hexyl)amino) methyl)benzoate

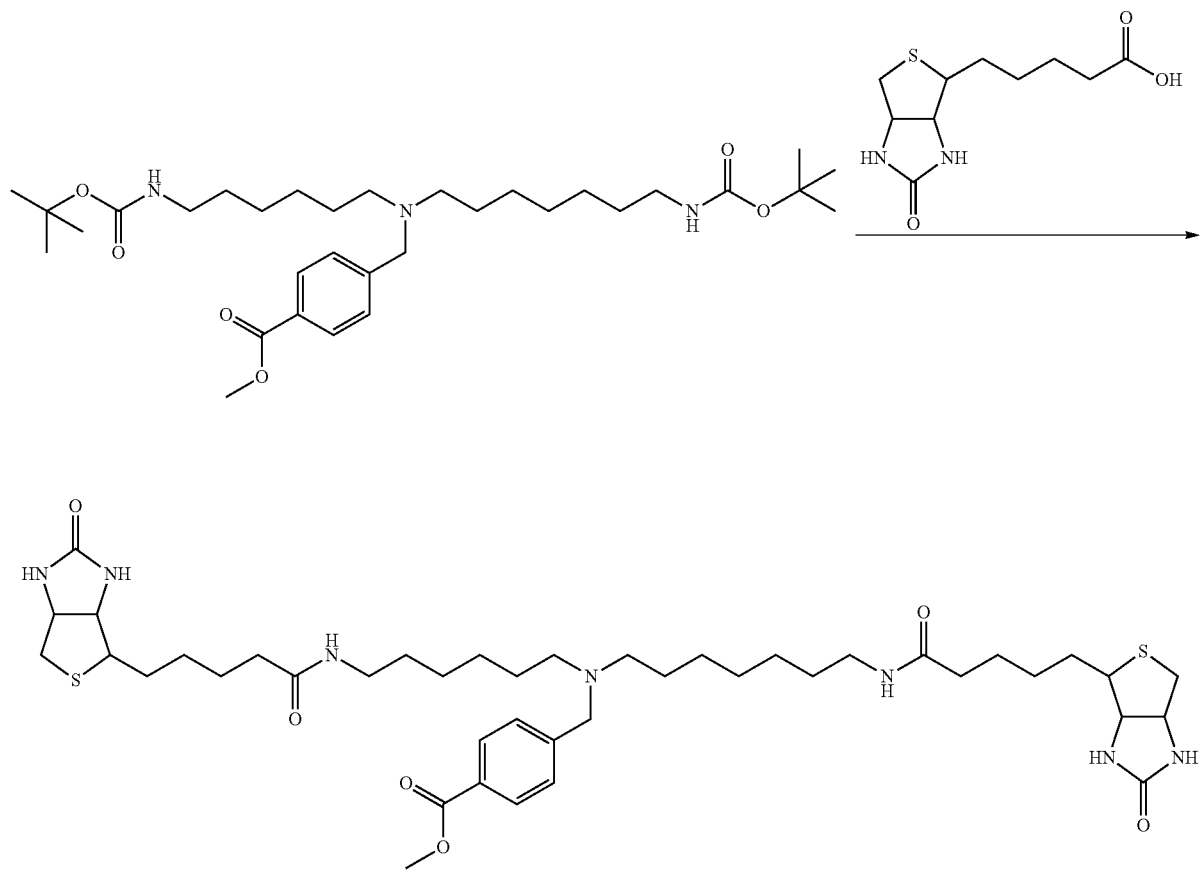

Synthesis was performed in accordance with Examples 3-4 and 3-5 by using 845 mg (1.46 mmol) of the 4-(((7-((tert-butoxycarbonyl)amino)heptyl)-(6-((tert-butoxycarbonyl)amino)hexyl)amino)methyl)benzoate synthesized as above to obtain 881 mg (73%) of a target reaction product of methyl 4-(((7-(biotinylamino)heptyl)-(6-(biotinylamino) hexyl)amino)methyl)benzoate.

(Analysis Values of Target Reaction Product)
1H-NMR (DMSO-d6): 7.92 (2H, d), 7.8-7.6 (2H, m), 7.45 (2H, m), 6.41 (2H, s), 6.34 (2H, s), 4.35-4.25 (2H, m), 4.15-4.1 (2H, m), 3.84 (3H, s), 3.2-2.9 (8H, m), 2.81 (2H, dd), 2.57 (2H, d), 2.35 (4H, br.t), 2.03 (4H, t), 1.7-1.1 (30H, m)

Example 4-3

Synthesis of 4-(((7-(Biotinylamino)heptyl)-(6-(biotinylamino)hexyl)amino)methyl) benzoic Acid

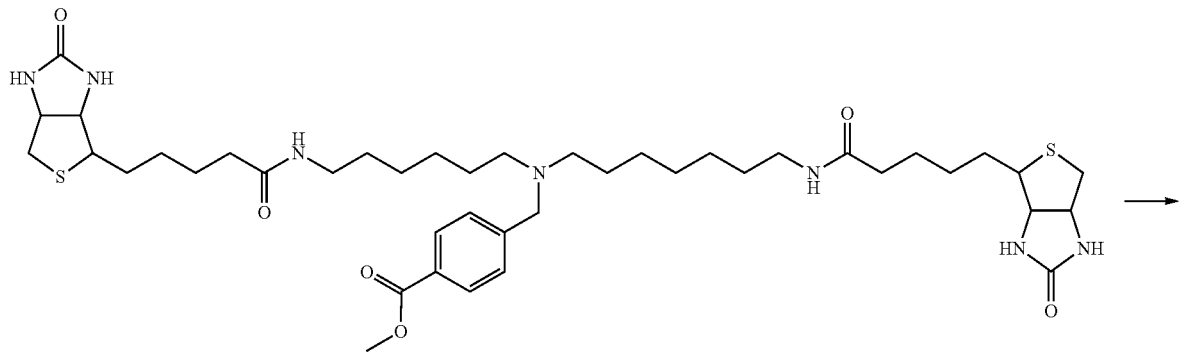

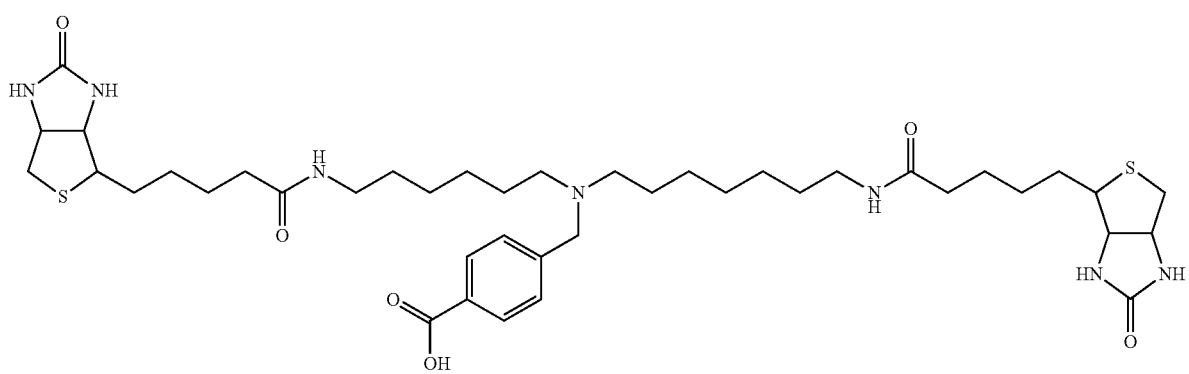

A reaction was performed in the same manner as in Example 3-6 by using 0.32 g (0.38 mmol) of the 4-(((7-(biotinylamino)heptyl)-(6-(biotinylamino)hexyl)amino) methyl) benzoate synthesized as above to obtain 303 mg (98%) of a target reaction product of methyl 4-(((7-(biotinylamino)heptyl)-(6-(biotinylamino)hexyl)amino)methyl) benzoic acid.

(Analysis Values of Target Reaction Product)

$^1$H-NMR (DMSO-d6): 7.83 (2H, d), 7.74 (2H, br), 7.36 (2H, d), 6.44 (2H, s), 6.37 (2H, s), 4.35-4.25 (2H, m), 4.15-4.1 (2H, m), 3.54 (2H, s), 3.2-3.0 (2H, m), 3.0-2.9 (4H, m), 2.81 (2H, dd), 2.57 (2H, d), 2.33 (4H, br.t), 2.04 (4H, t), 1.7-1.1 (30H, m)

Example 4-4

Synthesis of tert-Butyl 1-Oxo-1-(4-(((7-(biotinylamino)heptyl)-(6-(biotinylamino) hexyl)amino) methyl)phenyl)-5,8,11-trioxa-2-azatetradecan-14-oate

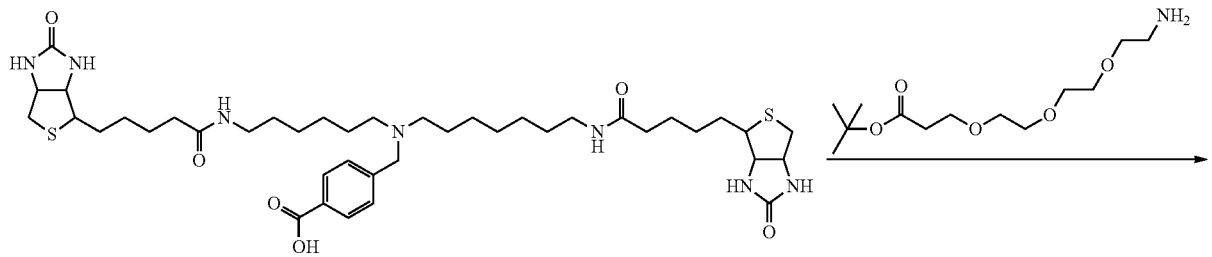

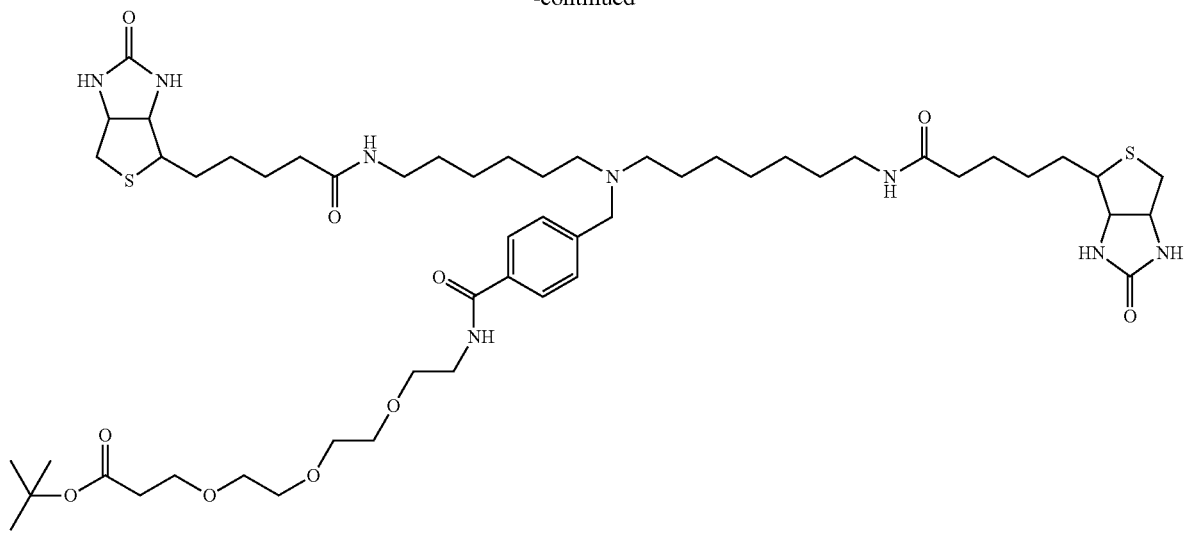

A reaction was performed in the same manner as in Example 3-7 by using 300 mg (0.368 mmol) of the 4-(((7-(biotinylamino)heptyl)-(6-(biotinylamino)hexyl)amino)methyl)benzoic acid synthesized as above to obtain 237 mg (60%) of a target reaction product of tert-butyl 1-oxo-1-(4-(((7-(biotinylamino)heptyl)(6-(biotinylamino)hexyl)amino)methyl)phenyl)-5,8,11-trioxa-2-azatetradecan-14-oate.

(Analysis Values of Target Reaction Product)
$^1$H-NMR (DMSO-d6): 7.93 (2H, d), 7.72 (2H, br), 7.60 (2H, d), 6.40 (2H, s), 6.36 (2H, s), 4.4-4.25 (4H, m), 4.15-4.1 (2H, m), 3.6-3.4 (12H, m), 3.2-2.9 (8H, m), 2.79 (2H, dd), 2.58 (2H, d), 2.40 (2H, t), 2.04 (4H, t), 1.8-1.2 (30H, m), 1.39 (9H, s).

HPLC Retention Time (Analysis Conditions B): 4.77 min (0.1% trifluoroacetic acid aqueous solution/CH$_3$CN=85/15 (7 min) 5/95)

Example 4-5

Synthesis of 1-Oxo-1-(4-(((7-(biotinylamino)heptyl)(6-(biotinylamino)hexyl) amino)methyl)phenyl)-5,8,11-trioxa-2-azatetradecan-14-oic Acid Sulfo-NHS Ester

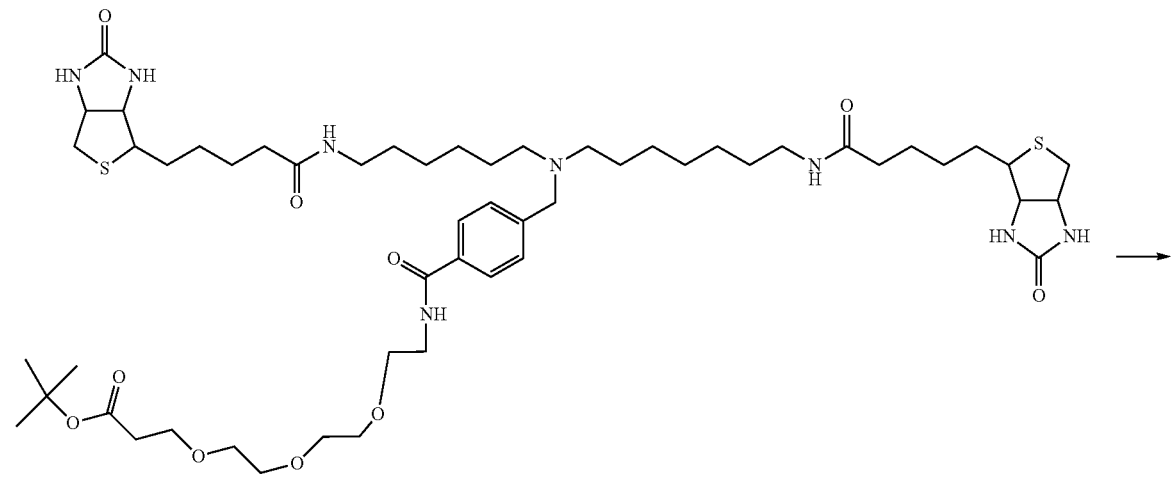

-continued

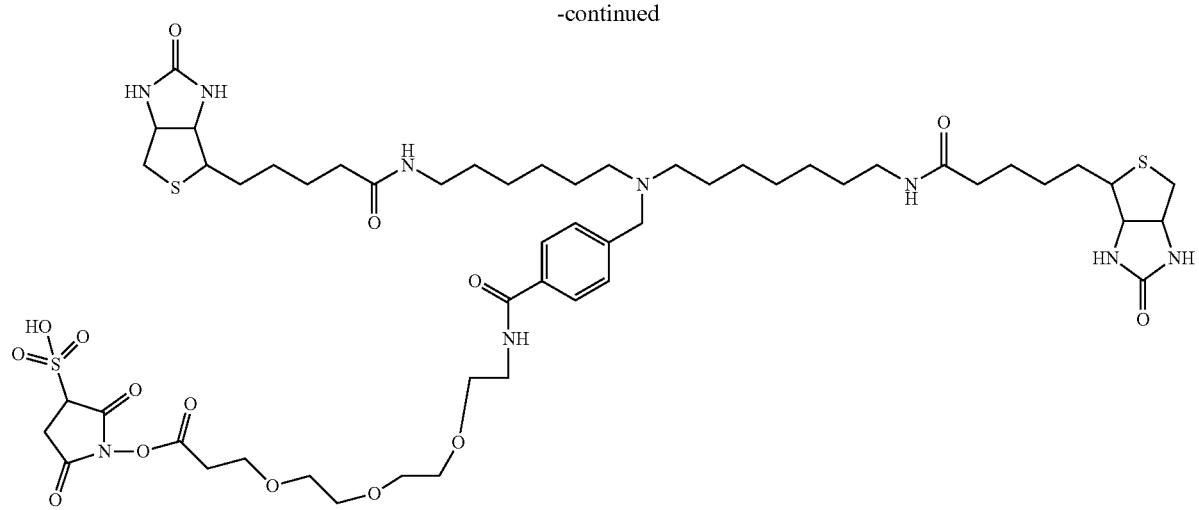

A reaction was performed in the same manner as in Examples 3-8 and 3-9 by using 80 mg (0.074 mmol) of the tert-butyl 1-oxo-1-(4-(((7-(biotinylamino)heptyl)(6-(biotinylamino)hexyl)amino)methyl)phenyl)-5,8,11-trioxa-2-azatetradecan-14-oate synthesized as above to obtain 83 mg (48%) of a target reaction product of 1-oxo-1-(4-(((7-(biotinylamino)heptyl)(6-(biotinylamino)hexyl)amino)methyl)phenyl)-5,8,11-trioxa-2-azatetradecan-14-oic acid sulfo-NHS ester.

(Analysis Values of Target Reaction Product)
$^1$H-NMR (DMSO-d6): 7.89 (2H, br.d), 7.77 (2H, br.s), 7.52 (2H, br.d), 6.4 (4H, br), 4.4-4.25 (2H, m), 4.15-4.1 (2H, m), 4.0-3.9 (1H, br.d), 3.69 (2H, t), 3.6-3.3 (14H, m), 3.2-2.9 (8H, m), 2.79 (2H, dd), 2.58 (2H, d), 2.05 (4H, t), 1.8-1.1 (30H, m)

HPLC Retention Time of De-t-butyl Esterified Carboxylic Acid of Intermediate (Analysis Conditions B): 3.92 min (0.1% trifluoroacetic acid aqueous solution/CH$_3$CN=85/15 (7 min) 5/95)

The target reaction product was reacted with N-butylamine and the HPLC analysis was performed. HPLC Retention Time of Butylamide Form (Analysis Conditions B): 4.31 min (0.1% trifluoroacetic acid aqueous solution/CH$_3$CN=85/15 (7 min) 5/95)

Example 5-1

Synthesis of 7-((tert-Butoxycarbonyl)amino)heptyl Methanesulfonate

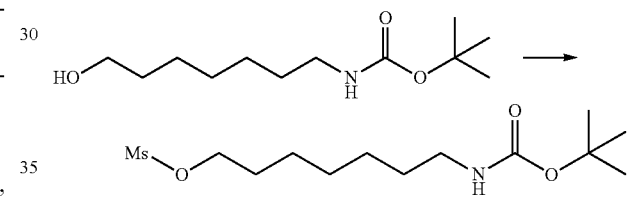

A reaction was performed in the same manner as in Example 3-1 by using 1.5 g (6.9 mmol) of tert-butyl (7-hydroxyheptyl)carbamate to obtain 1.29 g (63%) of a target reaction product of 7-((tert-butoxycarbonyl)amino)heptyl methanesulfonate.

(Analysis Values of Target Reaction Product)
$^1$H-NMR (CDCl$_3$): 4.22 (2H, t), 3.1 (2H, q), 3.01 (3H, s), 1.8-1.3 (10H, m), 1.44 (9H, s)

Example 5-2

Synthesis of Methyl 4-((Bis(7-((tert-butoxycarbonyl)amino)heptyl)amino)methyl) benzoate

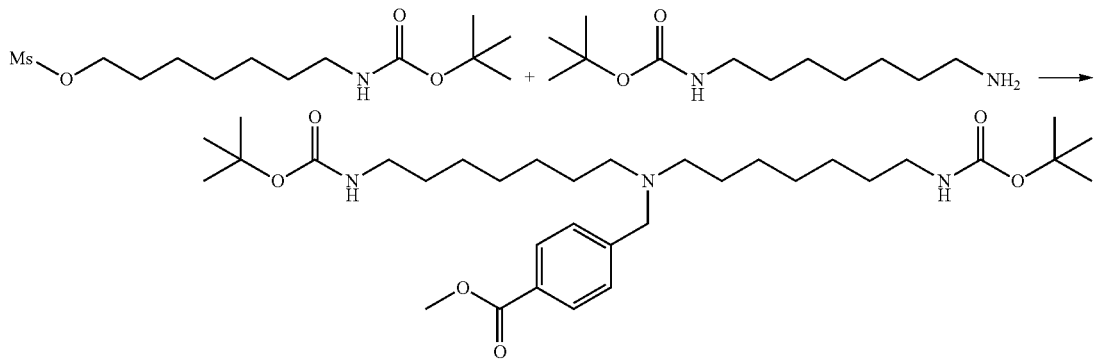

A reaction was performed in the same manner as in Example 4-1 by using 1.28 g (4.1 mmol) of the 7-((tert-butoxycarbonyl)amino)heptyl methanesulfonate synthesized as above and 1.78 g (7.7 mmol) of tert-butyl(7-aminoheptyl)carbamate to obtain 0.93 g (38%) of a target reaction product of methyl 4-((bis(7-((tert-butoxycarbonyl)amino)heptyl) amino)methyl)benzoate.

(Analysis Values of Target Reaction Product)
¹H-NMR (CDCl₃): 7.97 (2H, d), 7.42 (2H, d), 3.91 (3H, s), 3.56 (2H, s), 3.2-3.0 (4H, m), 2.41 (4H, t), 1.8-1.3 (20H, m), 1.44 (18H, s)

Example 5-3

Synthesis of Methyl 4-((Bis(7-(biotinylamino)heptyl)amino)methyl)benzoate

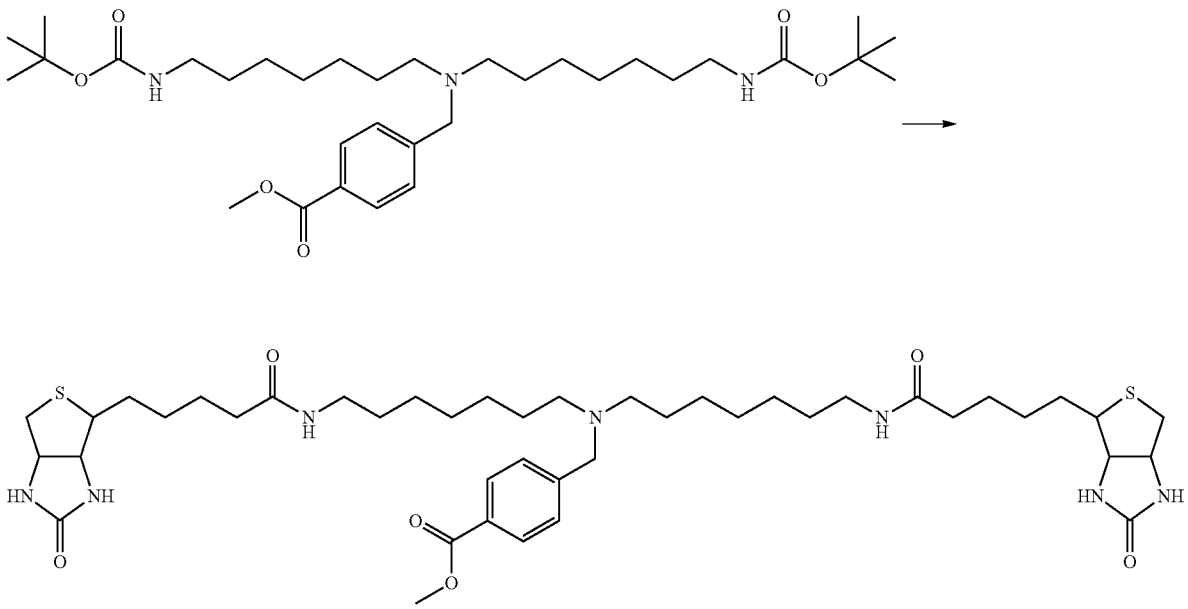

A reaction was performed in the same manner as in Example 4-2 by using 0.98 g (1.66 mmol) of the methyl 4-((bis(7-((tert-butoxycarbonyl)amino)heptyl)amino) methyl) benzoate synthesized as above to obtain 0.376 g (21%) of a target reaction product of methyl 4-((bis(7-(biotinylamino)heptyl)amino)methyl)benzoate.

(Analysis Values of Target Reaction Product)
¹H-NMR (DMSO-d6): 7.91 (2H, d), 7.8-7.6 (2H, m), 7.45 (2H, m), 6.41 (2H, s), 6.35 (2H, s), 4.35-4.25 (2H, m), 4.15-4.1 (2H, m), 3.84 (3H, s), 3.2-2.9 (8H, m), 2.81 (2H, dd), 2.57 (2H, d), 2.35 (4H, br.t), 2.03 (4H, t), 1.7-1.1 (32H, m)

Example 5-4

Synthesis of 4-((Bis(7-(biotinylamino)heptyl)amino)methyl)benzoic Acid

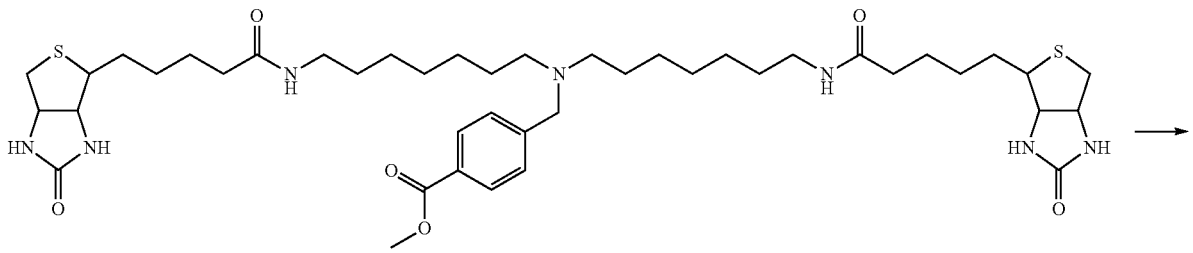

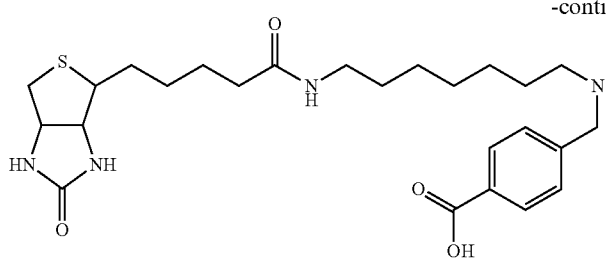
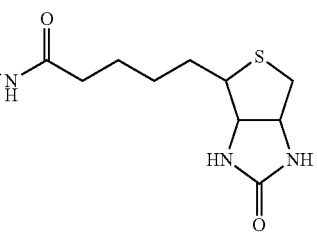

A reaction was performed in the same manner as in Example 3-6 by using 0.376 g (0.445 mmol) of the methyl 4-((bis(7-(biotinylamino)heptyl)amino)methyl)benzoate synthesized as above to obtain a target reaction product of 4-((bis(7-(biotinylamino)heptyl)amino)methyl)benzoic acid. This compound was not purified but directly used in the following step.

(Analysis Values of Target Reaction Product)
¹H-NMR (DMSO-d6): 7.81 (2H, d), 7.72 (2H, br), 7.34 (2H, d), 6.44 (2H, s), 6.37 (2H, s), 4.35-4.25 (2H, m), 4.15-4.1 (2H, m), 3.54 (2H, s), 3.2-3.0 (2H, m), 3.0-2.9 (4H, m), 2.81 (2H, dd), 2.57 (2H, d), 2.33 (4H, br.t), 2.04 (4H, t), 1.7-1.1 (32H, m)

Example 5-5

Synthesis of tert-Butyl 1-(4-((Bis(7-(biotinylamino)heptyl)amino)methyl)phenyl)-1-oxo-5,8,11-trioxa-2-azatetradecan-14-oate

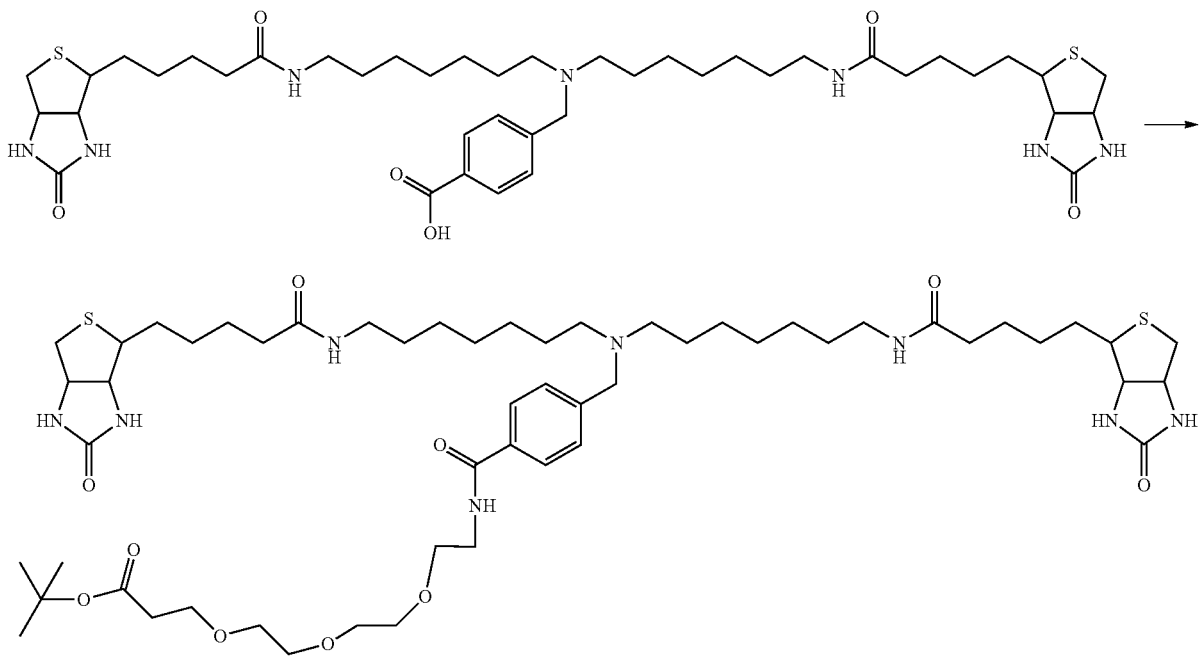

A reaction was performed in the same manner as in Example 3-7 by using the 4-((bis(7-(biotinylamino)heptyl)amino)methyl)benzoic acid synthesized as above to obtain 225 mg (47% through two steps) of a target reaction product of tert-butyl 1-(4-((bis(7-(biotinyl)heptyl)amino)methyl)phenyl)-1-oxo-5,8,11-trioxa-2-azatetradecan-14-oate.

(Analysis Values of Target Reaction Product)
¹H-NMR (DMSO-d6): 7.93 (2H, br.d), 7.72 (2H, br), 7.60 (2H, br.d), 6.35 (2H, s), 6.36 (2H, s), 4.4-4.25 (4H, m), 4.15-4.1 (2H, m), 3.6-3.4 (12H, m), 3.2-2.9 (8H, m), 2.79 (2H, dd), 2.58 (2H, d), 2.40 (2H, t), 2.04 (4H, t), 1.8-1.2 (32H, m), 1.39 (9H, s)
HPLC Retention Time (Analysis Conditions B): 4.89 min (0.1% trifluoroacetic acid aqueous solution/CH₃CN=85/15 (7 min) 5/95)

Example 5-6

Synthesis of 1-(4-((Bis(7-(biotinylamino)heptyl)amino)methyl)phenyl)-1-oxo-5,8,11-trioxa-2-azatetradecan-14-oic Acid Sulfo-NHS Ester

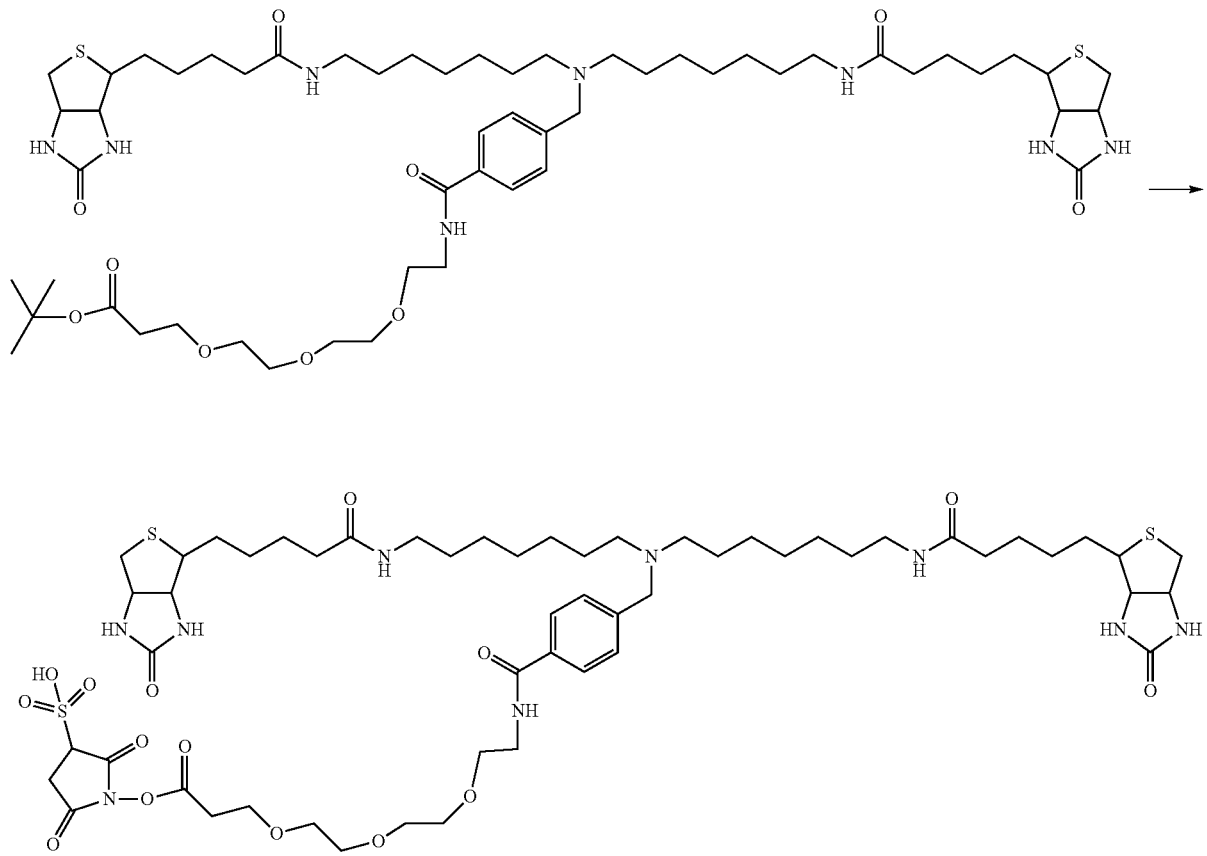

A reaction was performed in the same manner as in Examples 3-8 and 3-9 by using 76 mg (0.070 mmol) of the tert-butyl 1-(4-((bis(7-(biotinylamino)heptyl)amino)methyl)phenyl)-1-oxo-5,8,11-trioxa-2-azatetradecan-14-oate synthesized as above to obtain 50 mg (60%) of a target reaction product of 1-(4-((bis(7-(biotinylamino)heptyl)amino)methyl)phenyl)-1-oxo-5,8,11-trioxa-2-azatetradecan-14-oic acid sulfo-NHS ester.

(Analysis Values of Target Reaction Product)

$^1$H-NMR (DMSO-d6): 7.92 (2H, br.d), 7.78-7.76 (4H, br), 6.6-6.3 (4H, br), 4.4-4.25 (4H, m), 4.15-4.1 (2H, m), 4.0-3.9 (1H, br.d), 3.69 (2H, t), 3.6-3.3 (14H, m), 3.2-2.9 (8H, m), 2.79 (2H, dd), 2.58 (2H, d), 2.05 (4H, t), 1.8-1.1 (32H, m)

HPLC Retention Time of De-t-butyl Esterified Carboxylic Acid of Intermediate (Analysis Conditions B): 4.01 min (0.1% trifluoroacetic acid aqueous solution/CH$_3$CN=85/15 (7 min) 5/95)

The target reaction product was reacted with N-butylamine and the HPLC analysis was performed. HPLC Retention Time of Butylamide Form (Analysis Conditions B): 4.42 min (0.1% trifluoroacetic acid aqueous solution/CH$_3$CN=85/15 (7 min) 5/95)

Example 6-1

Synthesis of Methyl 4-(((7-((tert-Butoxycarbonyl)amino)heptyl)-(8-((tert-butoxycarbonyl)amino)octyl)amino)methyl)benzoate

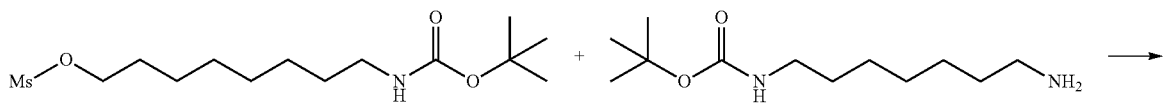

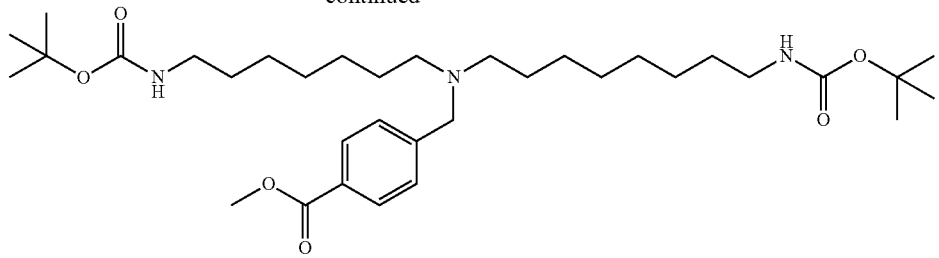

A reaction was performed in the same manner as in Example 4-1 by using 1.4 g (4.33 mmol) of 8-((tert-butoxycarbonyl)amino)octyl methanesulfonate and 1.74 g (7.6 mmol) of tert-butyl(7-aminoheptyl)carbamate to obtain 1.98 g (25.5%) of a target reaction product of methyl 4-(((7-((tert-butoxycarbonyl)amino)heptyl)-(8-((tert-butoxycarbonyl)amino)octyl)amino)methyl)benzoate.

(Analysis Values of Target Reaction Product)
$^1$H-NMR (CDCl3): 7.97 (2H, d), 7.42 (2H, d), 3.91 (3H, s), 3.56 (2H, s), 3.2-3.0 (4H, m), 2.41 (4H, t), 1.8-1.3 (24H, m), 1.44 (18H, s)

Example 6-2

Synthesis of Methyl 4-(((7-(Biotinylamino)heptyl)-(8-biotinylamino)octyl) amino)methyl)benzoate

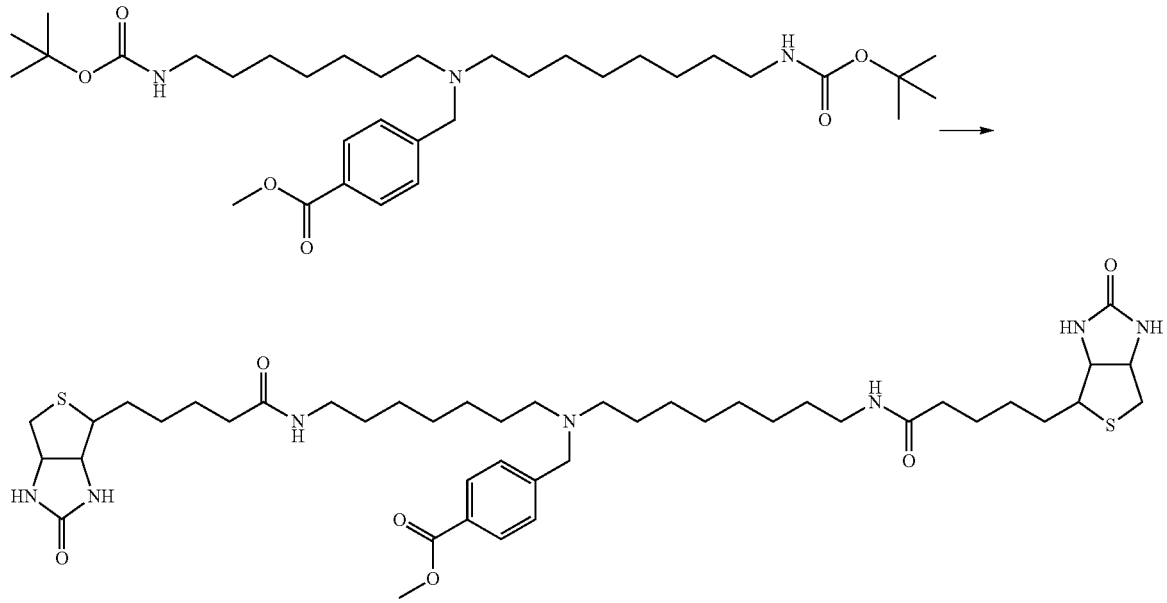

A reaction was performed in the same manner as in Example 4-2 by using 667 mg (1.10 mmol) of the 4-(((7-((tert-butoxycarbonyl)amino)heptyl)-(8-((tert-butoxycarbonyl)amino)octyl)amino)methyl)benzoate synthesized as above to obtain 321 mg (34%) of a target reaction product of methyl 4-(((7-(biotinylamino)heptyl)-(8-biotinylamino) octyl)amino)methyl)benzoate.

(Analysis Values of Target Reaction Product)
$^1$H-NMR (DMSO-d6): 7.90 (2H, d), 7.69 (2H, t), 7.43 (2H, m), 6.41 (2H, s), 6.35 (2H, s), 4.35-4.25 (2H, m), 4.15-4.1 (2H, m), 3.84 (3H, s), 3.2-2.9 (8H, m), 2.81 (2H, dd), 2.57 (2H, d), 2.34 (4H, br.t), 2.04 (4H, t), 1.7-1.1 (34H, m)

Example 6-3

Synthesis of 4-(((7-(Biotinylamino)heptyl)-(8-(biotinylamino)octyl)amino)methyl) benzoic Acid

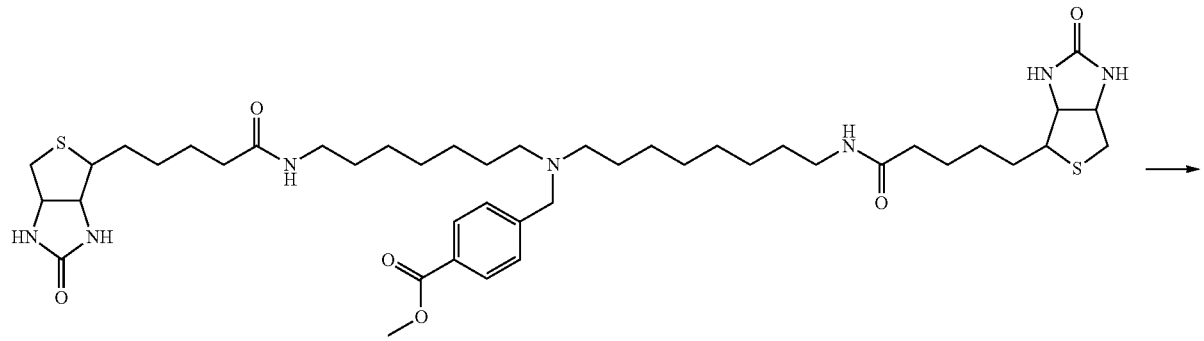

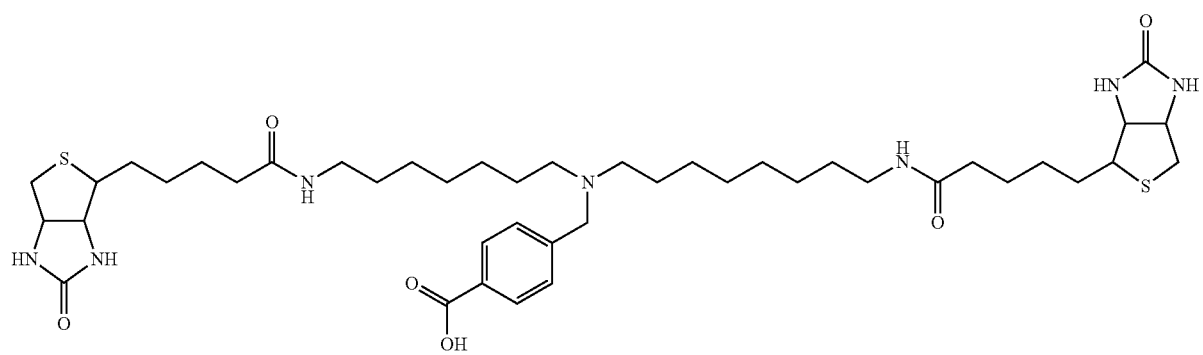

A reaction was performed in the same manner as in Example 3-6 by using 321 mg (0.374 mmol) of the methyl 4-(((7-(biotinylamino)heptyl)-(8-biotinylamino)octyl)amino)methyl)benzoate synthesized as above to obtain a target reaction product of 4-(((7-(biotinylamino)heptyl)-(8-(biotinylamino)octyl)amino)methyl)benzoic acid. This compound was not purified but directly used in the following step.

(Analysis Values of Target Reaction Product)
$^1$H-NMR (DMSO-d6): 7.86 (2H, d), 7.79 (2H, br.t), 7.36 (2H, d), 6.44 (2H, s), 6.38 (2H, s), 4.35-4.25 (2H, m), 4.15-4.1 (2H, m), 3.54 (2H, s), 3.2-3.0 (2H, m), 3.0-2.9 (4H, m), 2.81 (2H, dd), 2.57 (2H, d), 2.33 (4H, br.t), 2.04 (4H, t), 1.7-1.1 (34H, m)

Example 6-4

Synthesis of tert-Butyl 1-Oxo-1-(4-(((7-(biotinylamino)heptyl)-(8-(biotinylamino) octyl)amino)methyl)phenyl)-5,8,11-trioxa-2-azatetradecan-14-oate

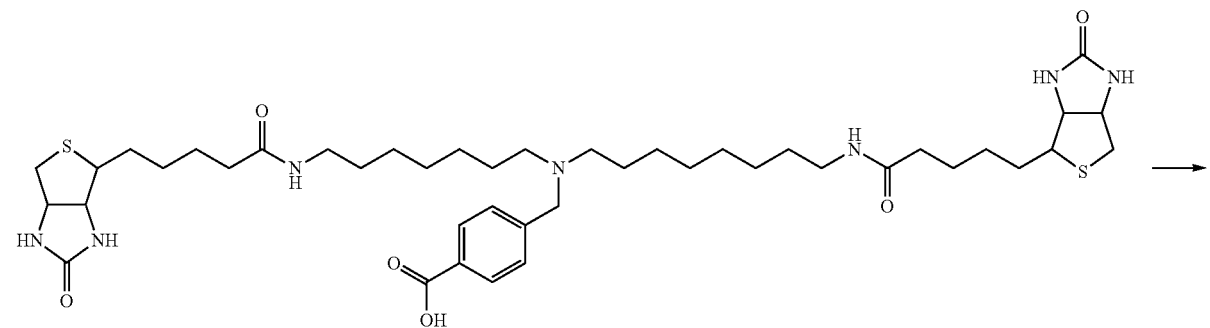

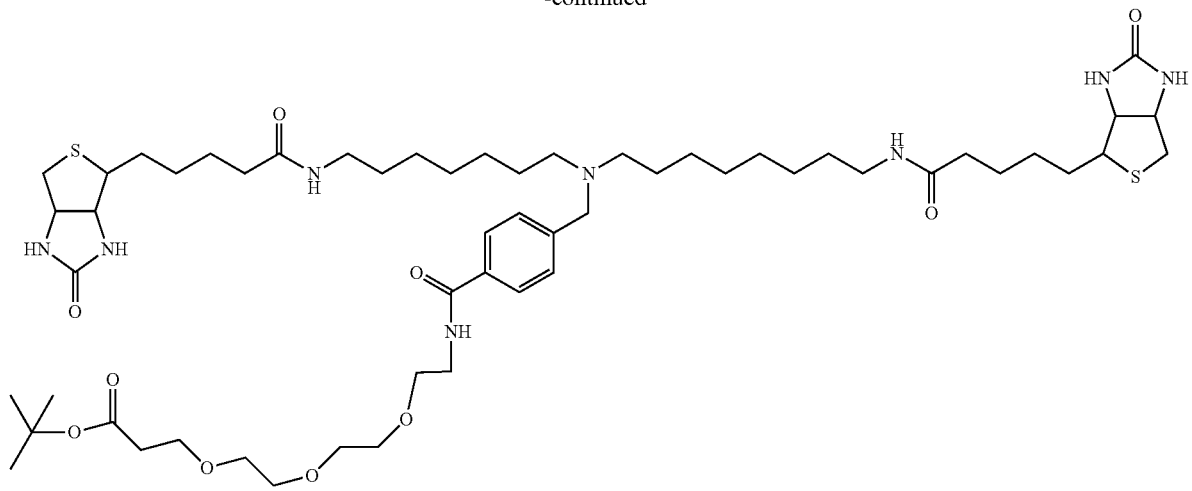

A reaction was performed in the same manner as in Example 3-7 by using the 4-(((7-(biotinylamino)heptyl)-(8-(biotinylamino)octyl)amino)methyl)benzoic acid synthesized as above to obtain 304 mg (74%) of a target reaction product of tert-butyl 1-oxo-1-(4-(((7-(biotinylamino)heptyl)-(8-(biotinylamino)octyl)amino)methyl)phenyl)-5,8,11-trioxa-2-azatetradecan-14-oate.

(Analysis Values of Target Reaction Product)

$^1$H-NMR (DMSO-d6): 8.0-7.8 (2H, br), 7.71 (2H, br.t), 7.6-7.4 (2H, br.t), 6.41 (2H, s), 6.36 (2H, s), 4.35-4.25 (2H, m), 4.15-4.1 (2H, m), 3.6-3.4 (12H, m), 3.2-2.9 (8H, m), 2.79 (2H, dd), 2.58 (2H, d), 2.40 (2H, t), 2.04 (4H, t), 1.8-1.2 (34H, m), 1.39 (9H, s)

HPLC Retention Time (Analysis Conditions B): 5.05 min (0.1% trifluoroacetic acid aqueous solution/CH$_3$CN=85/15 (7 min) 5/95)

Example 6-5

Synthesis of 1-(4-((7-(Biotinylamino)heptyl)-(8-(biotinylamino)octyl)amino) methyl)phenyl)-1-oxo-5,8,11-trioxa-2-azatetradecan-14-oic Acid Sulfo-NHS Ester

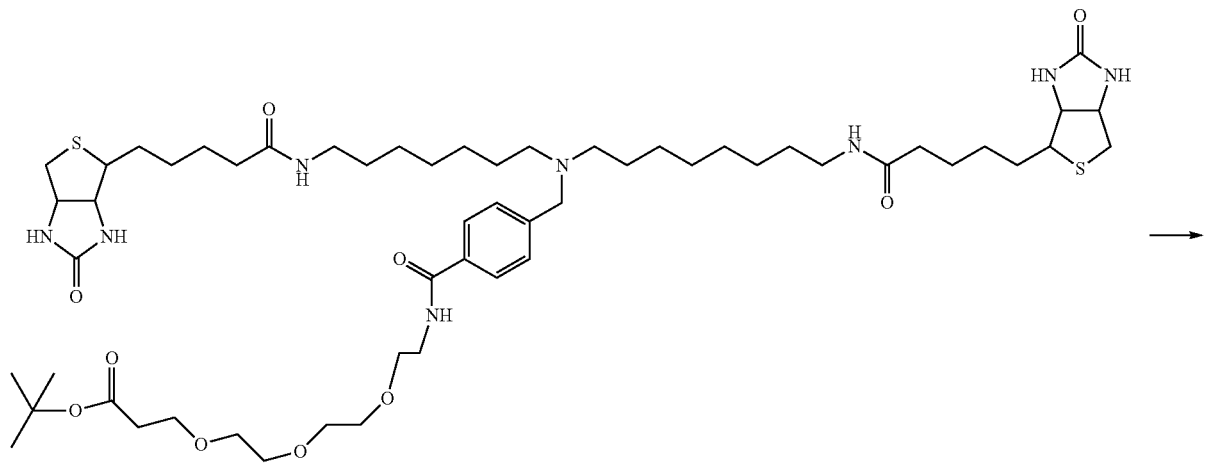

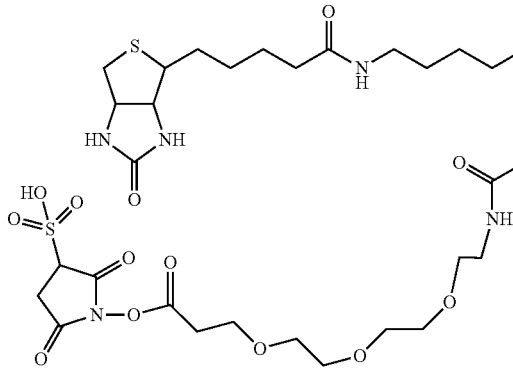

A reaction was performed in the same manner as in Examples 3-8 and 3-9 by using 82 mg (0.074 mmol) of the tert-butyl 1-oxo-1-(4-(((7-(biotinylamino)heptyl)-(8-(biotinylamino)octyl)amino)methyl)phenyl)-5,8,11-trioxa-2-azatetradecan-14-oate synthesized as above to obtain 61 mg (68%) of a target reaction product of 1444(7-(biotinylamino)heptyl)-(8-(biotinylamino)octyl)amino)methyl)phenyl)-1-oxo-5,8,11-trioxa-2-azatetradecan-14-oic acid sulfo-NHS ester.

(Analysis Values of Target Reaction Product)
$^1$H-NMR (DMSO-d6): 7.92 (2H, br.d), 7.78-7.76 (4H, br), 6.6-6.3 (4H, br), 4.4-4.25 (2H, m), 4.15-4.1 (2H, m), 4.0-3.9 (1H, br.d), 3.69 (2H, t), 3.6-3.3 (14H, m), 3.2-2.9 (8H, m), 2.79 (2H, dd), 2.58 (2H, d), 2.05 (4H, t), 1.8-1.1 (34H, m)

HPLC Retention Time of De-t-butyl Esterified Carboxylic Acid of Intermediate (Analysis Conditions B): 4.20 min (0.1% trifluoroacetic acid aqueous solution/CH$_3$CN=85/15 (7 min) 5/95)

The target reaction product was reacted with N-butylamine and the HPLC analysis was performed. HPLC Retention Time of Butylamide Form (Analysis Conditions B): 4.56 min (0.1% trifluoroacetic acid aqueous solution/CH$_3$CN=85/15 (7 min) 5/95)

Example 7-1

Synthesis of Methyl 4-((Bis(7-((tert-butoxycarbonyl)amino)octyl)amino)methyl) benzoate

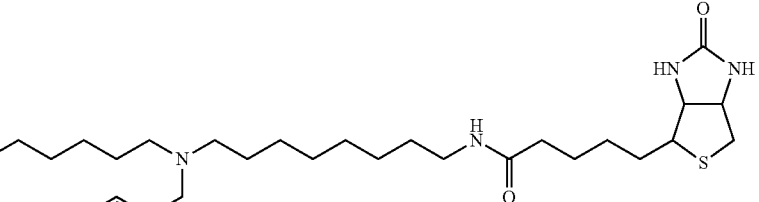

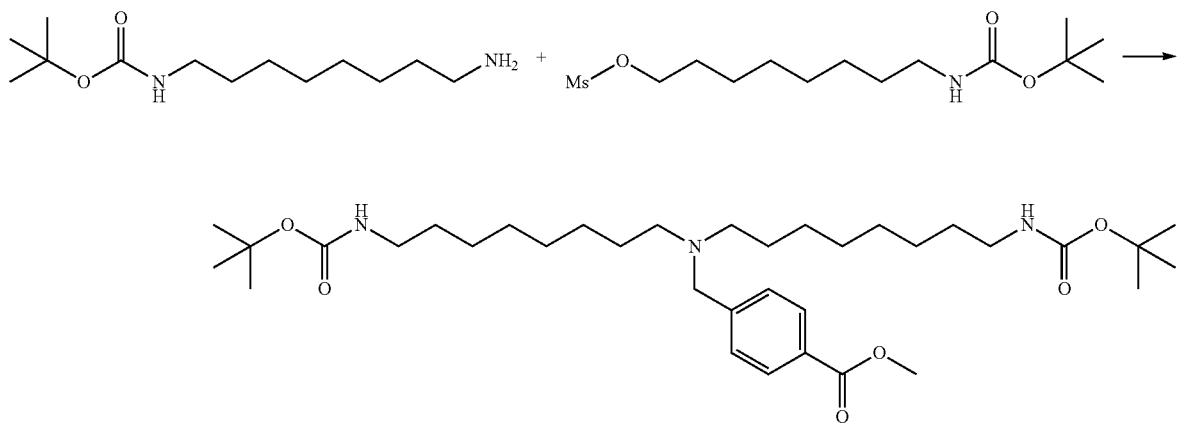

A reaction was performed in the same manner as in Example 4-1 by using 3.0 g (9.3 mmol) of 8-((tert-butoxycarbonyl)amino)octyl methanesulfonate and 3.97 g (16.2 mmol) of tert-butyl (7-aminooctyl)carbamate to obtain 2.76 g (48%) of a target reaction product of methyl 4-((bis(7-((tert-butoxycarbonyl)amino)octyl)amino)methyl)benzoate.

(Analysis Values of Target Reaction Product)
$^1$H-NMR (CDCl$_3$): 7.97 (2H, d), 7.42 (2H, d), 3.91 (3H, s), 3.56 (2H, s), 3.2-3.0 (4H, m), 2.41 (4H, t), 1.8-1.3 (28H, m), 1.44 (18H, s)

Example 7-2

Synthesis of Methyl 4-((Bis(7-(biotinylamino)octyl)amino)methyl)benzoate

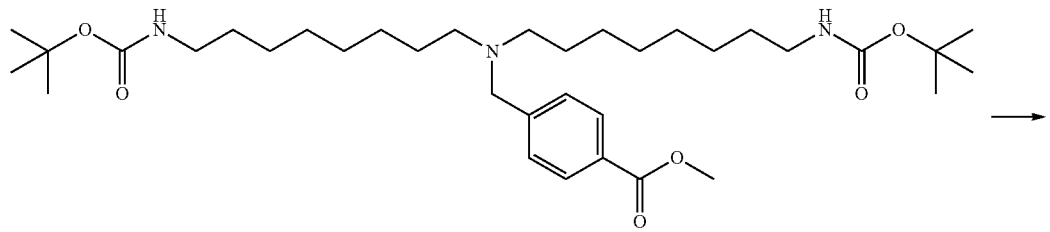

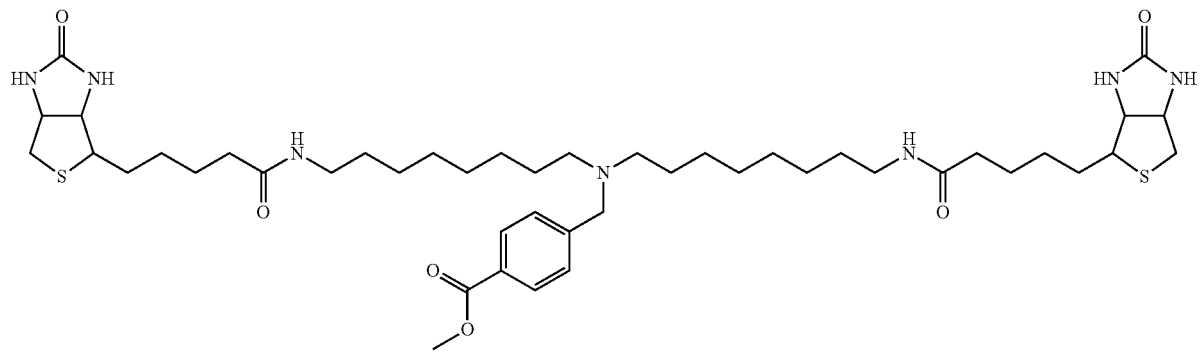

A reaction was performed in the same manner as in Example 4-2 by using 1.38 g (2.22 mmol) of the 4-((bis(7-((tert-butoxycarbonyl)amino)octyl)amino)methyl)benzoate synthesized as above to obtain 1.09 g (56%) of a target reaction product of methyl 4-((bis(7-(biotinylamino)octyl)amino)methyl)benzoate.

(Analysis Values of Target Reaction Product)
1H-NMR (DMSO-d6): 8.1-7.9 (2H, br), 7.71 (2H, t), 7.7-7.5 (2H, br), 6.42 (2H, s), 6.36 (2H, s), 4.35-4.25 (2H, m), 4.15-4.1 (2H, m), 3.84 (3H, s), 3.2-2.9 (8H, m), 2.81 (2H, dd), 2.57 (2H, d), 2.35 (4H, br.t), 2.03 (4H, t), 1.7-1.1 (36H, m)

Example 7-3

Synthesis of 4-((Bis(7-(biotinylamino)octyl)amino)methyl)benzoic Acid

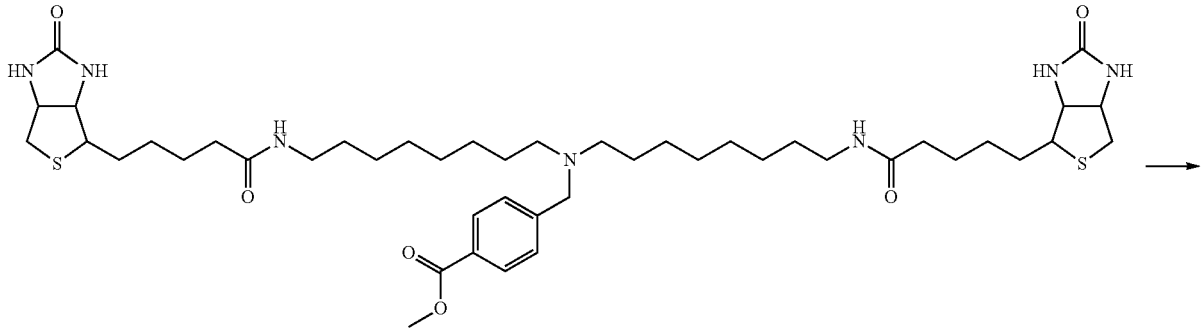

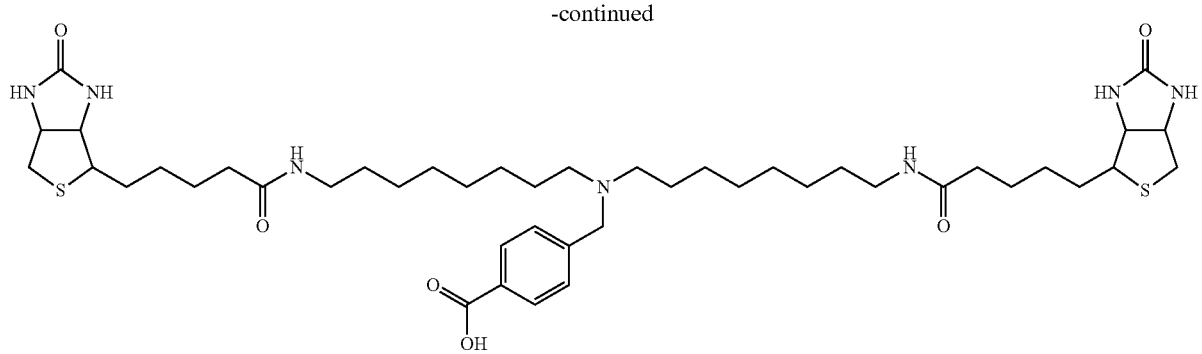

A reaction was performed in the same manner as in Example 3-6 by using 1.09 g (1.25 mmol) of the methyl 4-((bis(7-(biotinylamino)octyl)amino)methyl)benzoate synthesized as above to obtain 1.05 g (98%) of a target reaction product of 4-((bis(7-(biotinylamino)octyl)amino)methyl)benzoic acid.

(Analysis Values of Target Reaction Product)
$^1$H-NMR (DMSO-d6): 7.85 (2H, d), 7.75 (2H, br), 7.37 (2H, d), 6.44 (2H, s), 6.37 (2H, s), 4.35-4.25 (2H, m), 4.15-4.1 (2H, m), 3.54 (2H, s), 3.2-3.0 (2H, m), 3.0-2.9 (4H, m), 2.81 (2H, dd), 2.57 (2H, d), 2.33 (4H, br.t), 2.04 (4H, t), 1.7-1.1 (36H, m)

Example 7-4

Synthesis of tert-Butyl 1-(4-((Bis(7-(biotinylamino)octyl)amino)methyl)phenyl)-1-oxo-5,8,11-trioxa-2-azatetradecan-14-oate

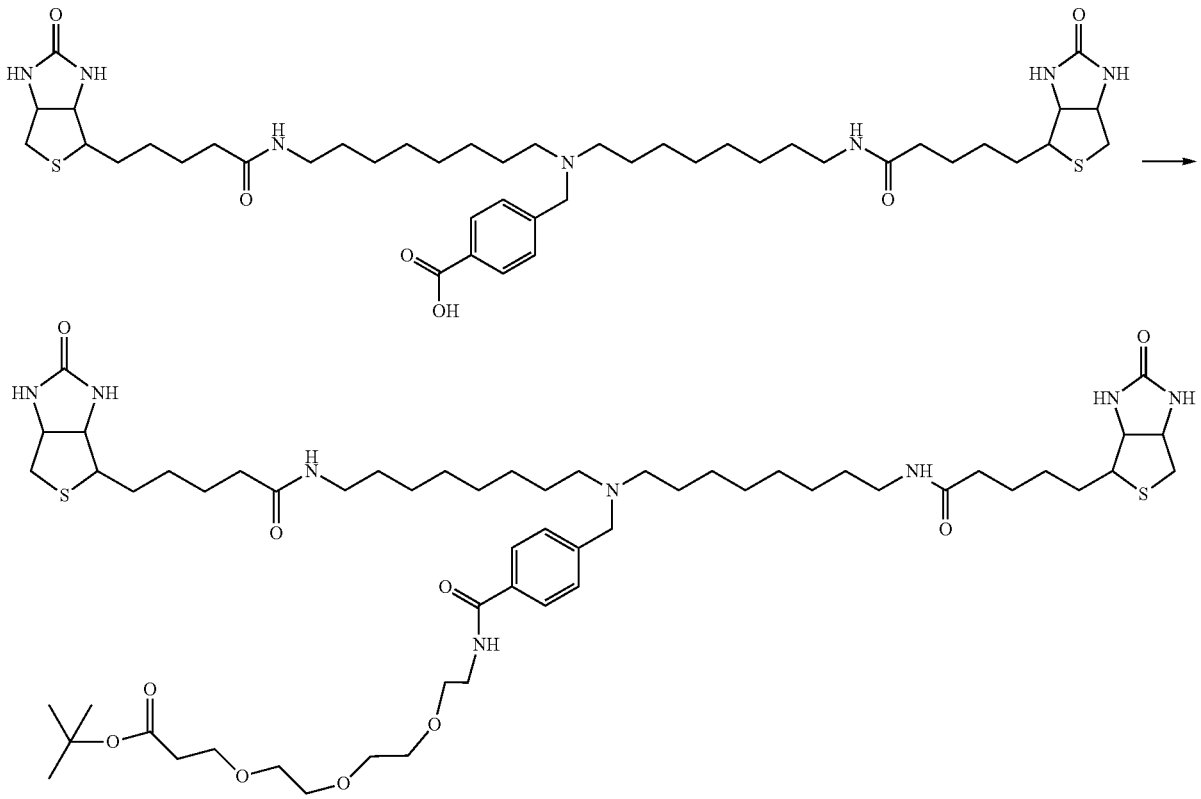

A reaction was performed in the same manner as in Example 3-7 by using 1.05 g (1.23 mmol) of the 4-((bis(7-(biotinylamino)octyl)amino)methyl)benzoic acid synthesized as above to obtain 891 mg (64%) of a target reaction product of tert-butyl 1-(4-((bis(7-(biotinylamino)octyl)amino)methyl)phenyl)-1-oxo-5,8,11-trioxa-2-azatetradecan-14-oate.

(Analysis Values of Target Reaction Product)
$^1$H-NMR (DMSO-d6): 8.42 (1H, br. T), 7.80 (2H, d), 7.70 (2H, t), 7.36 (2H, d), 6.41 (2H, s), 6.35 (2H, s), 4.4-4.25 (4H, m), 4.15-4.1 (2H, m), 3.6-3.4 (12H, m), 3.2-2.9 (8H, m), 2.79 (2H, dd), 2.58 (2H, d), 2.40 (2H, t), 2.04 (4H, t), 1.8-1.2 (36H, m), 1.44 (9H, s)
HPLC Retention Time (Analysis Conditions B): 5.09 min (0.1% trifluoroacetic acid aqueous solution/CH$_3$CN=85/15 (7 min) 5/95)

A reaction was performed in the same manner as in Examples 3-8 and 3-9 by using 75 mg (0.067 mmol) of the tert-butyl 1-(4-((bis(7-(biotinylamino)octyl)amino)methyl)phenyl)-1-oxo-5,8,11-trioxa-2-azatetradecan-14-oate synthesized as above to obtain 50 mg (60%) of a target reaction product of 1-(4-((bis(7-(biotinylamino)octyl)amino)methyl)phenyl)-1-oxo-5,8,11-trioxa-2-azatetradecan-14-oic acid sulfo-NHS ester.

(Analysis Values of Target Reaction Product)
$^1$H-NMR (DMSO-d6): 8.0-7.6 (6H, m), 6.6-6.3 (4H, br), 4.4-4.25 (4H, m), 4.15-4.1 (2H, m), 4.0-3.9 (1H, br.d), 3.69 (2H, t), 3.6-3.3 (14H, m), 3.2-2.9 (8H, m), 2.79 (2H, dd), 2.58 (2H, d), 2.05 (4H, t), 1.8-1.1 (36H, m)
HPLC Retention Time of De-t-butyl Esterified Carboxylic Acid of Intermediate (Analysis Conditions B): 4.37 min (0.1% trifluoroacetic acid aqueous solution/CH$_3$CN=85/15 (7 min) 5/95)
The target reaction product was reacted with N-butylamine and the HPLC analysis was performed. HPLC Retention Time of Butylamide Form (Analysis Conditions B): 4.69 min (0.1% trifluoroacetic acid aqueous solution/CH$_3$CN=85/15 (7 min) 5/95)

Example 7-5

Synthesis of 1-(4-((Bis(7-(biotinylamino)octyl)amino)methyl)phenyl)-1-oxo-5,8,11-trioxa-2-azatetradecan-14-oic Acid Sulfo-NHS Ester

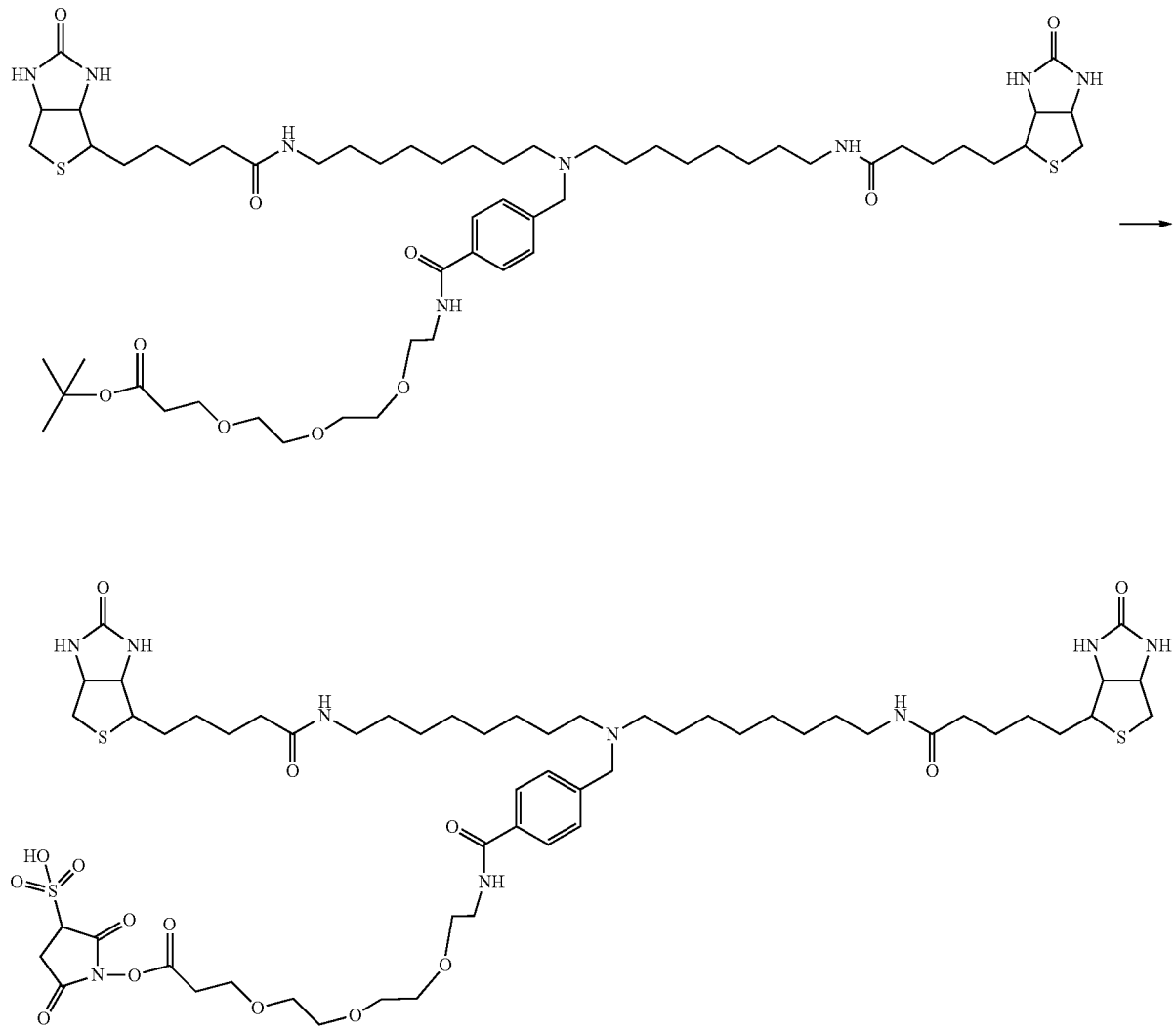

Example 8-1

Synthesis of Methyl 3,5-Bis(6-(biotinylamino)hexanamido)benzoate

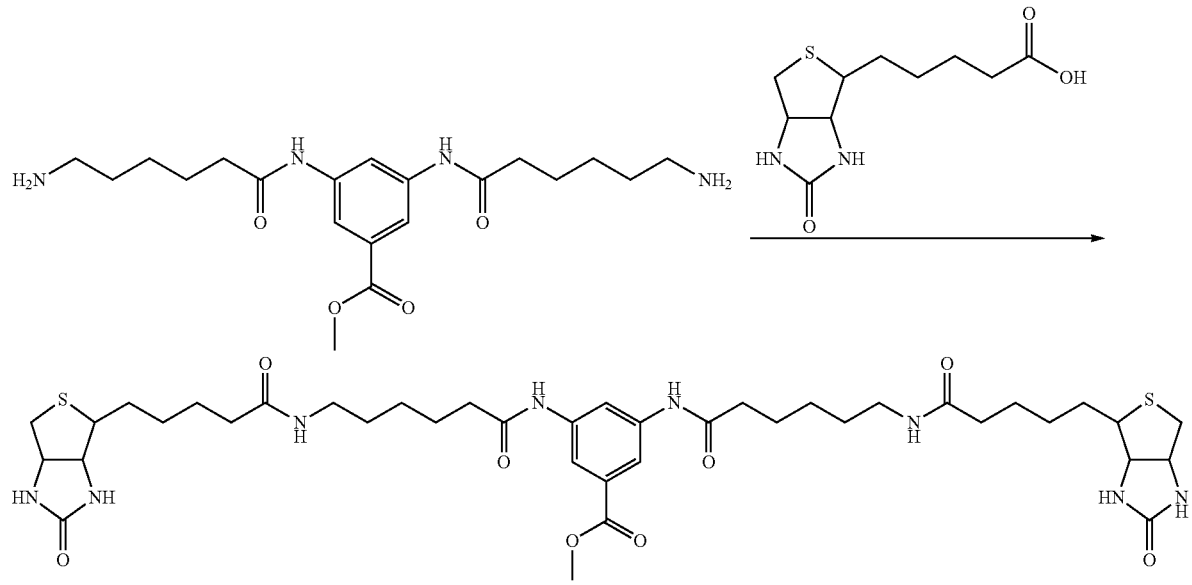

A reaction was performed in the same manner as in Example 1-2 by using 392 mg (0.84 mmol) of methyl 3,5-bis(6-aminohexanamido)benzoate dihydrochloride and 452 mg (1.85 mmol) of biotin to obtain 412 mg (58%) of a target reaction product of methyl 3,5-bis(6-(biotinylamino) hexanamido)benzoate.

(Analysis Values of Target Reaction Product)
$^1$H-NMR (DMSO-d6): 10.08 (2H, s), 8.19 (1H, s), 7.94 (2H, d), 7.74 (2H, t), 6.5-6.2 (4H, br.s), 4.35-4.25 (2H, m), 4.2-4.05 (2H, m), 3.84 (3H, s), 3.2-2.9 (6H, m), 2.81 (2H, dd), 2.57 (2H, d), 2.30 (4H, t), 2.04 (4H, t), 1.7-1.1 (24H, m)

Example 8-2

Synthesis of 3,5-Bis(6-(biotinylamino)hexanamido)benzoic Acid

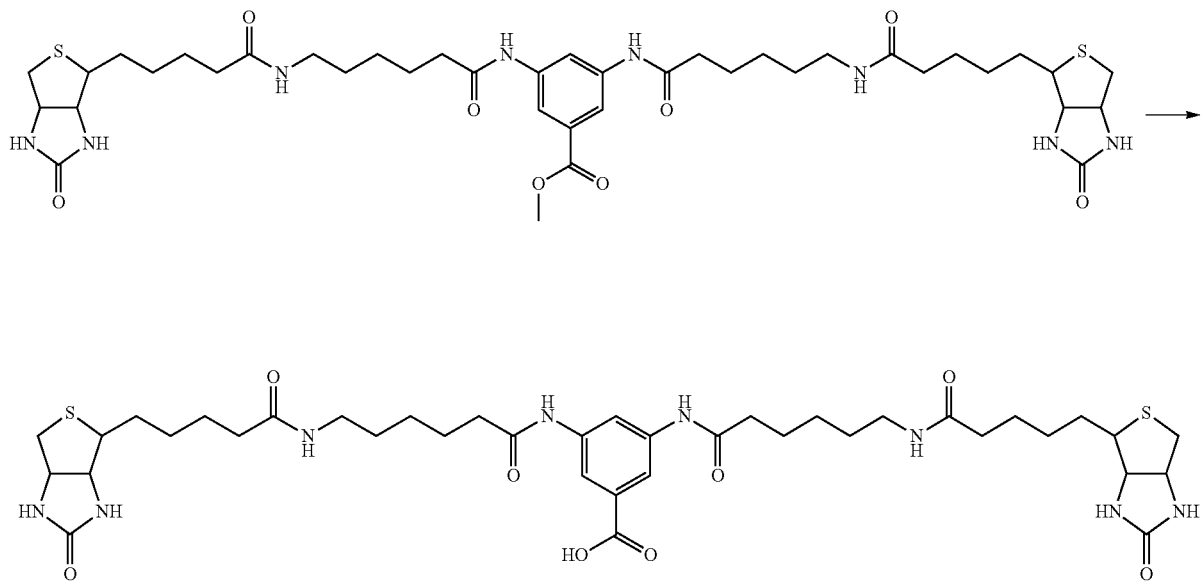

A reaction was performed in the same manner as in Example 3-6 by using 310 mg (0.367 mmol) of the methyl 3,5-bis(6-(biotinylamino)hexanamido)benzoate synthesized as above to obtain 282 mg (93%) of a target reaction product of 3,5-bis(6-(biotinylamino)hexanamido)benzoic acid. This compound was not purified but directly used in the following step.

(Analysis Values of Target Reaction Product)

$^1$H-NMR (DMSO-d6): 9.99 (2H, s), 8.15 (1H, s), 7.85 (2H, s), 7.75 (2H, br.s), 6.44 (2H, s), 6.36 (2H, s), 4.35-4.25 (2H, m), 4.2-4.05 (2H, m), 3.2-2.9 (6H, m), 2.81 (2H, dd), 2.57 (2H, d), 2.30 (4H, br.t), 2.04 (4H, br.t), 1.7-1.1 (24H, m)

Example 8-3

Synthesis of tert-Butyl 1-(3,5-Bis(6-(biotinyl) amino)hexanamido)phenyl)-1-oxo-5,8,11-trioxa-2-azatetradecan-14-oate

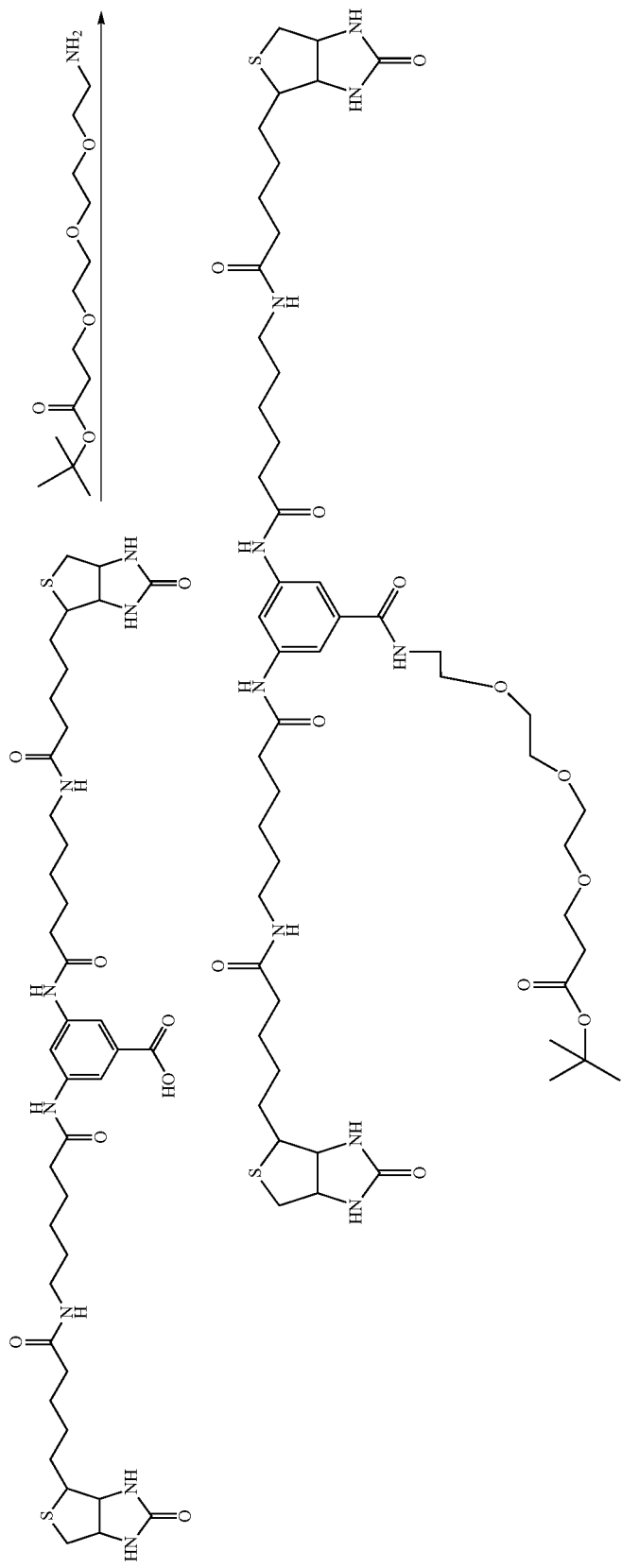

A reaction was performed in the same manner as in Example 3-7 by using 498 mg (0.599 mmol) of the 3,5-bis(6-(biotinylamino)hexanamido)benzoic acid obtained by the above-described synthesis method to obtain 407 mg (62%) of a target reaction product of tert-butyl 1-(3,5-bis(6-(biotinyl)amino)hexanamido)phenyl)-1-oxo-5,8,11-trioxa-2-azatetradecan-14-oate.

(Analysis Values of Target Reaction Product)
$^1$H-NMR (DMSO-d6): 9.97 (2H, s), 8.35 (1H, br.t), 8.04 (1H, s), 7.74 (2H, br.t), 7.66 (2H, d), 6.44 (2H, s), 6.35 (2H, s), 4.35-4.25 (2H, m), 4.2-4.05 (2H, m), 3.6-3.3 (14H, m), 3.2-2.9 (6H, m), 2.81 (2H, dd), 2.57 (2H, d), 2.40 (2H, t), 2.30 (4H, br.t), 2.04 (4H, br.t), 1.7-1.1 (33H, m)

Retention Time under HPLC Analysis Conditions A: 13.6 min (0.1% trifluoroacetic acid aqueous solution/CH$_3$CN=85/15 (12 min) 35/65)

Example 8-4

Synthesis of 1-(3,5-Bis(6-(biotinyl)amino)hexanamido)phenyl)-1-oxo-5,8,11-trioxa-2-azatetradecan-14-oic Acid Sulfo-NHS Ester

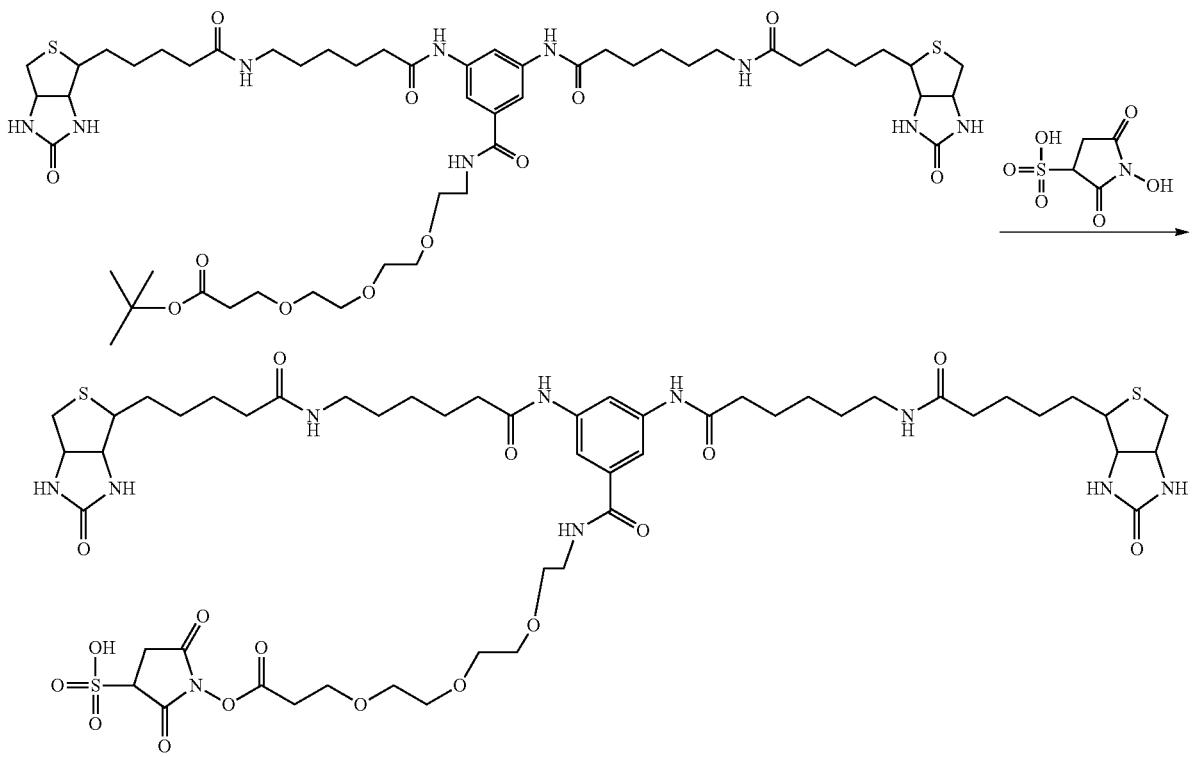 [SMILES: CC(C)(C)OC(=O)CCOCCOCCOCCNC(=O)c1cc(NC(=O)CCCCCNC(=O)CCCCC2SCC3NC(=O)NC32)cc(NC(=O)CCCCCNC(=O)CCCCC2SCC3NC(=O)NC32)c1 ; O=C1CC(S(=O)(=O)O)C(=O)N1O ; O=C(CCCCC1SCC2NC(=O)NC21)NCCCCCC(=O)Nc1cc(NC(=O)CCCCCNC(=O)CCCCC2SCC3NC(=O)NC32)cc(C(=O)NCCOCCOCCOCCC(=O)ON2C(=O)CC(S(=O)(=O)O)C2=O)c1]

A reaction was performed in the same manner as in Examples 3-8 and 3-9 by using 400 mg (0.367 mmol) of the tert-butyl 1-(3,5-bis(6-(biotinyl)amino)hexanamido) phenyl)-1-oxo-5,8,11-trioxa-2-azatetradecan-14-oate synthesized as above to obtain 493 mg of a target reaction product of 1-(3,5-bis(6-(biotinyl)amino)hexanamido)phenyl)-1-oxo-5,8,11-trioxa-2-azatetradecan-14-oic acid sulfo-NHS ester.

(Analysis Values of Target Reaction Product)
$^1$H-NMR (DMSO-d6): 9.96 (2H, s), 8.31 (2H, br), 8.08 (1H, s), 7.73 (2H, br.t), 7.64 (2H, d), 6.40 (2H, s), 6.34 (2H, s), 4.35-4.25 (2H, m), 4.2-4.05 (2H, m), 4.0-3.9 (1H, br.d), 3.7 (2H, t), 3.6-3.4 (10H, m), 3.4-3.3 (2H, m), 3.2-2.8 (8H, m), 2.81 (2H, dd), 2.57 (2H, d), 2.29 (4H, t), 2.04 (4H, t), 1.7-1.1 (24H, m)

HPLC Retention Time of De-t-butyl Esterified Carboxylic Acid of Intermediate under Analysis Conditions A: 11.1 min (0.1% trifluoroacetic acid aqueous solution/CH$_3$CN=85/15 (12 min) 35/65)

The target reaction product was reacted with N-butylamine and the HPLC analysis was performed. Retention Time of Butylamide Form under HPLC Analysis Conditions A: 12.0 min (0.1% trifluoroacetic acid aqueous solution/CH$_3$CN=85/15 (12 min) 35/65)

Example 9-1

Synthesis of Methyl 3,5-Bis(5-(biotinylamino)pentanamido)benzoate

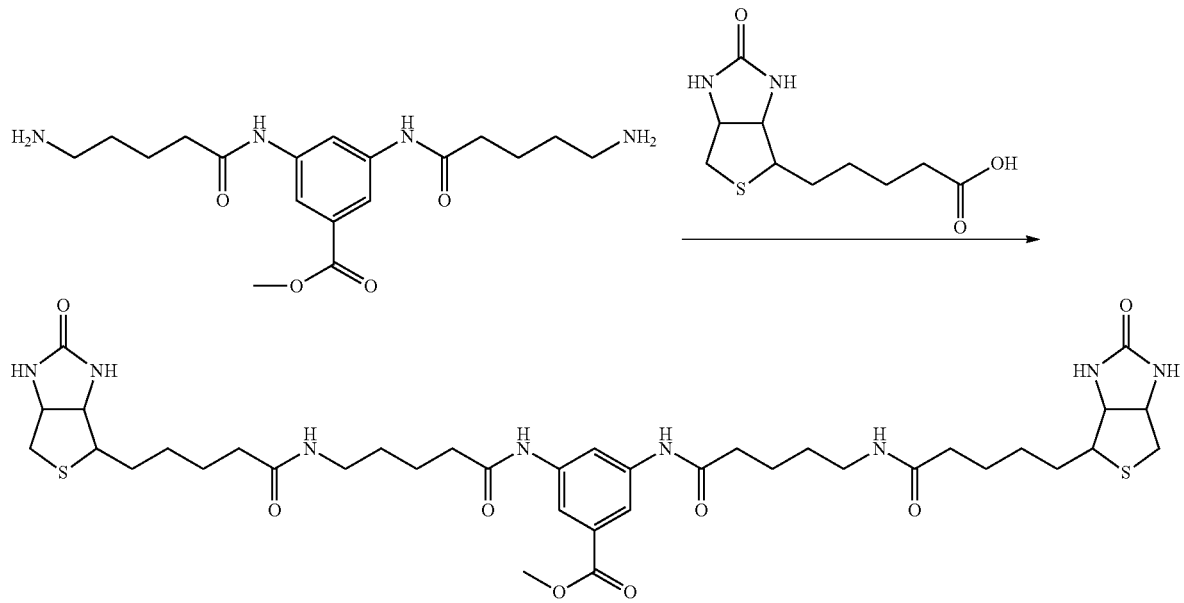

A reaction was performed in the same manner as in Example 1-2 by using 1.13 (3 mmol) of methyl 3,5-bis(6-aminopentanamido)benzoate dihydrochloride and 1.76 g (7.2 mmol) of biotin to obtain 1.5 g (63%) of a target reaction product of methyl 3,5-bis(5-(biotinylamino)pentanamido)benzoate.

(Analysis Values of Target Reaction Product)
$^1$H-NMR (DMSO-d6): 10.08 (2H, s), 8.19 (1H, s), 7.94 (2H, d), 7.74 (2H, t), 6.5-6.2 (4H, br.s), 4.35-4.25 (2H, m), 4.2-4.05 (2H, m), 3.84 (3H, s), 3.2-2.9 (6H, m), 2.81 (2H, dd), 2.57 (2H, d), 2.30 (4H, t), 2.04 (4H, t), 1.7-1.1 (20H, m)

Example 9-2

Synthesis of 3,5-Bis(5-(biotinylamino)pentanamido)benzoic Acid

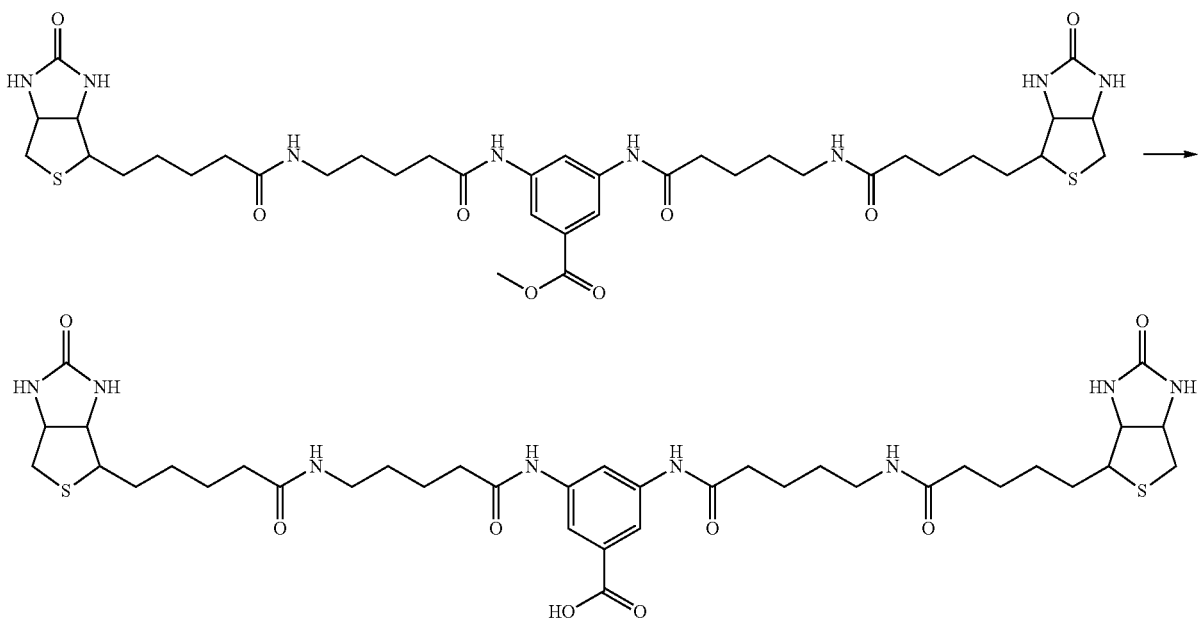

A reaction was performed in the same manner as in Example 3-6 by using 1.48 g (1.82 mmol) of the methyl 3,5-bis(5-(biotinylamino)pentanamido)benzoate synthesized as above to obtain 1.46 g (100%) of a target reaction product of 3,5-bis(5-(biotinylamino)pentanamido)benzoic acid. This compound was not purified but directly used in the following step.

(Analysis Values of Target Reaction Product)
$^1$H-NMR (DMSO-d6): 10.07 (2H, s), 8.17 (1H, s), 7.90 (2H, s), 7.80 (2H, br.s), 6.42 (2H, s), 6.35 (2H, s), 4.35-4.25 (2H, m), 4.2-4.05 (2H, m), 3.2-2.9 (6H, m), 2.81 (2H, dd), 2.57 (2H, d), 2.30 (4H, br.t), 2.04 (4H, br.t), 1.7-1.1 (20H, m)

Example 9-3

Synthesis of tert-Butyl 1-(3,5-Bis(5-(biotinylamino)pentanamido)phenyl)-1-oxo-5,8,11-trioxa-2-azatetradecan-14-oate

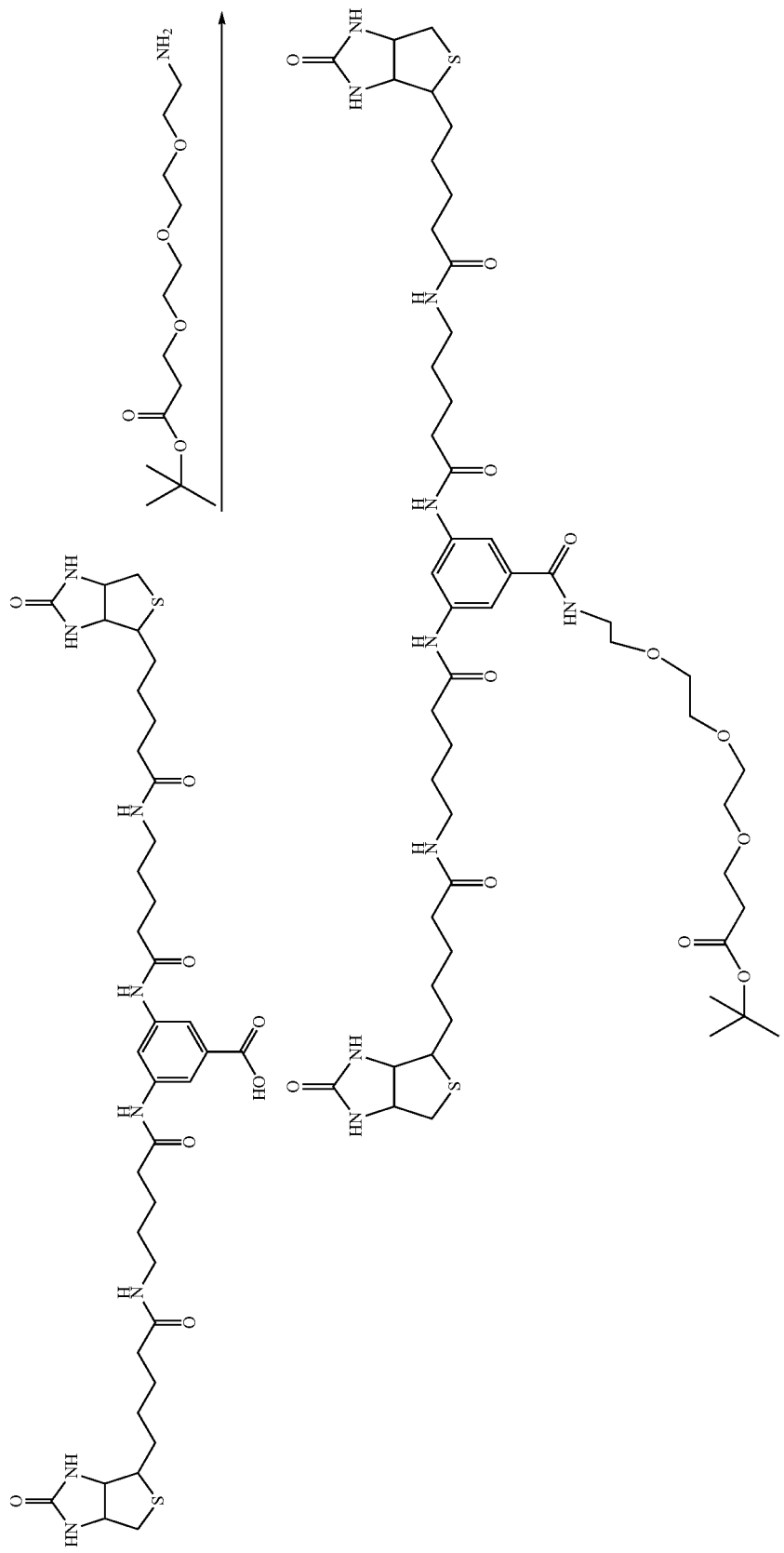

A reaction was performed in the same manner as in Example 3-7 by using 700 mg (0.782 mmol) of the 3,5-bis (5-(biotinylamino)pentanamido)benzoic acid obtained by the above-described synthesis method to obtain 537 mg (58%) of a target reaction product of tert-butyl 1-(3,5-bis (5-(biotinylamino)pentanamido)phenyl)-1-oxo-5,8,11-trioxa-2-azatetradecan-14-oate.

(Analysis Values of Target Reaction Product)

1H-NMR (DMSO-d6): 9.98 (2H, s), 8.33 (1H, br.t), 8.04 (1H, s), 7.74 (2H, br.t), 7.66 (2H, d), 6.5-6.2 (4H, br), 4.35-4.25 (2H, m), 4.2-4.05 (2H, m), 3.6-3.3 (14H, m), 3.2-2.9 (6H, m), 2.81 (2H, dd), 2.57 (2H, d), 2.40 (2H, t), 2.31 (4H, br.t), 2.05 (4H, br.t), 1.7-1.1 (29H, m)

Retention Time under HPLC Analysis Conditions A: 13.0 min (0.1% trifluoroacetic acid aqueous solution/CH$_3$CN=85/15 (12 min) 35/65)

Example 9-4

Synthesis of 1-(3,5-Bis(5-(biotinylamino)pentanamido)phenyl)-1-oxo-5,8,11-trioxa-2-azatetradecan-14-oic Acid Sulfo-NHS Ester 8,11-trioxa-2-azatetradecan-14-oate synthesized as above to obtain 404 mg (82%) of 1-(3,5-bis(5-(biotinylamino)pentanamido)phenyl)-1-oxo-5,8,11-trioxa-2-azatetradecan-14-oic acid. Then, a reaction was performed in the same manner as in Example 3-9 by using 100 mg (0.99 mmol) of the thus synthesized 1-(3,5-bis(5-(biotinylamino) pentanamido)phenyl)-1-oxo-5,8,11-trioxa-2-azatetradecan-14-oic acid to obtain 135 mg of a target reaction product of 1-(3,5-bis(5-(biotinylamino)pentanamido)phenyl)-1-oxo-5,8,11-trioxa-2-azatetradecan-14-oic acid sulfo-NHS ester.

(Analysis Values of Target Reaction Product)

$^1$H-NMR (DMSO-d6): 9.98 (2H, s), 8.31 (2H, br), 8.08 (1H, s), 7.76 (2H, br.t), 7.64 (2H, d), 6.40 (2H, s), 6.34 (2H, s), 4.35-4.25 (2H, m), 4.2-4.05 (2H, m), 4.0-3.9 (1H, br.d), 3.7 (2H, t), 3.6-3.4 (10H, m), 3.4-3.3 (2H, m), 3.2-2.8 (8H, m), 2.81 (2H, dd), 2.57 (2H, d), 2.31 (4H, t), 2.05 (4H, t), 1.7-1.1 (20H, m)

HPLC Retention Time of De-t-butyl Esterified Carboxylic Acid of Intermediate under Analysis Conditions A: 10.6 min (0.1% trifluoroacetic acid aqueous solution/CH$_3$CN=85/15 (12 min) 35/65)

The target reaction product was reacted with N-butylamine and the HPLC analysis was performed. Retention Time

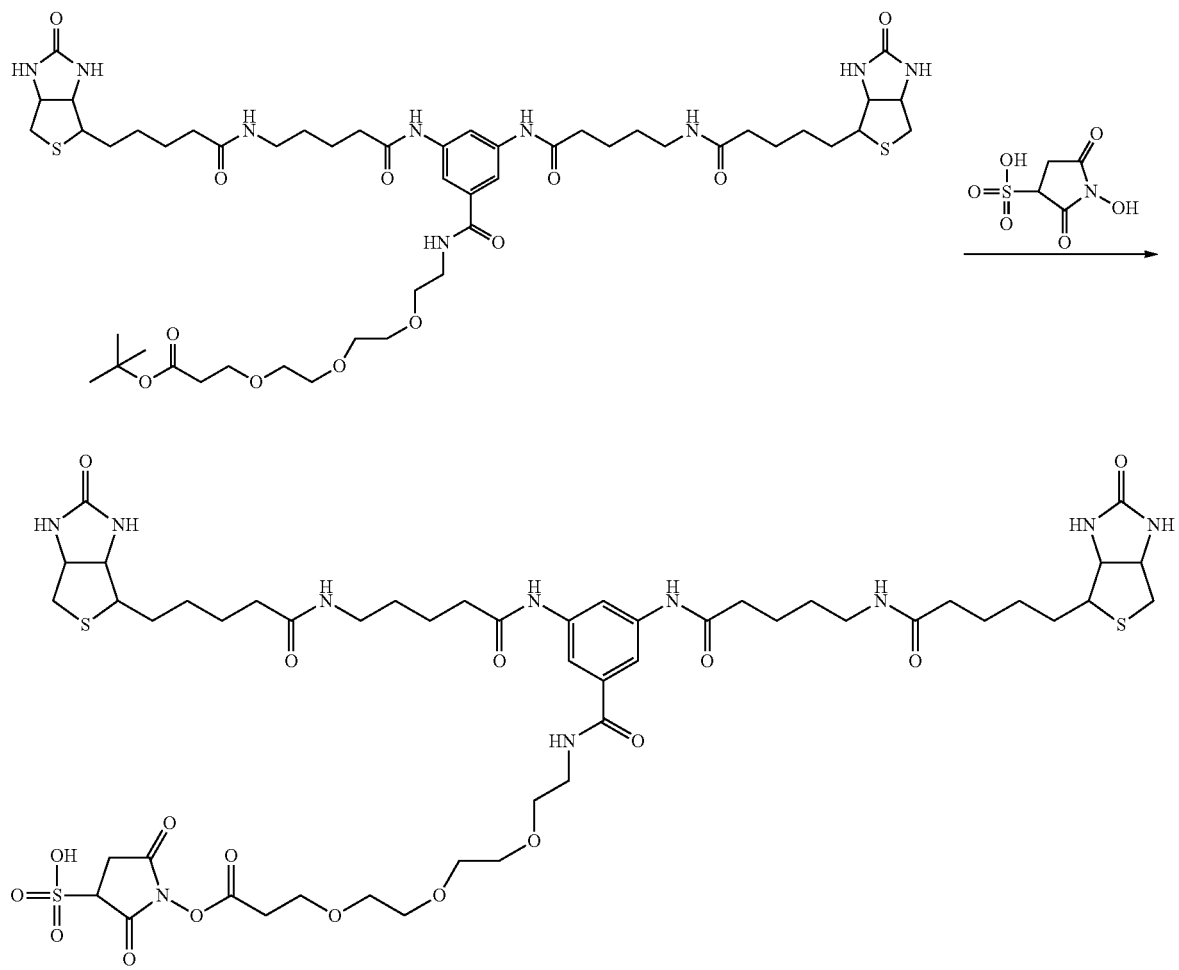 [SMILES: CC(C)(C)OC(=O)CCOCCOCCOCCNC(=O)c1cc(NC(=O)CCCCNC(=O)CCCCC2SCC3NC(=O)NC32)cc(NC(=O)CCCCNC(=O)CCCCC2SCC3NC(=O)NC32)c1 ; O=C1CC(S(=O)(=O)O)C(=O)N1O ; O=C(CCCCC1SCC2NC(=O)NC21)NCCCCC(=O)Nc1cc(NC(=O)CCCCNC(=O)CCCCC2SCC3NC(=O)NC32)cc(C(=O)NCCOCCOCCOCCC(=O)ON2C(=O)CC(S(=O)(=O)O)C2=O)c1]

A reaction was performed in the same manner as in Example 3-8 by using 520 mg (0.477 mmol) of the tert-butyl 1-(3,5-bis(5-(biotinylamino)pentanamido)phenyl)-1-oxo-5, of Butylamide Form under HPLC Analysis Conditions A: 11.6 min (0.1% trifluoroacetic acid aqueous solution/ CH$_3$CN=85/15 (12 min) 35/65)

Example 10-1

Synthesis of tert-Butyl 1-(3,5-Bis(5-(biotinylamino)pentanamido)phenyl)-1-oxo-5,8,11,14,17,20,23,26,29,32,35,38,41,44,47,50,53,56,59,62,65,68,71,74,77,80,83,86,89,92,95,98,101,104,107,110-hexatriacontaoxa-2-azatridecahectan-113-oate

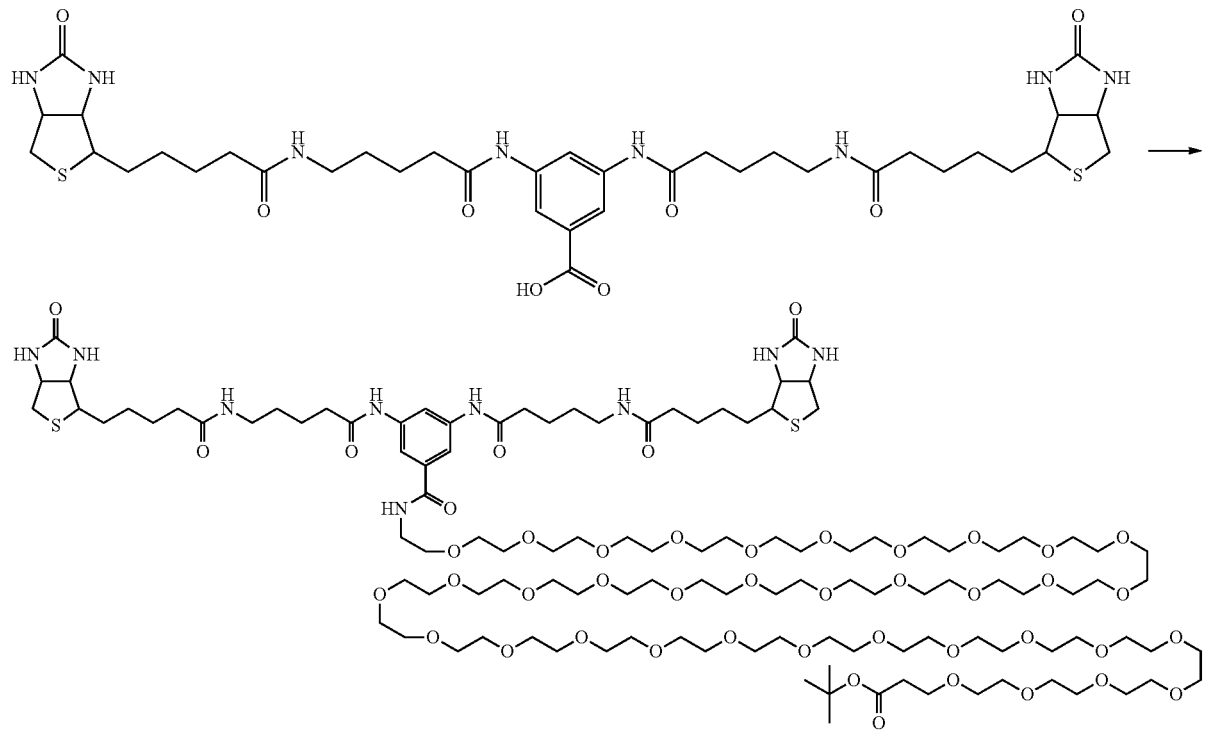

A reaction was performed in the same manner as in Example 3-7 by using 700 mg (0.782 mmol) of the 3,5-bis(5-(biotinylamino)pentanamido)benzoic acid synthesized in Example 9-2 and 700 mg (0.782 mmol) of amino-peg36-t-butyl ester to obtain 537 mg (58%) of a target reaction product of tert-butyl 1-(3,5-bis(5-(biotinylamino)pentanamido) phenyl)-1-oxo-5,8,11,14,17,20,23,26,29,32,35,38,41,44,47,50,53,56,59,62,65,68,71,74, 77,80,83,86,89,92,95,98, 101,104,107,110-hexatriacontaoxa-2-azatridecahectan-113-oate.

(Analysis Values of Target Reaction Product)
$^1$H-NMR (DMSO-d6): 9.98 (2H, s), 8.33 (1H, br.t), 8.04 (1H, s), 7.74 (2H, br.t), 7.66 (2H, d), 6.5-6.2 (4H, br), 4.35-4.25 (2H, m), 4.2-4.05 (2H, m), 3.6-3.3 (80H, m), 3.2-2.9 (6H, m), 2.81 (2H, dd), 2.57 (2H, d), 2.40 (2H, t), 2.31 (4H, br.t), 2.05 (4H, br.t), 1.7-1.1 (24H, m)

Example 10-2

Synthesis of 1-(3,5-Bis(5-(biotinylamino)pentanamido)phenyl)-1-oxo-5,8,11,14, 17,20,23,26,29,32,35,38,41,44,47,50,53,56,59,62,65,68,71,74,77,80,83,86,89,92,95,98,101,104,107,110-hexatriacontaoxa-2-azatridecahectan-113-oic Acid Sulfo-NHS Ester

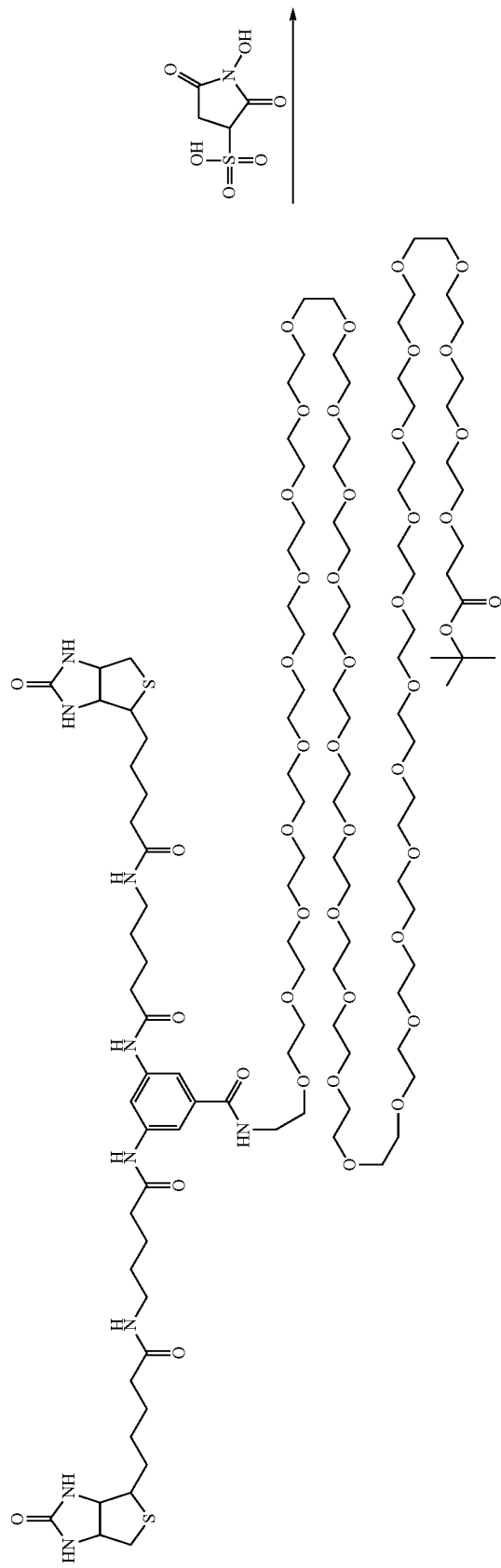

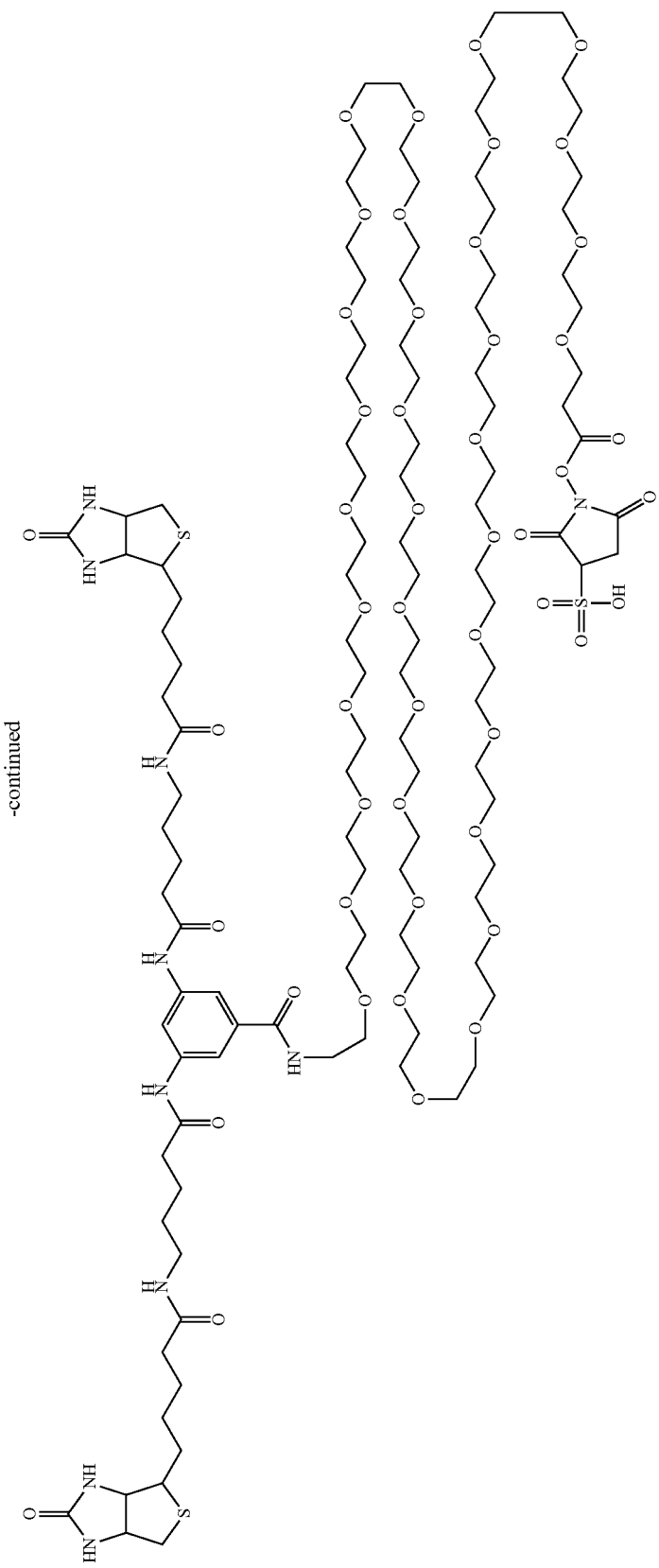

A reaction was performed in the same manner as in Example 3-8 by using 520 mg (0.477 mmol) of the tert-butyl 1-(3,5-bis(5-(biotinylamino)pentanamido)phenyl)-1-oxo-5,8,11,14,17,20,23,26,29,32,35,38,41,44,47,50,53,56,59,62,65,68,71,74,77,80,83,86,89,92,95,98,101,104,107,110-hexatriacontaoxa-2-azatridecahectan-113-oate synthesized as above to obtain 404 mg (82%) of 1-(3,5-bis(5-(biotinylamino)pentanamido)phenyl)-1-oxo-5,8,11-trioxa-2-azatetradecan-14-oic acid. A reaction was performed in the same manner as in Example 3-9 by using 100 mg (0.99 mmol) of the thus synthesized 1-(3,5-bis(5-(biotinylamino)pentanamido)phenyl)-1-oxo-5,8,11-trioxa-2-azatetradecan-14-oic acid to obtain 135 mg of a target reaction product of 1-(3,5-bis(5-(biotinylamino) pentanamido)phenyl)-1-oxo-5,8,11,14,17,20,23,26,29,32,35,38,41,44,47,50,53,56,59,62,65,68,71,74,77,80,83,86,89,92,95,98,101,104,107,110-hexatriacontaoxa-2-azatridecahectan-113-oic acid sulfo-NHS ester.

(Analysis Values of Target Reaction Product)
$^1$H-NMR (DMSO-d6): 9.98 (2H, s), 8.31 (2H, br), 8.08 (1H, s), 7.76 (2H, br.t), 7.64 (2H, d), 6.40 (2H, s), 6.34 (2H, s), 4.35-4.25 (2H, m), 4.2-4.05 (2H, m), 4.0-3.9 (1H, br.d), 3.7 (2H, t), 3.6-3.4 (76H, m), 3.4-3.3 (2H, m), 3.2-2.8 (8H, m), 2.81 (2H, dd), 2.57 (2H, d), 2.31 (4H, t), 2.05 (4H, t), 1.7-1.1 (20H, m)

HPLC Retention Time of De-t-butyl Esterified Carboxylic Acid of Intermediate under Analysis Conditions A: 10.6 min (0.1% trifluoroacetic acid aqueous solution/CH$_3$CN=85/15 (12 min) 35/65)

The target reaction product was reacted with N-butylamine and the HPLC analysis was performed. HPLC Retention Time of Butylamide Form under Analysis Conditions A: 11.6 min (0.1% trifluoroacetic acid aqueous solution/CH$_3$CN=85/15 (12 min) 35/65)

Example 11-1

Synthesis of tert-Butyl 1-(3,5-Bis(5-(biotinylamino) pentanamido)phenyl)-1-oxo-5,8,11,14,17,20,23,26,29,32,35,38-dodecaoxa-2-azahentetracontan-41-oate

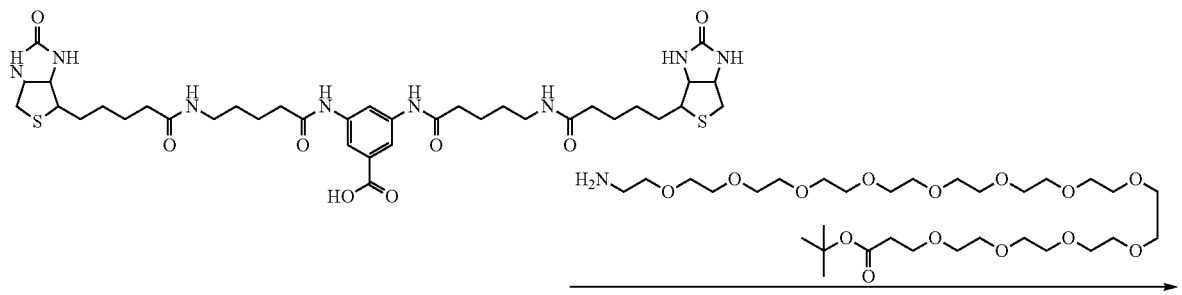

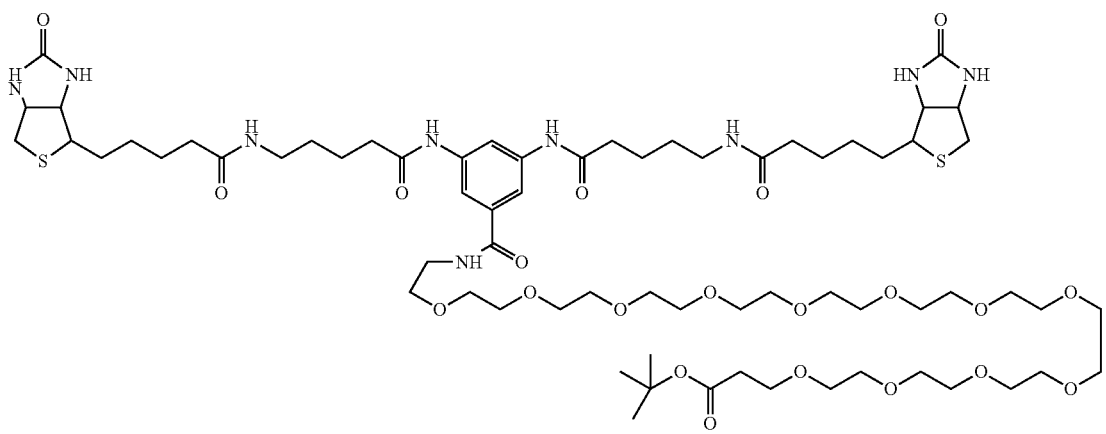

A reaction was performed in the same manner as in Example 3-7 by using 700 mg (0.782 mmol) of the 3,5-bis (5-(biotinylamino)pentanamido)benzoic acid synthesized in Example 9-2 and 700 mg (0.782 mmol) of amino-peg12-t-butyl ester to obtain 537 mg (58%) of a target reaction product of tert-butyl 1-(3,5-bis(5-(biotinylamino)pentanamido) phenyl)-1-oxo-5,8,11,14,17,20,23,26,29,32,35,38-dodecaoxa-2-azahentetracontan-41-oate.

(Analysis Values of Target Reaction Product)

$^1$H-NMR (DMSO-d6): 9.98 (2H, s), 8.33 (1H, br.t), 8.04 (1H, s), 7.74 (2H, br.t), 7.66 (2H, d), 6.5-6.2 (4H, br), 4.35-4.25 (2H, m), 4.2-4.05 (2H, m), 3.6-3.3 (32H, m), 3.2-2.9 (6H, m), 2.81 (2H, dd), 2.57 (2H, d), 2.40 (2H, t), 2.31 (4H, br.t), 2.05 (4H, br.t), 1.7-1.1 (24H, m)

Example 11-2

Synthesis of 1-(3,5-Bis(5-(biotinylamino)pentanamido)phenyl)-1-oxo-5,8,11,14,17,20,23,26,29,32,35,38-dodecaoxa-2-azahentetracontan-41-oic Acid Sulfo-NHS Ester

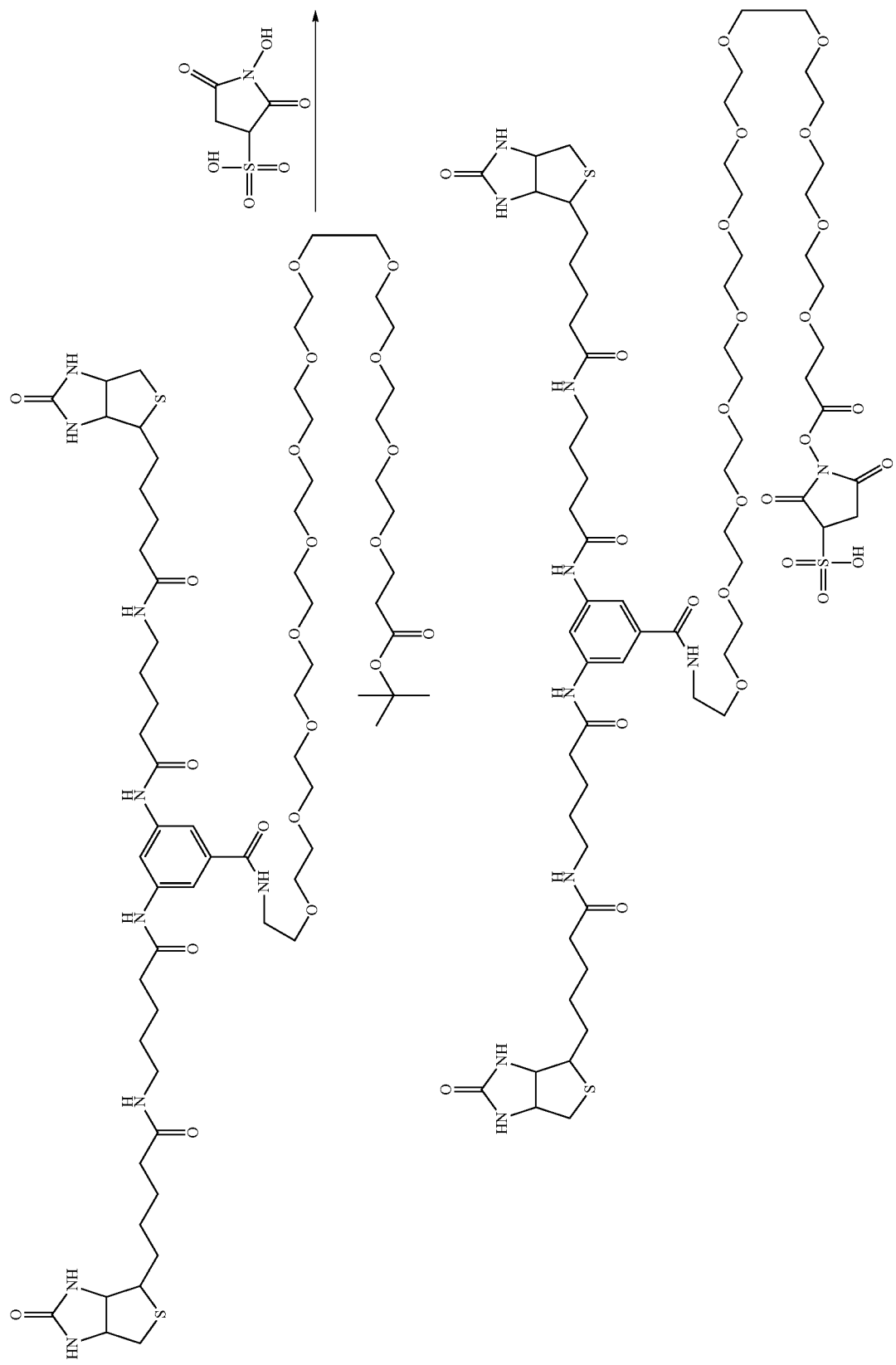

A reaction was performed in the same manner as in Example 3-8 by using 520 mg (0.477 mmol) of the tert-butyl 1-(3,5-bis(5-(biotinylamino)pentanamido)phenyl)-1-oxo-5,8,11,14,17,20,23,26,29,32,35,38-dodecaoxa-2-azahentetracontan-41-oate synthesized as above to obtain 404 mg (82%) of 1-(3,5-bis(5-(biotinylamino) pentanamido)phenyl)-1-oxo-5,8,11-trioxa-2-azatetradecan-14-oic acid. Then, a reaction was performed in the same manner as in Example 3-9 by using 100 mg (0.99 mmol) of the thus synthesized 1-(3,5-bis(5-(biotinylamino)pentanamido)phenyl)-1-oxo-5,8,11-trioxa-2-azatetradecan-14-oic acid to obtain 135 mg of a target reaction product of 1-(3,5-bis(5-(biotinylamino) pentanamido)phenyl)-1-oxo-5,8,11,14,17,20,23,26,29,32,35,38-dodecaoxa-2-azahentetracontan-41-oic acid sulfo-NHS ester.

(Analysis Values of Target Reaction Product)
$^1$H-NMR (DMSO-d6): 9.98 (2H, s), 8.31 (2H, br), 8.08 (1H, s), 7.76 (2H, br.t), 7.64 (2H, d), 6.40 (2H, s), 6.34 (2H, s), 4.35-4.25 (2H, m), 4.2-4.05 (2H, m), 4.0-3.9 (1H, br.d), 3.7 (2H, t), 3.6-3.4 (28H, m), 3.4-3.3 (2H, m), 3.2-2.8 (8H, m), 2.81 (2H, dd), 2.57 (2H, d), 2.31 (4H, t), 2.05 (4H, t), 1.7-1.1 (20H, m)

HPLC Retention Time of De-t-butyl Esterified Carboxylic Acid of Intermediate under Analysis Conditions A: 10.6 min (0.1% trifluoroacetic acid aqueous solution/CH$_3$CN=85/15 (12 min) 35/65)

The target reaction product was reacted with N-butylamine and the HPLC analysis was performed. HPLC Retention Time of Butylamide Form under Analysis Conditions A: 11.6 min (0.1% trifluoroacetic acid aqueous solution/CH$_3$CN=85/15 (12 min) 35/65)

Example 12-1

Synthesis of Methyl 3-(4-(Biotinylamino)butanamido)-5-(5-(biotinylamino) pentanamido)benzoate

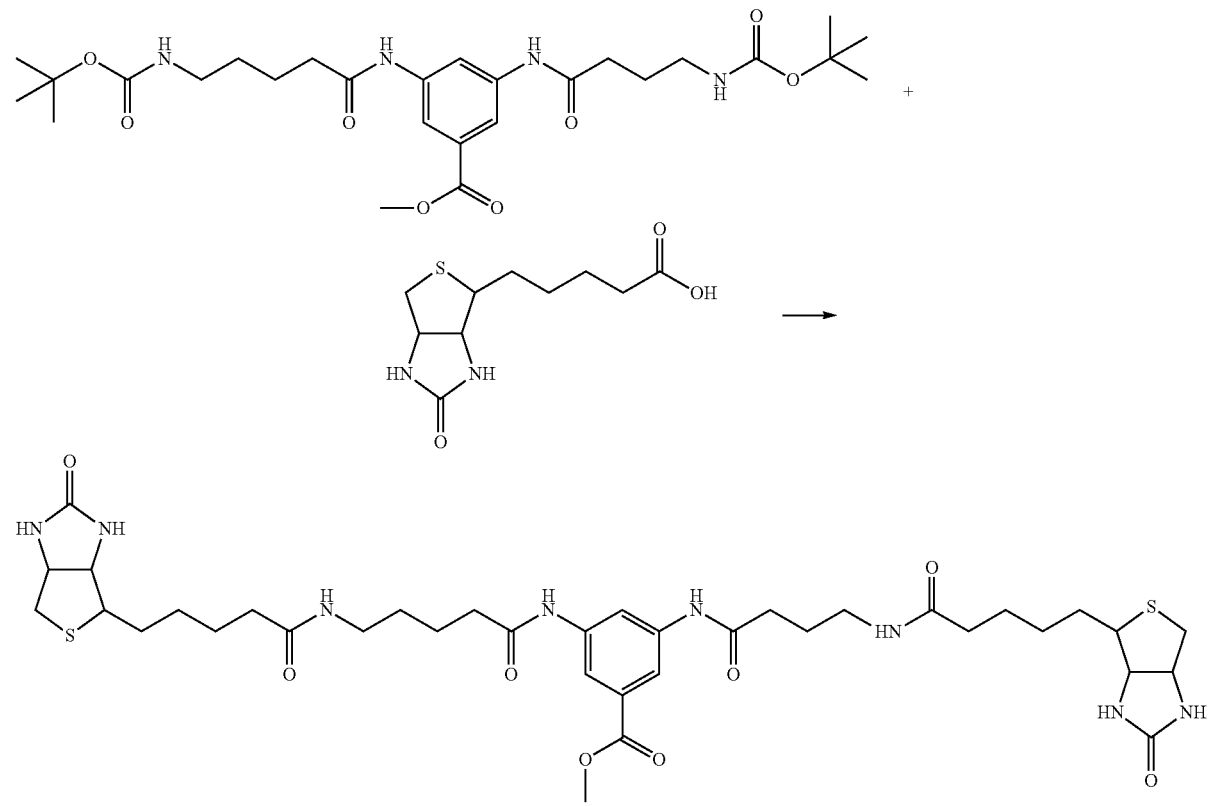

A reaction was performed in the same manner as in Examples 3-4 and 3-5 by using 1.32 (1.96 mmol) of methyl 3-(4-((tert-butoxycarbonyl)amino)butanamido)-5-(5-((tert-butoxycarbonyl)amino)pentanamido)benzoate and 1.20 (4.9 mmol) of biotin to obtain 861 mg (55%) of a target reaction product of methyl 3-(4-(biotinylamino) butanamido)-5-(5-(biotinylamino)pentanamido)benzoate.

(Analysis Values of Target Reaction Product)
$^1$H-NMR (DMSO-d6): 10.1 (2H, s), 8.18 (1H, s), 7.94 (2H, s), 7.8 (2H, br.t), 6.41 (2H, s), 6.35 (2H, s), 4.35-4.25 (2H, m), 4.2-4.05 (2H, m), 3.84 (3H, s), 3.2-2.9 (6H, m), 2.81 (2H, dd), 2.57 (2H, d), 2.31 (4H, t), 2.05 (4H, t), 1.7-1.1 (18H, m)

Example 12-2

Synthesis of 3-(4-(Biotinylamino)butanamido)-5-(5-(biotinylamino)pentanamido) benzoic Acid

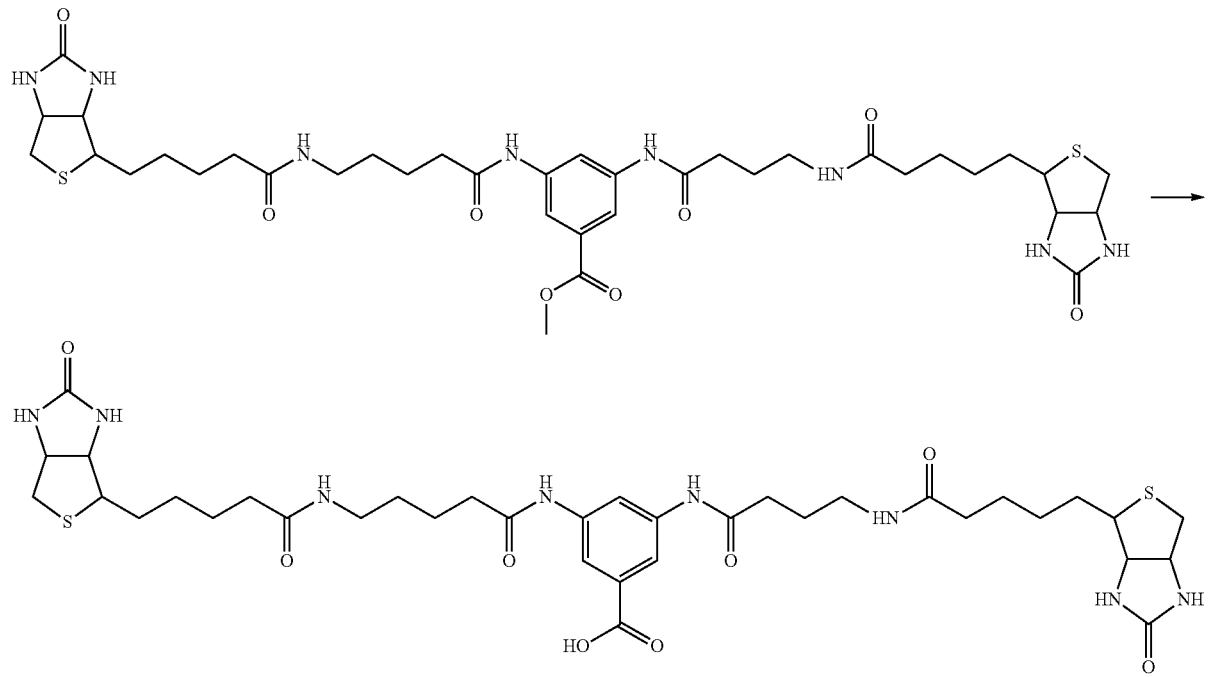

A reaction was performed in the same manner as in Example 3-6 by using 861 mg (1.07 mmol) of the methyl 3-(4-(biotinylamino)butanamido)-5-(5-(biotinylamino) pentanamido)benzoate synthesized as above to obtain 643 mg (76%) of a target reaction product of 3-(4-(biotinylamino) butanamido)-5-(5-(biotinylamino) pentanamido)benzoic acid. This compound was not purified but directly used in the following step.

(Analysis Values of Target Reaction Product)

$^1$H-NMR (DMSO-d6): 10.1 (2H, s), 8.17 (1H, s), 7.90 (2H, s), 7.8 (2H, br.t), 6.5-6.2 (4H, br), 4.35-4.25 (2H, m), 4.2-4.05 (2H, m), 3.2-2.9 (6H, m), 2.81 (2H, dd), 2.57 (2H, d), 2.31 (4H, br.t), 2.06 (4H, br.t), 1.7-1.1 (18H, m)

Example 12-3

Synthesis of tert-Butyl 1-Oxo-1-(3-(4-(biotinylamino)butanamido)-5-(5-(biotinylamino)pentanamido)phenyl)-5,8,11-trioxa-2-azatetradecan-14-oate

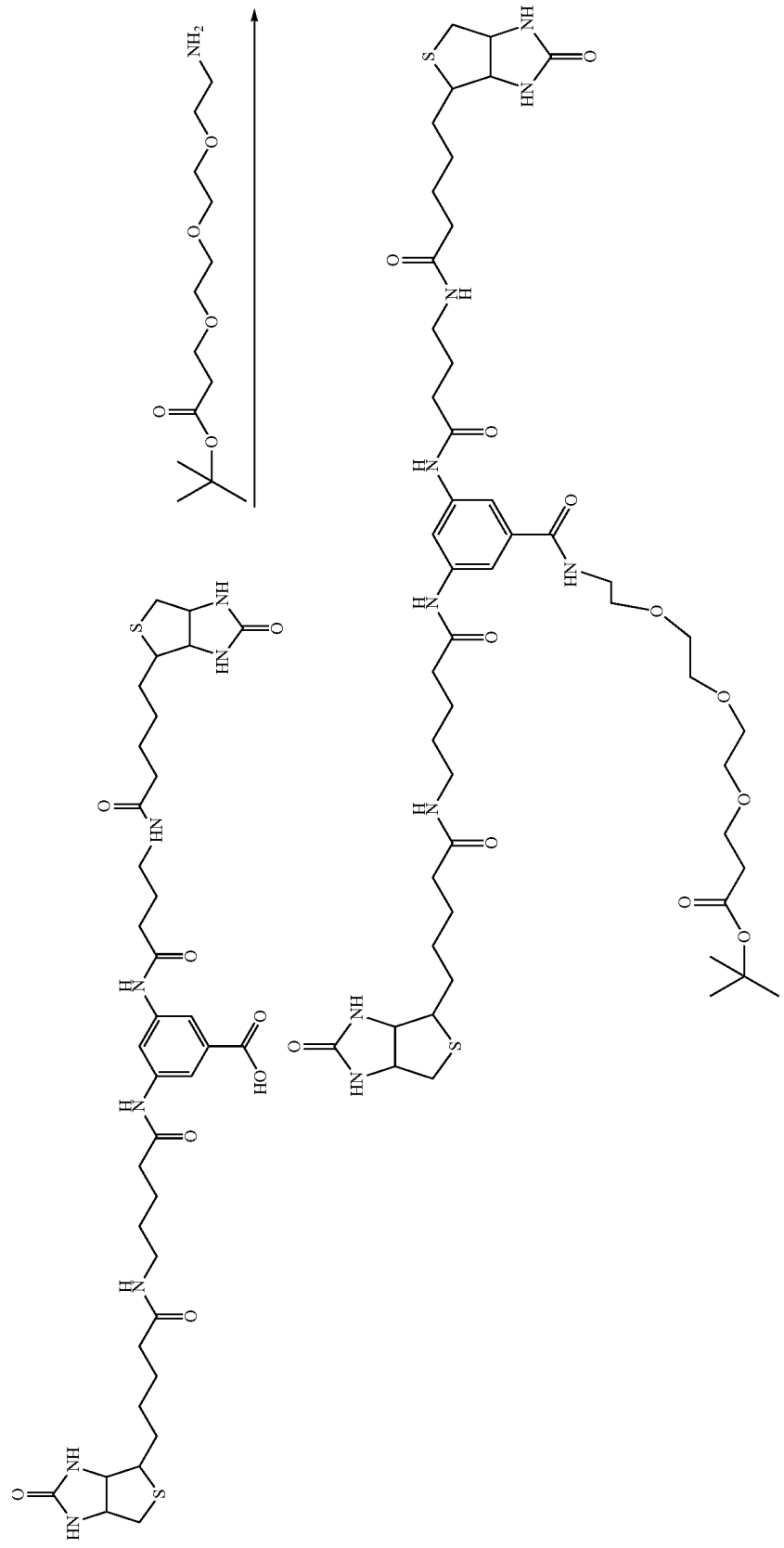

A reaction was performed in the same manner as in Example 3-7 by using 634 mg (0.804 mmol) of the 3-(4-(biotinylamino)butanamido)-5-(5-(biotinylamino) pentanamido)benzoic acid obtained by the above-described synthesis method to obtain 850 mg (100%) of a target reaction product of tert-butyl 1-oxo-1-(3-(4-(biotinylamino) butanamido)-5-(5-(biotinylamino)pentanamido)phenyl)-5,8,11-trioxa-2-azatetradecan-14-oate.

(Analysis Values of Target Reaction Product)
$^1$H-NMR (DMSO-d6): 10.03 (1H, s), 10.00 (1H, s), 8.34 (1H, br.t), 8.05 (1H, s), 7.9-7.6 (2H, m), 7.67 (2H, d), 6.42 (2H, s), 6.35 (2H, s), 4.35-4.25 (2H, m), 4.2-4.05 (2H, m), 3.6-3.3 (14H, m), 3.2-2.9 (6H, m), 2.81 (2H, dd), 2.57 (2H, d), 2.40 (2H, t), 2.31 (4H, br.t), 2.05 (4H, br.t), 1.7-1.1 (27H, m)

HPLC Retention Time (Analysis Conditions B): 4.54 min (0.1% trifluoroacetic acid aqueous solution/CH$_3$CN=85/15 (7 min) 5/95)

Example 12-4

Synthesis of 1-Oxo-1-(3-(4-(biotinylamino)butanamido)-5-(5-(biotinylamino) pentanamido)phenyl)-5,8,11-trioxa-2-azatetradecan-14-oic Acid Sulfo-NHS Ester A reaction was performed in the same manner as in Example 3-8 by using 100 mg (0.095 mmol) of the tert-butyl 1-oxo-1-(3-(4-(biotinylamino)butanamido)-5-(5-(biotinylamino)pentanamido)phenyl)-5,8,11-trioxa-2-azatetradecan-14-oate synthesized as above to obtain 1-oxo-1-(3-(4-(biotinylamino)butanamido)-5-(5-(biotinylamino) pentanamido)phenyl)-5,8,11-trioxa-2-azatetradecan-14-oic acid. Then, a reaction was performed in the same manner as in Example 3-9 by using the thus synthesized 1-oxo-1-(3-(4-(biotinylamino)butanamido)-5-(5-(biotinylamino)pentanamido)phenyl)-5,8,11-trioxa-2-azatetradecan-14-oic acid to obtain 95 mg of a target reaction product of 1-oxo-1-(3-(4-(biotinylamino)butanamido)-5-(5-(biotinylamino)pentanamido)phenyl)-5,8,11-trioxa-2-azatetradecan-14-oic acid sulfo-NHS ester.

(Analysis Values of Target Reaction Product)
$^1$H-NMR (DMSO-d6): 10.03 (1H, s), 10.00 (1H, s), 8.33 (2H, br), 8.08 (1H, s), 7.76 (2H, br.t), 7.64 (2H, d), 6.5-6.2 (4H, br), 4.35-4.25 (2H, m), 4.2-4.05 (2H, m), 4.0-3.9 (1H, br.d), 3.7 (2H, t), 3.6-3.4 (10H, m), 3.4-3.3 (2H, m), 3.2-2.8 (8H, m), 2.81 (2H, dd), 2.57 (2H, d), 2.31 (4H, t), 2.05 (4H, t), 1.7-1.1 (20H, m)

HPLC Retention Time of De-t-butyl Esterified Carboxylic Acid of Intermediate (Analysis Conditions B): 3.65 min (0.1% trifluoroacetic acid aqueous solution/CH$_3$CN=85/15 (7 min) 5/95)

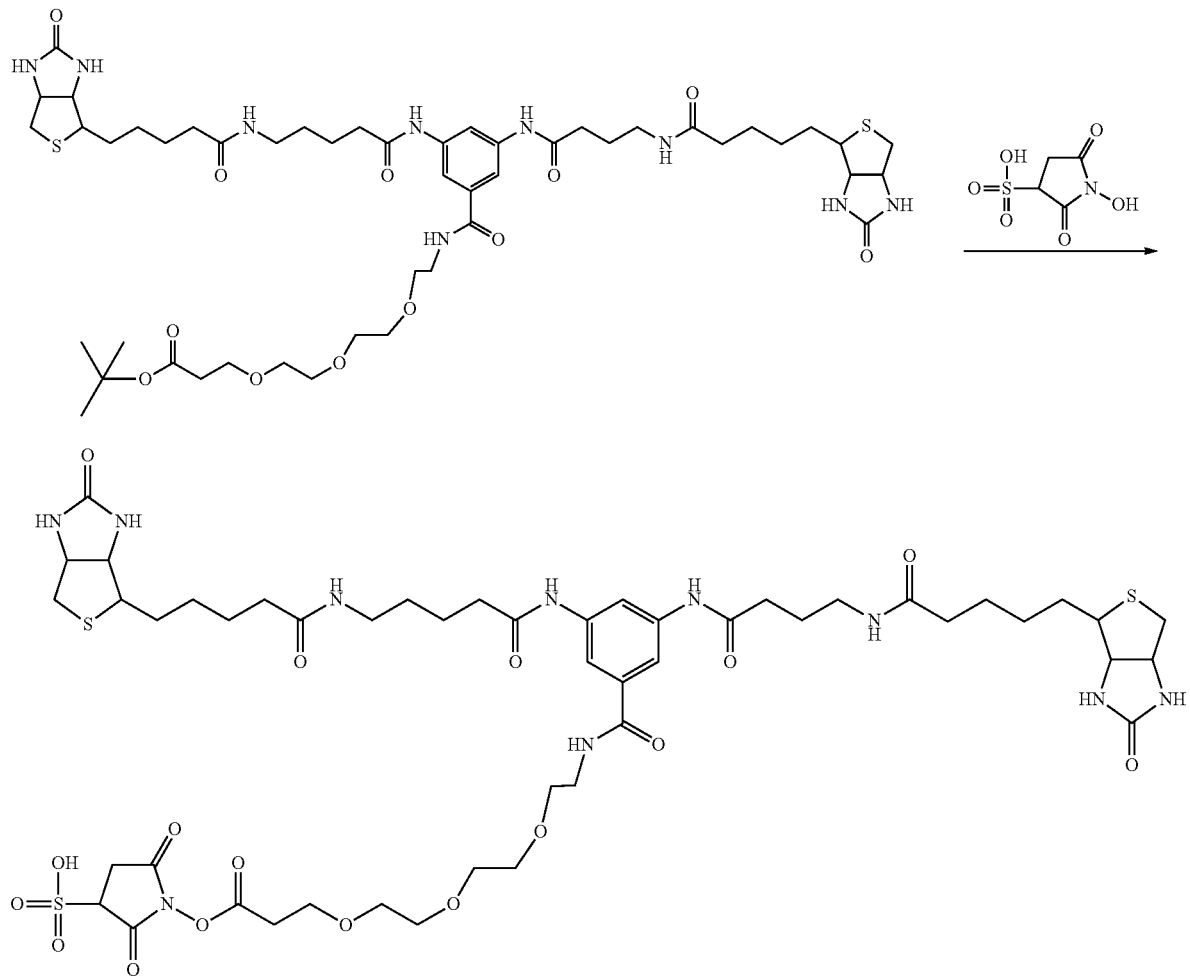

The target reaction product was reacted with N-butylamine and the HPLC analysis was performed. HPLC Retention Time of Butylamide Form (Analysis Conditions B): 4.07 min (0.1% trifluoroacetic acid aqueous solution/ CH₃CN=85/15 (7 min) 5/95)

Example 13-1

Synthesis of Methyl 3,5-Bis(5-(biotinylamino)butanamido)benzoate

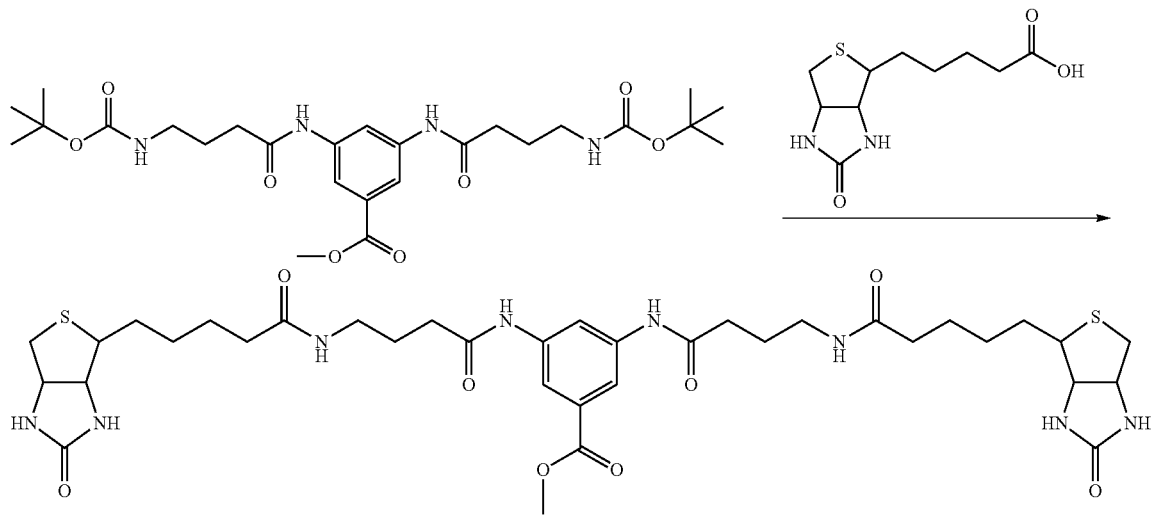

A reaction was performed in the same manner as in Examples 3-4 and 3-5 by using 1.0 g (1.86 mmol) of methyl 3,5-bis(4-((tert-butoxycarbonyl)amino)butanamido) benzoate and 1.36 g (5.58 mmol) of biotin to obtain 1.13 g (77%) of a target reaction product of methyl 3,5-bis(5-(biotinylamino)butanamido)benzoate.

(Analysis Values of Target Reaction Product)
¹H-NMR (DMSO-d6): 10.1 (2H, s), 8.17 (1H, s), 7.95 (2H, s), 7.83 (2H, br.t), 6.42 (2H, s), 6.36 (2H, s), 4.35-4.25 (2H, m), 4.2-4.05 (2H, m), 3.84 (3H, s), 3.2-2.9 (6H, m), 2.81 (2H, dd), 2.57 (2H, d), 2.29 (4H, t), 2.03 (4H, t), 1.7-1.1 (16H, m)

Example 13-2

Synthesis of 3,5-Bis(5-(biotinylamino)butanamido)benzoic Acid

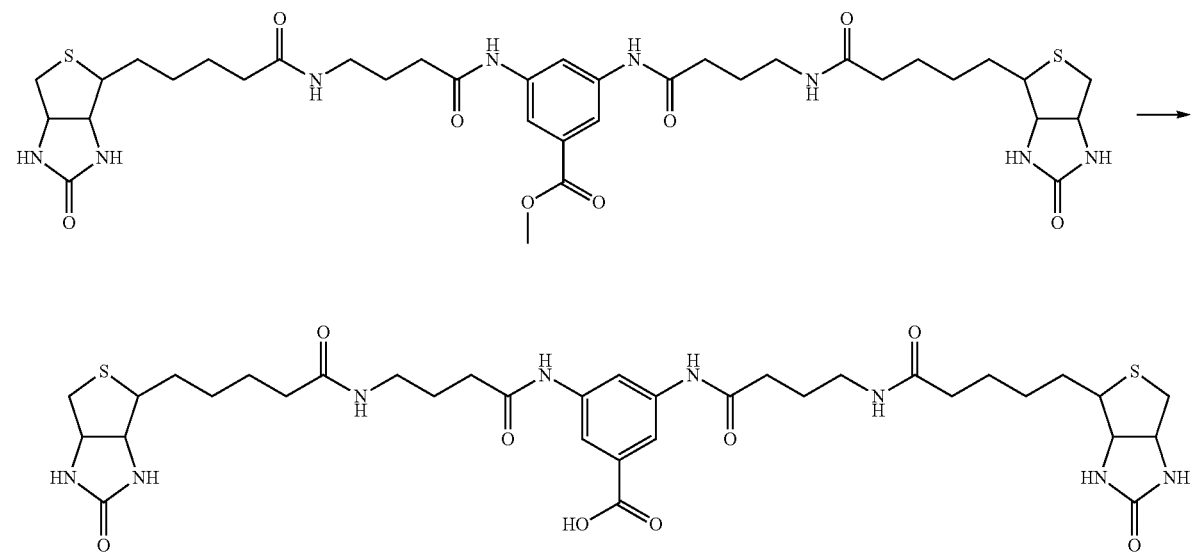

A reaction was performed in the same manner as in Example 3-6 by using 1.13 g (1.43 mmol) of the methyl 3,5-bis(5-(biotinylamino)butanamido)benzoate synthesized as above to obtain 650 mg (59%) of a target reaction product of 3,5-bis(5-(biotinylamino)butanamido)benzoic acid. This compound was not purified but directly used in the following step.

(Analysis Values of Target Reaction Product)

$^1$H-NMR (DMSO-d6): 10.1 (2H, s), 8.16 (1H, s), 7.95 (2H, s), 7.83 (2H, br.t), 6.6-6.2 (4H, br. s), 4.35-4.25 (2H, m), 4.2-4.05 (2H, m), 3.2-2.9 (6H, m), 2.81 (2H, dd), 2.57 (2H, d), 2.31 (4H, t), 2.06 (4H, t), 1.7-1.1 (16H, m)

Example 13-3

Synthesis of tert-Butyl 1-(3,5-Bis(5-(biotinylamino)buentanamido)phenyl)-1-oxo-5,8,11-trioxa-2-azatetradecan-14-oate

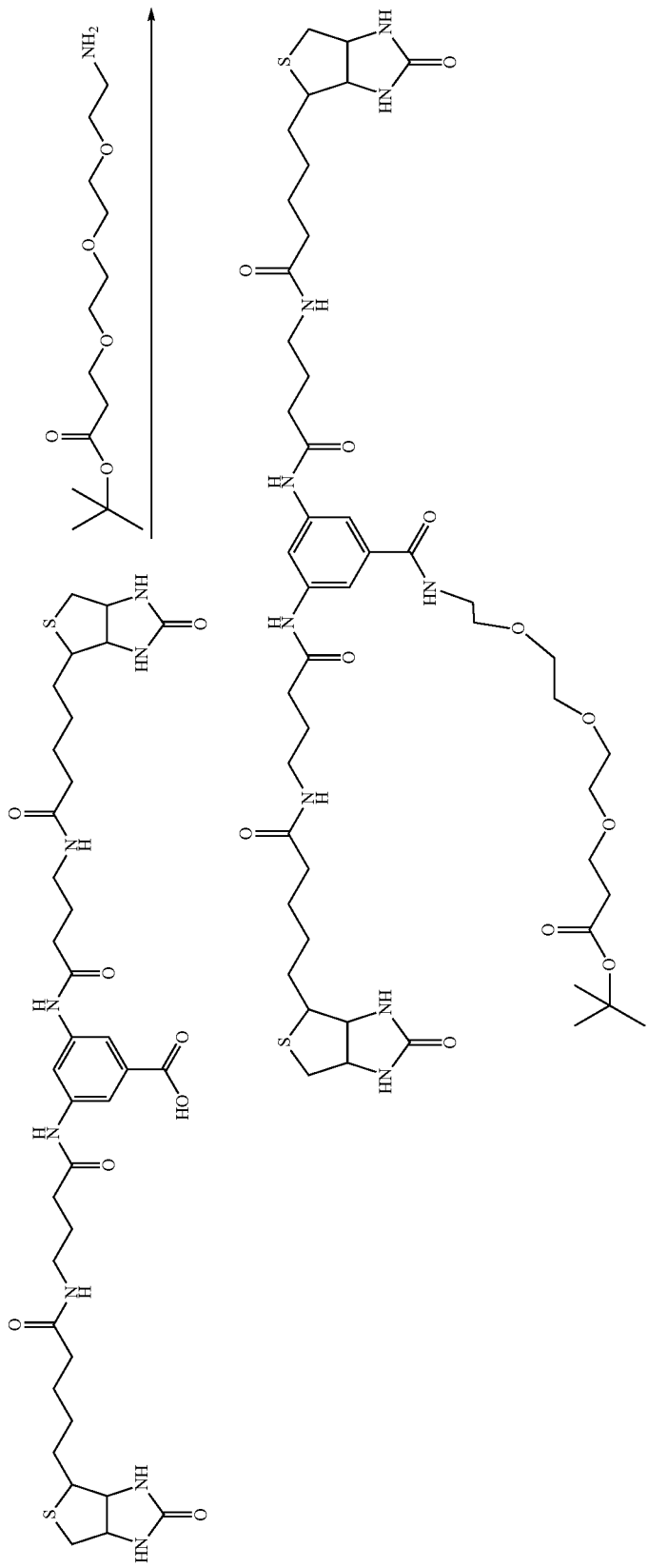

A reaction was performed in the same manner as in Example 3-7 by using 650 mg (0.839 mmol) of the 3,5-bis(5-(biotinylamino)butanamido)benzoic acid obtained by the above-described synthesis method to obtain 845 mg (97%) of a target reaction product of tert-butyl 1-(3,5-bis(5-(biotinylamino)butanamido)phenyl)-1-oxo-5,8,11-trioxa-2-azatetradecan-14-oate.

(Analysis Values of Target Reaction Product)
¹H-NMR (DMSO-d6): 10.03 (2H, s), 8.33 (1H, br.t), 8.03 (1H, s), 7.82 (2H, br.t), 7.67 (2H, s), 6.41 (2H, s), 6.35 (2H, s), 4.35-4.25 (2H, m), 4.2-4.05 (2H, m), 3.6-3.3 (14H, m), 3.2-2.9 (6H, m), 2.81 (2H, dd), 2.57 (2H, d), 2.38 (2H, t), 2.31 (4H, br.t), 2.06 (4H, br.t), 1.7-1.1 (25H, m)

HPLC Retention Time (Analysis Conditions B): 4.46 min (0.1% trifluoroacetic acid aqueous solution/CH₃CN=85/15 (7 min) 5/95)

Example 13-4

Synthesis of 1-(3,5-Bis(5-(biotinylamino)butanamido)phenyl)-1-oxo-5,8,11-trioxa-2-azatetradecan-14-oic Acid Sulfo-NHS Ester (Analysis Values of Target Reaction Product)
¹H-NMR (DMSO-d6): 10.03 (2H, s), 8.32 (2H, br), 8.08 (1H, s), 7.75 (2H, br.t), 7.66 (2H, d), 6.6-6.2 (4H, br), 4.35-4.25 (2H, m), 4.2-4.05 (2H, m), 4.0-3.9 (1H, br.d), 3.7 (2H, t), 3.6-3.4 (10H, m), 3.4-3.3 (2H, m), 3.2-2.8 (8H, m), 2.81 (2H, dd), 2.57 (2H, d), 2.31 (4H, t), 2.07 (4H, t), 1.7-1.1 (16H, m)

HPLC Retention Time of De-t-butyl Esterified Carboxylic Acid of Intermediate (Analysis Conditions B): 3.53 min (0.1% trifluoroacetic acid aqueous solution/CH₃CN=85/15 (7 min) 5/95)

The target reaction product was reacted with N-butylamine and the HPLC analysis was performed. HPLC Retention Time of Butylamide Form (Analysis Conditions B): 4.00 min (0.1% trifluoroacetic acid aqueous solution/CH₃CN=85/15 (7 min) 5/95)

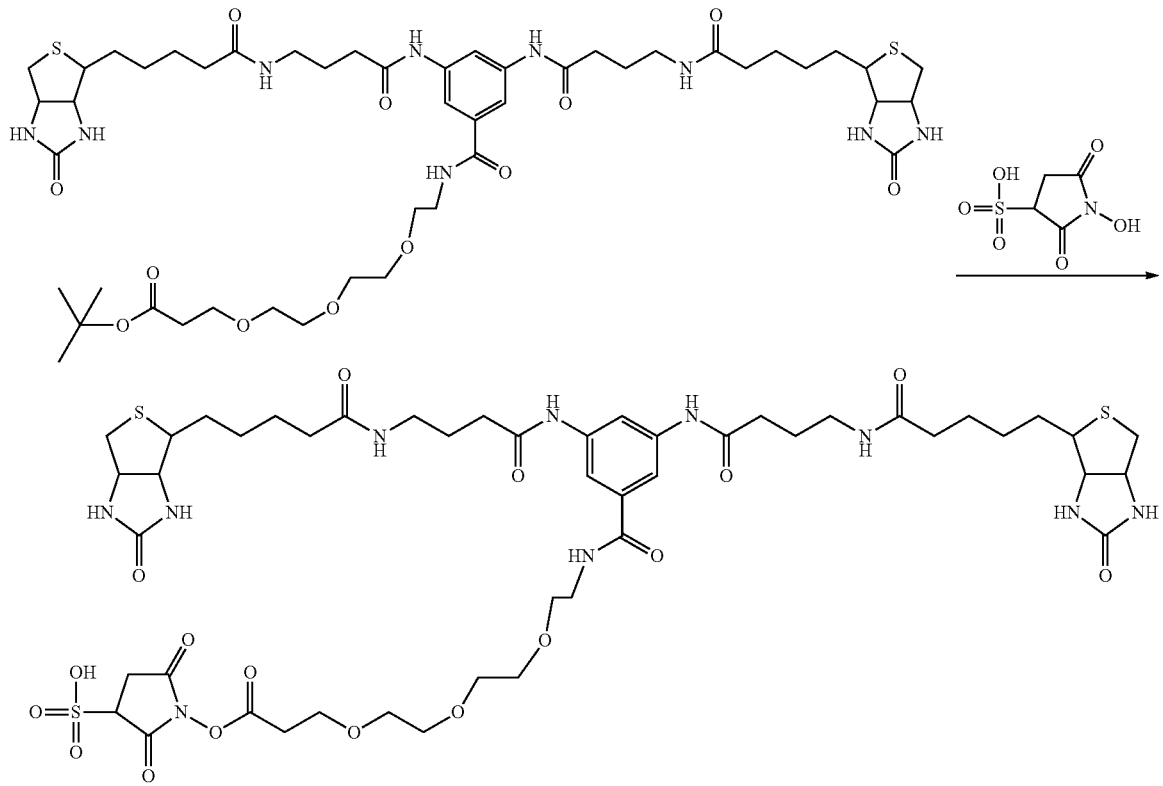 [SMILES: CC(C)(C)OC(=O)CCOCCOCCOCCNC(=O)c1cc(NC(=O)CCCNC(=O)CCCCC2SCC3NC(=O)NC32)cc(NC(=O)CCCNC(=O)CCCCC2SCC3NC(=O)NC32)c1 ; O=C1CC(S(=O)(=O)O)C(=O)N1O ; O=C(CCCCC1SCC2NC(=O)NC21)NCCCC(=O)Nc1cc(NC(=O)CCCNC(=O)CCCCC2SCC3NC(=O)NC32)cc(C(=O)NCCOCCOCCOCCC(=O)ON2C(=O)CC(S(=O)(=O)O)C2=O)c1]

A reaction was performed in the same manner as in Example 3-8 by using 100 mg (0.097 mmol) of the tert-butyl 1-(3,5-bis(5-(biotinylamino)butanamido)phenyl)-1-oxo-5,8,11-trioxa-2-azatetradecan-14-oate synthesized as above to obtain 1-(3,5-bis(5-(biotinylamino)butanamido)phenyl)-1-oxo-5,8,11-trioxa-2-azatetradecan-14-oic acid. Then, a reaction was performed in the same manner as in Example 3-9 by using the thus synthesized 1-(3,5-bis(5-(biotinylamino)butanamido)phenyl)-1-oxo-5,8,11-trioxa-2-azatetradecan-14-oic acid to obtain 112 mg of a target reaction product of 1-(3,5-bis(5-(biotinylamino)butanamido)phenyl)-1-oxo-5,8,11-trioxa-2-azatetradecan-14-oic acid sulfo-NHS ester.

Example 14-1

Synthesis of Di-tert-butyl N-(4-(Methoxycarbonyl)benzyl) Iminodiacetate

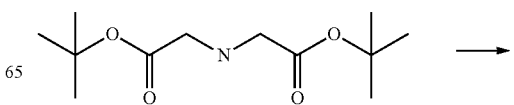

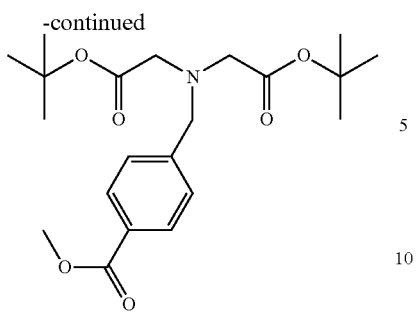

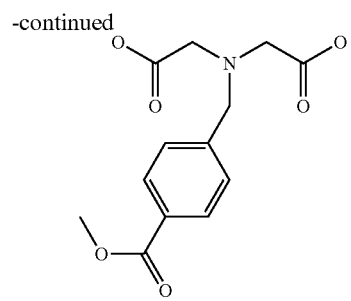

30 mL of chloroform was added to 2.5 g (10.2 mmol) of di-tert-butyl iminodiacetate and 3.13 g (13.7 mmol) of methyl 4-bromomethylbenzoate, and 1.54 g (15.3 mmol) of triethylamine was further added thereto. The resultant was heated at 65° C. for 4 hours, and then cooled, 40 mL of chloroform was added thereto, and the resultant was washed with 40 mL of a 5% citric acid aqueous solution and 30 mL of water. The resultant was dried over $Na_2SO_4$, and concentrated, and the thus obtained residue was purified by a silica gel column to obtain 1.45 g (36%) of a target reaction product of di-tert-butyl N-(4-(methoxycarbonyl)benzyl) iminodiacetate.

(Analysis Values of Target Reaction Product)
$^1$H-NMR ($CDCl_3$): 7.99 (2H, d), 7.48 (2H, d), 3.95 (2H, s), 3.91 (3H, s), 3.41 (4H, s), 1.46 (9H, s)

Example 14-2

Synthesis of N-(4-(Methoxycarbonyl)benzyl) Iminodiacetic Acid 9.2 mL of a 4N HCl/dioxane solution was added to 1.44 g (3.7 mmol) of the di-tert-butyl N-(4-(methoxycarbonyl) benzyl) iminodiacetate synthesized as above, and the resultant was allowed to stand still at room temperature for 2 days. The thus precipitated solid was filtered off, and washed with 10 mL of dioxane. The resultant was dried under reduced pressure at 50° C. to obtain 1.16 g of a target reaction product of N-(4-(methoxycarbonyl)benzyl) iminodiacetic acid. The product was not purified but directly used in the following step.

(Analysis Values of Target Reaction Product)
$^1$H-NMR (DMSO-d5): 7.97 (2H, d), 7.63 (2H, d), 4.30 (2H, br.s), 3.87 (3H, s), 3.41 (7H, br.s)

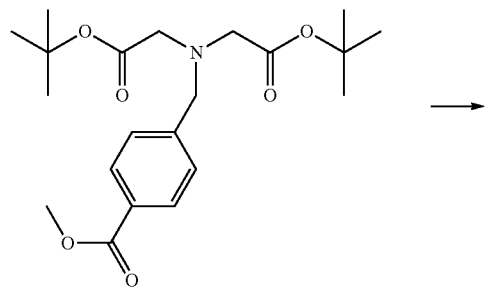

Example 14-3

Synthesis of Methyl 4-((Bis(2-oxo-2-((4-(biotinylamino)butyl)amino)ethyl)amino) methyl)benzoate

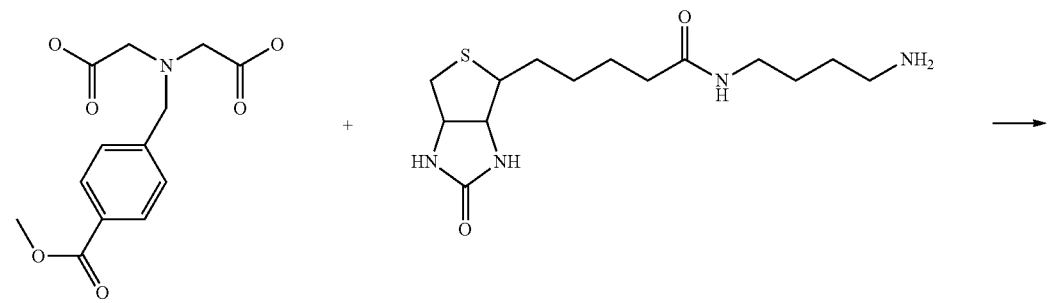

-continued

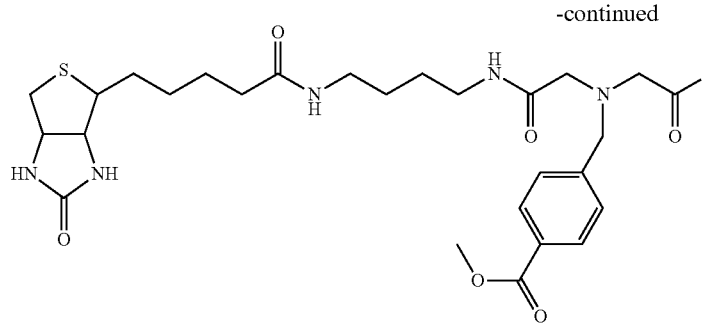

23 mL of DMF was added to 1.15 g (3.62 mmol) of the N-(4-(methoxycarbonyl)benzyl) iminodiacetic acid synthesized as above and 3.42 g (8.0 mmol) of 4-(biotinylamino)butylamine trifluoroacetate, and 2.2 g (22 mmol) of triethylamine and 4.12 (10.9 mmol) of HBTU were further added thereto, followed by stirring under heating at 45° C. for 4 hours. After concentration of the DMF, the resultant was neutralized with 1N hydrochloric acid water under ice cooling. The thus separated oil was separated, and the resultant aqueous layer was extracted with 30 mL of chloroform. The separated oil and the organic layer were combined, and the resultant was concentrated and purified by a silica gel column to obtain 1.28 g (90%) of a target reaction product of methyl 4-((bis(2-oxo-2-((4-(biotinylamino)butyl)amino)ethyl)amino)methyl)benzoate.

(Analysis Values of Target Reaction Product)
$^1$H-NMR (DMSO-d6): 8.19 (2H, br. S), 7.96 (2H, d), 7.76 (2H, t), 7.56 (2H, d), 6.6-6.2 (4H, br), 4.35-4.25 (2H, m), 4.15-4.1 (2H, m), 3.86 (3H, s), 3.2-2.9 (10H, m), 2.79 (2H, dd), 2.53 (2H, d), 2.04 (4H, t), 1.7-1.1 (20H, m)

Example 14-4

Synthesis of 4-((Bis(2-oxo-2-((4-(biotinylamino)butyl)amino)ethyl)amino)methyl) benzoic Acid

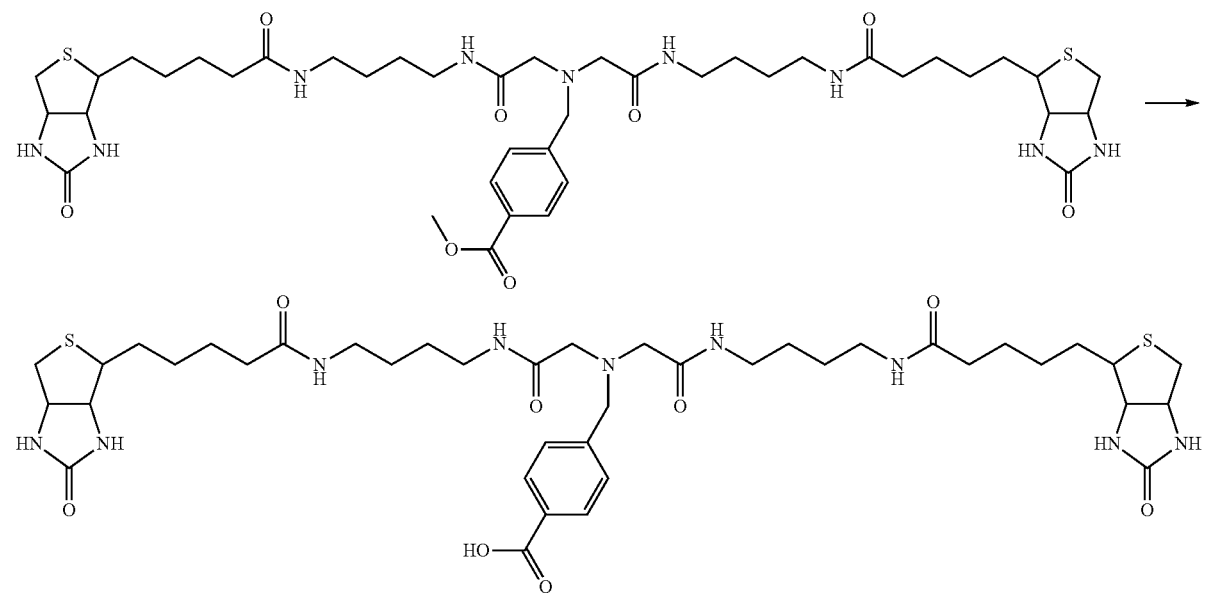

To 1.67 g (1.91 mmol) of the methyl 4-((bis(2-oxo-2-((4-(biotinylamino)butyl) amino)ethyl)amino)methyl)benzoate synthesized as above, 7 mL of methanol, 2 mL of water and 0.24 g (5.7 mmol) of a lithium hydroxide hydrate were added, followed by stirring under heating at 50° C. for 2.5 hours. The solvent was concentrated under reduced pressure, and the resultant was acidified with 1N hydrochloric acid. The thus precipitated gum was dried under reduced pressure to obtain 1.4 g (86%) of a target reaction product of 4-((bis(2-oxo-2-((4-(biotinylamino)butyl)amino)ethyl)amino)methyl) benzoic acid in an amorphous form.

(Analysis Values of Target Reaction Product)
$^1$H-NMR (DMSO-d6): 8.3 (2H, br. S), 7.95 (2H, d), 7.73 (2H, t), 7.55 (2H, d), 6.6-6.3 (4H, br), 4.35-4.25 (2H, m), 4.15-4.1 (2H, m), 3.8-3.6 (2H, br), 3.2-2.9 (10H, m), 2.79 (2H, dd), 2.53 (2H, d), 2.04 (4H, t), 1.7-1.1 (20H, m)

Example 14-5

Synthesis of tert-Butyl 1-(4-((Bis(2-oxo-2-((4-(biotinylamino)butyl)amino)ethyl) amino)methyl)phenyl)-1-oxo-5,8,11-trioxa-2-azatetradecan-14-oate

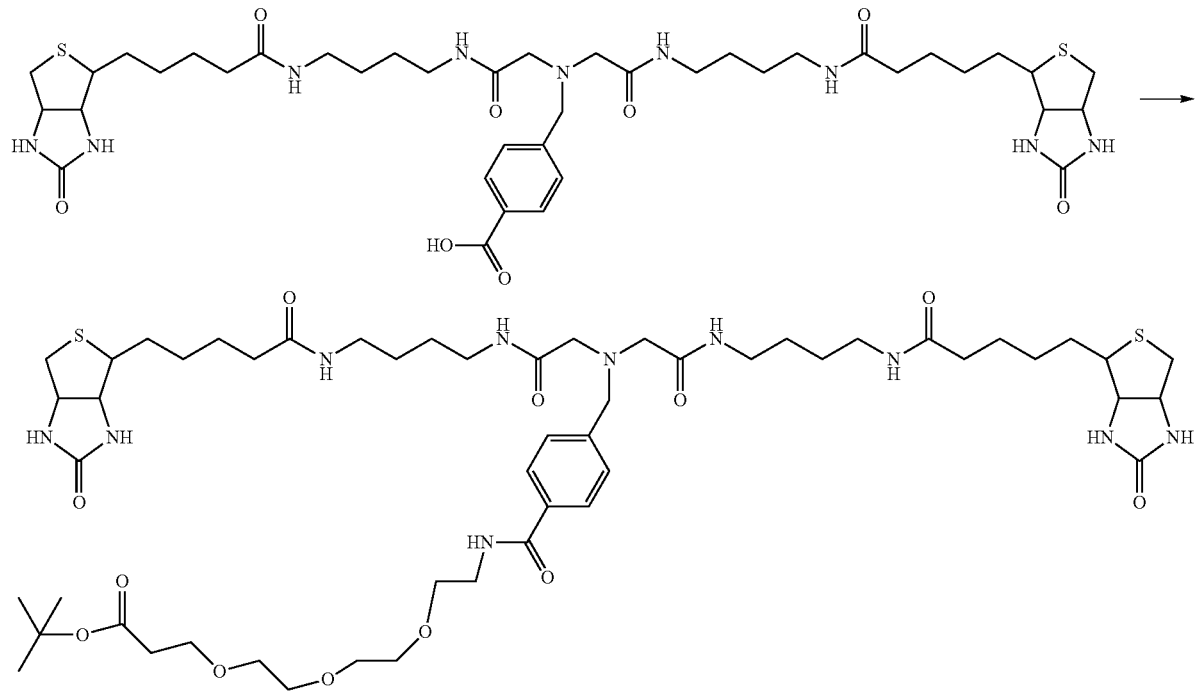

A reaction was performed in the same manner as in Example 3-7 by using 0.30 g (0.35 mmol) of the 4-((bis(2-oxo-2-((4-(biotinylamino)butyl)amino)ethyl)amino)methyl) benzoic acid synthesized as above to obtain 104 mg (27%) of a target reaction product of tert-butyl 1-(4-((bis(2-oxo-2-((4-(biotinylamino)butyl)amino)ethyl)amino)methyl)phenyl)-1-oxo-5,8,11-trioxa-2-azatetradecan-14-oate.

(Analysis Values of Target Reaction Product)
$^1$H-NMR (DMSO-d6): 8.5 (1H, br.t), 8.1 (2H, t), 7.9-7.7 (4H, m), 7.44 (2H, t), 6.41 (2H, s), 6.35 (2H, s), 4.35-4.25 (2H, m), 4.15-4.1 (2H, m), 3.69 (2H, s), 3.6-3.4 (16H, m), 3.2-2.9 (10H, m), 2.79 (2H, dd), 2.58 (2H, d), 2.40 (2H, t), 2.04 (4H, t), 1.8-1.2 (20H, m), 1.38 (9H, s)

HPLC Retention Time (Analysis Conditions B): 4.37 min (0.1% trifluoroacetic acid aqueous solution/CH$_3$CN=85/15 (7 min) 5/95)

Example 14-6

Synthesis of 1-(4-((Bis(2-oxo-2-((4-(biotinylamino) butyl)amino)ethyl)amino) methyl)phenyl)-1-oxo-5,8,11-trioxa-2-azatetradecan-14-oic Acid Sulfo-NHS Ester

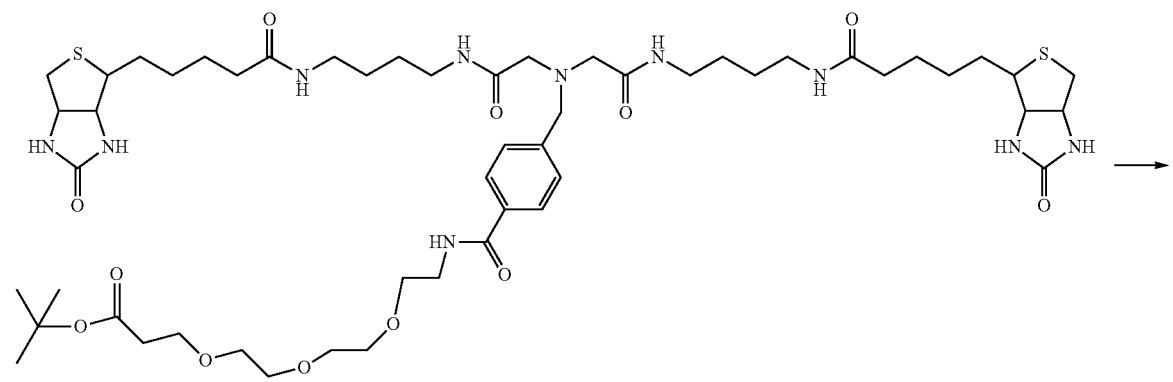

-continued

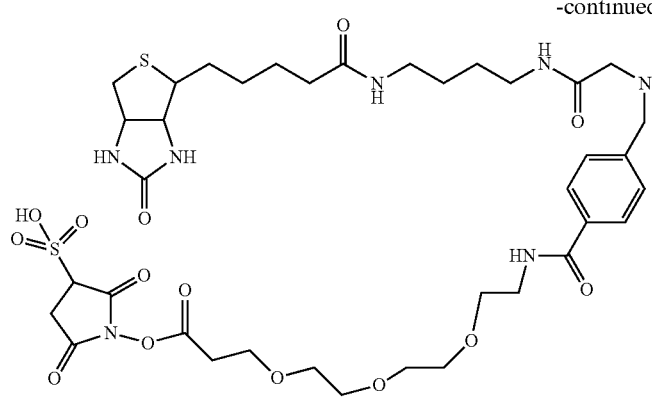
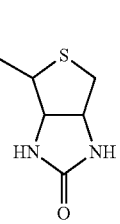

A reaction was performed in the same manner as in Examples 3-8 and 3-9 by using 100 mg (0.089 mmol) of the tert-butyl 1-(4-((bis(2-oxo-2-((4-(biotinylamino)butyl)amino)ethyl)amino)methyl)phenyl)-1-oxo-5,8,11-trioxa-2-azatetradecan-14-oate synthesized as above to obtain 44 mg (40%) of a target reaction product of 1-(4-((bis(2-oxo-2-((4-(biotinylamino)butyl)amino)ethyl)amino)methyl)phenyl)-1-oxo-5,8,11-trioxa-2-azatetradecan-14-oic acid sulfo-NHS ester.

(Analysis Values of Target Reaction Product)

$^1$H-NMR (DMSO-d6): 8.62 (1H, br.t), 7.93 (2H, br.d), 7.73 (2H, br.t), 7.65 (2H, br.d), 6.5-6.3 (4H, br), 4.4-4.25 (4H, m), 4.15-4.1 (2H, m), 4.0-3.9 (1H, br.d), 3.69 (2H, m), 3.6-3.3 (18H, m), 3.2-2.9 (10H, m), 2.79 (2H, dd), 2.58 (2H, d), 2.05 (4H, t), 1.8-1.1 (20H, m)

HPLC Retention Time of De-t-butyl Esterified Carboxylic Acid of Intermediate (Analysis Conditions B): 3.51 min (0.1% trifluoroacetic acid aqueous solution/CH$_3$CN=85/15 (7 min) 5/95)

The target reaction product was reacted with N-butylamine and the HPLC was performed. HPLC Retention Time of Butylamide Form (Analysis Conditions B): 3.92 min (0.1% trifluoroacetic acid aqueous solution/CH$_3$CN=85/15 (7 min) 5/95)

Example 14-7

Synthesis of 7-(3-(1-(3,5-Bis(6-(biotinyl)amino) hexanamido)phenyl)-1-oxo-5,8,11-trioxa-2-azatetradecan-14-amido)pyrrolidin-1-yl)-1-(2,4-difluorophenyl)-6-fluoro-4-oxo-1,4-dihydro-1,8-naphthyridine-3-carboxylic Acid 175
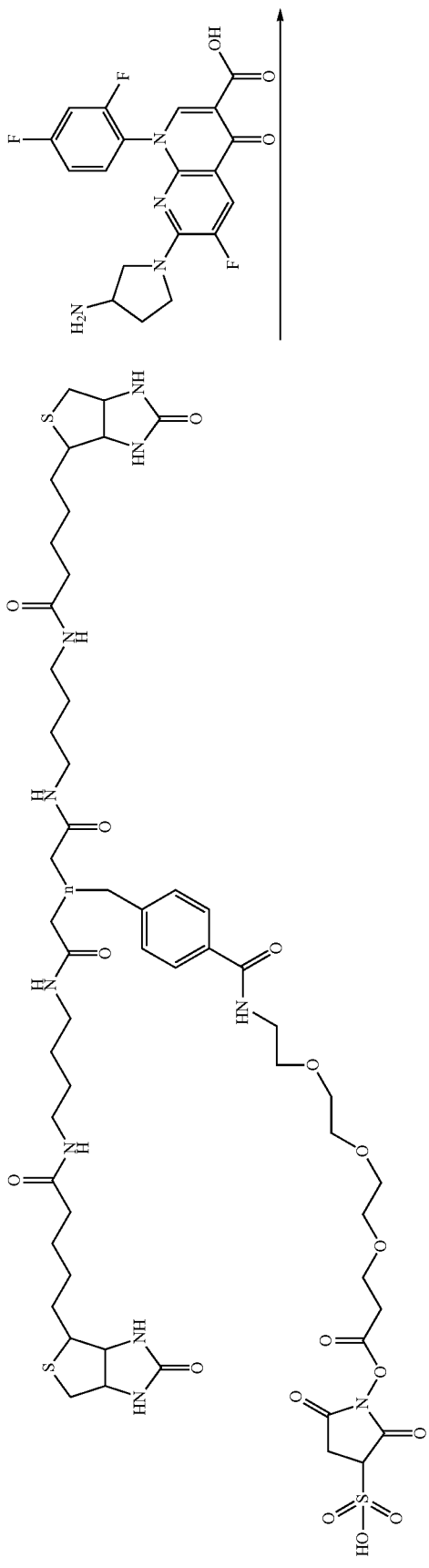
176
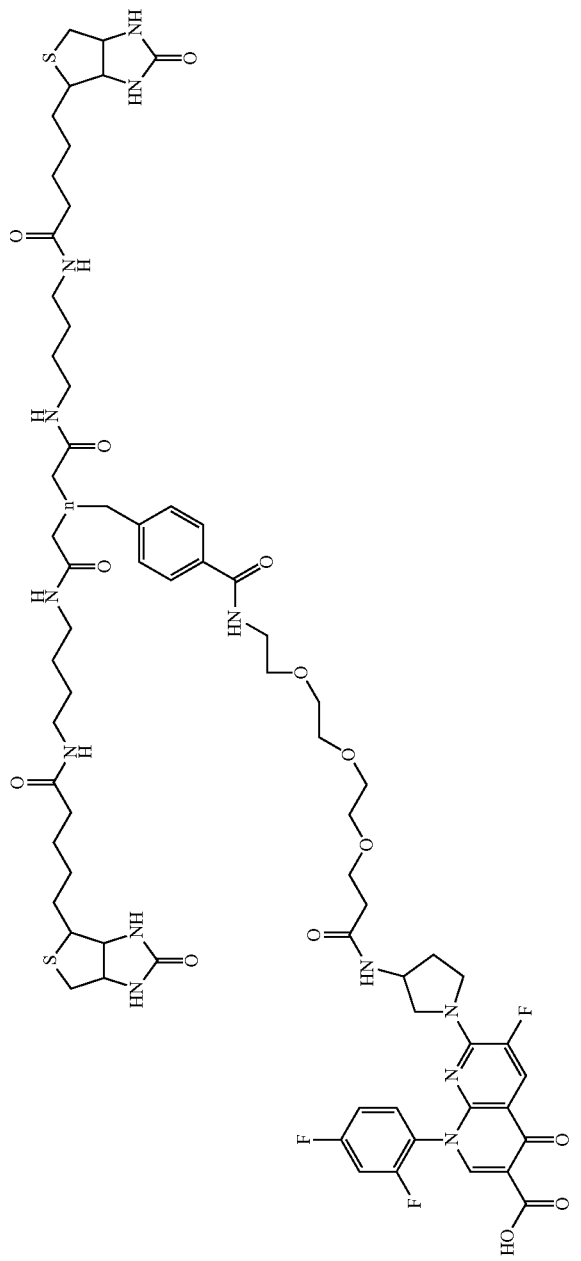

7 mg (5.8 μmol) of the 1-(3,5-bis(6-(biotinyl)amino) hexanamido)phenyl)-1-oxo-5,8,11-trioxa-2-azatetradecan-14-oic acid sulfo-NHS ester synthesized in Example 8-4 was dissolved in 1 mL of dehydrated DMF, 5 mg (8.7 μmol) of a new quinolone-based antibacterial agent of tosufloxacin tosylate and 20 μL of triethylamine were added thereto, followed by stirring at room temperature for 1 hour. The DMF was concentrated, and the resultant was washed with 1 mL of water. The thus obtained residue was purified by a silica gel column to obtain 3 mg of a target reaction product of 7-(3-(1-(3,5-bis(6-(biotinyl)amino)hexanamido)phenyl)-1-oxo-5,8,11-trioxa-2-azatetradecan-14-amido)pyrrolidin-1-yl)-1-(2,4-difluorophenyl)-6-fluoro-4-oxo-1,4-dihydro-1,8-naphthyridine-3-carboxylic acid.

(Analysis Values of Target Reaction Product)
$^1$H-NMR (DMSO-d6): 9.76 (2H, s), 8.81 (1H, s), 8.34 (2H, br), 8.15-8.0 (3H, br), 7.85-7.7 (3H, br), 7.66 (2H, d), 7.58 (2H, br.t), 7.33 (2H, br.t), 6.42 (2H, s), 6.36 (2H, s), 4.35-4.25 (2H, m), 4.2-4.05 (2H, m), 3.56 (2H, t), 3.5-3.4 (10H, m), 3.4-3.3 (2H, m), 3.2-2.9 (8H, m), 2.81 (2H, dd), 2.57 (2H, d), 2.27 (6H, br.t), 2.04 (4H, t), 1.7-1.1 (24H, m)

HPLC Retention Time (Analysis Conditions B): 4.92 min (0.1% trifluoroacetic acid aqueous solution/CH$_3$CN=85/15 (7 min) 5/95)

Example 14-8

Synthesis of tert-Butyl 17-(4-(1-Hydroxyethyl)-2-methoxy-5-nitrophenoxy)-14-oxo-4,7,10-trioxa-13-azaheptadecanoate

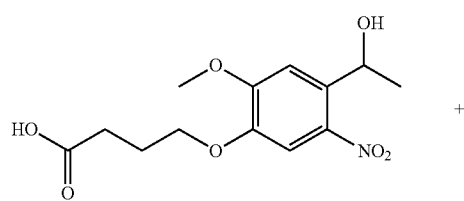

+

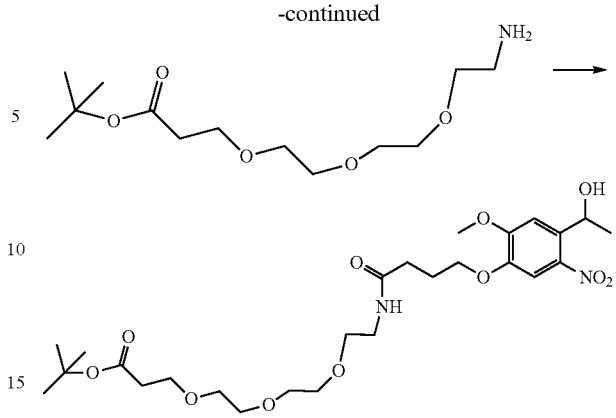

500 mg (1.67 mmol) of 4-(4-(1-hydroxyethyl)-2-methoxy-5-nitrophenoxy)butanoic acid, 309 mg (2.5 mmol) of tert-butyl 3-(2-(2-(2-aminoethoxy)ethoxy)ethoxy)propanoate and 507 mg (5 mmol) of triethylamine were added to 10 mL of THF, and 481 mg (2.5 mmol) of EDC hydrochloride was further added thereto. The resultant was stirred at room temperature overnight, and after confirming termination of the reaction, the solvent was distilled off. 5% citric acid and chloroform were added to the resultant, and the thus obtained organic layer was washed with water, dried and concentrated to obtain 579 mg (85%) of a target reaction product of tert-butyl 17-(4-(1-hydroxyethyl)-2-methoxy-5-nitrophenoxy)-14-oxo-4,7,10-trioxa-13-azaheptadecanoate.

(Analysis Values of Target Reaction Product)
$^1$H-NMR (CDCl$_3$): 9.57 (1H, s), 7.31 (1H, s), 6.3 (1H, br), 5.55 (1H, q), 4.11 (2H, t), 3.98 (3H, s), 3.69 (2H, t), 3.6-3.4 (12H, m), 2.49 (2H, t), 2.42 (2H, t), 2.3-2.2 (2H, m), 1.55 (3H, d), 1.44 (9H, s)

Example 14-9

Synthesis of tert-Butyl 17-(4-(1-((3,5-Bis(6-(biotinyl)amino)hexanamido)benzoyl) oxy)ethyl)-2-methoxy-5-nitrophenoxy)-14-oxo-4,7,10-trioxa-13-azaheptadecanoate

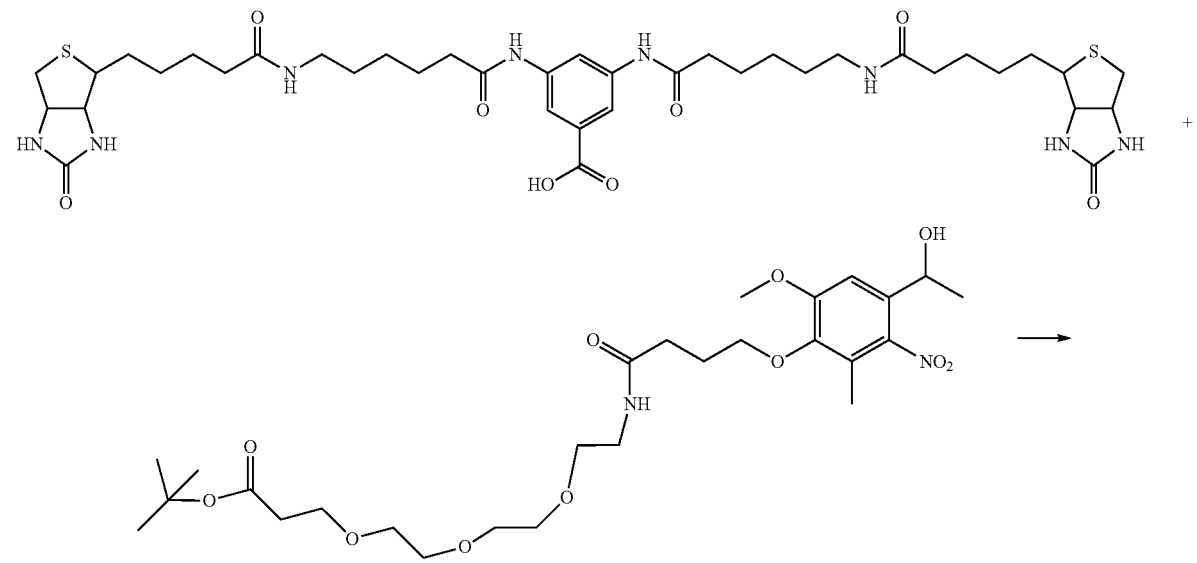

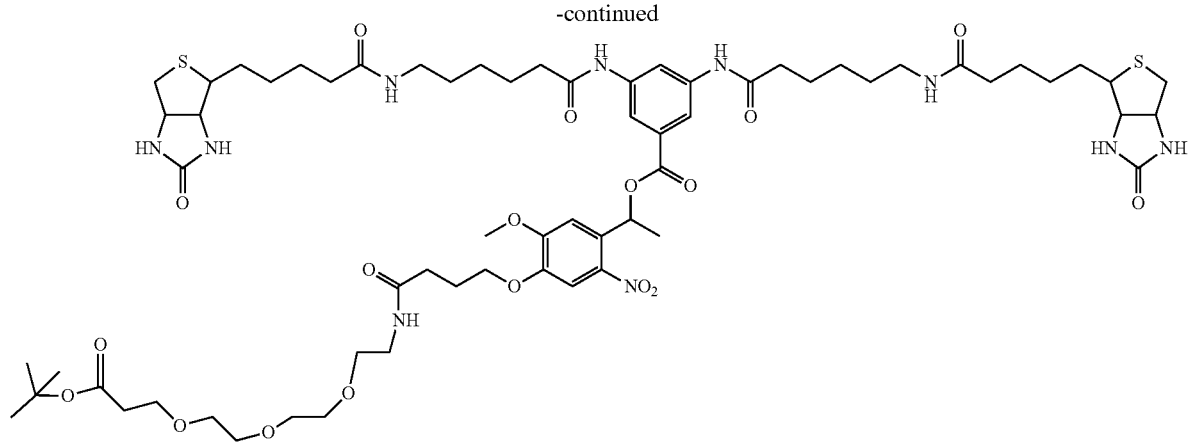

307 mg (0.37 mmol) of the 3,5-bis(6-(biotinylamino)hexanamido)benzoic acid synthesized in Example 8-2 and 246 mg (0.44 mmol) of tert-butyl 17-(4-(1-hydroxyethyl)-2-methoxy-5-nitrophenoxy)-14-oxo-4,7,10-trioxa-13-azaheptadecanoate synthesized as above were added to dry DMF. The resultant was subjected to condensation using 2-methyl-6-nitrobenzoic anhydride, triethylamine and dimethylaminopyridine by an ordinary method to obtain 307 mg (61%) of a target reaction product of tert-butyl 17-(4-(1-((3,5-bis(6-(biotinyl)amino)hexanamido)benzoyl)oxy)ethyl)-2-methoxy-5-nitrophenoxy)-14-oxo-4,7,10-trioxa-13-azaheptadecanoate.

(Analysis Values of Target Reaction Product)
$^1$H-NMR (DMSO-d6): 10.1 (2H, s), 8.15 (1H, s), 8.01 (2H, d), 7.91 (1H, br.t), 7.74 (2H, t), 7.61 (1H, s), 7.25 (1H, s), 6.49 (1H, q), 6.40 (2H, s), 6.35 (2H, s), 4.35-4.25 (2H, m), 4.2-4.0 (4H, m), 3.96 (3H, s), 3.54 (2H, t), 3.47 (2H, t), 3.45 (10H, d), 3.39 (2H, t), 3.2-2.9 (8H, m), 2.81 (2H, dd), 2.56 (2H, d), 2.4-2.2 (8H, m), 2.1-1.9 (6H, m), 1.7-1.2 (24H, m), 1.38 (9H, s)

HPLC Retention Time (Analysis Conditions B): 6.19 min (0.1% trifluoroacetic acid aqueous solution/CH$_3$CN=85/15 (7 min) 20/80)

Example 14-10

Synthesis of 1-((17-(4-(1-((3,5-Bis(6-(biotinyl)amino)hexanamido)benzoyl)oxy) ethyl)-2-methoxy-5-nitrophenoxy)-14-oxo-4,7,10-trioxa-13-azaheptadecanoic Acid Sulfo-NHS Ester

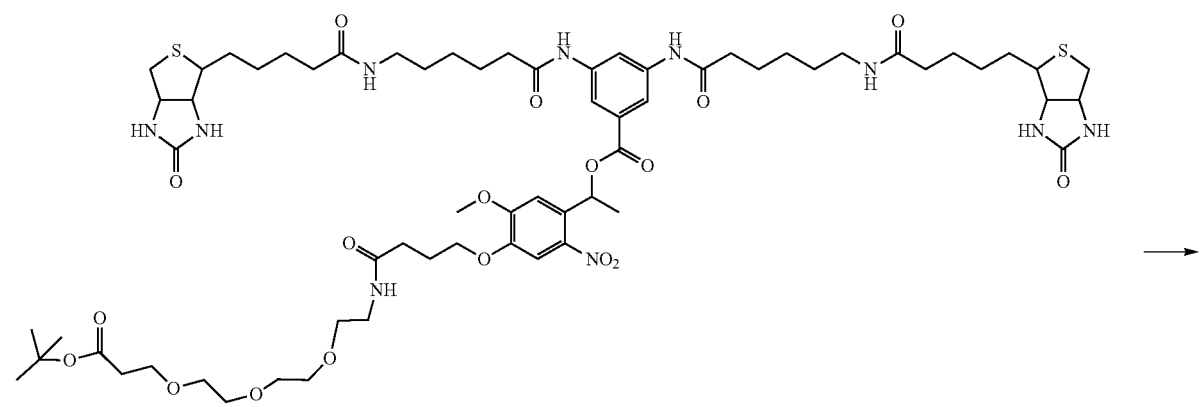

-continued

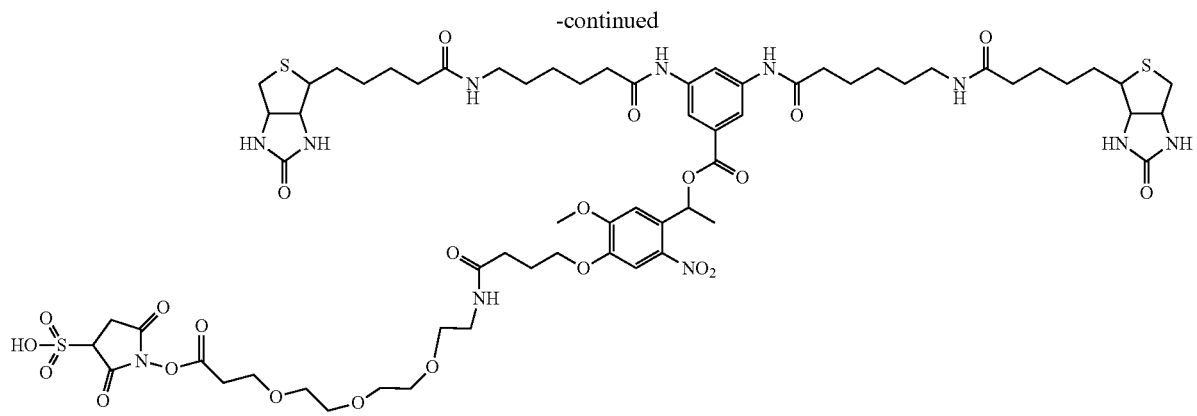

295 mg (0.215 mmol) of the tert-butyl 17-(4-(1-((3,5-bis(6-(biotinyl)amino) hexanamido)benzoyl)oxy)ethyl)-2-methoxy-5-nitrophenoxy)-14-oxo-4,7,10-trioxa-13-azaheptadecanoate synthesized as above was dissolved in 1 mL of trifluoroacetic acid, followed by stirring at room temperature for 30 minutes. After confirming removal of a t-butyl group by the HPLC, the resultant was concentrated under reduced pressure to obtain 17-(4-(1-((3,5-bis(6-(biotinyl)amino) hexanamido)benzoyl)oxy)ethyl)-2-methoxy-5-nitrophenoxy)-14-oxo-4,7,10-trioxa-13-azaheptadecanoic acid. This compound was not purified but directly used in a reaction performed in the same manner as in Example 3-9 to obtain 327 mg (quantitative) of a target reaction product of 1-((17-(4-(1-((3,5-bis(6-(biotinyl)amino)hexanamido)benzoyl) oxy)ethyl)-2-methoxy-5-nitrophenoxy)-14-oxo-4,7,10-trioxa-13-azaheptadecanoic acid sulfo-NHS ester.

(Analysis Values of Target Reaction Product)
$^1$H-NMR (DMSO-d6): 10.1 (2H, s), 8.17 (1H, s), 8.01 (2H, d), 7.95 (2H, br.d), 7.75 (2H, t), 7.61 (1H, s), 7.25 (1H, s), 6.49 (1H, q), 6.42 (2H, s), 6.35 (2H, s), 4.35-4.25 (2H, m), 4.2-4.0 (4H, m), 3.96 (3H, s), 3.93 (1H, br), 3.70 (2H, t), 3.49 (10H, d), 3.45-3.3 (8H, m), 3.25-2.95 (10H, m), 2.95-2.8 (4H, m), 2.60 (2H, d), 2.4-2.2 (6H, m), 2.04 (4H, t), 1.95 (2H, t), 1.7-1.2 (24H, m)

HPLC Retention Time (Analysis Conditions B): de-t-butyl esterified carboxylic acid of intermediate: 5.27 min (0.1% trifluoroacetic acid aqueous solution/CH$_3$CN=85/15 (7 min) 20/80)

HPLC Retention Time of Target Reaction Product (Analysis Conditions B): 4.88 min (0.1% trifluoroacetic acid aqueous solution/CH$_3$CN=85/15 (7 min) 20/80)

The product was reacted with N-butylamine and the HPLC analysis was performed.

HPLC Retention Time (Analysis Conditions B): butylamide form: 5.65 min (0.1% trifluoroacetic acid aqueous solution/CH$_3$CN=85/15 (7 min) 20/80)

[Example 14-11] PB-15 (Reductive Cleavage)

Synthesis of tert-Butyl 1-(3,5-Bis(6-(biotinyl) amino)hexanamido)phenyl)-7,10-dimethyl-1,6,11-trioxo-15,18,21-trioxa-8,9-dithia-2,5,12-triazatetracosan-24-oate

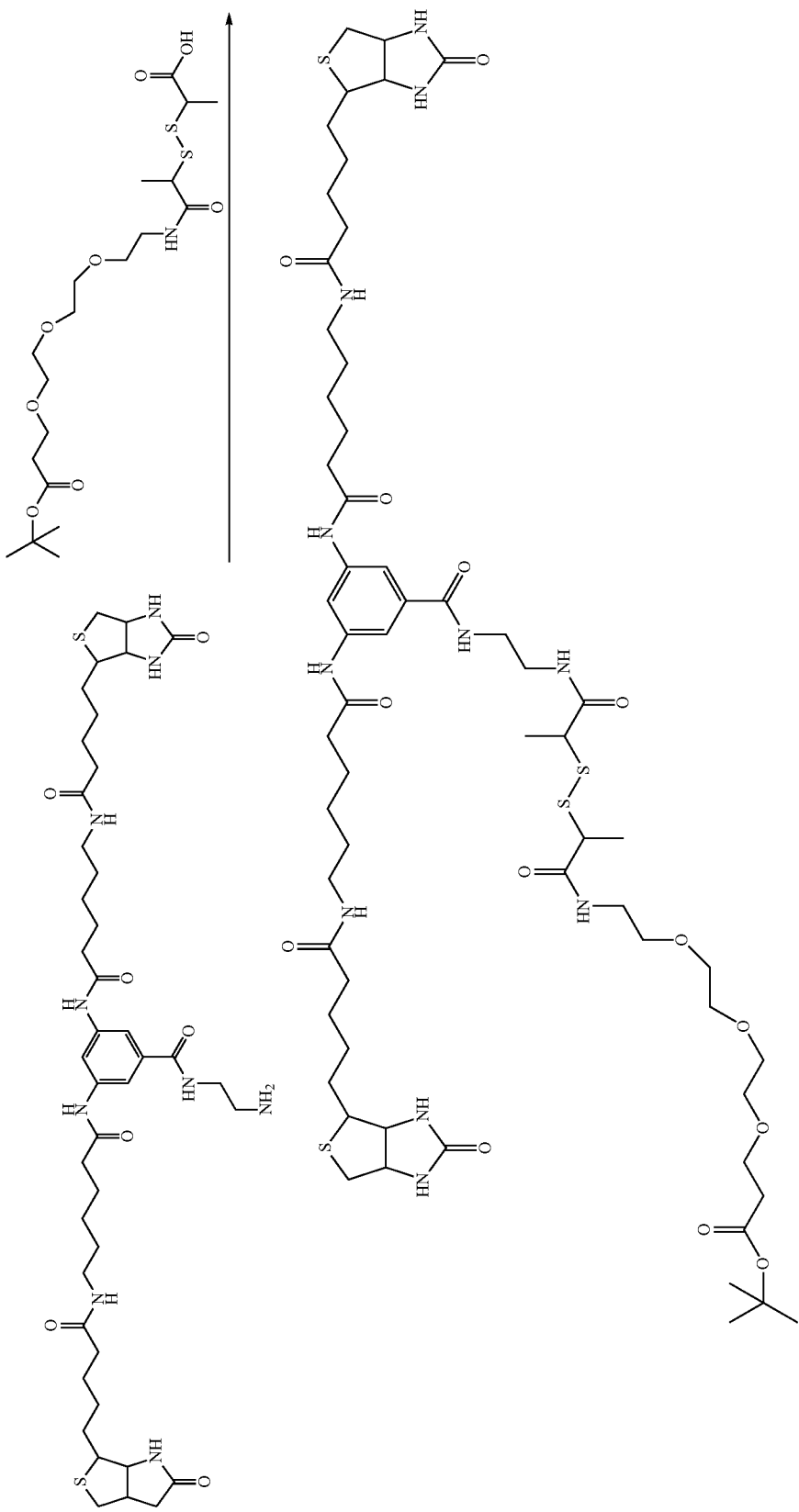

A reaction was performed in the same manner as in Example 3-7 by using 177 mg (0.18 mmol) of (3,5-bis(6-(biotinylamino)hexanamido)-N-(2-aminoethyl)benzamide and 126 mg (0.27 mmol) of 2,5,21,21-tetramethyl-6,19-dioxo-10,13,16,20-tetraoxa-3,4-dithia-7-azadocosanoic acid to obtain 85 mg (36%) of a target reaction product of tert-butyl 1-(3,5-bis(6-(biotinyl)amino)hexanamido)phenyl)-7,10-dimethyl-1,6,11-trioxo-15,18,21-trioxa-8,9-dithia-2,5,12-triazatetracosan-24-oate.

(Analysis Values of Target Reaction Product)
$^1$H-NMR (DMSO-d6): 9.98 (2H, s), 8.39 (1H, br.t), 8.2-8.0 (3H, m), 7.74 (2H, t), 7.68 (2H, s), 6.41 (2H, s), 6.35 (2H, s), 4.35-4.25 (2H, m), 4.2-4.05 (2H, m), 3.57 (2H, t), 3.6-3.4 (12H, m), 3.35-3.0 (10H, m), 2.81 (2H, dd), 2.57 (2H, d), 2.40 (2H, t), 2.30 (4H, t), 2.04 (4H, t), 1.7-1.2 (30H, m), 1.39 (9H, s)

Retention Time under HPLC Analysis Conditions A: 11.5 min (0.1% trifluoroacetic acid aqueous solution/CH$_3$CN=85/15 (12 min) 5/95)

[Example 14-12] PB-15 (Reductive Cleavage)

Synthesis of 1-((1-(3,5-Bis(6-(biotinyl)amino)hexanamido)phenyl)-7,10-dimethyl-1,6,11-trioxo-15,18,21-trioxa-8,9-dithia-2,5,12-triazatetracosan-24-oic Acid Sulfo-NHS Ester pound was not purified but directly used for performing a reaction in the same manner as in Example 3-9 to obtain 84 mg (94%) of a target reaction product of 1-((1-(3,5-bis(6-(biotinyl)amino)hexanamido) phenyl)-7,10-dimethyl-1,6,11-trioxo-15,18,21-trioxa-8,9-dithia-2,5,12-triazatetracosan-24-oic acid sulfo-NHS ester.

(Analysis Values of Target Reaction Product)
$^1$H-NMR (DMSO-d6): 9.97 (2H, s), 8.37 (1H, br.s), 8.2-8.0 (3H, m), 7.74 (2H, t), 7.67 (2H, s), 6.4 (3H, br), 4.35-4.25 (2H, m), 4.2-4.05 (2H, m), 4.0-3.9 (1H, br), 3.71 (2H, t), 3.6-3.4 (12H, m), 3.35-3.0 (12H, m), 2.9-2.75 (4H, m), 2.56 (2H, d), 2.30 (4H, t), 2.04 (4H, t), 1.7-1.2 (30H, m)

HPLC Retention Time of De-t-butyl Esterified Carboxylic Acid of Intermediate (Analysis Conditions A): 9.92 min (0.1% trifluoroacetic acid aqueous solution/CH$_3$CN=85/15 (12 min) 5/95)

HPLC Retention Time of De-t-butyl Esterified Carboxylic Acid of Intermediate (Analysis Conditions A): 13.8 min (0.1% trifluoroacetic acid aqueous solution/CH$_3$CN=85/15 (12 min) 55/45)

HPLC Retention Time of Target Reaction Product (Analysis Conditions A): 13.2 min (0.1% trifluoroacetic acid aqueous solution/CH$_3$CN=85/15 (12 min) 55/45)

The product was reacted with N-butylamine and the HPLC analysis was performed.

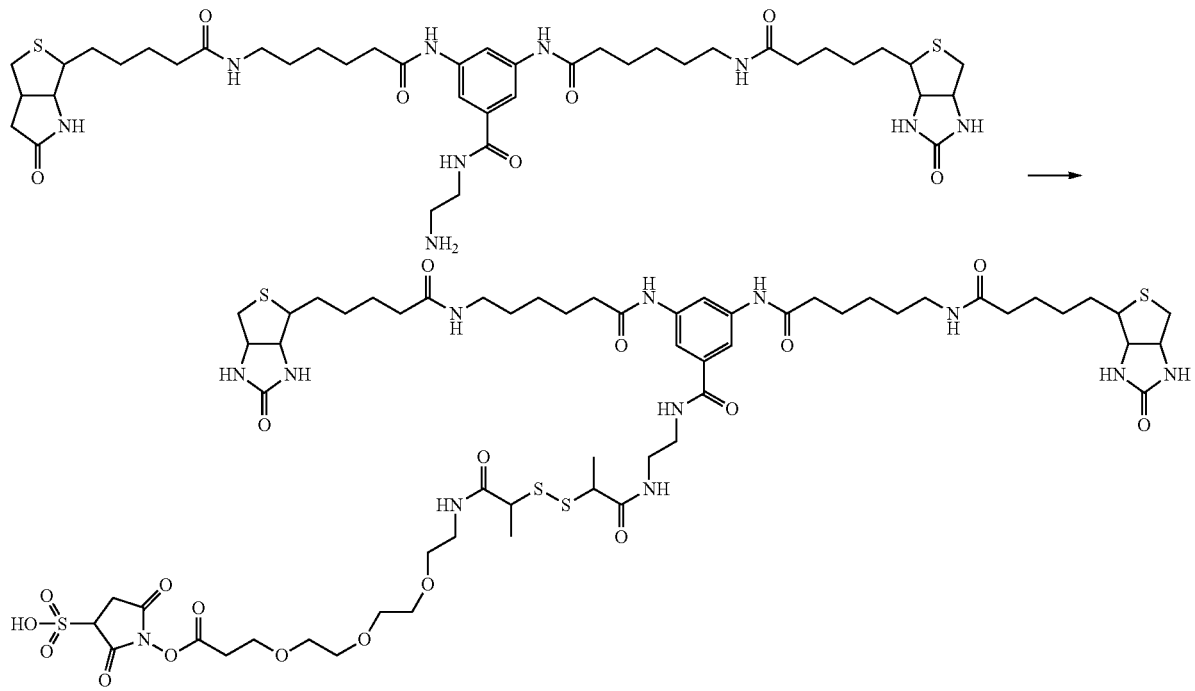

85 mg (0.064 mmol) of the tert-butyl 1-(3,5-bis(6-(biotinyl)amino)hexanamido) phenyl)-7,10-dimethyl-1,6,11-trioxo-15,18,21-trioxa-8,9-dithia-2,5,12-triazatetracosan-24-oate synthesized as above was dissolved in 1 mL of trifluoroacetic acid, followed by stirring at room temperature for 30 minutes. After confirming removal of a t-butyl group by the HPLC, the resultant was concentrated under reduced pressure to obtain 1-(3,5-bis(6-(biotinyl)amino)hexanamido)phenyl)-7,10-dimethyl-1,6,11-trioxo-15,18,21-trioxa-8,9-dithia-2,5,12-triazatetracosan-24-oic acid. This com- HPLC Retention Time (Analysis Conditions A): butylamide form: 15.4 min (0.1% trifluoroacetic acid aqueous solution/CH$_3$CN=85/15 (12 min) 55/45)

Example 15

(Preparation of Streptavidin Mutant Immobilized Beads)
A streptavidin mutant C obtained by causing mutation in Y10S/Y71S/R72K/E89D/R91K/E104N/N11D/S15D/S33N/N37G of streptavidin was produced by a method described in WO2015/125820.

The streptavidin mutant C was diluted to 150 µg/mL with a binding buffer (0.1 M phosphate buffer pH 8.0, 0.5 M NaCl). 10 mL of 1 mM hydrochloric acid was added to and mixed with 2 mL of NHS sepharose beads (NHS-activate Sepharose™ 4 Fast Flow, GE Healthcare), and the resultant was centrifuged at 700 rpm for 1 minute to remove a supernatant. A similar operation was repeated to activate the beads. 10 mL of the binding buffer was added to and mixed with the beads, and the resultant was centrifuged at 700 rpm for 1 minute to remove a supernatant. A 150 µg/mL Cupid solution was added to the thus equilibrated beads, and a reaction was performed by stirring the resultant by inversion at 4° C. for 16 hours. Thereafter, the resultant was centrifuged at 700 rpm for 1 minute to remove a supernatant, and 10 mL of a blocking buffer (0.1 M Tri-HCl pH 8.5, 0.5 NaCl, 0.1 M ethanolamine) was added thereto, followed by stirring by inversion at 4° C. for 2 hours. The resultant was centrifuged at 700 rpm for 1 minute to remove a supernatant, 10 mL of the binding buffer was added thereto and mixed therewith, and the resultant was centrifuged at 700 rpm for 1 minute to remove a supernatant. After the centrifugation at 700 rpm for 1 minute to remove a supernatant, 10 mL of a wash buffer (0.1 M acetate buffer pH 4.0, 0.5 M NaCl) was added thereto and mixed therewith, and the resultant was centrifuged at 700 rpm for 1 minute to remove a supernatant. The resultant was washed repeatedly three times with the binding buffer and the wash buffer, and 1 mL of the binding buffer was added to the resultant to obtain 50% v/v streptavidin mutant C immobilized beads.

Example 16

(Labeling of Surface Protein of Karpas Cell)

A supernatant was removed from Karpas cells derived from human lymphoma statically cultured in a 75 cm² flask, and the cells were washed with 1×PBS. The bis(Boc-iminobiotin)-DBCO-sulfo-NHS 6 synthesized in Example 1-8 in a concentration of 725 µM was dissolved in 50 µL of DMSO, the resultant was diluted with 1×PBS to 5 mL, and the thus obtained solution was added to the washed cells, followed by a labeling reaction performed at room temperature for 1 hour. After the reaction, 300 µL of 1M Tris-HCl pH 7.4 was added thereto to complete the labeling reaction. The cells thus subjected to the labeling reaction were collected in a 15 mL tube, and the thus obtained cell pellet was washed with 10 mL of 1×PBS. 2 mL of a lysis buffer (1×PBS pH 7.4, 0.2% w/v SDS (sodium dodecyl sulfate), 2% v/v NP-40 (Nonidet P40), 10 mM EDTA) was added to the cell pellet, and the resultant was suspended by gently pipetting. Thereafter, the resultant was allowed to stand still for 30 minutes on ice while suspending with a Voltex mixer every 5 minutes, and thus, the cells were dissolved. After dissolving, the resultant solution was dispensed into two 1.5 mL Eppendorf tubes, and centrifuged at room temperature at 13200 rpm for 10 minutes. After the centrifugation, a supernatant was collected to a new 1.5 mL Eppendorf tube, and stored at −30° C.

Subsequently, for reductive alkylation, 100 mM TCEP (tris(2-carboxyethyl)phosphine hydrochloride) was added to 1 mL of the sample to a final concentration of 5 mM, and the resultant was allowed to stand still at room temperature for 15 minutes, and then at 95° C. for 15 minutes. Next, 100 mM iodoacetamide was added thereto to a final concentration of 10 mM, and the resultant was allowed to stand still at room temperature for 15 minutes in a dark room. Next, 100 mM L-cysteine was added thereto in an equimolar amount to the iodoacetamide, and the resultant was allowed to stand still at room temperature for 15 minutes. After standing still, the resultant was centrifuged at room temperature at 13000 g for 10 minutes, and a supernatant was collected in a new 2 mL tube as a labeled protein.

The thus collected labeled protein was subjected to reductive alkylation using TCEP (tris(2-carboxyethyl)phosphine hydrochloride) and iodoacetamide. A sample resulting from the alkylation was mixed with the beads prepared in Example 15, and the resultant was stirred by inversion at room temperature for 20 minutes. After stirring, the sample was washed with a buffer A (1×PBS pH 7.4, 0.1% w/v SDS, 1% v/v NP-40) twice, with a buffer B (1×PBS pH 7.4, 0.1% w/v SDS, 2M NaCl) twice, and with a digestion buffer (50 mM Tris-HCl pH 8.0, 1 mM CaCl$_2$)) eight times. Thereafter, the resultant was suspended in 200 µL of the digestion buffer, and digested with 80 µg/mL trypsin (Promega) at 37° C. at 1200 rpm for 16 hours.

The sample resulting from the digestion with trypsin was filtered through a 0.45 µm centrifugal filter, and 2.2 µL of 10% TFA (trifluoroacetic acid) was added thereto. The thus obtained peptide was collected with a peptide collection tip (OMIX C18 pipette tips, 10 to 100 µL, Agilent Technologies Inc.), and the solvent was evaporated therefrom using a vacuum centrifugal concentrator (CC-105, TOMY). The thus obtained peptide sample was dried, and dissolved again in 25 µL of 2% v/v acetonitrile and 0.1% v/v TFA to be used in identification of a surface protein in Example 18-1.

Reference Example 1

Labeling of Surface Protein of Karpas Cell by Conventional Method

Wild type streptavidin was immobilized on beads in the same manner as in Example 15. Commercially available sulfo-NHS-LC-biotin was used to label the surface protein of Karpas cells in the same manner as in Example 16 to obtain a peptide sample, and the sample was used in the identification of the surface protein in Example 18-1.

Example 17

(Labeling 2 of Surface Protein of Mouse Blood Vessel)

A solution was prepared by dissolving the bis-iminobiotin-triazole-sulfo-NHS 10 synthesized in Example 1-11 in a concentration of 725 µM in 150 µL and diluting the resultant with 1×PBS to 15 mL. The resultant solution was administered, from the left ventricle of an anesthetized mouse, to be circulated at a rate of 1 mL/min. After the circulation, a quenching perfusion buffer (1×PBS pH 7.4, 50 mM Tris, 10% w/v Dextran 40) was caused to circulate in the mouse again to wash out bis-iminobiotin-triazole-sulfo-NHS 10 not binding to the surface protein and a degradation product thereof. After completing the circulation, the liver was removed from the mouse, and the tissue was homogenized with a lysis buffer (50 mM Tris-HCl pH 7.4, 2% w/v SDS, 10 mM EDTA, 1 tablet/50 mL Complete EDTA free protease inhibitor cocktail (Roche)). The protein was dissolved using an ultrasonic pulverizer (Vibra-Cell™, SONICS), followed by performing a reaction at 95° C. for 20 minutes. A residue not dissolved was centrifuged at room temperature at 11000 rpm for 20 minutes, and the thus obtained supernatant sample solution was used in the experiment. The labeled protein was collected from the sample, and purified and identified by a method according to that described in Example 16.

Reference Example 2

(Labeling of Surface Protein of Mouse Blood Vessel by Conventional Method)

Wild type streptavidin was immobilized on beads in the same manner as in Example 15. Commercially available sulfo-NHS-LC-biotin was used to label the surface protein of a mouse blood vessel in the same manner as in Example 17 to obtain a peptide sample, and the sample was used in the identification of a surface protein in Example 18-2.

Example 18-1

(Identification of Surface Protein of Samples of Example 16 and Reference Example 1)

The samples prepared in Example 16 and Reference Example 1 were analyzed by LC-MS/MS. As an auto sampler, HTC-PAL (CTC) was used, as an LC apparatus, UltiMate 3000 (Dionex) was used, and as an MS apparatus, Q Exactive™ (Thermo Scientific) was used. The peptide was separated using a silica gel capillary column (C18, 200 mm×100 μm) to be subjected to MS/MS analysis. As a mobile phase, a buffer A (0.1% formic acid, 2% acetonitrile) and a buffer B (0.1% formic acid, 90% acetonitrile) were used. The peptide sample obtained in each of Examples 16 and Reference Example 1 was dissolved in 25 μL of the buffer A, the resultant was centrifuged to remove undesired matter, and the thus obtained analysis sample was set on the auto sampler. After loading in a trap column (Acclaim PepMap® 100, 75 μm×2 cm, nanoViper, C18, 3 μm, 100 angstroms), the peptide was eluted from the trap column at a flow rate of 280 nL/m in with a linear gradient (A:B=95:5 to A:B=35:65, 120 min). Scanning conditions in the Q Exactive™ are shown in Table 2 below.

TABLE 2

Properties of Full MS/dd-MS2 (TopN)

General

| Runtime | Polarity | Default charge state |
|---|---|---|
| 0 to 120 min | positive | 2 |

Full MS

| Resolution | AGC target | Maximum IT | Scan range |
|---|---|---|---|
| 70,000 | 3.00E+06 | 100 ms | 350 to 1800 m/z | dd-MS2/dd-SIM

| Resolution | AGC target | Maximum IT | Loop count | Isolation window | Fixed first mass | NCE/stepped NCE |
|---|---|---|---|---|---|---|
| 35,000 | 1.00E+05 | 120 ms | 12 | 3.0 m/z | 100.0 m/z | 25 |

The thus obtained MS/MS spectral data was analyzed using Proteome Discoverer (Thermo Scientific) with a Mascot database engine. As database, a data set of Uniprot_human was used. The measurement criteria for the MS/MS are as follows: Maximum Missed Cleavage Site: 2; Precursor Mass Tolerance: 5 ppm; Fragment Mass Tolerance: 0.01 Da; Dynamic Modification: Oxidation (Met), Actyl (N-term); and Static set are as follows: Maximum Delta Cn: 0.05: Target FDR (False Positive Rate): 0.01 (strict), 0.05 (relaxed); and Validation based on q-Value.

Top 30 proteins identified from the sample of Example 16 are shown in Table 3 below.

TABLE 3

Top 30 Proteins Identified from Sample of Example 16

| Detection Order | Accession | Name of Protein |
|---|---|---|
| 1 | P16150 | Leukosialin |
| 2 | P05141 | ADP/ATP translocase 2 |
| 3 | P12236 | ADP/ATP translocase 3 |
| 4 | Q14761 | Protein tyrosine phosphatase receptor type C-associated protein |
| 5 | Q96AG4 | Leucine-rich repeat-containing protein 59 |
| 6 | P14209-3 | Isoform 3 of CD99 antigen |
| 7 | O15260-2 | Isoform 2 of Surfeit locus protein 4 |
| 8 | Q9H3N1 | Thioredoxin-related transmembrane protein 1 |
| 9 | Q6P9G4 | Transmembrane protein 154 |
| 10 | P28908 | Tumor necrosis factor receptor superfamily member 8 |
| 11 | Q00325-2 | Isoform B of Phosphate carrier protein, mitochondrial |
| 12 | P42167 | Lamina-associated polypeptide 2, isoforms beta/gamma |
| 13 | P08675-2 | Isoform 2 of Receptor-type tyrosine-protein phosphatase C |
| 14 | Q96AQ6-3 | Isoform 3 of Pre-B-cell leukemia transcription factor-interacting protein 1 |
| 15 | Q13596 | Sorting nexin-1 |

TABLE 3-continued

Top 30 Proteins Identified from Sample of Example 16

| Detection Order | Accession | Name of Protein |
|---|---|---|
| 16 | Q9HDC9 | Adipocyte plasma membrane-associated protein |
| 17 | O75381 | Peroxisomal membrane protein PEX14 |
| 18 | Q86UE4 | Protein LYRIC |
| 19 | P13073 | Cytochrome c oxidase subunit 4 isoform 1, mitochondrial |
| 20 | P04844-2 | Isoform 2 of Dolichyl-diohosphooligosaccharide--protein glycosyltransferase subunit 2 |
| 21 | Q13586 | Stromal interaction molecule 1 |
| 22 | P49755 | Transmembrane emp24 domain-containing protein 10 |
| 23 | Q9NYL4 | Peptidyl-proyl cis-trans isomerase FKBP11 |
| 24 | P02786 | Transferrin receptor protein 1 |
| 25 | P05023-3 | Isoform 3 of Sodium/potassium-transporting ATPase subunit alpha-1 |
| 26 | Q01650 | Large neutral amino acids transporter small subunit 1 |
| 27 | O76390 | Citrate synthase, mitochondrial |
| 28 | Q86UP2 | Kinectin |
| 29 | P13164 | Interferon-induced transmembrane protein 1 |
| 30 | P60903 | Protein S100-A10 |

CD30 known as tumor necrosis factor receptor family and tumor marker is detected in the 10th rank.

Top 30 proteins identified from the sample of Reference Example 1 are shown in Table 4 below.

TABLE 4

Top 30 Proteins Identifted from Sample of Reference Example 1

| Detection Order | Accession | Name of Protein |
|---|---|---|
| 1 | P16150 | Leukosialin |
| 2 | P13164 | Interferon-induced transmembrane protein 1 |
| 3 | Q14761 | Protein tyrosine phosphatase receptor type C-associated protein |
| 4 | P60903 | Protein S100-A10 |
| 5 | Q15762 | CD226 antigen |
| 6 | O43169 | Cytochrome b5 type B |
| 7 | Q96AG4 | Leucine-rich repeat-containing protein 59 |
| 8 | P56385 | ATP synthase subunit e, mitochondrial |
| 9 | P14209-3 | Isoform 3 of CD99 antigen |
| 10 | P08575-2 | Isoform 2 of Receptor-type tyrosine-protein phosphatase C |
| 11 | P05107 | Integrin beta-2 |
| 12 | Q9UM00-2 | Isoform 2 of Transmembrane and coiled-coil domain-containing protein 1 |
| 13 | Q01628 | Interferon-induced transmembrane protein 3 |
| 14 | P51572 | B-cell receptor-associated protein 31 |
| 15 | P42167 | Lamina-associated polypeptide 2, isoforms beta/gamma |
| 16 | Q6GTX8-3 | Isoform 3 of Leukocyte-associated immunoglobuiin-like receptor 1 |
| 17 | Q9P0L0 | Vesicle-associated membrane protein-associated protein A |
| 18 | Q9H0X4 | Proten ITFG3 |
| 19 | Q86UP2 | Kinectin |
| 20 | Q9P0U1 | Mitochondrial import receptor subunit TOM7 homolog |
| 21 | Q6P9G4 | Transmembrane protein 154 |
| 22 | Q9UDW1 | Cytochrome b-c1 complex subunit 9 |
| 23 | Q15223 | Poliovirus receptor-related protein 1 |
| 24 | P30519 | Heme oxygenase 2 |
| 25 | Q5JTV8 | Torsin-1A-interacting protein 1 |
| 26 | P28908 | Tumor necrosis factor receptor superfamily member 8 |
| 27 | O00264 | Membrane-associated progesterone receptor component 1 |
| 28 | O14949 | Cytochrome b-c1 complex subunit 8 |
| 29 | Q9NS69 | Mitochondrial import receptor subunit TOM22 homolog |
| 30 | P78310 | Coxsackievirus and adenovirus receptor |

Although CD30 was detected, the rank was the 26th.

Example 18-2

(Comparison of Surface Protein Between Samples of Example 17 and Reference Example 2)

The samples prepared in Example 17 and Reference Example 2 were analyzed by the LC-MS/MS in the same manner as in Example 18-1.

The types and the identified amounts of top 10 proteins are shown in Table 5 below. From the sample of Reference Example 2, three types of endogenous biotinylated proteins, i.e., Pyruvate carboxylase, mitochondrial; Propionyl-CoA carboxylase alpha chain, mitochondrial; and Methylcrotonoyl-CoA carboxylase subunit alpha, mitochondrial, were detected in upper ranks, while, from the sample of Example 17, Pyruvate carboxylase, mitochondrial was detected in the 6th rank, and the detection amount thereof was largely reduced. It is also understood that surface proteins were preferentially detected.

TABLE 5

Top 10 Proteins of Reference Example 2

| | Name of Identified Protein | Amount Identified |
|---|---|---|
| 1 | Pyruvate carboxylase, mitochondrial | 27518.84 |
| 2 | Strepavidin | 8378.54 |
| 3 | Propionyl-CoA carboxylase alpha chain, mitochondrial | 7640.96 |
| 4 | Methylcrotonoyl-CoA carboxylase subunit alpha, mitochondrial | 6087.47 |
| 5 | Fatty acid synthase | 4378.28 |
| 6 | Carbamoyl-phosphate synthase [ammonia], mitochondrial | 4274.22 |
| 7 | 3-ketoacyl-CoA thiolase A, peroxisomal | 4103.91 |
| 8 | 3-ketoacyl-CoA thiolase B, peroxisomal | 4077.33 |
| 9 | Fibronectin | 3783.52 |
| 10 | Basement membrane-specific heparan sulfate proteoglycan core protein | 3735.95 |

Top 10 Proteins of Example 1-7

| | Name of Identified Protein | Amount Identified |
|---|---|---|
| 1 | Fibronectin | 4718.17 |
| 2 | Basement membrane-specific heparan sulfate proteoglycan core protein | 4561.43 |
| 3 | Strepavidin | 3970.20 |
| 4 | Carbamoyl-phosphate synthase [ammonia], mitochondrial | 2827.04 |
| 5 | Trypsin | 2285.83 |
| 6 | Pyruvate carboxylase, mitochondrial | 2094.97 |
| 7 | ATP-binding cassette sub-family A member 8-A | 1806.12 |
| 8 | Serum albumin | 1310.84 |
| 9 | Apolipoprotein B-100 | 1194.19 |
| 10 | Keratin, type I cytoskeletal 14 | 1168.30 |

Thus, it was found that when a surface protein was labeled with a bis-iminobiotin and an immobilized streptavidin mutant was used, endogenous biotinylated proteins ware significantly reduced as compared in the conventional method using biotin and wild type streptavidin, and the analysis accuracy for the surface protein could be thus improved.

Example 19

(Production of Anti-CD30 Antibody)

In order to make an antibody against CD30 identified in Example 18-1, a plasm id encoding CD30 gene (pHRm30c) under CMV promoter control was subcutaneously administered twice to a 6-week old Balb/c mouse for DNA immunization. Thereafter, recombinant protein of CD30 extracellular domain was intravenously administered (twice) every two weeks for booster immunization. Three days after boosting the antigen, the spleen was collected to be fused with mouse-derived SP2/0 myeloma cell. An antibody contained in a culture supernatant was measured by ELISA, and antibody producing hybridomas were screened. Each of the thus obtained hybridomas was cloned to obtain a monoclonal antibody. The binding of such a monoclonal antibody to CD30 on membrane was analyzed by flow cytometry using a CD30 expressing cell. The obtained results are shown in Table 6.

Table 6
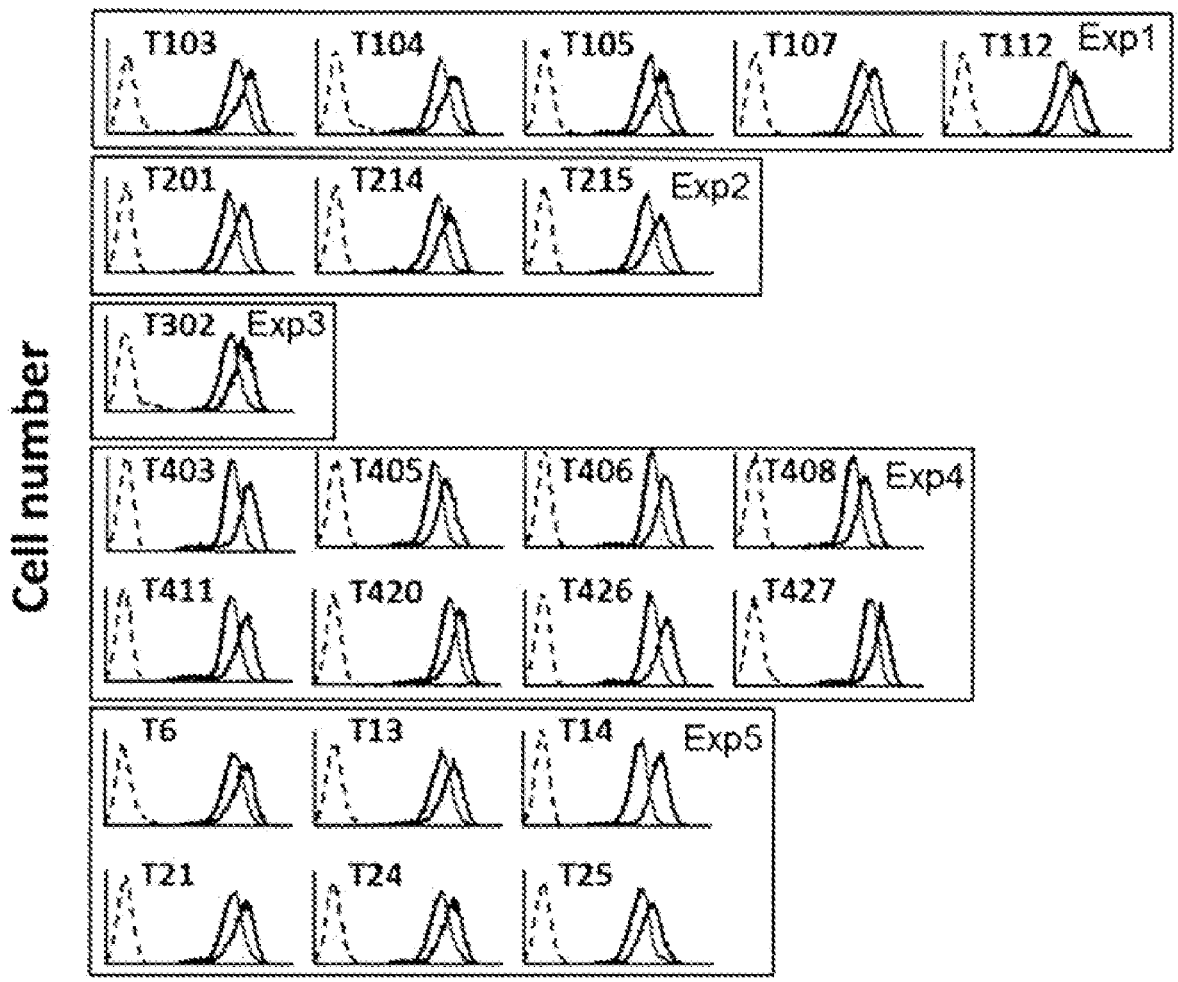

For the analysis by the flow cytometry, L540, Karpas 299 and Ramos cells were used. The L540 and Karpas 299 cells were used as positive controls for expressing CD30, and the Ramos cell was used as a negative control.

Each antibody against CD30 was added to each of the three types of cells. Besides, as a secondary antibody, a PE-labeled goat-derived anti-mouse IgG antibody was added.

The ordinate indicates the number of cells, and the abscissa indicates the PE strength (A cell more strongly expressing CD30 being shifted more rightward). In the results shown above, cells corresponding to a right solid line were the L540 cell, cells corresponding to a left solid line were the Karpas 299 cell, and cells corresponding to a left dotted light were the Ramos cell. It was found that all the selected antibodies bind to the cells expressing CD30.

Example 20

(Preparation of Streptavidin Mutant)

A N11D/S15A/S33A mutant obtained from the natural amino acid sequence set forth in SEQ ID NO: 2 was prepared by a method described in WO2015/125820. An oligo DNA used here was designed in accordance with an instruction attached to QuikChange Site-Directed Mutagenesis Kit (Agilent Technologies Japan Ltd.). For a polymerase chain reaction, KOD plus neo (Toyobo Co., Ltd.) was used. Amino acid sequence conversion was performed by using the following primers, using, as a template, a pET21a vector into which a wild type streptavidin cDNA of the natural amino acid sequence set forth in SEQ ID NO: 2 had been inserted, and changing codon sequence by substitution of a nucleotide sequence by a site-directed mutagenesis method. Thereafter, the template plasmid was cleaved with a restriction enzyme DpnI for transformation of E. coli.

Primer Set for Introducing N11D Mutation:
(SEQ ID NO: 3)
Fw: TTACCGGCACCTGGTATGATCAGCTGGGCAGCACCTTTATTGTG (SEQ ID NO: 4)
RV: AAGGTGCTGCCCAGCTGATCATACCAGGTGCCGGTAATACCTGC Primer Set for Introducing S15A Mutation:
(SEQ ID NO: 5)
Fw: GGTATGATCAGCTGGGCGCGACCTTTATTGTGACCGCCGGCGCAG (SEQ ID NO: 6)
Rv: GCGGTCACAATAAAGGTCGCGCCCAGCTGATCATACCAGGTGCCG Primer Set for Introducing S33A Mutation:
(SEQ ID NO: 7)
Fw: TGACCGGCACCTATGAAGCGGCCGTGGGTAATGCGGAAAGCCG (SEQ ID NO: 8)
Rv: TCCGCATTACCCACGGCCGCTTCATAGGTGCCGGTCAGCGCACC The structure of the thus obtained N11D/S15A/S33A mutant was confirmed by X-ray crystal structure analysis performed in accordance with a method described in Bioscience, Biotechnology, and Biochemistry, 79:4, 640-642 (2015). The thus obtained X-ray crystal structure analysis data is as follows:

[X-ray Crystal Structure Analysis Data]

```
HEADER    ----                                                    23-NOV-17   2018
COMPND    ---
REMARK 3
REMARK 3 REFINEMENT.
REMARK 3   PROGRAM     : REFMAC 5.8.0189
REMARK 3   AUTHORS     : MURSHUDOV,SKUBAK,LEBEDEV,PANNU,
REMARK 3                 STEINER,NICHOLLS,WINN,LONG,VAGIN
REMARK 3
REMARK 3  REFINEMENT TARGET : MAXIMUM LIKELIHOOD
REMARK 3
REMARK 3  DATA USED IN REFINEMENT.
REMARK 3   RESOLUTION RANGE HIGH (ANGSTROMS) :   1.46
REMARK 3   RESOLUTION RANGE LOW  (ANGSTROMS) :  55.09
REMARK 3   DATA CUTOFF            (SIGMA(F)) : NONE
REMARK 3   COMPLETENESS FOR RANGE        (%) :  80.36
REMARK 3   NUMBER OF REFLECTIONS             :  20861
REMARK 3
REMARK 3  FIT TO DATA USED IN REFINEMENT.
REMARK 3   CROSS-VALIDATION METHOD          : THROUGHOUT
REMARK 3   FREE R VALUE TEST SET SELECTION  : RANDOM
REMARK 3   R VALUE     (WORKING + TEST SET) : 0.21891
REMARK 3   R VALUE            (WORKING SET) : 0.21752
REMARK 3   FREE R VALUE                     : 0.24607
REMARK 3   FREE R VALUE TEST SET SIZE   (%) : 4.8
REMARK 3   FREE R VALUE TEST SET COUNT      : 1041
REMARK 3
REMARK 3  FIT IN THE HIGHEST RESOLUTION BIN.
REMARK 3   TOTAL NUMBER OF BINS USED           :      20
REMARK 3   BIN RESOLUTION RANGE HIGH           :   1.465
REMARK 3   BIN RESOLUTION RANGE LOW            :   1.503
REMARK 3   REFLECTION IN BIN    (WORKING SET) :    1089
REMARK 3   BIN COMPLETENESS (WORKING+TEST) (%) :   58.19
REMARK 3   BIN R VALUE          (WORKING SET) :   0.416
REMARK 3   BIN FREE R VALUE SET COUNT          :      59
REMARK 3   BIN FREE R VALUE                    :   0.461
REMARK 3
REMARK 3  NUMBER OF NON-HYDROGEN ATOMS USED IN REFINEMENT.
REMARK 3   ALL ATOMS              :     970
REMARK 3
REMARK 3  B VALUES.
REMARK 3   FROM WILSON PLOT          (A**2) : NULL
```

[X-ray Crystal Structure Analysis Data]

```
REMARK 3 MEAN B VALUE       (OVERALL, A**2) :  22.320
REMARK 3 OVERALL ANISOTROPIC B VALUE.
REMARK 3 B11 (A**2):   -0.01
REMARK 3 B22 (A**2):   -0.01
REMARK 3 B33 (A**2):    0.02
REMARK 3 B12 (A**2):    0.00
REMARK 3 B13 (A**2):   -0.00
REMARK 3 B23 (A**2):    0.00
REMARK 3
REMARK 3 ESTIMATED OVERALL COORDINATE ERROR.
REMARK 3 ESU BASED ON R VALUE            (A): 0.083
REMARK 3 ESU BASED ON FREE R VALUE       (A): 0.085
REMARK 3 ESU BASED ON MAXIMUM LIKELIHOOD     (A): 0.067
REMARK 3 ESU FOR B VALUES BASED ON MAXIMUM LIKELIHOOD (A**2):1.888
REMARK 3
REMARK 3 CORRELATION COEFFICIENTS.
REMARK 3 CORRELATION COEFFICIENT FO-FC : 0.946
REMARK 3 CORRELATION COEFFICIENT FO-FC FREE: 0.939
REMARK 3
REMARK 3 RMS DEVIATIONS FROM IDEAL VALUES COUNT RMS WEIGHT
REMARK 3 BOND LENGTHS REFINED ATOMS (A): 953; 0.024; 0.020
REMARK 3 BOND LENGTHS OTHERS         (A): 820; 0.004; 0.020
REMARK 3 BOND ANGLES REFINED ATOMS (DEGREES): 1304; 2.118; 1.909
REMARK 3 BOND ANGLES OTHERS         (DEGREES): 1891; 1.121; 3.000
REMARK 3 TORSION ANGLES, PERIOD 1 (DEGREES): 122; 7.577; 5.000
REMARK 3 TORSION ANGLES, PERIOD 2 (DEGREES): 39; 29.700; 23.846
REMARK 3 TORSION ANGLES, PERIOD 3 (DEGREES): 125; 12.590; 15.000
REMARK 3 TORSION ANGLES, PERIOD 4 (DEGREES): 4; 9.460; 15.000
REMARK 3 CHIRAL-CENTER RESTRAINTS (A**3): 146; 0.140; 0.200
REMARK 3 GENERAL PLANES REFINED ATOMS (A): 1099; 0.012; 0.020
REMARK 3 GENERAL PLANES OTHERS      (A): 215; 0.002; 0.020
REMARK 3
REMARK 3 ISOTROPIC THERMAL FACTOR RESTRAINTS.  COUNT    RMS WEIGHT
REMARK 3 MAIN-CHAIN BOND REFINED ATOMS (A**2):491; 2.301; 2.112
REMARK 3 MAIN-CHAIN BOND OTHER ATOMS      (A**2):490; 2.301; 2.106
REMARK 3 MAIN-CHAIN ANGLE REFINED ATOMS (A**2):612; 3.672; 3.155
REMARK 3 MAIN-CHAIN ANGLE OTHER ATOMS (A**2):613; 3.670; 3.162
REMARK 3 SIDE-CHAIN BOND REFINED ATOMS   (A**2):461; 2.879; 2.336
REMARK 3 SIDE-CHAIN BOND OTHER ATOMS   (A**2):459; 2.882; 2.335
REMARK 3 SIDE-CHAIN ANGLE OTHER ATOMS (A**2):692; 4.372; 3.379
REMARK 3 LONG RANGE B REFINED ATOMS (A**2):1025; 8.931;24.362
REMARK 3 LONG RANGE B OTHER ATOMS (A**2):1026; 8.926; 24.369
REMARK 3
REMARK 3 NCS RESTRAINTS STATISTICS
REMARK 3 NUMBER OF NCS GROUPS : NULL
REMARK 3
REMARK 3 TWIN DETAILS
REMARK 3 NUMBER OF TWIN DOMAINS : NULL
REMARK 3
REMARK 3
REMARK 3 TLS DETAILS
REMARK 3 NUMBER OF TLS GROUPS : NULL
REMARK 3
REMARK 3
REMARK 3 BULK SOLVENT MODELLING.
REMARK 3 METHOD USED:   MASK
REMARK 3 PARAMETERS FOR MASK CALCULATION
REMARK 3 VDW PROBE RADIUS   :   1.20
REMARK 3 ION PROBE RADIUS   :   0.80
REMARK 3 SHRINKAGE RADIUS   :   0.80
REMARK 3
REMARK 3 OTHER REFINEMENT REMARKS:
REMARK 3 HYDROGENS HAVE BEEN ADDED IN THE RIDING POSITIONS
REMARK 3 U VALUES      : REFINED INDIVIDUALLY
REMARK 3
```

| CRYST1 | 57.765    | 57.765    | 182.995  | 90.00   | 90.00 | 90.00 | I | 41    | 2 | 2 |
|--------|-----------|-----------|----------|---------|-------|-------|---|-------|---|---|
| SCALE1 | 0.017312  | 0.000000  | 0.000000 | 0.00000 |       |       |   |       |   |   |
| SCALE2 | -0.000000 | 0.017312  | 0.000000 | 0.00000 |       |       |   |       |   |   |
| SCALE3 | 0.000000  | -0.000000 | 0.005465 | 0.00000 |       |       |   |       |   |   |

| ATOM | 1 | N  | SER A | 12 | -24.590 | -2.136 | -14.698 | 1.00 | 35.05 | A | N |
|------|---|----|-------|----|---------|--------|---------|------|-------|---|---|
| ATOM | 2 | CA | SER A | 12 | -23.588 | -3.207 | -14.347 | 1.00 | 33.49 | A | C |
| ATOM | 3 | CB | SER A | 12 | -22.153 | -2.639 | -14.241 | 1.00 | 33.09 | A | C |
| ATOM | 4 | OG | SER A | 12 | -21.983 | -1.835 | -13.070 | 1.00 | 30.54 | A | O |
| ATOM | 5 | C  | SER A | 12 | -23.968 | -3.950 | -13.037 | 1.00 | 31.12 | A | C |
| ATOM | 6 | O  | SER A | 12 | -24.733 | -3.462 | -12.190 | 1.00 | 30.11 | A | O |

-continued

| | | | | | | | | | | | |
|---|---|---|---|---|---|---|---|---|---|---|---|
| [X-ray Crystal Structure Analysis Data] | | | | | | | | | | | |
| ATOM | 7 | N | ALA A | 13 | −23.428 | −5.160 | −12.930 | 1.00 | 29.20 | A | N |
| ATOM | 8 | CA | ALA A | 13 | −23.551 | −5.963 | −11.733 | 1.00 | 30.72 | A | C |
| ATOM | 9 | CB | ALA A | 13 | −22.807 | −7.302 | −11.935 | 1.00 | 31.55 | A | C |
| ATOM | 10 | C | ALA A | 13 | −22.956 | −5.216 | −10.548 | 1.00 | 29.10 | A | C |
| ATOM | 11 | O | ALA A | 13 | −23.547 | −5.230 | −9.455 | 1.00 | 25.75 | A | O |
| ATOM | 12 | N | GLU A | 14 | −21.741 | −4.642 | −10.716 | 1.00 | 28.93 | A | N |
| ATOM | 13 | CA | GLU A | 14 | −21.111 | −3.807 | −9.638 | 1.00 | 31.91 | A | C |
| ATOM | 14 | CB | GLU A | 14 | −19.895 | −2.999 | −10.134 | 1.00 | 36.91 | A | C |
| ATOM | 15 | CG | GLU A | 14 | −18.657 | −3.765 | −10.567 | 1.00 | 42.41 | A | C |
| ATOM | 16 | CD | GLU A | 14 | −18.797 | −4.576 | −11.885 | 1.00 | 49.72 | A | C |
| ATOM | 17 | OE1 | GLU A | 14 | −19.786 | −4.411 | −12.652 | 1.00 | 55.11 | A | O |
| ATOM | 18 | OE2 | GLU A | 14 | −17.887 | −5.403 | −12.160 | 1.00 | 56.64 | A | O |
| ATOM | 19 | C | GLU A | 14 | −22.091 | −2.767 | −9.064 | 1.00 | 27.77 | A | C |
| ATOM | 20 | O | GLU A | 14 | −22.267 | −2.671 | −7.871 | 1.00 | 26.78 | A | O |
| ATOM | 21 | N | ALA A | 15 | −22.671 | −1.960 | −9.931 | 1.00 | 26.16 | A | N |
| ATOM | 22 | CA | ALA A | 15 | −23.635 | −0.888 | −9.519 | 1.00 | 25.76 | A | C |
| ATOM | 23 | CB | ALA A | 15 | −23.947 | −0.032 | −10.723 | 1.00 | 26.10 | A | C |
| ATOM | 24 | C | ALA A | 15 | −24.961 | −1.468 | −8.907 | 1.00 | 27.06 | A | C |
| ATOM | 25 | O | ALA A | 15 | −25.538 | −0.929 | −7.960 | 1.00 | 27.82 | A | O |
| ATOM | 26 | N | GLY A | 16 | −25.382 | −2.636 | −9.384 | 1.00 | 23.31 | A | N |
| ATOM | 27 | CA | GLY A | 16 | −26.585 | −3.276 | −8.880 | 1.00 | 20.86 | A | C |
| ATOM | 28 | C | GLY A | 16 | −26.470 | −3.913 | −7.500 | 1.00 | 19.56 | A | C |
| ATOM | 29 | O | GLY A | 16 | −27.341 | −3.754 | −6.628 | 1.00 | 21.64 | A | O |
| ATOM | 30 | N | ILE A | 17 | −25.346 | −4.636 | −7.290 | 1.00 | 18.86 | A | N |
| ATOM | 31 | CA | ILE A | 17 | −25.126 | −5.350 | −6.023 | 1.00 | 18.29 | A | C |
| ATOM | 32 | CB | ILE A | 17 | −24.065 | −6.498 | −6.276 | 1.00 | 18.33 | A | C |
| ATOM | 33 | CG1 | ILE A | 17 | −24.595 | −7.482 | −7.323 | 1.00 | 20.90 | A | C |
| ATOM | 34 | CD1 | ILE A | 17 | −23.510 | −8.321 | −7.991 | 1.00 | 22.55 | A | C |
| ATOM | 35 | CG2 | ILE A | 17 | −23.753 | −7.294 | −5.007 | 1.00 | 18.05 | A | C |
| ATOM | 36 | C | ILE A | 17 | −24.686 | −4.510 | −4.851 | 1.00 | 17.39 | A | C |
| ATOM | 37 | O | ILE A | 17 | −25.107 | −4.711 | −3.681 | 1.00 | 16.83 | A | O |
| ATOM | 38 | N | THR A | 18 | −23.744 | −3.605 | −5.135 | 1.00 | 18.43 | A | N |
| ATOM | 39 | CA | THR A | 18 | −23.161 | −2.732 | −4.137 | 1.00 | 19.39 | A | C |
| ATOM | 40 | CB | THR A | 18 | −22.080 | −1.821 | −4.736 | 1.00 | 19.58 | A | C |
| ATOM | 41 | OG1 | THR A | 18 | −20.980 | −2.599 | −5.205 | 1.00 | 19.34 | A | O |
| ATOM | 42 | CG2 | THR A | 18 | −21.605 | −0.829 | −3.680 | 1.00 | 19.51 | A | C |
| ATOM | 43 | C | THR A | 18 | −24.223 | −1.961 | −3.308 | 1.00 | 19.04 | A | C |
| ATOM | 44 | O | THR A | 18 | −25.147 | −1.258 | −3.836 | 1.00 | 19.94 | A | O |
| ATOM | 45 | N | GLY A | 19 | −24.134 | −2.154 | −1.986 | 1.00 | 17.89 | A | N |
| ATOM | 46 | CA | GLY A | 19 | −25.052 | −1.485 | −1.045 | 1.00 | 19.62 | A | C |
| ATOM | 47 | C | GLY A | 19 | −25.570 | −2.388 | 0.071 | 1.00 | 19.08 | A | C |
| ATOM | 48 | O | GLY A | 19 | −24.962 | −3.456 | 0.397 | 1.00 | 19.84 | A | O |
| ATOM | 49 | N | THR A | 20 | −26.737 | −2.020 | 0.588 | 1.00 | 18.95 | A | N |
| ATOM | 50 | CA | THR A | 20 | −27.285 | −2.619 | 1.820 | 1.00 | 18.73 | A | C |
| ATOM | 51 | CB | THR A | 20 | −27.709 | −1.550 | 2.847 | 1.00 | 21.02 | A | C |
| ATOM | 52 | OG1 | THR A | 20 | −26.602 | −0.714 | 3.145 | 1.00 | 22.51 | A | O |
| ATOM | 53 | CG2 | THR A | 20 | −28.207 | −2.144 | 4.106 | 1.00 | 20.02 | A | C |
| ATOM | 54 | C | THR A | 20 | −28.511 | −3.466 | 1.420 | 1.00 | 18.52 | A | C |
| ATOM | 55 | O | THR A | 20 | −29.399 | −3.027 | 0.657 | 1.00 | 18.77 | A | O |
| ATOM | 56 | N | TRP A | 21 | −28.520 | −4.680 | 1.913 | 1.00 | 16.07 | A | N |
| ATOM | 57 | CA | TRP A | 21 | −29.570 | −5.679 | 1.659 | 1.00 | 16.67 | A | C |
| ATOM | 58 | CB | TRP A | 21 | −29.058 | −6.726 | 0.779 | 1.00 | 14.71 | A | C |
| ATOM | 59 | CG | TRP A | 21 | −28.595 | −6.339 | −0.626 | 1.00 | 14.06 | A | C |
| ATOM | 60 | CD1 | TRP A | 21 | −27.318 | −5.936 | −1.001 | 1.00 | 12.92 | A | C |
| ATOM | 61 | NE1 | TRP A | 21 | −27.293 | −5.777 | −2.388 | 1.00 | 13.91 | A | N |
| ATOM | 62 | CE2 | TRP A | 21 | −28.562 | −6.031 | −2.852 | 1.00 | 13.09 | A | C |
| ATOM | 63 | CD2 | TRP A | 21 | −29.353 | −6.416 | −1.777 | 1.00 | 13.43 | A | C |
| ATOM | 64 | CE3 | TRP A | 21 | −30.668 | −6.775 | −2.029 | 1.00 | 13.60 | A | C |
| ATOM | 65 | CZ3 | TRP A | 21 | −31.110 | −6.764 | −3.338 | 1.00 | 14.71 | A | C |
| ATOM | 66 | CH2 | TRP A | 21 | −30.327 | −6.396 | −4.348 | 1.00 | 14.45 | A | C |
| ATOM | 67 | CZ2 | TRP A | 21 | −29.028 | −6.043 | −4.161 | 1.00 | 12.52 | A | C |
| ATOM | 68 | C | TRP A | 21 | −30.125 | −6.244 | 2.935 | 1.00 | 16.40 | A | C |
| ATOM | 69 | O | TRP A | 21 | −29.470 | −6.291 | 3.938 | 1.00 | 15.82 | A | O |
| ATOM | 70 | N | TYR A | 22 | −31.423 | −6.573 | 2.892 | 1.00 | 16.68 | A | N |
| ATOM | 71 | CA | TYR A | 22 | −32.216 | −6.969 | 4.074 | 1.00 | 18.74 | A | C |
| ATOM | 72 | CB | TYR A | 22 | −33.321 | −5.965 | 4.398 | 1.00 | 16.19 | A | C |
| ATOM | 73 | CG | TYR A | 22 | −32.751 | −4.630 | 4.644 | 1.00 | 16.43 | A | C |
| ATOM | 74 | CD1 | TYR A | 22 | −32.623 | −3.744 | 3.626 | 1.00 | 17.29 | A | C |
| ATOM | 75 | CE1 | TYR A | 22 | −32.050 | −2.510 | 3.829 | 1.00 | 16.46 | A | C |
| ATOM | 76 | CZ | TYR A | 22 | −31.627 | −2.104 | 5.109 | 1.00 | 16.82 | A | C |
| ATOM | 77 | OH | TYR A | 22 | −31.085 | −0.777 | 5.332 | 1.00 | 19.07 | A | O |
| ATOM | 78 | CE2 | TYR A | 22 | −31.728 | −2.997 | 6.123 | 1.00 | 19.14 | A | C |
| ATOM | 79 | CD2 | TYR A | 22 | −32.291 | −4.273 | 5.883 | 1.00 | 15.90 | A | C |
| ATOM | 80 | C | TYR A | 22 | −32.939 | −8.263 | 3.761 | 1.00 | 19.33 | A | C |
| ATOM | 81 | O | TYR A | 22 | −33.442 | −8.397 | 2.679 | 1.00 | 19.38 | A | O |
| ATOM | 82 | N | ASP A | 23 | −32.934 | −9.211 | 4.675 | 1.00 | 24.41 | A | N |
| ATOM | 83 | CA | ASP A | 23 | −33.676 | −10.460 | 4.431 | 1.00 | 30.45 | A | C |

[X-ray Crystal Structure Analysis Data]

| ATOM | 84 | CB | ASP A | 23 | −32.816 | −11.744 | 4.655 | 1.00 | 32.46 | A | C |
|---|---|---|---|---|---|---|---|---|---|---|---|
| ATOM | 85 | CG | ASP A | 23 | −32.658 | −12.130 | 6.139 | 1.00 | 37.26 | A | C |
| ATOM | 86 | OD1 | ASP A | 23 | −33.238 | −11.395 | 7.012 | 1.00 | 35.20 | A | O |
| ATOM | 87 | OD2 | ASP A | 23 | −31.973 | −13.198 | 6.372 | 1.00 | 36.81 | A | O |
| ATOM | 88 | C | ASP A | 23 | −35.001 | −10.460 | 5.142 | 1.00 | 36.82 | A | C |
| ATOM | 89 | O | ASP A | 23 | −35.399 | −9.453 | 5.700 | 1.00 | 36.77 | A | O |
| ATOM | 90 | N | GLN A | 24 | −35.692 | −11.585 | 5.029 | 1.00 | 44.93 | A | N |
| ATOM | 91 | CA | GLN A | 24 | −36.949 | −11.861 | 5.738 | 1.00 | 55.45 | A | C |
| ATOM | 92 | CB | GLN A | 24 | −37.653 | −13.106 | 5.096 | 1.00 | 58.99 | A | C |
| ATOM | 93 | CG | GLN A | 24 | −36.949 | −14.494 | 5.178 | 1.00 | 60.34 | A | C |
| ATOM | 94 | CD | GLN A | 24 | −35.621 | −14.648 | 4.374 | 1.00 | 61.29 | A | C |
| ATOM | 95 | OE1 | GLN A | 24 | −35.556 | −14.365 | 3.177 | 1.00 | 58.08 | A | O |
| ATOM | 96 | NE2 | GLN A | 24 | −34.568 | −15.109 | 5.045 | 1.00 | 63.91 | A | N |
| ATOM | 97 | C | GLN A | 24 | −36.731 | −11.989 | 7.280 | 1.00 | 59.95 | A | C |
| ATOM | 98 | O | GLN A | 24 | −37.360 | −11.256 | 8.048 | 1.00 | 62.75 | A | O |
| ATOM | 99 | N | LEU A | 25 | −35.776 | −12.841 | 7.698 | 1.00 | 61.98 | A | N |
| ATOM | 100 | CA | LEU A | 25 | −35.413 | −13.068 | 9.142 | 1.00 | 58.71 | A | C |
| ATOM | 101 | CB | LEU A | 25 | −34.196 | −14.091 | 9.286 | 1.00 | 48.56 | A | C |
| ATOM | 102 | CG | LEU A | 25 | −34.254 | −15.540 | 8.633 | 1.00 | 48.98 | A | C |
| ATOM | 103 | CD1 | LEU A | 25 | −32.913 | −16.281 | 8.430 | 1.00 | 42.11 | A | C |
| ATOM | 104 | CD2 | LEU A | 25 | −35.213 | −16.513 | 9.342 | 1.00 | 46.59 | A | C |
| ATOM | 105 | C | LEU A | 25 | −35.221 | −11.692 | 9.947 | 1.00 | 62.94 | A | C |
| ATOM | 106 | O | LEU A | 25 | −35.708 | −11.573 | 11.089 | 1.00 | 67.22 | A | O |
| ATOM | 107 | N | GLY A | 26 | −34.631 | −10.655 | 9.310 | 1.00 | 52.67 | A | N |
| ATOM | 108 | CA | GLY A | 26 | −34.225 | −9.359 | 9.952 | 1.00 | 39.54 | A | C |
| ATOM | 109 | C | GLY A | 26 | −32.696 | −9.088 | 9.899 | 1.00 | 33.50 | A | C |
| ATOM | 110 | O | GLY A | 26 | −32.171 | −8.284 | 10.672 | 1.00 | 31.06 | A | O |
| ATOM | 111 | N | ALA A | 27 | −31.982 | −9.768 | 8.998 | 1.00 | 25.56 | A | N |
| ATOM | 112 | CA | ALA A | 27 | −30.562 | −9.598 | 8.788 | 1.00 | 23.69 | A | C |
| ATOM | 113 | CB | ALA A | 27 | −29.961 | −10.862 | 8.168 | 1.00 | 27.35 | A | C |
| ATOM | 114 | C | ALA A | 27 | −30.277 | −8.419 | 7.873 | 1.00 | 21.86 | A | C |
| ATOM | 115 | O | ALA A | 27 | −31.062 | −8.099 | 7.038 | 1.00 | 22.74 | A | O |
| ATOM | 116 | N | THR A | 28 | −29.071 | −7.875 | 7.968 | 1.00 | 23.35 | A | N |
| ATOM | 117 | CA | THR A | 28 | −28.613 | −6.771 | 7.111 | 1.00 | 25.58 | A | C |
| ATOM | 118 | CB | THR A | 28 | −28.470 | −5.468 | 7.925 | 1.00 | 28.45 | A | C |
| ATOM | 119 | OG1 | THR A | 28 | −29.683 | −5.191 | 8.605 | 1.00 | 30.56 | A | O |
| ATOM | 120 | CG2 | THR A | 28 | −28.147 | −4.287 | 7.022 | 1.00 | 30.95 | A | C |
| ATOM | 121 | C | THR A | 28 | −27.212 | −7.161 | 6.573 | 1.00 | 21.48 | A | C |
| ATOM | 122 | O | THR A | 28 | −26.330 | −7.536 | 7.340 | 1.00 | 24.83 | A | O |
| ATOM | 123 | N | PHE A | 29 | −27.046 | −7.121 | 5.252 | 1.00 | 19.91 | A | N |
| ATOM | 124 | CA | PHE A | 29 | −25.823 | −7.589 | 4.520 | 1.00 | 23.45 | A | C |
| ATOM | 125 | CB | PHE A | 29 | −26.354 | −8.709 | 3.588 | 1.00 | 24.59 | A | C |
| ATOM | 126 | CG | PHE A | 29 | −25.577 | −9.010 | 2.403 | 1.00 | 23.33 | A | C |
| ATOM | 127 | CD1 | PHE A | 29 | −24.266 | −9.484 | 2.485 | 1.00 | 25.55 | A | C |
| ATOM | 128 | CE1 | PHE A | 29 | −23.570 | −9.847 | 1.335 | 1.00 | 21.65 | A | C |
| ATOM | 129 | CZ | PHE A | 29 | −24.205 | −9.886 | 0.103 | 1.00 | 21.41 | A | C |
| ATOM | 130 | CE2 | PHE A | 29 | −25.548 | −9.500 | 0.051 | 1.00 | 22.80 | A | C |
| ATOM | 131 | CD2 | PHE A | 29 | −26.215 | −9.098 | 1.164 | 1.00 | 25.38 | A | C |
| ATOM | 132 | C | PHE A | 29 | −25.404 | −6.252 | 3.821 | 1.00 | 21.83 | A | C |
| ATOM | 133 | O | PHE A | 29 | −26.229 | −5.633 | 3.083 | 1.00 | 22.06 | A | O |
| ATOM | 134 | N | ILE A | 30 | −24.186 | −5.776 | 4.069 | 1.00 | 18.73 | A | N |
| ATOM | 135 | CA | ILE A | 30 | −23.683 | −4.545 | 3.467 | 1.00 | 22.00 | A | C |
| ATOM | 136 | CB | ILE A | 30 | −23.250 | −3.551 | 4.514 | 1.00 | 26.06 | A | C |
| ATOM | 137 | CG1 | ILE A | 30 | −24.409 | −3.262 | 5.453 | 1.00 | 26.43 | A | C |
| ATOM | 138 | CD1 | ILE A | 30 | −23.967 | −2.447 | 6.637 | 1.00 | 27.01 | A | C |
| ATOM | 139 | CG2 | ILE A | 30 | −22.851 | −2.235 | 3.851 | 1.00 | 26.77 | A | C |
| ATOM | 140 | C | ILE A | 30 | −22.512 | −4.946 | 2.636 | 1.00 | 21.76 | A | C |
| ATOM | 141 | O | ILE A | 30 | −21.604 | −5.510 | 3.147 | 1.00 | 20.88 | A | O |
| ATOM | 142 | N | VAL A | 31 | −22.576 | −4.749 | 1.328 | 1.00 | 21.38 | A | N |
| ATOM | 143 | CA | VAL A | 31 | −21.585 | −5.346 | 0.441 | 1.00 | 19.41 | A | C |
| ATOM | 144 | CB | VAL A | 31 | −22.141 | −6.604 | −0.235 | 1.00 | 20.60 | A | C |
| ATOM | 145 | CG1 | VAL A | 31 | −23.369 | −6.301 | −1.150 | 1.00 | 20.12 | A | C |
| ATOM | 146 | CG2 | VAL A | 31 | −21.085 | −7.406 | −0.970 | 1.00 | 20.28 | A | C |
| ATOM | 147 | C | VAL A | 31 | −21.103 | −4.347 | −0.624 | 1.00 | 19.13 | A | C |
| ATOM | 148 | O | VAL A | 31 | −21.811 | −3.468 | −1.073 | 1.00 | 19.64 | A | O |
| ATOM | 149 | N | THR A | 32 | −19.824 | −4.425 | −0.926 | 1.00 | 19.88 | A | N |
| ATOM | 150 | CA | THR A | 32 | −19.277 | −3.777 | −2.098 | 1.00 | 19.80 | A | C |
| ATOM | 151 | CB | THR A | 32 | −18.039 | −2.930 | −1.742 | 1.00 | 23.25 | A | C |
| ATOM | 152 | OG1 | THR A | 32 | −18.410 | −2.002 | −0.742 | 1.00 | 23.99 | A | O |
| ATOM | 153 | CG2 | THR A | 32 | −17.507 | −2.216 | −2.929 | 1.00 | 23.25 | A | C |
| ATOM | 154 | C | THR A | 32 | −18.882 | −4.854 | −3.095 | 1.00 | 21.65 | A | C |
| ATOM | 155 | O | THR A | 32 | −18.138 | −5.805 | −2.769 | 1.00 | 17.13 | A | O |
| ATOM | 156 | N | ALA A | 33 | −19.306 | −4.638 | −4.358 | 1.00 | 18.89 | A | N |
| ATOM | 157 | CA | ALA A | 33 | −18.936 | −5.520 | −5.469 | 1.00 | 20.18 | A | C |
| ATOM | 158 | CB | ALA A | 33 | −20.182 | −5.833 | −6.273 | 1.00 | 19.54 | A | C |
| ATOM | 159 | C | ALA A | 33 | −17.884 | −4.834 | −6.340 | 1.00 | 22.60 | A | C |
| ATOM | 160 | O | ALA A | 33 | −18.185 | −3.777 | −6.895 | 1.00 | 24.21 | A | O |

-continued

| [X-ray Crystal Structure Analysis Data] | | | | | | | | | | |
|---|---|---|---|---|---|---|---|---|---|---|
| ATOM | 161 | N | GLY A | 34 | −16.685 | −5.419 | −6.434 | 1.00 | 22.16 | A | N |
| ATOM | 162 | CA | GLY A | 34 | −15.539 | −4.815 | −7.103 | 1.00 | 28.16 | A | C |
| ATOM | 163 | C | GLY A | 34 | −15.658 | −5.122 | −8.567 | 1.00 | 34.23 | A | C |
| ATOM | 164 | O | GLY A | 34 | −16.350 | −6.098 | −8.963 | 1.00 | 35.35 | A | O |
| ATOM | 165 | N | ALA A | 35 | −15.031 | −4.288 | −9.421 | 1.00 | 40.74 | A | N |
| ATOM | 166 | CA | ALA A | 35 | −15.121 | −4.486 | −10.904 | 1.00 | 36.86 | A | C |
| ATOM | 167 | CB | ALA A | 35 | −14.540 | −3.314 | −11.671 | 1.00 | 38.16 | A | C |
| ATOM | 168 | C | ALA A | 35 | −14.491 | −5.855 | −11.345 | 1.00 | 39.96 | A | C |
| ATOM | 169 | O | ALA A | 35 | −14.820 | −6.407 | −12.402 | 1.00 | 42.31 | A | O |
| ATOM | 170 | N | ASP A | 36 | −13.632 | −6.383 | −10.475 | 1.00 | 35.03 | A | N |
| ATOM | 171 | CA | ASP A | 36 | −12.929 | −7.604 | −10.659 | 1.00 | 37.23 | A | C |
| ATOM | 172 | CB | ASP A | 36 | −11.757 | −7.561 | −9.678 | 1.00 | 40.42 | A | C |
| ATOM | 173 | CG | ASP A | 36 | −12.161 | −7.043 | −8.294 | 1.00 | 52.41 | A | C |
| ATOM | 174 | OD1 | ASP A | 36 | −12.839 | −5.983 | −8.195 | 1.00 | 60.10 | A | O |
| ATOM | 175 | OD2 | ASP A | 36 | −11.784 | −7.683 | −7.294 | 1.00 | 63.05 | A | O |
| ATOM | 176 | C | ASP A | 36 | −13.759 | −8.903 | −10.407 | 1.00 | 30.76 | A | C |
| ATOM | 177 | O | ASP A | 36 | −13.377 | −9.952 | −10.879 | 1.00 | 34.66 | A | O |
| ATOM | 178 | N | GLY A | 37 | −14.871 | −8.843 | −9.672 | 1.00 | 21.89 | A | N |
| ATOM | 179 | CA | GLY A | 37 | −15.551 | −10.060 | −9.209 | 1.00 | 20.15 | A | C |
| ATOM | 180 | C | GLY A | 37 | −15.533 | −10.207 | −7.695 | 1.00 | 17.31 | A | C |
| ATOM | 181 | O | GLY A | 37 | −16.056 | −11.199 | −7.181 | 1.00 | 16.84 | A | O |
| ATOM | 182 | N | ALA A | 38 | −14.927 | −9.276 | −6.992 | 1.00 | 16.44 | A | N |
| ATOM | 183 | CA | ALA A | 38 | −14.906 | −9.415 | −5.505 | 1.00 | 17.16 | A | C |
| ATOM | 184 | CB | ALA A | 38 | −13.640 | −8.842 | −4.915 | 1.00 | 19.72 | A | C |
| ATOM | 185 | C | ALA A | 38 | −16.161 | −8.887 | −4.773 | 1.00 | 19.43 | A | C |
| ATOM | 186 | O | ALA A | 38 | −16.685 | −7.805 | −5.103 | 1.00 | 20.74 | A | O |
| ATOM | 187 | N | LEU A | 39 | −16.529 | −9.582 | −3.687 | 1.00 | 17.46 | A | N |
| ATOM | 188 | CA | LEU A | 39 | −17.506 | −9.154 | −2.767 | 1.00 | 17.84 | A | C |
| ATOM | 189 | CB | LEU A | 39 | −18.679 | −10.132 | −2.610 | 1.00 | 18.13 | A | C |
| ATOM | 190 | CG | LEU A | 39 | −19.509 | −10.393 | −3.873 | 1.00 | 18.35 | A | C |
| ATOM | 191 | CD1 | LEU A | 39 | −20.555 | −11.424 | −3.484 | 1.00 | 17.68 | A | C |
| ATOM | 192 | CD2 | LEU A | 39 | −20.204 | −9.202 | −4.424 | 1.00 | 18.29 | A | C |
| ATOM | 193 | C | LEU A | 39 | −16.848 | −9.021 | −1.430 | 1.00 | 16.96 | A | C |
| ATOM | 194 | O | LEU A | 39 | −16.134 | −9.883 | −0.994 | 1.00 | 19.04 | A | O |
| ATOM | 195 | N | THR A | 40 | −17.032 | −7.874 | −0.848 | 1.00 | 16.16 | A | N |
| ATOM | 196 | CA | THR A | 40 | −16.562 | −7.639 | 0.517 | 1.00 | 17.71 | A | C |
| ATOM | 197 | CB | THR A | 40 | −15.236 | −6.848 | 0.478 | 1.00 | 18.35 | A | C |
| ATOM | 198 | OG1 | THR A | 40 | −15.466 | −5.589 | −0.139 | 1.00 | 22.04 | A | O |
| ATOM | 199 | CG2 | THR A | 40 | −14.269 | −7.443 | −0.368 | 1.00 | 18.36 | A | C |
| ATOM | 200 | C | THR A | 40 | −17.603 | −6.859 | 1.293 | 1.00 | 19.09 | A | C |
| ATOM | 201 | O | THR A | 40 | −18.278 | −5.989 | 0.752 | 1.00 | 20.33 | A | O |
| ATOM | 202 | N | GLY A | 41 | −17.686 | −7.111 | 2.593 | 1.00 | 18.42 | A | N |
| ATOM | 203 | CA | GLY A | 41 | −18.555 | −6.335 | 3.394 | 1.00 | 17.80 | A | C |
| ATOM | 204 | C | GLY A | 41 | −18.743 | −6.916 | 4.762 | 1.00 | 16.42 | A | C |
| ATOM | 205 | O | GLY A | 41 | −17.860 | −7.536 | 5.317 | 1.00 | 18.14 | A | O |
| ATOM | 206 | N | THR A | 42 | −19.954 | −6.730 | 5.301 | 1.00 | 18.17 | A | N |
| ATOM | 207 | CA | THR A | 42 | −20.325 | −7.236 | 6.622 | 1.00 | 17.52 | A | C |
| ATOM | 208 | CB | THR A | 42 | −20.249 | −6.119 | 7.695 | 1.00 | 19.32 | A | C |
| ATOM | 209 | OG1 | THR A | 42 | −21.150 | −5.065 | 7.404 | 1.00 | 20.00 | A | O |
| ATOM | 210 | CG2 | THR A | 42 | −18.829 | −5.613 | 7.800 | 1.00 | 20.09 | A | C |
| ATOM | 211 | C | THR A | 42 | −21.716 | −7.772 | 6.607 | 1.00 | 18.63 | A | C |
| ATOM | 212 | O | THR A | 42 | −22.513 | −7.336 | 5.803 | 1.00 | 18.01 | A | O |
| ATOM | 213 | N | TYR A | 43 | −21.987 | −8.678 | 7.534 | 1.00 | 18.20 | A | N |
| ATOM | 214 | CA | TYR A | 43 | −23.257 | −9.326 | 7.657 | 1.00 | 13.58 | A | C |
| ATOM | 215 | CB | TYR A | 43 | −23.137 | −10.824 | 7.249 | 1.00 | 15.03 | A | C |
| ATOM | 216 | CG | TYR A | 43 | −24.521 | −11.468 | 7.036 | 1.00 | 15.25 | A | C |
| ATOM | 217 | CD1 | TYR A | 43 | −25.256 | −11.958 | 8.114 | 1.00 | 17.63 | A | C |
| ATOM | 218 | CE1 | TYR A | 43 | −26.563 | −12.487 | 7.933 | 1.00 | 16.32 | A | C |
| ATOM | 219 | CZ | TYR A | 43 | −27.079 | −12.625 | 6.619 | 1.00 | 17.17 | A | C |
| ATOM | 220 | OH | TYR A | 43 | −28.340 | −13.221 | 6.353 | 1.00 | 21.04 | A | O |
| ATOM | 221 | CE2 | TYR A | 43 | −26.340 | −12.181 | 5.557 | 1.00 | 16.77 | A | C |
| ATOM | 222 | CD2 | TYR A | 43 | −25.024 | −11.645 | 5.750 | 1.00 | 16.43 | A | C |
| ATOM | 223 | C | TYR A | 43 | −23.676 | −9.188 | 9.118 | 1.00 | 15.26 | A | C |
| ATOM | 224 | O | TYR A | 43 | −22.916 | −9.460 | 9.966 | 1.00 | 17.69 | A | O |
| ATOM | 225 | N | GLU A | 44 | −24.950 | −8.848 | 9.386 | 1.00 | 16.42 | A | N |
| ATOM | 226 | CA | GLU A | 44 | −25.432 | −8.847 | 10.793 | 1.00 | 19.27 | A | C |
| ATOM | 227 | CB | GLU A | 44 | −25.684 | −7.414 | 11.215 | 1.00 | 22.51 | A | C |
| ATOM | 228 | CG | GLU A | 44 | −26.222 | −7.320 | 12.629 | 1.00 | 27.05 | A | C |
| ATOM | 229 | CD | GLU A | 44 | −26.109 | −5.918 | 13.200 | 1.00 | 32.58 | A | C |
| ATOM | 230 | OE1 | GLU A | 44 | −26.066 | −4.943 | 12.437 | 1.00 | 28.73 | A | O |
| ATOM | 231 | OE2 | GLU A | 44 | −26.058 | −5.770 | 14.446 | 1.00 | 32.12 | A | O |
| ATOM | 232 | C | GLU A | 44 | −26.745 | −9.708 | 10.791 | 1.00 | 20.57 | A | C |
| ATOM | 233 | O | GLU A | 44 | −27.705 | −9.375 | 10.090 | 1.00 | 21.96 | A | O |
| ATOM | 234 | N | ALA A | 45 | −26.736 | −10.823 | 11.542 | 1.00 | 22.25 | A | N |
| ATOM | 235 | CA | ALA A | 45 | −27.834 | −11.751 | 11.624 | 1.00 | 21.97 | A | C |
| ATOM | 236 | CB | ALA A | 45 | −27.349 | −13.199 | 11.791 | 1.00 | 23.41 | A | C |
| ATOM | 237 | C | ALA A | 45 | −28.627 | −11.403 | 12.812 | 1.00 | 25.14 | A | C |

-continued

| [X-ray Crystal Structure Analysis Data] | | | | | | | | | | |
|---|---|---|---|---|---|---|---|---|---|---|
| ATOM | 238 | O | ALA A | 45 | −28.053 | −11.009 | 13.822 | 1.00 | 32.36 | A | O |
| ATOM | 239 | N | ALA A | 46 | −29.927 | −11.637 | 12.702 | 1.00 | 24.46 | A | N |
| ATOM | 240 | CA | ALA A | 46 | −30.873 | −11.444 | 13.786 | 1.00 | 28.03 | A | C |
| ATOM | 241 | CB | ALA A | 46 | −32.047 | −10.622 | 13.312 | 1.00 | 31.09 | A | C |
| ATOM | 242 | C | ALA A | 46 | −31.348 | −12.760 | 14.402 | 1.00 | 28.43 | A | C |
| ATOM | 243 | O | ALA A | 46 | −32.006 | −12.748 | 15.426 | 1.00 | 29.54 | A | O |
| ATOM | 244 | N | VAL A | 47 | −31.019 | −13.883 | 13.796 | 1.00 | 23.52 | A | N |
| ATOM | 245 | CA | VAL A | 47 | −31.224 | −15.202 | 14.439 | 1.00 | 22.19 | A | C |
| ATOM | 246 | CB | VAL A | 47 | −32.282 | −16.071 | 13.730 | 1.00 | 23.12 | A | C |
| ATOM | 247 | CG1 | VAL A | 47 | −33.557 | −15.259 | 13.621 | 1.00 | 22.67 | A | C |
| ATOM | 248 | CG2 | VAL A | 47 | −31.837 | −16.487 | 12.334 | 1.00 | 22.80 | A | C |
| ATOM | 249 | C | VAL A | 47 | −29.892 | −15.903 | 14.555 | 1.00 | 24.69 | A | C |
| ATOM | 250 | O | VAL A | 47 | −28.965 | −15.567 | 13.819 | 1.00 | 27.40 | A | O |
| ATOM | 251 | N | GLY A | 48 | −29.814 | −16.875 | 15.451 | 1.00 | 22.30 | A | N |
| ATOM | 252 | CA | GLY A | 48 | −28.646 | −17.733 | 15.555 | 1.00 | 24.01 | A | C |
| ATOM | 253 | C | GLY A | 48 | −27.682 | −17.267 | 16.611 | 1.00 | 23.81 | A | C |
| ATOM | 254 | O | GLY A | 48 | −27.931 | −16.296 | 17.325 | 1.00 | 25.68 | A | O |
| ATOM | 255 | N | ASN A | 49 | −26.557 | −17.963 | 16.693 | 1.00 | 23.09 | A | N |
| ATOM | 256 | CA | ASN A | 49 | −25.539 | −17.682 | 17.711 | 1.00 | 22.53 | A | C |
| ATOM | 257 | CB | ASN A | 49 | −24.810 | −18.960 | 18.065 | 1.00 | 24.14 | A | C |
| ATOM | 258 | CG | ASN A | 49 | −23.906 | −18.802 | 19.264 | 1.00 | 24.89 | A | C |
| ATOM | 259 | OD1 | ASN A | 49 | −23.816 | −17.735 | 19.937 | 1.00 | 25.32 | A | O |
| ATOM | 260 | ND2 | ASN A | 49 | −23.187 | −19.868 | 19.512 | 1.00 | 26.43 | A | N |
| ATOM | 261 | C | ASN A | 49 | −24.580 | −16.623 | 17.154 | 1.00 | 22.24 | A | C |
| ATOM | 262 | O | ASN A | 49 | −23.444 | −16.935 | 16.701 | 1.00 | 21.06 | A | O |
| ATOM | 263 | N | ALA A | 50 | −25.072 | −15.398 | 17.188 | 1.00 | 21.77 | A | N |
| ATOM | 264 | CA | ALA A | 0 | −24.443 | −14.280 | 16.504 | 1.00 | 22.01 | A | C |
| ATOM | 265 | CB | ALA A | 50 | −24.824 | −14.258 | 15.014 | 1.00 | 23.55 | A | C |
| ATOM | 266 | C | ALA A | 50 | −24.843 | −13.014 | 17.138 | 1.00 | 23.23 | A | C |
| ATOM | 267 | O | ALA A | 50 | −25.967 | −12.875 | 17.637 | 1.00 | 21.90 | A | O |
| ATOM | 268 | N | GLU A | 51 | −23.915 | −12.085 | 17.172 | 1.00 | 22.60 | A | N |
| ATOM | 269 | CA | GLU A | 51 | −24.303 | −10.732 | 17.448 | 1.00 | 23.25 | A | C |
| ATOM | 270 | CB | GLU A | 51 | −24.362 | −10.516 | 18.979 | 1.00 | 28.34 | A | C |
| ATOM | 271 | CG | GLU A | 51 | −23.134 | −9.906 | 19.594 | 1.00 | 29.94 | A | C |
| ATOM | 272 | CD | GLU A | 51 | −23.241 | −9.756 | 21.110 | 1.00 | 35.05 | A | C |
| ATOM | 273 | OE1 | GLU A | 51 | −23.233 | −8.595 | 21.556 | 1.00 | 41.25 | A | O |
| ATOM | 274 | OE2 | GLU A | 51 | −23.383 | −10.786 | 21.825 | 1.00 | 38.53 | A | O |
| ATOM | 275 | C | GLU A | 51 | −23.320 | −9.745 | 16.771 | 1.00 | 21.42 | A | C |
| ATOM | 276 | O | GLU A | 51 | −22.138 | −10.041 | 16.573 | 1.00 | 22.31 | A | O |
| ATOM | 277 | N | SER A | 52 | −23.865 | −8.604 | 16.426 | 1.00 | 22.32 | A | N |
| ATOM | 278 | CA | SER A | 52 | −23.186 | −7.511 | 15.803 | 1.00 | 23.10 | A | C |
| ATOM | 279 | CB | SER A | 52 | −21.982 | −7.027 | 16.658 | 1.00 | 26.33 | A | C |
| ATOM | 280 | OG | SER A | 52 | −21.397 | −5.843 | 16.111 | 1.00 | 27.68 | A | O |
| ATOM | 281 | C | SER A | 52 | −22.801 | −7.947 | 14.355 | 1.00 | 22.62 | A | C |
| ATOM | 282 | O | SER A | 52 | −23.340 | −8.947 | 13.780 | 1.00 | 20.26 | A | O |
| ATOM | 283 | N | ARG A | 53 | −21.800 | −7.244 | 13.823 | 1.00 | 21.63 | A | N |
| ATOM | 284 | CA | ARG A | 53 | −21.360 | −7.444 | 12.410 | 1.00 | 21.71 | A | C |
| ATOM | 285 | CB | ARG A | 53 | −20.913 | −6.120 | 11.777 | 1.00 | 26.94 | A | C |
| ATOM | 286 | CG | ARG A | 53 | −22.033 | −5.113 | 11.591 | 1.00 | 32.15 | A | C |
| ATOM | 287 | CD | ARG A | 53 | −21.732 | −3.956 | 10.667 | 1.00 | 41.47 | A | C |
| ATOM | 288 | NE | ARG A | 53 | −21.065 | −2.835 | 11.352 | 1.00 | 54.96 | A | N |
| ATOM | 289 | CZ | ARG A | 53 | −20.755 | −1.651 | 10.788 | 1.00 | 56.22 | A | C |
| ATOM | 290 | NH1 | ARG A | 53 | −21.050 | −1.378 | 9.511 | 1.00 | 51.50 | A | N |
| ATOM | 291 | NH2 | ARG A | 53 | −20.141 | −0.726 | 11.524 | 1.00 | 60.44 | A | N |
| ATOM | 292 | C | ARG A | 53 | −20.217 | −8.478 | 12.308 | 1.00 | 20.08 | A | C |
| ATOM | 293 | O | ARG A | 53 | −19.367 | −8.593 | 13.188 | 1.00 | 18.17 | A | O |
| ATOM | 294 | N | TYR A | 54 | −20.265 | −9.281 | 11.241 | 1.00 | 18.46 | A | N |
| ATOM | 295 | CA | TYR A | 54 | −19.254 | −10.267 | 10.882 | 1.00 | 16.08 | A | C |
| ATOM | 296 | CB | TYR A | 54 | −19.825 | −11.729 | 10.879 | 1.00 | 15.32 | A | C |
| ATOM | 297 | CG | TYR A | 54 | −20.284 | −12.144 | 12.255 | 1.00 | 16.94 | A | C |
| ATOM | 298 | CD1 | TYR A | 54 | −21.542 | −11.766 | 12.705 | 1.00 | 14.12 | A | C |
| ATOM | 299 | CE1 | TYR A | 54 | −21.920 | −12.072 | 14.023 | 1.00 | 15.58 | A | C |
| ATOM | 300 | CZ | TYR A | 54 | −21.134 | −12.808 | 14.789 | 1.00 | 18.44 | A | C |
| ATOM | 301 | OH | TYR A | 54 | −21.509 | −13.120 | 16.060 | 1.00 | 18.97 | A | O |
| ATOM | 302 | CE2 | TYR A | 54 | −19.919 | −13.234 | 14.353 | 1.00 | 18.64 | A | C |
| ATOM | 303 | CD2 | TYR A | 54 | −19.506 | −12.914 | 13.074 | 1.00 | 16.26 | A | C |
| ATOM | 304 | C | TYR A | 54 | −18.713 | −9.978 | 9.463 | 1.00 | 15.04 | A | C |
| ATOM | 305 | O | TYR A | 54 | −19.423 | −9.541 | 8.584 | 1.00 | 16.36 | A | O |
| ATOM | 306 | N | VAL A | 55 | −17.405 | −10.205 | 9.282 | 1.00 | 14.03 | A | N |
| ATOM | 307 | CA | VAL A | 55 | −16.832 | −10.038 | 7.957 | 1.00 | 15.87 | A | C |
| ATOM | 308 | CB | VAL A | 55 | −15.281 | −10.209 | 8.003 | 1.00 | 17.23 | A | C |
| ATOM | 309 | CG1 | VAL A | 55 | −14.677 | −10.261 | 6.588 | 1.00 | 17.72 | A | C |
| ATOM | 310 | CG2 | VAL A | 55 | −14.699 | −9.057 | 8.757 | 1.00 | 19.72 | A | C |
| ATOM | 311 | C | VAL A | 55 | −17.383 | −10.996 | 6.954 | 1.00 | 16.79 | A | C |
| ATOM | 312 | O | VAL A | 55 | −17.656 | −12.191 | 7.247 | 1.00 | 17.29 | A | O |
| ATOM | 313 | N | LEU A | 56 | −17.505 | −10.525 | 5.720 | 1.00 | 19.39 | A | N |
| ATOM | 314 | CA | LEU A | 56 | −17.899 | −11.500 | 4.691 | 1.00 | 22.53 | A | C |

[X-ray Crystal Structure Analysis Data]

| ATOM | 315 | CB  | LEU A | 56 | −19.358 | −11.358 | 4.279   | 1.00 | 22.49 | A | C |
|------|-----|-----|-------|----|---------|---------|---------|------|-------|---|---|
| ATOM | 316 | CG  | LEU A | 56 | −19.806 | −10.155 | 3.459   | 1.00 | 19.77 | A | C |
| ATOM | 317 | CD1 | LEU A | 56 | −19.782 | −10.273 | 1.881   | 1.00 | 18.92 | A | C |
| ATOM | 318 | CD2 | LEU A | 56 | −21.211 | −9.844  | 3.832   | 1.00 | 24.33 | A | C |
| ATOM | 319 | C   | LEU A | 56 | −17.107 | −11.241 | 3.488   | 1.00 | 21.24 | A | C |
| ATOM | 320 | O   | LEU A | 56 | −16.717 | −10.106 | 3.250   | 1.00 | 19.27 | A | O |
| ATOM | 321 | N   | THR A | 57 | −16.904 | −12.303 | 2.730   | 1.00 | 16.28 | A | N |
| ATOM | 322 | CA  | THR A | 57 | −16.209 | −12.164 | 1.501   | 1.00 | 16.59 | A | C |
| ATOM | 323 | CB  | THR A | 57 | −14.685 | −12.409 | 1.732   | 1.00 | 16.53 | A | C |
| ATOM | 324 | OG1 | THR A | 57 | −14.036 | −12.117 | 0.532   | 1.00 | 23.86 | A | O |
| ATOM | 325 | CG2 | THR A | 57 | −14.344 | −13.872 | 1.998   | 1.00 | 16.65 | A | C |
| ATOM | 326 | C   | THR A | 57 | −16.810 | −13.083 | 0.489   | 1.00 | 16.06 | A | C |
| ATOM | 327 | O   | THR A | 57 | −17.233 | −14.168 | 0.830   | 1.00 | 15.61 | A | O |
| ATOM | 328 | N   | GLY A | 58 | −16.704 | −12.771 | −0.806  | 1.00 | 15.90 | A | N |
| ATOM | 329 | CA  | GLY A | 58 | −17.231 | −13.649 | −1.793  | 1.00 | 13.46 | A | C |
| ATOM | 330 | C   | GLY A | 58 | −16.854 | −13.187 | −3.152  | 1.00 | 14.30 | A | C |
| ATOM | 331 | O   | GLY A | 58 | −15.916 | −12.393 | −3.294  | 1.00 | 14.85 | A | O |
| ATOM | 332 | N   | ARG A | 59 | −17.563 | −13.701 | −4.124  | 1.00 | 13.42 | A | N |
| ATOM | 333 | CA  | ARG A | 59 | −17.294 | −13.505 | −5.559  | 1.00 | 13.58 | A | C |
| ATOM | 334 | CB  | ARG A | 59 | −16.514 | −14.70  | −6.134  | 1.00 | 15.75 | A | C |
| ATOM | 335 | CG  | ARG A | 59 | −15.134 | −14.937 | −5.565  | 1.00 | 16.64 | A | C |
| ATOM | 336 | CD  | ARG A | 59 | −14.020 | −13.925 | −5.773  | 1.00 | 13.78 | A | C |
| ATOM | 337 | NE  | ARG A | 59 | −13.722 | −13.854 | −7.223  | 1.00 | 14.26 | A | N |
| ATOM | 338 | CZ  | ARG A | 59 | −13.023 | −12.887 | −7.794  | 1.00 | 19.57 | A | C |
| ATOM | 339 | NH1 | ARG A | 59 | −12.592 | −11.861 | −7.108  | 1.00 | 20.45 | A | N |
| ATOM | 340 | NH2 | ARG A | 59 | −12.838 | −12.886 | −9.107  | 1.00 | 20.51 | A | N |
| ATOM | 341 | C   | ARG A | 59 | −18.658 | −13.352 | −6.294  | 1.00 | 15.96 | A | C |
| ATOM | 342 | O   | ARG A | 59 | −19.696 | −13.972 | −5.915  | 1.00 | 17.20 | A | O |
| ATOM | 343 | N   | TYR A | 60 | −18.661 | −12.660 | −7.465  | 1.00 | 16.16 | A | N |
| ATOM | 344 | CA  | TYR A | 60 | −19.863 | −12.589 | −8.308  | 1.00 | 15.24 | A | C |
| ATOM | 345 | CB  | TYR A | 60 | −20.623 | −11.288 | −7.993  | 1.00 | 18.01 | A | C |
| ATOM | 346 | CG  | TYR A | 60 | −20.007 | −10.033 | −8.448  | 1.00 | 19.37 | A | C |
| ATOM | 347 | CD1 | TYR A | 60 | −18.931 | −9.480  | −7.768  | 1.00 | 20.00 | A | C |
| ATOM | 348 | CE1 | TYR A | 60 | −18.344 | −8.307  | −8.209  | 1.00 | 23.72 | A | C |
| ATOM | 349 | CZ  | TYR A | 60 | −18.801 | −7.751  | −9.397  | 1.00 | 24.97 | A | C |
| ATOM | 350 | OH  | TYR A | 60 | −18.233 | −6.623  | −9.806  | 1.00 | 30.56 | A | O |
| ATOM | 351 | CE2 | TYR A | 60 | −19.870 | −8.231  | −10.054 | 1.00 | 25.42 | A | C |
| ATOM | 352 | CD2 | TYR A | 60 | −20.464 | −9.394  | −9.615  | 1.00 | 22.87 | A | C |
| ATOM | 353 | C   | TYR A | 60 | −19.325 | −12.599 | −9.753  | 1.00 | 13.87 | A | C |
| ATOM | 354 | O   | TYR A | 60 | −18.110 | −12.255 | −9.972  | 1.00 | 15.00 | A | O |
| ATOM | 355 | N   | ASP A | 61 | −20.194 | −12.860 | −10.705 | 1.00 | 14.02 | A | N |
| ATOM | 356 | CA  | ASP A | 61 | −19.944 | −12.789 | −12.125 | 1.00 | 14.36 | A | C |
| ATOM | 357 | CB  | ASP A | 61 | −20.998 | −13.619 | −12.840 | 1.00 | 15.26 | A | C |
| ATOM | 358 | CG  | ASP A | 61 | −20.851 | −13.603 | −14.378 | 1.00 | 16.51 | A | C |
| ATOM | 359 | OD1 | ASP A | 61 | −19.945 | −12.917 | −14.829 | 1.00 | 19.73 | A | O |
| ATOM | 360 | OD2 | ASP A | 61 | −21.722 | −14.173 | −14.987 | 1.00 | 17.72 | A | O |
| ATOM | 361 | C   | ASP A | 61 | −20.003 | −11.288 | −12.518 | 1.00 | 17.15 | A | C |
| ATOM | 362 | O   | ASP A | 61 | −21.056 | −10.705 | −12.508 | 1.00 | 19.35 | A | O |
| ATOM | 363 | N   | SER A | 62 | −18.842 | −10.745 | −12.807 | 1.00 | 19.28 | A | N |
| ATOM | 364 | CA  | SER A | 62 | −18.697 | −9.337  | −13.203 | 1.00 | 20.58 | A | C |
| ATOM | 365 | CB  | SER A | 62 | −17.294 | −8.844  | −12.865 | 1.00 | 22.24 | A | C |
| ATOM | 366 | OG  | SER A | 62 | −16.296 | −9.650  | −13.371 | 1.00 | 24.82 | A | O |
| ATOM | 367 | C   | SER A | 62 | −18.979 | −9.128  | −14.684 | 1.00 | 22.52 | A | C |
| ATOM | 368 | O   | SER A | 62 | −18.953 | −8.022  | −15.107 | 1.00 | 24.22 | A | O |
| ATOM | 369 | N   | ALA A | 63 | −19.244 | −10.166 | −15.441 | 1.00 | 23.33 | A | N |
| ATOM | 370 | CA  | ALA A | 63 | −19.693 | −9.993  | −16.854 | 1.00 | 23.68 | A | C |
| ATOM | 371 | CB  | ALA A | 63 | −18.596 | −10.298 | −17.824 | 1.00 | 23.75 | A | C |
| ATOM | 372 | C   | ALA A | 63 | −20.885 | −10.897 | −17.123 | 1.00 | 22.86 | A | C |
| ATOM | 373 | O   | ALA A | 63 | −20.750 | −11.912 | −17.840 | 1.00 | 22.66 | A | O |
| ATOM | 374 | N   | PRO A | 64 | −22.020 | −10.622 | −16.474 | 1.00 | 22.56 | A | N |
| ATOM | 375 | CA  | PRO A | 64 | −23.161 | −11.523 | −16.577 | 1.00 | 21.49 | A | C |
| ATOM | 376 | CB  | PRO A | 64 | −24.074 | −11.079 | −15.430 | 1.00 | 21.77 | A | C |
| ATOM | 377 | CG  | PRO A | 64 | −23.775 | −9.605  | −15.323 | 1.00 | 21.35 | A | C |
| ATOM | 378 | CD  | PRO A | 64 | −22.309 | −9.472  | −15.587 | 1.00 | 24.56 | A | C |
| ATOM | 379 | C   | PRO A | 64 | −23.805 | −11.460 | −17.974 | 1.00 | 23.78 | A | C |
| ATOM | 380 | O   | PRO A | 64 | −23.546 | −10.540 | −18.718 | 1.00 | 24.16 | A | O |
| ATOM | 381 | N   | ALA A | 65 | −24.555 | −12.499 | −18.307 | 1.00 | 22.56 | A | N |
| ATOM | 382 | CA  | ALA A | 65 | −25.262 | −12.592 | −19.579 | 1.00 | 27.60 | A | C |
| ATOM | 383 | CB  | ALA A | 65 | −25.974 | −13.919 | −19.690 | 1.00 | 26.99 | A | C |
| ATOM | 384 | C   | ALA A | 65 | −26.233 | −11.428 | −19.657 | 1.00 | 30.08 | A | C |
| ATOM | 385 | O   | ALA A | 65 | −26.701 | −10.907 | −18.646 | 1.00 | 31.03 | A | O |
| ATOM | 386 | N   | THR A | 66 | −26.490 | −10.964 | −20.871 | 1.00 | 33.71 | A | N |
| ATOM | 387 | CA  | THR A | 66 | −27.342 | −9.791  | −21.038 | 1.00 | 36.18 | A | C |
| ATOM | 388 | CB  | THR A | 66 | −26.654 | −8.768  | −21.957 | 1.00 | 34.93 | A | C |
| ATOM | 389 | OG1 | THR A | 66 | −26.540 | −9.331  | −23.242 | 1.00 | 33.52 | A | O |
| ATOM | 390 | CG2 | THR A | 66 | −25.245 | −8.437  | −21.517 | 1.00 | 37.15 | A | C |
| ATOM | 391 | C   | THR A | 66 | −28.710 | −10.218 | −21.595 | 1.00 | 37.97 | A | C |

-continued

[X-ray Crystal Structure Analysis Data]

| ATOM | 392 | O | THR A | 66 | −29.387 | −9.417 | −22.223 | 1.00 | 40.69 | A | O |
|------|-----|-----|-------|----|---------|--------|---------|------|-------|---|---|
| ATOM | 393 | N | ASP A | 67 | −29.130 | −11.456 | −21.319 | 1.00 | 33.68 | A | N |
| ATOM | 394 | CA | ASP A | 67 | −30.317 | −12.113 | −21.917 | 1.00 | 32.13 | A | C |
| ATOM | 395 | CB | ASP A | 67 | −29.937 | −13.522 | −22.412 | 1.00 | 32.24 | A | C |
| ATOM | 396 | CG | ASP A | 67 | −29.592 | −14.483 | −21.282 | 1.00 | 33.84 | A | C |
| ATOM | 397 | OD1 | ASP A | 67 | −29.545 | −14.060 | −20.103 | 1.00 | 32.63 | A | O |
| ATOM | 398 | OD2 | ASP A | 67 | −29.376 | −15.670 | −21.577 | 1.00 | 36.09 | A | O |
| ATOM | 399 | C | ASP A | 67 | −31.548 | −12.193 | −20.986 | 1.00 | 32.11 | A | C |
| ATOM | 400 | O | ASP A | 67 | −32.459 | −12.967 | −21.223 | 1.00 | 33.62 | A | O |
| ATOM | 401 | N | GLY A | 68 | −31.539 | −11.416 | −19.907 | 1.00 | 30.44 | A | N |
| ATOM | 402 | CA | GLY A | 68 | −32.501 | −11.549 | −18.83 | 1.00 | 31.92 | A | C |
| ATOM | 403 | C | GLY A | 68 | −32.133 | −12.473 | −17.679 | 1.00 | 28.89 | A | C |
| ATOM | 404 | O | GLY A | 68 | −32.903 | −12.596 | −16.739 | 1.00 | 31.13 | A | O |
| ATOM | 405 | N | SER A | 69 | −30.971 | −13.101 | −17.733 | 1.00 | 25.39 | A | N |
| ATOM | 406 | CA | SER A | 69 | −30.542 | −13.967 | −16.650 | 1.00 | 22.55 | A | C |
| ATOM | 407 | CB | SER A | 69 | −29.503 | −14.934 | −17.123 | 1.00 | 25.44 | A | C |
| ATOM | 408 | OG | SER A | 69 | −30.104 | −15.772 | −18.120 | 1.00 | 27.24 | A | O |
| ATOM | 409 | C | SER A | 69 | −30.050 | −13.203 | −15.513 | 1.00 | 19.12 | A | C |
| ATOM | 410 | O | SER A | 69 | −29.577 | −12.041 | −15.669 | 1.00 | 19.68 | A | O |
| ATOM | 411 | N | GLY A | 70 | −30.132 | −13.821 | −14.338 | 1.00 | 17.46 | A | N |
| ATOM | 412 | CA | GLY A | 70 | −29.626 | −13.212 | −13.124 | 1.00 | 17.75 | A | C |
| ATOM | 413 | C | GLY A | 70 | −28.086 | −13.203 | −13.131 | 1.00 | 18.15 | A | C |
| ATOM | 414 | O | GLY A | 70 | −27.433 | −13.834 | −13.998 | 1.00 | 19.62 | A | O |
| ATOM | 415 | N | THR A | 71 | −27.533 | −12.628 | −12.074 | 1.00 | 16.48 | A | N |
| ATOM | 416 | CA | THR A | 71 | −26.083 | −12.590 | −11.947 | 1.00 | 16.65 | A | C |
| ATOM | 417 | CB | THR A | 71 | −25.610 | −11.164 | −11.618 | 1.00 | 17.07 | A | C |
| ATOM | 418 | OG1 | THR A | 71 | −25.967 | −10.234 | −12.705 | 1.00 | 18.85 | A | O |
| ATOM | 419 | CG2 | THR A | 71 | −24.130 | −11.132 | −11.344 | 1.00 | 17.20 | A | C |
| ATOM | 420 | C | THR A | 71 | −25.663 | −13.555 | −10.839 | 1.00 | 14.35 | A | C |
| ATOM | 421 | O | THR A | 71 | −25.952 | −13.289 | −9.654 | 1.00 | 15.70 | A | O |
| ATOM | 422 | N | ALA A | 72 | −24.848 | −14.550 | −11.128 | 1.00 | 18.08 | A | N |
| ATOM | 423 | CA | ALA A | 72 | −24.476 | −15.522 | −10.105 | 1.00 | 16.77 | A | C |
| ATOM | 424 | CB | ALA A | 72 | −23.888 | −16.757 | −10.771 | 1.00 | 17.75 | A | C |
| ATOM | 425 | C | ALA A | 72 | −23.494 | −14.948 | −9.113 | 1.00 | 16.31 | A | C |
| ATOM | 426 | O | ALA A | 72 | −22.580 | −14.177 | −9.449 | 1.00 | 16.01 | A | O |
| ATOM | 427 | N | LEU A | 73 | −23.693 | −15.287 | −7.841 | 1.00 | 16.00 | A | N |
| ATOM | 428 | CA | LEU A | 73 | −22.808 | −14.821 | −6.796 | 1.00 | 18.83 | A | C |
| ATOM | 429 | CB | LEU A | 73 | −23.145 | −13.325 | −6.407 | 1.00 | 18.62 | A | C |
| ATOM | 430 | CG | LEU A | 73 | −24.344 | −13.052 | −5.538 | 1.00 | 22.18 | A | C |
| ATOM | 431 | CD1 | LEU A | 73 | −24.634 | −11.547 | −5.450 | 1.00 | 23.44 | A | C |
| ATOM | 432 | CD2 | LEU A | 73 | −25.560 | −13.696 | −6.010 | 1.00 | 21.87 | A | C |
| ATOM | 433 | C | LEU A | 73 | −22.811 | −15.777 | −5.592 | 1.00 | 17.40 | A | C |
| ATOM | 434 | O | LEU A | 73 | −23.638 | −16.748 | −5.518 | 1.00 | 17.94 | A | O |
| ATOM | 435 | N | GLY A | 74 | −21.766 | −15.645 | −4.775 | 1.00 | 15.31 | A | N |
| ATOM | 436 | CA | GLY A | 74 | −21.767 | −16.236 | −3.442 | 1.00 | 15.54 | A | C |
| ATOM | 437 | C | GLY A | 74 | −20.853 | −15.640 | −2.457 | 1.00 | 13.62 | A | C |
| ATOM | 438 | O | GLY A | 74 | −20.028 | −14.852 | −2.800 | 1.00 | 16.00 | A | O |
| ATOM | 439 | N | TRP A | 75 | −21.077 | −15.887 | −1.167 | 1.00 | 14.11 | A | N |
| ATOM | 440 | CA | TRP A | 75 | −20.254 | −15.326 | −0.184 | 1.00 | 12.96 | A | C |
| ATOM | 441 | CB | TRP A | 75 | −20.643 | −13.831 | 0.171 | 1.00 | 14.00 | A | C |
| ATOM | 442 | CG | TRP A | 75 | −21.888 | −13.678 | 0.861 | 1.00 | 12.48 | A | C |
| ATOM | 443 | CD1 | TRP A | 75 | −22.093 | −13.659 | 2.224 | 1.00 | 13.45 | A | C |
| ATOM | 444 | NE1 | TRP A | 75 | −23.433 | −13.496 | 2.477 | 1.00 | 12.74 | A | N |
| ATOM | 445 | CE2 | TRP A | 75 | −24.090 | −13.413 | 1.288 | 1.00 | 13.13 | A | C |
| ATOM | 446 | CD2 | TRP A | 75 | −23.161 | −13.474 | 0.280 | 1.00 | 10.73 | A | C |
| ATOM | 447 | CE3 | TRP A | 75 | −23.605 | −13.392 | −1.063 | 1.00 | 10.66 | A | C |
| ATOM | 448 | CZ3 | TRP A | 75 | −25.058 | −13.244 | −1.275 | 1.00 | 13.04 | A | C |
| ATOM | 449 | CH2 | TRP A | 75 | −25.893 | −13.170 | −0.237 | 1.00 | 13.87 | A | C |
| ATOM | 450 | CZ2 | TRP A | 75 | −25.462 | −13.207 | 1.044 | 1.00 | 13.00 | A | C |
| ATOM | 451 | C | TRP A | 75 | −20.310 | −16.147 | 1.071 | 1.00 | 14.17 | A | C |
| ATOM | 452 | O | TRP A | 75 | −21.141 | −17.038 | 1.211 | 1.00 | 13.15 | A | O |
| ATOM | 453 | N | THR A | 76 | −19.320 | −15.941 | 1.939 | 1.00 | 13.58 | A | N |
| ATOM | 454 | CA | THR A | 76 | −19.153 | −16.640 | 3.194 | 1.00 | 13.35 | A | C |
| ATOM | 455 | CB | THR A | 76 | −17.822 | −17.502 | 3.176 | 1.00 | 13.60 | A | C |
| ATOM | 456 | OG1 | THR A | 76 | −17.818 | −18.322 | 2.037 | 1.00 | 14.67 | A | O |
| ATOM | 457 | CG2 | THR A | 76 | −17.651 | −18.293 | 4.382 | 1.00 | 13.14 | A | C |
| ATOM | 458 | C | THR A | 76 | −19.061 | −15.691 | 4.332 | 1.00 | 13.74 | A | C |
| ATOM | 459 | O | THR A | 76 | −18.381 | −14.644 | 4.258 | 1.00 | 13.39 | A | O |
| ATOM | 460 | N | VAL A | 77 | −19.554 | −16.146 | 5.452 | 1.00 | 14.79 | A | N |
| ATOM | 461 | CA | VAL A | 77 | −19.354 | −15.556 | 6.762 | 1.00 | 16.07 | A | C |
| ATOM | 462 | CB | VAL A | 77 | −20.627 | −14.915 | 7.318 | 1.00 | 15.64 | A | C |
| ATOM | 463 | CG1 | VAL A | 77 | −20.469 | −14.678 | 8.863 | 1.00 | 15.86 | A | C |
| ATOM | 464 | CG2 | VAL A | 77 | −20.953 | −13.599 | 6.619 | 1.00 | 17.81 | A | C |
| ATOM | 465 | C | VAL A | 77 | −18.914 | −16.661 | 7.698 | 1.00 | 16.25 | A | C |
| ATOM | 466 | O | VAL A | 77 | −19.582 | −17.691 | 7.840 | 1.00 | 14.79 | A | O |
| ATOM | 467 | N | ALA A | 78 | −17.760 | −16.493 | 8.354 | 1.00 | 17.31 | A | N |
| ATOM | 468 | CA | ALA A | 78 | −17.360 | −17.328 | 9.505 | 1.00 | 16.85 | A | C |

[X-ray Crystal Structure Analysis Data]

| | | | | | | | | | | |
|---|---|---|---|---|---|---|---|---|---|---|
| ATOM | 469 | CB | ALA A | 78 | −15.847 | −17.445 | 9.605 | 1.00 | 16.28 | A C |
| ATOM | 470 | C | ALA A | 78 | −17.848 | −16.590 | 10.737 | 1.00 | 15.93 | A C |
| ATOM | 471 | O | ALA A | 78 | −17.496 | −15.428 | 10.925 | 1.00 | 15.72 | A O |
| ATOM | 472 | N | TRP A | 79 | −18.532 | −17.278 | 11.613 | 1.00 | 15.43 | A N |
| ATOM | 473 | CA | TRP A | 79 | −19.276 | −16.691 | 12.733 | 1.00 | 15.50 | A C |
| ATOM | 474 | CB | TRP A | 79 | −20.562 | −17.493 | 13.012 | 1.00 | 14.81 | A C |
| ATOM | 475 | CG | TRP A | 79 | −21.497 | −17.495 | 11.858 | 1.00 | 16.50 | A C |
| ATOM | 476 | CD1 | TRP A | 79 | −21.711 | −18.501 | 11.002 | 1.00 | 17.06 | A C |
| ATOM | 477 | NE1 | TRP A | 79 | −22.608 | −18.129 | 10.052 | 1.00 | 17.03 | A N |
| ATOM | 478 | CE2 | TRP A | 79 | −23.001 | −16.834 | 10.275 | 1.00 | 16.87 | A C |
| ATOM | 479 | CD2 | TRP A | 79 | −22.345 | −16.421 | 11.472 | 1.00 | 15.24 | A C |
| ATOM | 480 | CE3 | TRP A | 79 | −22.515 | −15.107 | 11.908 | 1.00 | 15.07 | A C |
| ATOM | 481 | CZ3 | TRP A | 79 | −23.480 | −14.307 | 11.261 | 1.00 | 17.46 | A C |
| ATOM | 482 | CH2 | TRP A | 79 | −24.144 | −14.775 | 10.100 | 1.00 | 17.01 | A C |
| ATOM | 483 | CZ2 | TRP A | 79 | −23.960 | −16.046 | 9.632 | 1.00 | 15.22 | A C |
| ATOM | 484 | C | TRP A | 79 | −18.419 | −16.493 | 13.974 | 1.00 | 16.09 | A C |
| ATOM | 485 | O | TRP A | 79 | −18.774 | −16.885 | 15.101 | 1.00 | 15.87 | A O |
| ATOM | 486 | N | LYS A | 80 | −17.332 | −15.747 | 13.731 | 1.00 | 16.59 | A N |
| ATOM | 487 | CA | LYS A | 80 | −16.359 | −15.317 | 14.729 | 1.00 | 17.83 | A C |
| ATOM | 488 | CB | LYS A | 80 | −14.980 | −16.044 | 14.616 | 1.00 | 18.82 | A C |
| ATOM | 489 | CG | LYS A | 80 | −13.922 | −15.486 | 15.531 | 1.00 | 21.76 | A C |
| ATOM | 490 | CD | LYS A | 80 | −12.625 | −16.237 | 15.397 | 1.00 | 21.35 | A C |
| ATOM | 491 | CE | LYS A | 80 | −11.570 | −15.750 | 16.376 | 1.00 | 27.27 | A C |
| ATOM | 492 | NZ | LYS A | 80 | −11.240 | −14.331 | 16.151 | 1.00 | 28.66 | A N |
| ATOM | 493 | C | LYS A | 80 | −16.223 | −13.813 | 14.524 | 1.00 | 16.06 | A C |
| ATOM | 494 | O | LYS A | 80 | −15.965 | −13.357 | 13.402 | 1.00 | 17.08 | A O |
| ATOM | 495 | N | ASN A | 81 | −16.368 | −13.082 | 15.611 | 1.00 | 14.95 | A N |
| ATOM | 496 | CA | ASN A | 81 | −16.057 | −11.634 | 15.583 | 1.00 | 16.12 | A C |
| ATOM | 497 | CB | ASN A | 81 | −17.286 | −10.777 | 15.127 | 1.00 | 17.96 | A C |
| ATOM | 498 | CG | ASN A | 81 | −18.388 | −10.753 | 16.104 | 1.00 | 18.61 | A C |
| ATOM | 499 | OD1 | ASN A | 81 | −18.223 | −11.244 | 17.223 | 1.00 | 19.62 | A O |
| ATOM | 500 | ND2 | ASN A | 81 | −19.544 | −10.151 | 15.703 | 1.00 | 17.57 | A N |
| ATOM | 501 | C | ASN A | 81 | −15.515 | −11.315 | 16.969 | 1.00 | 17.19 | A C |
| ATOM | 502 | O | ASN A | 81 | −15.120 | −12.214 | 17.680 | 1.00 | 20.06 | A O |
| ATOM | 503 | N | ASN A | 82 | −15.439 | −10.051 | 17.330 | 1.00 | 17.87 | A N |
| ATOM | 504 | CA | ASN A | 82 | −14.879 | −9.763 | 18.683 | 1.00 | 22.34 | A C |
| ATOM | 505 | CB | ASN A | 82 | −14.355 | −8.318 | 18.741 | 1.00 | 24.12 | A C |
| ATOM | 506 | CG | ASN A | 82 | −13.101 | −8.138 | 17.892 | 1.00 | 28.20 | A C |
| ATOM | 507 | OD1 | ASN A | 82 | −12.962 | −7.133 | 17.246 | 1.00 | 38.07 | A O |
| ATOM | 508 | ND2 | ASN A | 82 | −12.189 | −9.122 | 17.894 | 1.00 | 31.84 | A N |
| ATOM | 509 | C | ASN A | 82 | −15.727 | −10.125 | 19.856 | 1.00 | 21.87 | A C |
| ATOM | 510 | O | ASN A | 82 | −15.200 | −10.118 | 21.004 | 1.00 | 24.02 | A O |
| ATOM | 511 | N | TYR A | 83 | −17.002 | −10.487 | 19.632 | 1.00 | 21.94 | A N |
| ATOM | 512 | CA | TYR A | 83 | −17.992 | −10.735 | 20.673 | 1.00 | 22.27 | A C |
| ATOM | 513 | CB | TYR A | 83 | −19.325 | −10.081 | 20.280 | 1.00 | 25.09 | A C |
| ATOM | 514 | CG | TYR A | 83 | −19.220 | −8.594 | 20.114 | 1.00 | 26.11 | A C |
| ATOM | 515 | CD1 | TYR A | 83 | −19.179 | −7.766 | 21.219 | 1.00 | 33.29 | A C |
| ATOM | 516 | CE1 | TYR A | 83 | −19.059 | −6.381 | 21.089 | 1.00 | 35.35 | A C |
| ATOM | 517 | CZ | TYR A | 83 | −18.941 | −5.833 | 19.835 | 1.00 | 37.95 | A C |
| ATOM | 518 | OH | TYR A | 83 | −18.801 | −4.470 | 19.710 | 1.00 | 33.88 | A O |
| ATOM | 519 | CE2 | TYR A | 83 | −18.970 | −6.646 | 18.701 | 1.00 | 33.39 | A C |
| ATOM | 520 | CD2 | TYR A | 83 | −19.101 | −8.026 | 18.852 | 1.00 | 30.39 | A C |
| ATOM | 521 | C | TYR A | 83 | −18.267 | −12.203 | 20.883 | 1.00 | 21.14 | A C |
| ATOM | 522 | O | TYR A | 83 | −18.446 | −12.661 | 22.014 | 1.00 | 19.32 | A O |
| ATOM | 523 | N | ARG A | 84 | −18.304 | −12.942 | 19.803 | 1.00 | 18.05 | A N |
| ATOM | 524 | CA | ARG A | 84 | −18.693 | −14.340 | 19.841 | 1.00 | 21.22 | A C |
| ATOM | 525 | CB | ARG A | 84 | −20.139 | −14.450 | 19.468 | 1.00 | 25.01 | A C |
| ATOM | 526 | CG | ARG A | 84 | −21.096 | −13.638 | 20.291 | 1.00 | 29.95 | A C |
| ATOM | 527 | CD | ARG A | 84 | −22.364 | −14.447 | 20.386 | 1.00 | 34.03 | A C |
| ATOM | 528 | NE | ARG A | 84 | −23.415 | −13.701 | 21.042 | 1.00 | 34.10 | A N |
| ATOM | 529 | CZ | ARG A | 84 | −24.663 | −14.090 | 21.117 | 1.00 | 31.11 | A C |
| ATOM | 530 | NH1 | ARG A | 84 | −25.531 | −13.331 | 21.751 | 1.00 | 39.24 | A N |
| ATOM | 531 | NH2 | ARG A | 84 | −25.056 | −15.221 | 20.582 | 1.00 | 33.47 | A N |
| ATOM | 532 | C | ARG A | 84 | −17.928 | −15.204 | 18.857 | 1.00 | 20.17 | A C |
| ATOM | 533 | O | ARG A | 84 | −17.398 | −14.725 | 17.852 | 1.00 | 20.60 | A O |
| ATOM | 534 | N | ASN A | 85 | −17.984 | −16.486 | 19.088 | 1.00 | 19.41 | A N |
| ATOM | 535 | CA | ASN A | 85 | −17.507 | −17.460 | 18.123 | 1.00 | 18.43 | A C |
| ATOM | 536 | CB | ASN A | 85 | −16.015 | −17.812 | 18.344 | 1.00 | 18.24 | A C |
| ATOM | 537 | CG | ASN A | 85 | −15.423 | −18.651 | 17.242 | 1.00 | 20.74 | A C |
| ATOM | 538 | OD1 | ASN A | 85 | −16.094 | −19.114 | 16.349 | 1.00 | 18.84 | A O |
| ATOM | 539 | ND2 | ASN A | 85 | −14.093 | −18.767 | 17.262 | 1.00 | 18.92 | A N |
| ATOM | 540 | C | ASN A | 85 | −18.356 | −18.704 | 18.173 | 1.00 | 18.92 | A C |
| ATOM | 541 | O | ASN A | 85 | −18.242 | −19.467 | 19.113 | 1.00 | 19.47 | A O |
| ATOM | 542 | N | ALA A | 86 | −19.239 | −18.884 | 17.175 | 1.00 | 17.92 | A N |
| ATOM | 543 | CA | ALA A | 86 | −20.095 | −20.020 | 17.081 | 1.00 | 17.69 | A C |
| ATOM | 544 | CB | ALA A | 86 | −21.390 | −19.654 | 16.331 | 1.00 | 17.69 | A C |
| ATOM | 545 | C | ALA A | 86 | −19.450 | −21.253 | 16.488 | 1.00 | 17.54 | A C |

-continued

[X-ray Crystal Structure Analysis Data]

| ATOM | 546 | O   | ALA A | 86 | −20.107 | −22.248 | 16.418  | 1.00 | 17.38 | A | O |
|------|-----|-----|-------|----|---------|---------|---------|------|-------|---|---|
| ATOM | 547 | N   | HIS A | 87 | −18.184 | −21.154 | 16.046  | 1.00 | 16.01 | A | N |
| ATOM | 548 | CA  | HIS A | 87 | −17.432 | −22.252 | 15.479  | 1.00 | 19.04 | A | C |
| ATOM | 549 | CB  | HIS A | 87 | −17.100 | −23.300 | 16.498  | 1.00 | 20.58 | A | C |
| ATOM | 550 | CG  | HIS A | 87 | −16.312 | −22.775 | 17.657  | 1.00 | 19.99 | A | C |
| ATOM | 551 | ND1 | HIS A | 87 | −15.116 | −22.096 | 17.528  | 1.00 | 21.42 | A | N |
| ATOM | 552 | CE1 | HIS A | 87 | −14.644 | −21.807 | 18.733  | 1.00 | 23.43 | A | C |
| ATOM | 553 | NE2 | HIS A | 87 | −15.516 | −22.240 | 19.630  | 1.00 | 21.31 | A | N |
| ATOM | 554 | CD2 | HIS A | 87 | −16.552 | −22.869 | 18.986  | 1.00 | 21.83 | A | C |
| ATOM | 555 | C   | HIS A | 87 | −18.216 | −22.804 | 14.322  | 1.00 | 17.42 | A | C |
| ATOM | 556 | O   | HIS A | 87 | −18.611 | −24.025 | 14.257  | 1.00 | 17.49 | A | O |
| ATOM | 557 | N   | SER A | 88 | −18.495 | −21.884 | 13.406  | 1.00 | 17.30 | A | N |
| ATOM | 558 | CA  | SER A | 88 | −19.449 | −22.198 | 12.309  | 1.00 | 17.06 | A | C |
| ATOM | 559 | CB  | SER A | 88 | −20.933 | −22.153 | 12.740  | 1.00 | 18.01 | A | C |
| ATOM | 560 | OG  | SER A | 88 | −21.349 | −20.813 | 13.082  | 1.00 | 17.58 | A | O |
| ATOM | 561 | C   | SER A | 88 | −19.214 | −21.209 | 11.198  | 1.00 | 15.34 | A | C |
| ATOM | 562 | O   | SER A | 88 | −18.656 | −20.132 | 11.410  | 1.00 | 16.11 | A | O |
| ATOM | 563 | N   | ALA A | 89 | −19.639 | −21.599 | 10.017  | 1.00 | 15.46 | A | N |
| ATOM | 564 | CA  | ALA A | 89 | −19.554 | −20.778 | 8.842   | 1.00 | 15.99 | A | C |
| ATOM | 565 | CB  | ALA A | 89 | −18.241 | −21.029 | 8.075   | 1.00 | 16.91 | A | C |
| ATOM | 566 | C   | ALA A | 89 | −20.783 | −21.036 | 7.924   | 1.00 | 14.84 | A | C |
| ATOM | 567 | O   | ALA A | 89 | −21.207 | −22.161 | 7.761   | 1.00 | 15.00 | A | O |
| ATOM | 568 | N   | THR A | 90 | −21.324 | −19.977 | 7.365   | 1.00 | 13.80 | A | N |
| ATOM | 569 | CA  | THR A | 90 | −22.291 | −20.101 | 6.317   | 1.00 | 13.02 | A | C |
| ATOM | 570 | CB  | THR A | 90 | −23.537 | −19.252 | 6.701   | 1.00 | 14.30 | A | C |
| ATOM | 571 | OG1 | THR A | 90 | −24.025 | −19.635 | 7.979   | 1.00 | 14.70 | A | O |
| ATOM | 572 | CG2 | THR A | 90 | −24.629 | −19.357 | 5.694   | 1.00 | 14.26 | A | C |
| ATOM | 573 | C   | THR A | 90 | −21.820 | −19.633 | 4.984   | 1.00 | 13.14 | A | C |
| ATOM | 574 | O   | THR A | 90 | −21.181 | −18.553 | 4.866   | 1.00 | 12.97 | A | O |
| ATOM | 575 | N   | THR A | 91 | −22.204 | −20.310 | 3.954   | 1.00 | 12.67 | A | N |
| ATOM | 576 | CA  | THR A | 91 | −22.071 | −19.858 | 2.612   | 1.00 | 12.42 | A | C |
| ATOM | 577 | CB  | THR A | 91 | −21.202 | −20.742 | 1.745   | 1.00 | 15.77 | A | C |
| ATOM | 578 | OG1 | THR A | 91 | −21.809 | −22.026 | 1.542   | 1.00 | 16.02 | A | O |
| ATOM | 579 | CG2 | THR A | 91 | −19.780 | −20.911 | 2.340   | 1.00 | 15.45 | A | C |
| ATOM | 580 | C   | THR A | 91 | −23.439 | −19.667 | 1.973   | 1.00 | 14.07 | A | C |
| ATOM | 581 | O   | THR A | 91 | −24.299 | −20.504 | 2.114   | 1.00 | 12.71 | A | O |
| ATOM | 582 | N   | TRP A | 92 | −23.602 | −18.551 | 1.251   | 1.00 | 13.47 | A | N |
| ATOM | 583 | CA  | TRP A | 92 | −24.826 | −18.367 | 0.473   | 1.00 | 12.27 | A | C |
| ATOM | 584 | CB  | TRP A | 92 | −25.378 | −16.896 | 0.702   | 1.00 | 11.42 | A | C |
| ATOM | 585 | CG  | TRP A | 92 | −25.935 | −16.642 | 2.095   | 1.00 | 10.76 | A | C |
| ATOM | 586 | CD1 | TRP A | 92 | −27.297 | −16.521 | 2.390   | 1.00 | 10.99 | A | C |
| ATOM | 587 | NE1 | TRP A | 92 | −27.448 | −16.294 | 3.722   | 1.00 | 12.14 | A | N |
| ATOM | 588 | CE2 | TRP A | 92 | −26.199 | −16.150 | 4.272   | 1.00 | 11.60 | A | C |
| ATOM | 589 | CD2 | TRP A | 92 | −25.245 | −16.346 | 3.298   | 1.00 | 13.63 | A | C |
| ATOM | 590 | CE3 | TRP A | 92 | −23.874 | −16.243 | 3.642   | 1.00 | 13.21 | A | C |
| ATOM | 591 | CZ3 | TRP A | 92 | −23.541 | −15.954 | 4.979   | 1.00 | 13.11 | A | C |
| ATOM | 592 | CH2 | TRP A | 92 | −24.515 | −15.689 | 5.900   | 1.00 | 13.75 | A | C |
| ATOM | 593 | CZ2 | TRP A | 92 | −25.862 | −15.841 | 5.616   | 1.00 | 11.60 | A | C |
| ATOM | 594 | C   | TRP A | 92 | −24.390 | −18.440 | −1.001  | 1.00 | 12.69 | A | C |
| ATOM | 595 | O   | TRP A | 92 | −23.439 | −17.765 | −1.428  | 1.00 | 14.32 | A | O |
| ATOM | 596 | N   | SER A | 93 | −25.189 | −19.085 | −1.785  | 1.00 | 11.07 | A | N |
| ATOM | 597 | CA  | SER A | 93 | −25.019 | −19.227 | −3.260  | 1.00 | 11.20 | A | C |
| ATOM | 598 | CB  | SER A | 93 | −24.634 | −20.716 | −3.527  | 1.00 | 9.73  | A | C |
| ATOM | 599 | OG  | SER A | 93 | −24.489 | −20.870 | −4.986  | 1.00 | 12.21 | A | O |
| ATOM | 600 | C   | SER A | 93 | −26.361 | −18.793 | −3.889  | 1.00 | 12.66 | A | C |
| ATOM | 601 | O   | SER A | 93 | −27.443 | −19.192 | −3.527  | 1.00 | 14.66 | A | O |
| ATOM | 602 | N   | GLY A | 94 | −26.265 | −17.930 | −4.889  | 1.00 | 16.74 | A | N |
| ATOM | 603 | CA  | GLY A | 94 | −27.508 | −17.364 | −5.420  | 1.00 | 15.90 | A | C |
| ATOM | 604 | C   | GLY A | 94 | −27.321 | −16.543 | −6.651  | 1.00 | 15.93 | A | C |
| ATOM | 605 | O   | GLY A | 94 | −26.289 | −16.593 | −7.275  | 1.00 | 17.33 | A | O |
| ATOM | 606 | N   | GLN A | 95 | −28.279 | −15.657 | −6.877  | 1.00 | 15.61 | A | N |
| ATOM | 607 | CA  | GLN A | 95 | −28.136 | −14.766 | −8.014  | 1.00 | 14.49 | A | C |
| ATOM | 608 | CB  | GLN A | 95 | −28.625 | −15.351 | −9.303  | 1.00 | 16.88 | A | C |
| ATOM | 609 | CG  | GLN A | 95 | −30.096 | −15.793 | −9.363  | 1.00 | 14.86 | A | C |
| ATOM | 610 | CD  | GLN A | 95 | −30.462 | −16.468 | −10.663 | 1.00 | 17.65 | A | C |
| ATOM | 611 | OE1 | GLN A | 95 | −30.160 | −15.981 | −11.729 | 1.00 | 16.49 | A | O |
| ATOM | 612 | NE2 | GLN A | 95 | −31.183 | −17.605 | −10.586 | 1.00 | 21.66 | A | N |
| ATOM | 613 | C   | GLN A | 95 | −28.801 | −13.445 | −7.692  | 1.00 | 16.08 | A | C |
| ATOM | 614 | O   | GLN A | 95 | −29.848 | −13.420 | −6.988  | 1.00 | 14.65 | A | O |
| ATOM | 615 | N   | TYR A | 96 | −28.194 | −12.420 | −8.254  | 1.00 | 15.51 | A | N |
| ATOM | 616 | CA  | TYR A | 96 | −28.782 | −11.055 | −8.177  | 1.00 | 15.30 | A | C |
| ATOM | 617 | CB  | TYR A | 96 | −27.604 | −10.051 | −8.157  | 1.00 | 16.94 | A | C |
| ATOM | 618 | CG  | TYR A | 96 | −27.985 | −8.670  | −8.535  | 1.00 | 18.16 | A | C |
| ATOM | 619 | CD1 | TYR A | 96 | −28.543 | −7.802  | −7.615  | 1.00 | 19.11 | A | C |
| ATOM | 620 | CE1 | TYR A | 96 | −28.936 | −6.501  | −7.953  | 1.00 | 18.74 | A | C |
| ATOM | 621 | CZ  | TYR A | 96 | −28.794 | −6.092  | −9.242  | 1.00 | 20.04 | A | C |
| ATOM | 622 | OH  | TYR A | 96 | −29.173 | −4.798  | −9.613  | 1.00 | 23.69 | A | O |

-continued

| | | | | | [X-ray Crystal Structure Analysis Data] | | | | | |
|---|---|---|---|---|---|---|---|---|---|---|---|
| ATOM | 623 | CE2 | TYR A | 96 | −28.253 | −6.917 | −10.167 | 1.00 | 23.25 | A | C |
| ATOM | 624 | CD2 | TYR A | 96 | −27.849 | −8.229 | −9.824 | 1.00 | 20.21 | A | C |
| ATOM | 625 | C | TYR A | 96 | −29.679 | −10.862 | −9.347 | 1.00 | 16.62 | A | C |
| ATOM | 626 | O | TYR A | 96 | −29.252 | −11.103 | −10.482 | 1.00 | 17.40 | A | O |
| ATOM | 627 | N | VAL A | 97 | −30.900 | −10.344 | −9.110 | 1.00 | 18.07 | A | N |
| ATOM | 628 | CA | VAL A | 97 | −31.849 | −9.998 | −10.156 | 1.00 | 20.76 | A | C |
| ATOM | 629 | CB | VAL A | 97 | −33.137 | −10.764 | −9.910 | 1.00 | 23.01 | A | C |
| ATOM | 630 | CG1 | VAL A | 97 | −34.251 | −10.387 | −10.888 | 1.00 | 25.43 | A | C |
| ATOM | 631 | CG2 | VAL A | 97 | −32.855 | −12.287 | −9.920 | 1.00 | 23.41 | A | C |
| ATOM | 632 | C | VAL A | 97 | −32.140 | −8.494 | −10.034 | 1.00 | 20.45 | A | C |
| ATOM | 633 | O | VAL A | 97 | −32.552 | −8.055 | −8.954 | 1.00 | 22.10 | A | O |
| ATOM | 634 | N | GLY A | 98 | −31.901 | −7.732 | −11.087 | 1.00 | 23.07 | A | N |
| ATOM | 635 | CA | GLY A | 98 | −31.956 | −6.238 | −10.974 | 1.00 | 24.31 | A | C |
| ATOM | 636 | C | GLY A | 98 | −33.345 | −5.673 | −11.231 | 1.00 | 25.89 | A | C |
| ATOM | 637 | O | GLY A | 98 | −34.301 | −6.416 | −11.318 | 1.00 | 27.64 | A | O |
| ATOM | 638 | N | GLY A | 99 | −33.468 | −4.345 | −11.294 | 1.00 | 28.00 | A | N |
| ATOM | 639 | CA | GLY A | 99 | −34.746 | −3.689 | −11.603 | 1.00 | 27.00 | A | C |
| ATOM | 640 | C | GLY A | 99 | −35.406 | −3.099 | −10.371 | 1.00 | 26.18 | A | C |
| ATOM | 641 | O | GLY A | 99 | −34.851 | −3.116 | −9.264 | 1.00 | 26.21 | A | O |
| ATOM | 642 | N | ALA A | 100 | −36.634 | −2.585 | −10.543 | 1.00 | 28.67 | A | N |
| ATOM | 643 | CA | ALA A | 100 | −37.236 | −1.743 | −9.528 | 1.00 | 27.31 | A | C |
| ATOM | 644 | CB | ALA A | 100 | −38.537 | −1.148 | −10.051 | 1.00 | 29.27 | A | C |
| ATOM | 645 | C | ALA A | 100 | −37.446 | −2.466 | −8.222 | 1.00 | 30.01 | A | C |
| ATOM | 646 | O | ALA A | 100 | −37.389 | −1.840 | −7.145 | 1.00 | 29.14 | A | O |
| ATOM | 647 | N | GLU A | 101 | −37.641 | −3.794 | −8.305 | 1.00 | 30.89 | A | N |
| ATOM | 648 | CA | GLU A | 101 | −37.816 | −4.670 | −7.151 | 1.00 | 34.24 | A | C |
| ATOM | 649 | CB | GLU A | 101 | −39.238 | −5.263 | −7.176 | 1.00 | 38.59 | A | C |
| ATOM | 650 | CG | GLU A | 101 | −40.279 | −4.110 | −7.185 | 1.00 | 46.83 | A | C |
| ATOM | 651 | CD | GLU A | 101 | −41.762 | −4.510 | −7.320 | 1.00 | 50.44 | A | C |
| ATOM | 652 | OE1 | GLU A | 101 | −42.423 | −4.769 | −6.284 | 1.00 | 52.52 | A | O |
| ATOM | 653 | OE2 | GLU A | 101 | −42.293 | −4.488 | −8.459 | 1.00 | 56.15 | A | O |
| ATOM | 654 | C | GLU A | 101 | −36.652 | −5.711 | −7.132 | 1.00 | 28.59 | A | C |
| ATOM | 655 | O | GLU A | 101 | −36.822 | −6.936 | −7.207 | 1.00 | 28.05 | A | O |
| ATOM | 656 | N | ALA A | 102 | −35.445 | −5.173 | −7.000 | 1.00 | 24.10 | A | N |
| ATOM | 657 | CA | ALA A | 102 | −34.257 | −5.972 | −7.121 | 1.00 | 22.09 | A | C |
| ATOM | 658 | CB | ALA A | 102 | −32.979 | −5.095 | −7.198 | 1.00 | 22.18 | A | C |
| ATOM | 659 | C | ALA A | 102 | −34.178 | −6.956 | −5.936 | 1.00 | 21.29 | A | C |
| ATOM | 660 | O | ALA A | 102 | −34.649 | −6.670 | −4.827 | 1.00 | 20.75 | A | O |
| ATOM | 661 | N | ARG A | 103 | −33.494 | −8.078 | −6.169 | 1.00 | 20.06 | A | N |
| ATOM | 662 | CA | ARG A | 103 | −33.503 | −9.243 | −5.277 | 1.00 | 21.78 | A | C |
| ATOM | 663 | CB | ARG A | 103 | −34.497 | −10.227 | −5.836 | 1.00 | 29.62 | A | C |
| ATOM | 664 | CG | ARG A | 103 | −35.316 | −10.993 | −4.849 | 1.00 | 41.78 | A | C |
| ATOM | 665 | CD | ARG A | 103 | −36.730 | −11.119 | −5.390 | 1.00 | 47.80 | A | C |
| ATOM | 666 | NE | ARG A | 103 | −37.381 | −9.807 | −5.264 | 1.00 | 53.91 | A | N |
| ATOM | 667 | CZ | ARG A | 103 | −38.175 | −9.395 | −4.262 | 1.00 | 47.22 | A | C |
| ATOM | 668 | NH1 | ARG A | 103 | −38.500 | −10.192 | −3.249 | 1.00 | 43.98 | A | N |
| ATOM | 669 | NH2 | ARG A | 103 | −38.659 | −8.145 | −4.296 | 1.00 | 44.61 | A | N |
| ATOM | 670 | C | ARG A | 103 | −32.140 | −9.889 | −5.340 | 1.00 | 19.29 | A | C |
| ATOM | 671 | O | ARG A | 103 | −31.542 | −9.974 | −6.419 | 1.00 | 18.81 | A | O |
| ATOM | 672 | N | ILE A | 104 | −31.656 | −10.375 | −4.217 | 1.00 | 17.81 | A | N |
| ATOM | 673 | CA | ILE A | 104 | −30.676 | −11.489 | −4.237 | 1.00 | 18.58 | A | C |
| ATOM | 674 | CB | ILE A | 104 | −29.422 | −11.139 | −3.444 | 1.00 | 20.17 | A | C |
| ATOM | 675 | CG1 | ILE A | 104 | −28.714 | −9.929 | −4.036 | 1.00 | 19.35 | A | C |
| ATOM | 676 | CD1 | ILE A | 104 | −27.588 | −9.417 | −3.164 | 1.00 | 22.31 | A | C |
| ATOM | 677 | CG2 | ILE A | 104 | −28.432 | −12.304 | −3.431 | 1.00 | 21.36 | A | C |
| ATOM | 678 | C | ILE A | 104 | −31.391 | −12.718 | −3.679 | 1.00 | 15.96 | A | C |
| ATOM | 679 | O | ILE A | 104 | −31.748 | −12.782 | −2.494 | 1.00 | 15.71 | A | O |
| ATOM | 680 | N | ASN A | 105 | −31.581 | −13.714 | −4.518 | 1.00 | 16.03 | A | N |
| ATOM | 681 | CA | ASN A | 105 | −32.177 | −15.004 | −4.136 | 1.00 | 15.47 | A | C |
| ATOM | 682 | CB | ASN A | 105 | −33.018 | −15.486 | −5.273 | 1.00 | 18.76 | A | C |
| ATOM | 683 | CG | ASN A | 105 | −34.249 | −14.630 | −5.481 | 1.00 | 19.99 | A | C |
| ATOM | 684 | OD1 | ASN A | 105 | −34.895 | −14.242 | −4.514 | 1.00 | 24.04 | A | O |
| ATOM | 685 | ND2 | ASN A | 105 | −34.533 | −14.319 | −6.742 | 1.00 | 19.00 | A | N |
| ATOM | 686 | C | ASN A | 105 | −31.055 | −16.047 | −3.885 | 1.00 | 16.56 | A | C |
| ATOM | 687 | O | ASN A | 105 | −30.288 | −16.308 | −4.767 | 1.00 | 16.66 | A | O |
| ATOM | 688 | N | THR A | 106 | −31.009 | −16.568 | −2.677 | 1.00 | 13.86 | A | N |
| ATOM | 689 | CA | THR A | 106 | −29.981 | −17.494 | −2.206 | 1.00 | 14.08 | A | C |
| ATOM | 690 | CB | THR A | 106 | −29.104 | −16.888 | −1.141 | 1.00 | 15.41 | A | C |
| ATOM | 691 | OG1 | THR A | 106 | −29.739 | −16.895 | 0.146 | 1.00 | 16.37 | A | O |
| ATOM | 692 | CG2 | THR A | 106 | −28.592 | −15.491 | −1.592 | 1.00 | 15.99 | A | C |
| ATOM | 693 | C | THR A | 106 | −30.512 | −18.791 | −1.590 | 1.00 | 13.69 | A | C |
| ATOM | 694 | O | THR A | 106 | −31.666 | −18.894 | −1.116 | 1.00 | 12.85 | A | O |
| ATOM | 695 | N | GLN A | 107 | −29.609 | −19.762 | −1.632 | 1.00 | 14.47 | A | N |
| ATOM | 696 | CA | GLN A | 107 | −29.631 | −20.948 | −0.783 | 1.00 | 15.52 | A | C |
| ATOM | 697 | CB | GLN A | 107 | −29.852 | −22.224 | −1.591 | 1.00 | 16.42 | A | C |
| ATOM | 698 | CG | GLN A | 107 | −31.333 | −22.243 | −2.032 | 1.00 | 19.73 | A | C |
| ATOM | 699 | CD | GLN A | 107 | −31.740 | −23.384 | −2.868 | 1.00 | 21.18 | A | C |

-continued

[X-ray Crystal Structure Analysis Data]

| ATOM | 700 | OE1 | GLN A | 107 | −31.560 | −23.368 | −4.126 | 1.00 | 25.61 | A | O |
|------|-----|-----|-------|-----|---------|---------|--------|------|-------|---|---|
| ATOM | 701 | NE2 | GLN A | 107 | −32.319 | −24.378 | −2.237 | 1.00 | 24.54 | A | N |
| ATOM | 702 | C   | GLN A | 107 | −28.359 | −20.974 | −0.005 | 1.00 | 14.36 | A | C |
| ATOM | 703 | O   | GLN A | 107 | −27.365 | −20.464 | −0.422 | 1.00 | 15.33 | A | O |
| ATOM | 704 | N   | TRP A | 108 | −28.449 | −21.425 | 1.246  | 1.00 | 14.84 | A | N |
| ATOM | 705 | CA  | TRP A | 108 | −27.307 | −21.358 | 2.119  | 1.00 | 14.28 | A | C |
| ATOM | 706 | CB  | TRP A | 108 | −27.352 | −20.258 | 3.171  | 1.00 | 13.46 | A | C |
| ATOM | 707 | CG  | TRP A | 108 | −28.624 | −20.187 | 3.968  | 1.00 | 14.36 | A | C |
| ATOM | 708 | CD1 | TRP A | 108 | −29.636 | −19.304 | 3.815  | 1.00 | 16.85 | A | C |
| ATOM | 709 | NE1 | TRP A | 108 | −30.589 | −19.513 | 4.771  | 1.00 | 15.52 | A | N |
| ATOM | 710 | CE2 | TRP A | 108 | −30.189 | −20.536 | 5.583  | 1.00 | 17.21 | A | C |
| ATOM | 711 | CD2 | TRP A | 108 | −28.891 | −20.905 | 5.156  | 1.00 | 15.08 | A | C |
| ATOM | 712 | CE3 | TRP A | 108 | −28.254 | −21.970 | 5.786  | 1.00 | 14.60 | A | C |
| ATOM | 713 | CZ3 | TRP A | 108 | −28.805 | −22.492 | 6.933  | 1.00 | 14.45 | A | C |
| ATOM | 714 | CH2 | TRP A | 108 | −30.119 | −22.103 | 7.355  | 1.00 | 15.96 | A | C |
| ATOM | 715 | CZ2 | TRP A | 108 | −30.744 | −21.027 | 6.772  | 1.00 | 14.96 | A | C |
| ATOM | 716 | C   | TRP A | 108 | −27.009 | −22.706 | 2.767  | 1.00 | 13.11 | A | C |
| ATOM | 717 | O   | TRP A | 108 | −27.874 | −23.561 | 2.887  | 1.00 | 13.13 | A | O |
| ATOM | 718 | N   | LEU A | 109 | −25.726 | −22.872 | 3.131  | 1.00 | 13.09 | A | N |
| ATOM | 719 | CA  | LEU A | 109 | −25.259 | −24.004 | 3.924  | 1.00 | 14.34 | A | C |
| ATOM | 720 | CB  | LEU A | 109 | −24.288 | −24.944 | 3.181  | 1.00 | 17.02 | A | C |
| ATOM | 721 | CG  | LEU A | 109 | −24.738 | −25.544 | 1.878  | 1.00 | 16.95 | A | C |
| ATOM | 722 | CD1 | LEU A | 109 | −23.621 | −26.114 | 1.087  | 1.00 | 18.74 | A | C |
| ATOM | 723 | CD2 | LEU A | 109 | −25.835 | −26.513 | 2.191  | 1.00 | 17.06 | A | C |
| ATOM | 724 | C   | LEU A | 109 | −24.532 | −23.427 | 5.144  | 1.00 | 14.59 | A | C |
| ATOM | 725 | O   | LEU A | 109 | −23.503 | −22.744 | 4.993  | 1.00 | 15.41 | A | O |
| ATOM | 726 | N   | LEU A | 110 | −24.949 | −23.834 | 6.335  | 1.00 | 15.54 | A | N |
| ATOM | 727 | CA  | LEU A | 110 | −24.330 | −23.479 | 7.600  | 1.00 | 16.92 | A | C |
| ATOM | 728 | CB  | LEU A | 110 | −25.356 | −22.940 | 8.515  | 1.00 | 17.99 | A | C |
| ATOM | 729 | CG  | LEU A | 110 | −25.057 | −22.779 | 10.005 | 1.00 | 19.52 | A | C |
| ATOM | 730 | CD1 | LEU A | 110 | −23.722 | −22.122 | 10.280 | 1.00 | 20.33 | A | C |
| ATOM | 731 | CD2 | LEU A | 110 | −26.217 | −22.002 | 10.597 | 1.00 | 21.65 | A | C |
| ATOM | 732 | C   | LEU A | 110 | −23.658 | −24.748 | 8.233  | 1.00 | 14.53 | A | C |
| ATOM | 733 | O   | LEU A | 110 | −24.331 | −25.622 | 8.686  | 1.00 | 17.43 | A | O |
| ATOM | 734 | N   | THR A | 111 | −22.339 | −24.812 | 8.187  | 1.00 | 15.77 | A | N |
| ATOM | 735 | CA  | THR A | 111 | −21.565 | −25.995 | 8.731  | 1.00 | 15.93 | A | C |
| ATOM | 736 | CB  | THR A | 111 | −20.422 | −26.415 | 7.842  | 1.00 | 16.12 | A | C |
| ATOM | 737 | OG1 | THR A | 111 | −20.911 | −26.710 | 6.526  | 1.00 | 15.27 | A | O |
| ATOM | 738 | CG2 | THR A | 111 | −19.619 | −27.656 | 8.376  | 1.00 | 15.86 | A | C |
| ATOM | 739 | C   | THR A | 111 | −20.959 | −25.592 | 10.070 | 1.00 | 16.43 | A | C |
| ATOM | 740 | O   | THR A | 111 | −20.358 | −24.494 | 10.182 | 1.00 | 14.55 | A | O |
| ATOM | 741 | N   | SER A | 112 | −21.153 | −26.443 | 11.056 | 1.00 | 14.09 | A | N |
| ATOM | 742 | CA  | SER A | 112 | −20.563 | −26.210 | 12.366 | 1.00 | 15.81 | A | C |
| ATOM | 743 | CB  | SER A | 112 | −21.510 | −26.517 | 13.445 | 1.00 | 17.22 | A | C |
| ATOM | 744 | OG  | SER A | 112 | −22.603 | −25.605 | 13.420 | 1.00 | 18.98 | A | O |
| ATOM | 745 | C   | SER A | 112 | −19.353 | −27.086 | 12.493 | 1.00 | 18.10 | A | C |
| ATOM | 746 | O   | SER A | 112 | −19.366 | −28.228 | 12.031 | 1.00 | 17.67 | A | O |
| ATOM | 747 | N   | GLY A | 113 | −18.315 | −26.589 | 13.169 | 1.00 | 17.50 | A | N |
| ATOM | 748 | CA  | GLY A | 113 | −17.254 | −27.539 | 13.602 | 1.00 | 19.63 | A | C |
| ATOM | 749 | C   | GLY A | 113 | −17.820 | −28.640 | 14.535 | 1.00 | 20.31 | A | C |
| ATOM | 750 | O   | GLY A | 113 | −18.546 | −28.324 | 15.510 | 1.00 | 21.97 | A | O |
| ATOM | 751 | N   | THR A | 114 | −17.533 | −29.901 | 14.218 | 1.00 | 20.34 | A | N |
| ATOM | 752 | CA  | THR A | 114 | −17.992 | −31.027 | 14.999 | 1.00 | 20.32 | A | C |
| ATOM | 753 | CB  | THR A | 114 | −19.175 | −31.785 | 14.362 | 1.00 | 20.70 | A | C |
| ATOM | 754 | OG1 | THR A | 114 | −18.814 | −32.402 | 13.117 | 1.00 | 20.53 | A | O |
| ATOM | 755 | CG2 | THR A | 114 | −20.395 | −30.849 | 14.106 | 1.00 | 23.49 | A | C |
| ATOM | 756 | C   | THR A | 114 | −16.886 | −32.010 | 15.178 | 1.00 | 21.36 | A | C |
| ATOM | 757 | O   | THR A | 114 | −15.908 | −32.042 | 14.422 | 1.00 | 19.92 | A | O |
| ATOM | 758 | N   | THR A | 115 | −17.080 | −32.917 | 16.107 | 1.00 | 20.65 | A | N |
| ATOM | 759 | CA  | THR A | 115 | −16.240 | −34.130 | 16.076 | 1.00 | 21.85 | A | C |
| ATOM | 760 | CB  | THR A | 115 | −16.438 | −34.934 | 17.363 | 1.00 | 25.24 | A | C |
| ATOM | 761 | OG1 | THR A | 115 | −17.802 | −35.393 | 17.424 | 1.00 | 26.73 | A | O |
| ATOM | 762 | CG2 | THR A | 115 | −16.143 | −34.091 | 18.559 | 1.00 | 24.62 | A | C |
| ATOM | 763 | C   | THR A | 115 | −16.598 | −35.024 | 14.870 | 1.00 | 25.14 | A | C |
| ATOM | 764 | O   | THR A | 115 | −17.652 | −34.876 | 14.242 | 1.00 | 22.79 | A | O |
| ATOM | 765 | N   | GLU A | 116 | −15.742 | −35.966 | 14.520 | 1.00 | 27.47 | A | N |
| ATOM | 766 | CA  | GLU A | 116 | −16.034 | −36.879 | 13.380 | 1.00 | 32.64 | A | C |
| ATOM | 767 | CB  | GLU A | 116 | −14.839 | −37.801 | 13.061 | 1.00 | 38.08 | A | C |
| ATOM | 768 | CG  | GLU A | 116 | −13.627 | −37.022 | 12.537 | 1.00 | 44.94 | A | C |
| ATOM | 769 | CD  | GLU A | 116 | −12.452 | −37.905 | 12.110 | 1.00 | 54.90 | A | C |
| ATOM | 770 | OE1 | GLU A | 116 | −12.669 | −39.069 | 11.680 | 1.00 | 58.99 | A | O |
| ATOM | 771 | OE2 | GLU A | 116 | −11.297 | −37.417 | 12.187 | 1.00 | 54.36 | A | O |
| ATOM | 772 | C   | GLU A | 116 | −17.324 | −37.324 | 13.619 | 1.00 | 28.77 | A | C |
| ATOM | 773 | O   | GLU A | 116 | −18.077 | −37.894 | 12.725 | 1.00 | 27.68 | A | O |
| ATOM | 774 | N   | ALA A | 117 | −17.531 | −38.112 | 14.860 | 1.00 | 27.12 | A | N |
| ATOM | 775 | CA  | ALA A | 117 | −18.723 | −38.795 | 15.302 | 1.00 | 26.78 | A | C |
| ATOM | 776 | CB  | ALA A | 117 | −18.684 | −38.939 | 16.826 | 1.00 | 28.01 | A | C |

-continued

[X-ray Crystal Structure Analysis Data]

| ATOM | 777 | C   | ALA A | 117 | −19.980 | −38.040 | 14.908 | 1.00 | 28.23 | A | C |
| ---- | --- | --- | ----- | --- | ------- | ------- | ------ | ---- | ----- | - | - |
| ATOM | 778 | O   | ALA A | 117 | −20.933 | −38.664 | 14.443 | 1.00 | 27.53 | A | O |
| ATOM | 779 | N   | ASN A | 118 | −19.932 | −36.705 | 15.051 | 1.00 | 22.78 | A | N |
| ATOM | 780 | CA  | ASN A | 118 | −21.099 | −35.776 | 14.837 | 1.00 | 23.58 | A | C |
| ATOM | 781 | CB  | ASN A | 118 | −21.103 | −34.743 | 15.948 | 1.00 | 22.16 | A | C |
| ATOM | 782 | CG  | ASN A | 118 | −21.402 | −35.362 | 17.291 | 1.00 | 25.14 | A | C |
| ATOM | 783 | OD1 | ASN A | 118 | −22.066 | −36.418 | 17.360 | 1.00 | 24.57 | A | O |
| ATOM | 784 | ND2 | ASN A | 118 | −20.897 | −34.752 | 18.354 | 1.00 | 26.59 | A | N |
| ATOM | 785 | C   | ASN A | 118 | −21.118 | −35.054 | 13.479 | 1.00 | 20.46 | A | C |
| ATOM | 786 | O   | ASN A | 118 | −21.957 | −34.156 | 13.261 | 1.00 | 19.35 | A | O |
| ATOM | 787 | N   | ALA A | 119 | −20.212 | −35.432 | 12.585 | 1.00 | 21.42 | A | N |
| ATOM | 788 | CA  | ALA A | 119 | −20.081 | −34.770 | 11.307 | 1.00 | 22.38 | A | C |
| ATOM | 789 | CB  | ALA A | 119 | −18.781 | −35.204 | 10.576 | 1.00 | 24.20 | A | C |
| ATOM | 790 | C   | ALA A | 119 | −21.351 | −34.920 | 10.437 | 1.00 | 20.78 | A | C |
| ATOM | 791 | O   | ALA A | 119 | −21.721 | −33.992 | 9.705  | 1.00 | 17.06 | A | O |
| ATOM | 792 | N   | TRP A | 120 | −22.027 | −36.068 | 10.543 | 1.00 | 18.34 | A | N |
| ATOM | 793 | CA  | TRP A | 120 | −23.251 | −36.327 | 9.745  | 1.00 | 18.13 | A | C |
| ATOM | 794 | CB  | TRP A | 120 | −23.881 | −37.742 | 9.994  | 1.00 | 17.84 | A | C |
| ATOM | 795 | CG  | TRP A | 120 | −24.425 | −37.834 | 11.374 | 1.00 | 16.96 | A | C |
| ATOM | 796 | CD1 | TRP A | 120 | −23.730 | −38.106 | 12.477 | 1.00 | 18.89 | A | C |
| ATOM | 797 | NE1 | TRP A | 120 | −24.487 | −38.029 | 13.578 | 1.00 | 19.07 | A | N |
| ATOM | 798 | CE2 | TRP A | 120 | −25.761 | −37.694 | 13.223 | 1.00 | 18.30 | A | C |
| ATOM | 799 | CD2 | TRP A | 120 | −25.763 | −37.559 | 11.808 | 1.00 | 18.25 | A | C |
| ATOM | 800 | CE3 | TRP A | 120 | −26.962 | −37.233 | 11.157 | 1.00 | 20.65 | A | C |
| ATOM | 801 | CZ3 | TRP A | 120 | −28.061 | −37.046 | 11.911 | 1.00 | 20.59 | A | C |
| ATOM | 802 | CH2 | TRP A | 120 | −28.035 | −37.215 | 13.309 | 1.00 | 19.14 | A | C |
| ATOM | 803 | CZ2 | TRP A | 120 | −26.886 | −37.555 | 13.973 | 1.00 | 19.60 | A | C |
| ATOM | 804 | C   | TRP A | 120 | −24.289 | −35.230 | 9.992  | 1.00 | 19.12 | A | C |
| ATOM | 805 | O   | TRP A | 120 | −25.021 | −34.905 | 9.059  | 1.00 | 21.69 | A | O |
| ATOM | 806 | N   | LYS A | 121 | −24.367 | −34.687 | 11.210 | 1.00 | 18.67 | A | N |
| ATOM | 807 | CA  | LYS A | 121 | −25.297 | −33.568 | 11.553 | 1.00 | 19.57 | A | C |
| ATOM | 808 | CB  | LYS A | 121 | −26.080 | −33.860 | 12.818 | 1.00 | 21.73 | A | C |
| ATOM | 809 | CG  | LYS A | 121 | −25.275 | −34.143 | 14.032 | 1.00 | 22.88 | A | C |
| ATOM | 810 | CD  | LYS A | 121 | −26.137 | −34.197 | 15.266 | 1.00 | 25.20 | A | C |
| ATOM | 811 | CE  | LYS A | 121 | −25.270 | −34.826 | 16.321 | 1.00 | 25.79 | A | C |
| ATOM | 812 | NZ  | LYS A | 121 | −26.063 | −35.080 | 17.507 | 1.00 | 28.98 | A | N |
| ATOM | 813 | C   | LYS A | 121 | −24.638 | −32.163 | 11.607 | 1.00 | 19.75 | A | C |
| ATOM | 814 | O   | LYS A | 121 | −25.098 | −31.318 | 12.366 | 1.00 | 17.68 | A | O |
| ATOM | 815 | N   | SER A | 122 | −23.539 | −31.945 | 10.851 | 1.00 | 16.26 | A | N |
| ATOM | 816 | CA  | SER A | 122 | −22.831 | −30.678 | 10.872 | 1.00 | 16.42 | A | C |
| ATOM | 817 | CB  | SER A | 122 | −21.349 | −30.917 | 10.441 | 1.00 | 16.04 | A | C |
| ATOM | 818 | OG  | SER A | 122 | −21.254 | −31.226 | 9.035  | 1.00 | 18.48 | A | O |
| ATOM | 819 | C   | SER A | 122 | −23.433 | −29.536 | 10.069 | 1.00 | 15.34 | A | C |
| ATOM | 820 | O   | SER A | 122 | −23.125 | −28.367 | 10.309 | 1.00 | 15.66 | A | O |
| ATOM | 821 | N   | THR A | 123 | −24.221 | −29.846 | 9.026  | 1.00 | 14.71 | A | N |
| ATOM | 822 | CA  | THR A | 123 | −24.557 | −28.839 | 8.065  | 1.00 | 14.13 | A | C |
| ATOM | 823 | CB  | THR A | 123 | −24.003 | −29.274 | 6.711  | 1.00 | 14.70 | A | C |
| ATOM | 824 | OG1 | THR A | 123 | −22.557 | −29.479 | 6.880  | 1.00 | 16.48 | A | O |
| ATOM | 825 | CG2 | THR A | 123 | −24.219 | −28.237 | 5.667  | 1.00 | 14.95 | A | C |
| ATOM | 826 | C   | THR A | 123 | −26.113 | −28.680 | 7.943  | 1.00 | 13.40 | A | C |
| ATOM | 827 | O   | THR A | 123 | −26.781 | −29.587 | 7.542  | 1.00 | 12.91 | A | O |
| ATOM | 828 | N   | LEU A | 124 | −26.539 | −27.471 | 8.216  | 1.00 | 14.07 | A | N |
| ATOM | 829 | CA  | LEU A | 124 | −27.878 | −26.960 | 8.029  | 1.00 | 15.15 | A | C |
| ATOM | 830 | CB  | LEU A | 124 | −28.215 | −25.898 | 9.055  | 1.00 | 17.87 | A | C |
| ATOM | 831 | CG  | LEU A | 124 | −28.425 | −26.359 | 10.506 | 1.00 | 17.97 | A | C |
| ATOM | 832 | CD1 | LEU A | 124 | −28.593 | −25.115 | 11.347 | 1.00 | 20.25 | A | C |
| ATOM | 833 | CD2 | LEU A | 124 | −29.689 | −27.221 | 10.628 | 1.00 | 17.31 | A | C |
| ATOM | 834 | C   | LEU A | 124 | −28.020 | −26.382 | 6.603  | 1.00 | 13.30 | A | C |
| ATOM | 835 | O   | LEU A | 124 | −27.063 | −25.781 | 6.086  | 1.00 | 15.49 | A | O |
| ATOM | 836 | N   | VAL A | 125 | −29.258 | −26.468 | 6.040  | 1.00 | 13.21 | A | N |
| ATOM | 837 | CA  | VAL A | 125 | −29.479 | −25.932 | 4.687  | 1.00 | 13.43 | A | C |
| ATOM | 838 | CB  | VAL A | 125 | −29.634 | −26.995 | 3.647  | 1.00 | 12.41 | A | C |
| ATOM | 839 | CG1 | VAL A | 125 | −30.868 | −27.900 | 3.851  | 1.00 | 13.73 | A | C |
| ATOM | 840 | CG2 | VAL A | 125 | −29.673 | −26.444 | 2.218  | 1.00 | 13.59 | A | C |
| ATOM | 841 | C   | VAL A | 125 | −30.759 | −25.057 | 4.798  | 1.00 | 13.06 | A | C |
| ATOM | 842 | O   | VAL A | 125 | −31.659 | −25.380 | 5.543  | 1.00 | 14.17 | A | O |
| ATOM | 843 | N   | GLY A | 126 | −30.746 | −23.920 | 4.097  | 1.00 | 13.02 | A | N |
| ATOM | 844 | CA  | GLY A | 126 | −31.936 | −23.128 | 3.984  | 1.00 | 14.12 | A | C |
| ATOM | 845 | C   | GLY A | 126 | −31.880 | −22.193 | 2.821  | 1.00 | 15.80 | A | C |
| ATOM | 846 | O   | GLY A | 126 | −31.083 | −22.371 | 1.900  | 1.00 | 15.54 | A | O |
| ATOM | 847 | N   | HIS A | 127 | −32.749 | −21.173 | 2.877  | 1.00 | 18.26 | A | N |
| ATOM | 848 | CA  | HIS A | 127 | −32.830 | −20.204 | 1.772  | 1.00 | 18.62 | A | C |
| ATOM | 849 | CB  | HIS A | 127 | −33.848 | −20.669 | 0.726  | 1.00 | 20.41 | A | C |
| ATOM | 850 | CG  | HIS A | 127 | −35.171 | −21.041 | 1.309  | 1.00 | 22.15 | A | C |
| ATOM | 851 | ND1 | HIS A | 127 | −36.208 | −20.134 | 1.414  | 1.00 | 25.17 | A | N |
| ATOM | 852 | CE1 | HIS A | 127 | −37.232 | −20.739 | 1.999  | 1.00 | 27.19 | A | C |
| ATOM | 853 | NE2 | HIS A | 127 | −36.894 | −21.993 | 2.273  | 1.00 | 26.82 | A | N |

[X-ray Crystal Structure Analysis Data]

| | | | | | | | | | | | |
|---|---|---|---|---|---|---|---|---|---|---|---|
| ATOM | 854 | CD2 | HIS A | 127 | −35.603 | −22.202 | 1.863 | 1.00 | 27.56 | A | C |
| ATOM | 855 | C | HIS A | 127 | −33.123 | −18.804 | 2.310 | 1.00 | 20.81 | A | C |
| ATOM | 856 | O | HIS A | 127 | −33.778 | −18.690 | 3.319 | 1.00 | 22.23 | A | O |
| ATOM | 857 | N | ASP A | 128 | −32.605 | −17.769 | 1.678 | 1.00 | 22.34 | A | N |
| ATOM | 858 | CA | ASP A | 128 | −32.721 | −16.333 | 2.136 | 1.00 | 21.50 | A | C |
| ATOM | 859 | CB | ASP A | 128 | −31.458 | −15.752 | 2.815 | 1.00 | 25.45 | A | C |
| ATOM | 860 | CG | ASP A | 128 | −31.237 | −16.133 | 4.372 | 1.00 | 29.55 | A | C |
| ATOM | 861 | OD1 | ASP A | 128 | −32.209 | −16.549 | 5.075 | 1.00 | 30.31 | A | O |
| ATOM | 862 | OD2 | ASP A | 128 | −30.013 | −16.030 | 4.876 | 1.00 | 25.11 | A | O |
| ATOM | 863 | C | ASP A | 128 | −32.997 | −15.560 | 0.846 | 1.00 | 18.17 | A | C |
| ATOM | 864 | O | ASP A | 128 | −32.337− | 15.746 | −0.126 | 1.00 | 17.75 | A | O |
| ATOM | 865 | N | THR A | 129 | −34.003 | −14.695 | 0.870 | 1.00 | 18.53 | A | N |
| ATOM | 866 | CA | THR A | 129 | −34.213 | −13.671 | −0.151 | 1.00 | 19.69 | A | C |
| ATOM | 867 | CB | THR A | 129 | −35.617 | −13.728 | −0.763 | 1.00 | 23.10 | A | C |
| ATOM | 868 | OG1 | THR A | 129 | −35.773 | −15.011 | −1.338 | 1.00 | 29.35 | A | O |
| ATOM | 869 | CG2 | THR A | 129 | −35.739 | −12.663 | −1.928 | 1.00 | 22.92 | A | C |
| ATOM | 870 | C | THR A | 129 | −33.992 | −12.287 | 0.426 | 1.00 | 17.24 | A | C |
| ATOM | 871 | O | THR A | 129 | −34.547 | −11.970 | 1.472 | 1.00 | 17.62 | A | O |
| ATOM | 872 | N | PHE A | 130 | −33.021 | −11.583 | −0.175 | 1.00 | 16.12 | A | N |
| ATOM | 873 | CA | PHE A | 130 | −32.684 | −10.209 | 0.157 | 1.00 | 16.86 | A | C |
| ATOM | 874 | CB | PHE A | 130 | −31.161 | −10.058 | 0.174 | 1.00 | 17.52 | A | C |
| ATOM | 875 | CG | PHE A | 130 | −30.461 | −10.992 | 1.108 | 1.00 | 18.59 | A | C |
| ATOM | 876 | CD1 | PHE A | 130 | −30.000 | −12.249 | 0.660 | 1.00 | 19.91 | A | C |
| ATOM | 877 | CE1 | PHE A | 130 | −29.300 | −13.114 | 1.524 | 1.00 | 20.36 | A | C |
| ATOM | 878 | CZ | PHE A | 130 | −29.083 | −12.741 | 2.845 | 1.00 | 19.23 | A | C |
| ATOM | 879 | CE2 | PHE A | 130 | −29.504 | −11.489 | 3.280 | 1.00 | 18.63 | A | C |
| ATOM | 880 | CD2 | PHE A | 130 | −30.211 | −10.632 | 2.408 | 1.00 | 19.70 | A | C |
| ATOM | 881 | C | PHE A | 130 | −33.252 | −9.197 | −0.819 | 1.00 | 15.55 | A | C |
| ATOM | 882 | O | PHE A | 130 | −33.250 | −9.406 | −2.063 | 1.00 | 16.92 | A | O |
| ATOM | 883 | N | THR A | 131 | −33.716 | −8.053 | −0.254 | 1.00 | 17.19 | A | N |
| ATOM | 884 | CA | THR A | 131 | −34.213 | −6.902 | −1.005 | 1.00 | 18.16 | A | C |
| ATOM | 885 | CB | THR A | 131 | −35.736 | −6.742 | −0.850 | 1.00 | 20.34 | A | C |
| ATOM | 886 | OG1 | THR A | 131 | −36.030 | −6.515 | 0.543 | 1.00 | 23.94 | A | O |
| ATOM | 887 | CG2 | THR A | 131 | −36.360 | −8.065 | −1.253 | 1.00 | 19.94 | A | C |
| ATOM | 888 | C | THR A | 131 | −33.507 | −5.656 | −0.513 | 1.00 | 19.30 | A | C |
| ATOM | 889 | O | THR A | 131 | −32.930 | −5.635 | 0.578 | 1.00 | 19.07 | A | O |
| ATOM | 890 | N | LYS A | 132 | −33.641 | −4.603 | −1.299 | 1.00 | 20.04 | A | N |
| ATOM | 891 | CA | LYS A | 132 | −33.107 | −3.309 | −0.974 | 1.00 | 20.15 | A | C |
| ATOM | 892 | CB | LYS A | 132 | −33.052 | −2.493 | −2.272 | 1.00 | 22.47 | A | C |
| ATOM | 893 | CG | LYS A | 132 | −32.100 | −3.060 | −3.281 | 1.00 | 27.50 | A | C |
| ATOM | 894 | CD | LYS A | 132 | −30.649 | −2.758 | −3.000 | 1.00 | 30.10 | A | C |
| ATOM | 895 | CE | LYS A | 132 | −29.899 | −2.695 | −4.342 | 1.00 | 37.90 | A | C |
| ATOM | 896 | NZ | LYS A | 132 | −28.388 | −2.573 | −4.217 | 1.00 | 41.27 | A | N |
| ATOM | 897 | C | LYS A | 132 | −33.914 | −2.539 | 0.075 | 1.00 | 21.30 | A | C |
| ATOM | 898 | O | LYS A | 132 | −33.438 | −1.582 | 0.617 | 1.00 | 19.98 | A | O |
| ATOM | 899 | N | VAL A | 133 | −35.181 | −2.913 | 0.305 | 1.00 | 24.58 | A | N |
| ATOM | 900 | CA | VAL A | 133 | −35.979 | −2.250 | 1.308 | 1.00 | 28.80 | A | C |
| ATOM | 901 | CB | VAL A | 133 | −37.363 | −1.933 | 0.732 | 1.00 | 30.13 | A | C |
| ATOM | 902 | CG1 | VAL A | 133 | −38.020 | −0.880 | 1.609 | 1.00 | 32.94 | A | C |
| ATOM | 903 | CG2 | VAL A | 133 | −37.277 | −1.538 | −0.754 | 1.00 | 30.74 | A | C |
| ATOM | 904 | C | VAL A | 133 | −36.183 | −3.018 | 2.627 | 1.00 | 33.51 | A | C |
| ATOM | 905 | O | VAL A | 133 | −36.589 | −4.169 | 2.626 | 1.00 | 34.41 | A | O |
| ATOM | 906 | N | LYS A | 134 | −35.990 | −2.315 | 3.747 | 1.00 | 42.93 | A | N |
| ATOM | 907 | CA | LYS A | 134 | −36.196 | −2.854 | 5.105 | 1.00 | 47.50 | A | C |
| ATOM | 908 | CB | LYS A | 134 | −35.860 | −1.760 | 6.136 | 1.00 | 49.06 | A | C |
| ATOM | 909 | CG | LYS A | 134 | −35.180 | −2.244 | 7.404 | 1.00 | 46.76 | A | C |
| ATOM | 910 | CD | LYS A | 134 | −34.388 | −1.118 | 8.042 | 1.00 | 49.49 | A | C |
| ATOM | 911 | CE | LYS A | 134 | −33.641 | −1.577 | 9.285 | 1.00 | 52.80 | A | C |
| ATOM | 912 | NZ | LYS A | 134 | −34.516 | −1.570 | 10.482 | 1.00 | 55.60 | A | N |
| ATOM | 913 | C | LYS A | 134 | −37.612 | −3.397 | 5.359 | 1.00 | 48.89 | A | C |
| ATOM | 914 | O | LYS A | 134 | −37.814 | −4.600 | 5.440 | 1.00 | 51.03 | A | O |
| TER | 915 | | LYS A | 134 | | | | | | | |
| HETATM | 956 | O3 | BTN B | 1 | −29.368 | −14.209 | 8.519 | 1.00 | 22.29 | | O |
| HETATM | 957 | C3 | BTN B | 1 | −29.310 | −15.495 | 8.628 | 1.00 | 21.59 | | C |
| HETATM | 958 | N1 | BTN B | 1 | −29.346 | −16.433 | 7.643 | 1.00 | 18.94 | | N |
| HETATM | 959 | N2 | BTN B | 1 | −29.217 | −16.144 | 9.783 | 1.00 | 19.86 | | N |
| HETATM | 960 | C4 | BTN B | 1 | −29.185 | −17.573 | 9.670 | 1.00 | 19.14 | | C |
| HETATM | 961 | C5 | BTN B | 1 | −29.340 | −17.756 | 8.148 | 1.00 | 19.62 | | C |
| HETATM | 962 | C6 | BTN B | 1 | −28.175 | −18.542 | 7.651 | 1.00 | 19.93 | | C |
| HETATM | 963 | Si | BTN B | 1 | −26.812 | −18.019 | 8.637 | 1.00 | 21.47 | | S |
| HETATM | 964 | C2 | BTN B | 1 | −27.875 | −18.232 | 10.050 | 1.00 | 20.92 | | C |
| HETATM | 965 | C7 | BTN B | 1 | −27.277 | −17.647 | 11.305 | 1.00 | 22.18 | | C |
| HETATM | 966 | C8 | BTN B | 1 | −25.917 | −18.135 | 11.659 | 1.00 | 25.46 | | C |
| HETATM | 967 | C9 | BTN B | 1 | −25.722 | −18.054 | 13.163 | 1.00 | 29.25 | | C |
| HETATM | 968 | C10 | BTN B | 1 | −24.338 | −18.579 | 13.619 | 1.00 | 25.31 | | C |
| HETATM | 969 | C11 | BTN B | 1 | −24.662 | −19.889 | 14.260 | 1.00 | 24.71 | | C |
| HETATM | 970 | O11 | BTN B | 1 | −25.732 | −19.984 | 14.911 | 1.00 | 26.64 | | O |

[X-ray Crystal Structure Analysis Data]

| HETATM | 971 | O12 | BTN B | 1 | −23.906 | −20.875 | 14.130 | 1.00 | 22.85 | O |
|--------|-----|-----|-------|---|---------|---------|--------|------|-------|---|
| END | | | | | | | | | | |

It was confirmed, based on the X-ray crystal structure analysis data, that the mutant of interest was obtained. Besides, it was confirmed, by a method described in Bioscience, Biotechnology, and Biochemistry, 79:4, 640-642 (2015), that the obtained mutant had a weakened affinity for biotin as compared with wild type streptavidin having the natural amino acid sequence set forth in SEQ ID NO: 2.

The oligo DNA used for introducing further mutation into the N11D/S15A/S33A mutant was designed in accordance with the instruction attached to QuikChange Site-Directed Mutagenesis Kit (Agilent Technologies Japan Ltd.). For the polymerase chain reaction, KOD plus neo (Toyobo Co., Ltd.) was used. Amino acid sequence conversion was performed by using a primer for introducing desired mutation selected from the following primers, using, as a template, a vector into which a DNA encoding the N11D/S15A/S33A mutant had been inserted, and changing codon sequence by substitution of a nucleotide sequence by the site-directed mutagenesis method. Thereafter, the template plasmid was cleaved with the restriction enzyme DpnI for transformation of E. coli. In this manner, various mutants including the mutant of having the mutation of N11D/S15A/S33N were produced. It was confirmed, based on the X-ray crystal structure in the same manner as described above, that each mutant of interest was obtained. Besides, it was confirmed, in the same manner as described above, that the obtained mutants had a weakened affinity for biotin as compared with wild type streptavidin having the natural amino acid sequence set forth in SEQ ID NO: 2.

Primer Set for Introducing S33N Mutation:
(SEQ ID NO: 9)
FW: TGACCGGCACCTATGAAAACGCCGTGGGTAATGCGGAAAGCCG (SEQ ID NO: 10)
RV: TCCGCATTACCCACGGCGTTTTCATAGGTGCCGGTCAGCGCACC Primer Set for Introducing N37G Mutation:
(SEQ ID NO: 11)
FW: ATGAAGCGGCCGTGGGTGGCGCGGAAAGCCGTTATGTTCTGACCG (SEQ ID NO: 12)
RV: ACATAACGGCTTTCCGCGCCACCCACGGCCGCTTCATAGGTGCCG Primer Set for Introducing S76G Mutation:
(SEQ ID NO: 13)
FW: CAATTATCGTAACGCCCATGGCGCGACCACCTGGAGCGGCCAG (SEQ ID NO: 14)
RV: GCTCCAGGTGGTCGCGCCATGGGCGTTACGATAATTGTTTTTC Primer Set for Introducing S76R Mutation:
(SEQ ID NO: 15)
FW: CAATTATCGTAACGCCCATCGTGCGACCACCTGGAGCGGCCAG (SEQ ID NO: 16)
RV: GCTCCAGGTGGTCGCACGATGGGCGTTACGATAATTGTTTTTC Primer Set for Introducing S100L Mutation:
(SEQ ID NO: 17)
FW: CCCAGTGGCTGCTGACCCTGGGCACCACCGAAGCCAATGCGTG (SEQ ID NO: 18)
RV: GGCTTCGGTGGTGCCCAGGGTCAGCAGCCACTGGGTGTTAATG Primer Set for Introducing S100I Mutation:
(SEQ ID NO: 19)
FW: CCCAGTGGCTGCTGACCATTGGCACCACCAATGCCAATGCGTG (SEQ ID NO: 20)
RV: GGCATTGGTGGTGCCAATGGTCAGCAGCCACTGGGTGTTAATG Primer Set for Introducing S100V Mutation:
(SEQ ID NO: 21)
FW: CCCAGTGGCTGCTGACCGTGGGCACCACCAATGCCAATGCGTG (SEQ ID NO: 22)
RV: GGCATTGGTGGTGCCCACGGTCAGCAGCCACTGGGTGTTAATG Primer Set for Introducing S100M Mutation:
(SEQ ID NO: 23)
FW: CCCAGTGGCTGCTGACCATGGGCACCACCAATGCCAATGCGTG (SEQ ID NO: 24)
RV: GGCATTCGGTGGTGCCCATGGTCAGCAGCCACTGGGTGTTAATG Primer Set for Introducing S100R Mutation:
(SEQ ID NO: 25)
FW: CCCAGTGGCTGCTGACCCGTGGCACCACCGAAGCCAATGCGTG (SEQ ID NO: 26)
RV: GGCTTCGGTGGTGCCACGGGTCAGCAGCCACTGGGTGTTAATG Primer Set for Introducing K109M Mutation:
(SEQ ID NO: 27)
FW: CCGAAGCCAATGCGTGGATGAGCACCCTGGTGGGTCATGATAC (SEQ ID NO: 28)
RV: TGACCCACCAGGGTGCTCATCCACGCATTGGCTTCGGTGGTGC Primer Set for Introducing K109R Mutation:
(SEQ ID NO: 29)
FW: CCGAAGCCAATGCGTGGCGTAGCACCCTGGTGGGTCATGATAC (SEQ ID NO: 30)
RV: TGACCCACCAGGGTGCTACGCCACGCATTGGCTTCGGTGGTGC Primer Set for Introducing K109E Mutation:
(SEQ ID NO: 31)
FW: CCGAAGCCAATGCGTGGGAAAGCACCCTGGTGGGTCATGATAC (SEQ ID NO: 32)
RV: TGACCCACCAGGGTGCTTTCCCACGCATTGGCTTCGGTGGTGC Primer Set for Introducing L112N Mutation:
(SEQ ID NO: 33)
FW: CAATGCGTGGAAAAGCACCAACGTGGGTCATGATACCTTTACC (SEQ ID NO: 34)
RV: AGGTATCATGACCCACGTTGGTGCTTTTCCACGCATTGGCTTC Primer Set for Introducing L112Q Mutation:
(SEQ ID NO: 35)
FW: CAATGCGTGGAAAAGCACCCAGGTGGGTCATGATACCTTTACC (SEQ ID NO: 36)
RV: AGGTATCATGACCCACCTGGGTGCTTTTCCACGCATTGGCTTC

The invention claimed is:
1. A bis-iminobiotin compound selected from the group consisting of compounds shown in following Tables A3 to A10:
TABLE A3
1
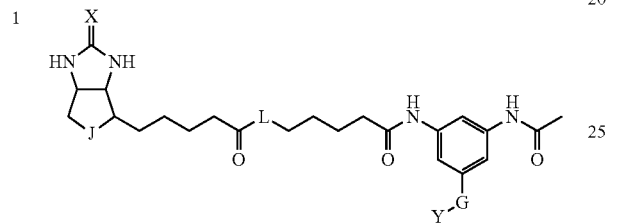
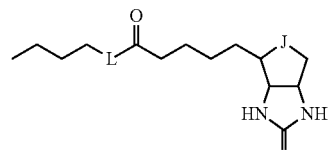
2
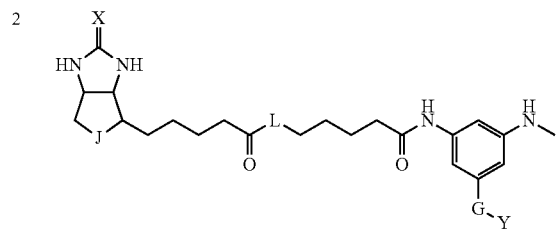
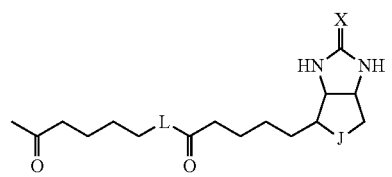
TABLE A3-continued
3
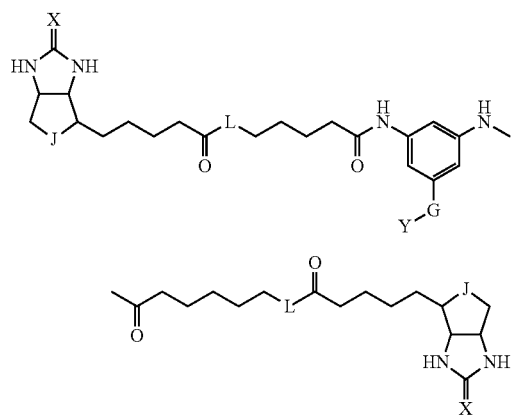
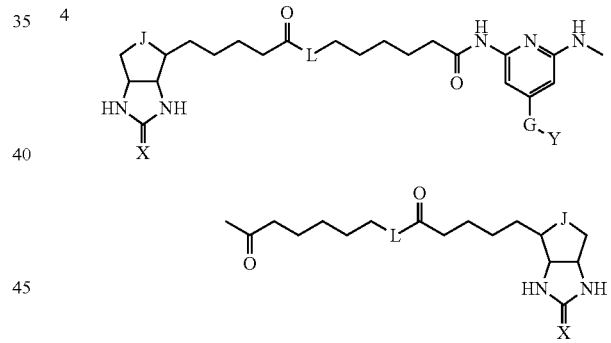
4
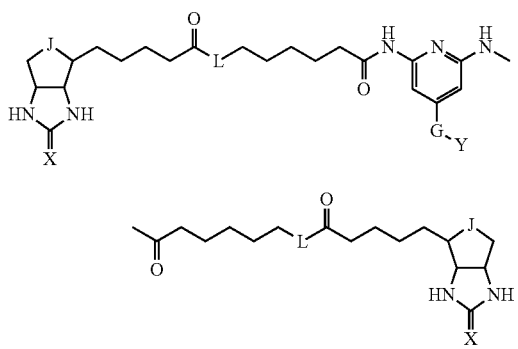
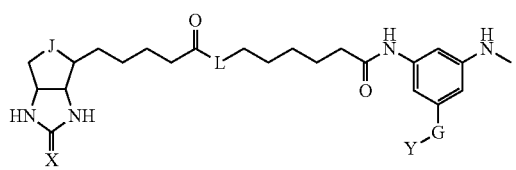
5
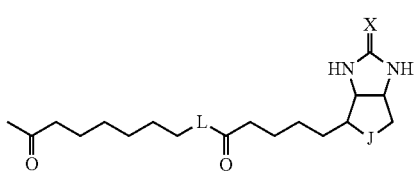

TABLE A3-continued
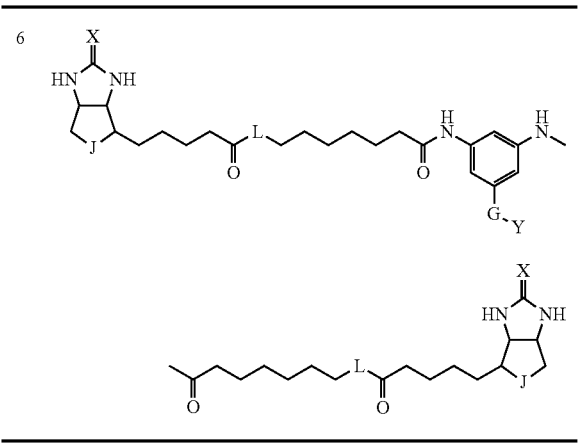
TABLE A4
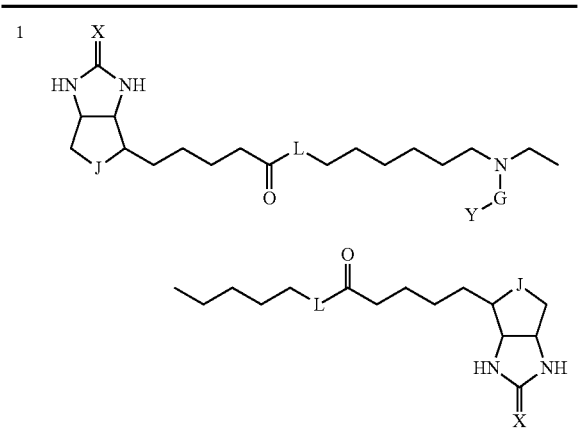
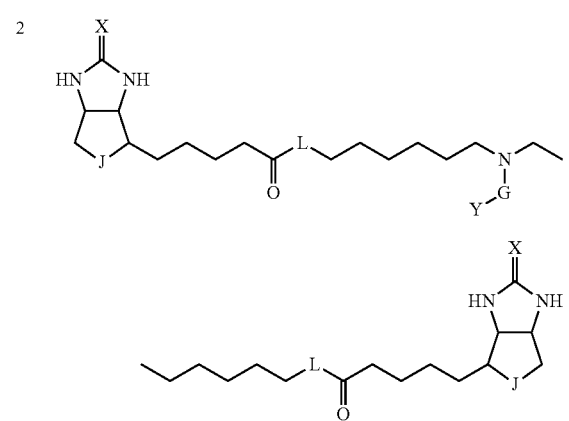
TABLE A4-continued
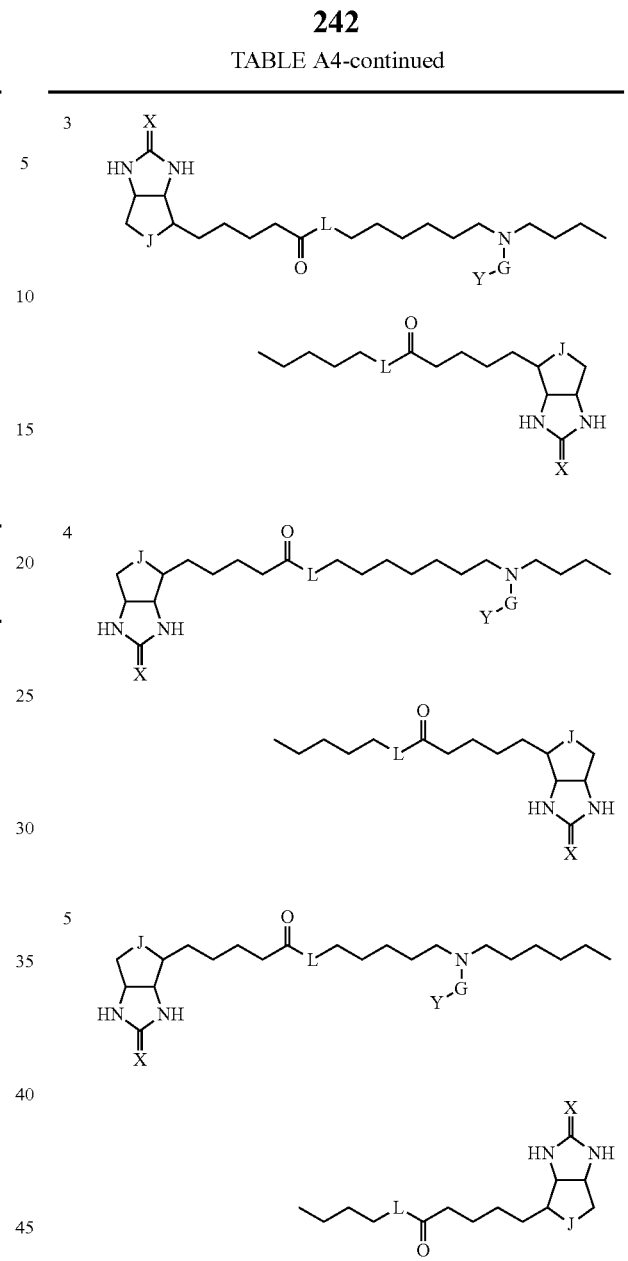
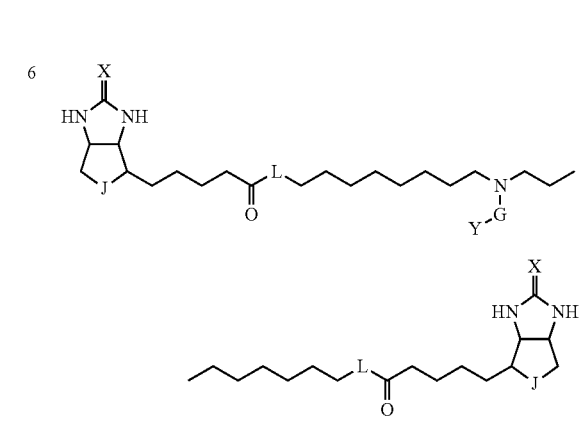

TABLE A4-continued
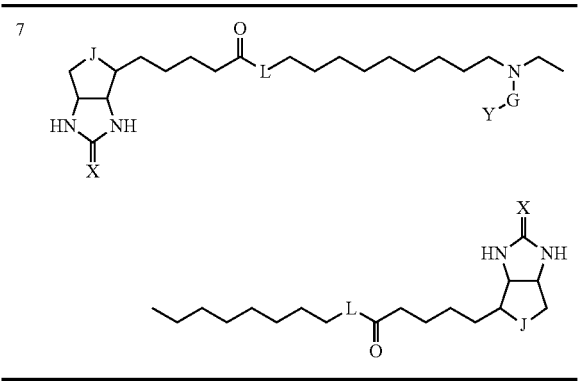
TABLE A5
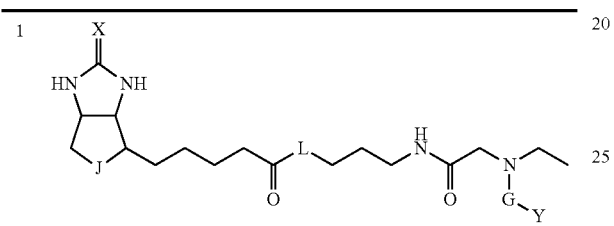
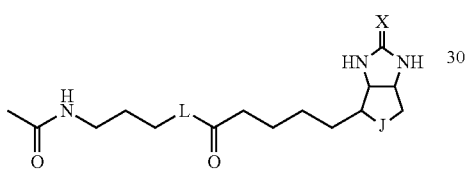
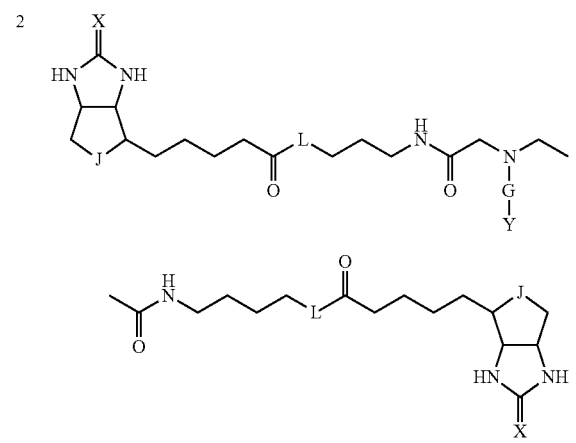
TABLE A5-continued
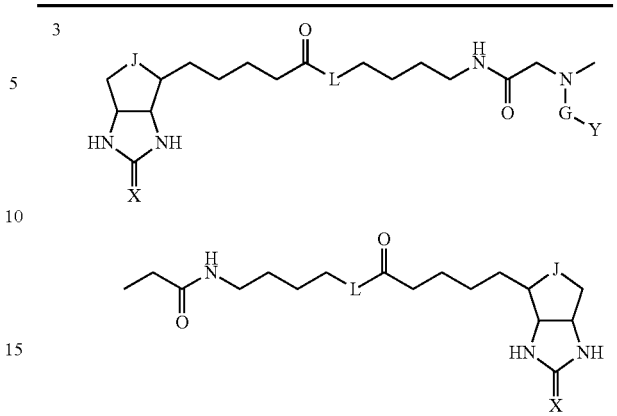
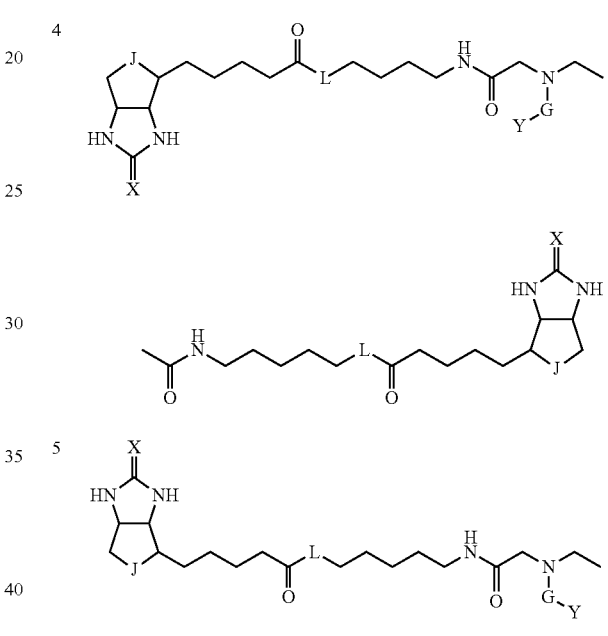
TABLE A6
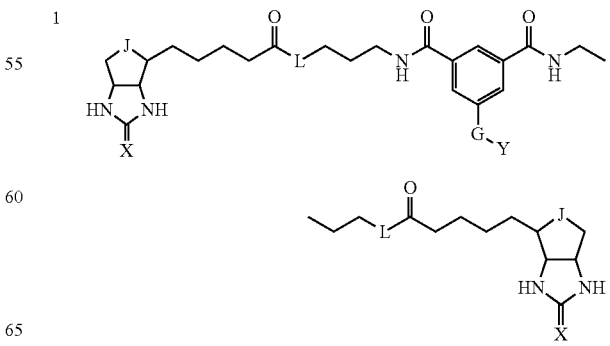

TABLE A6-continued
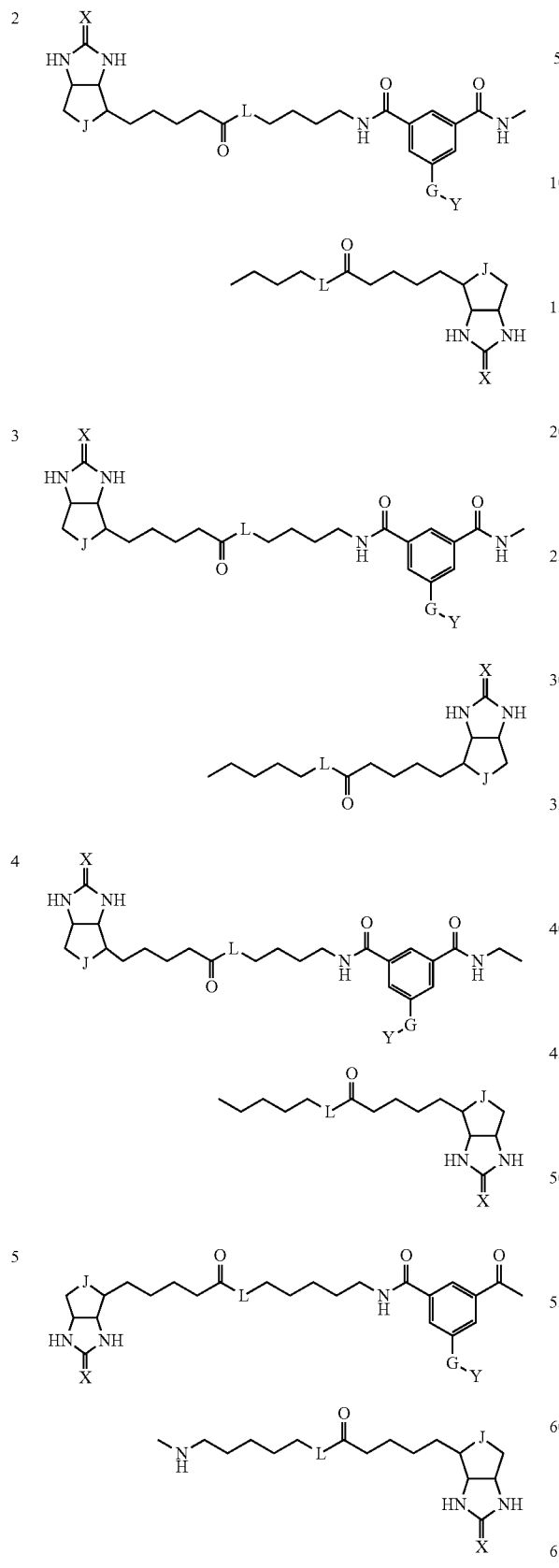
TABLE A7
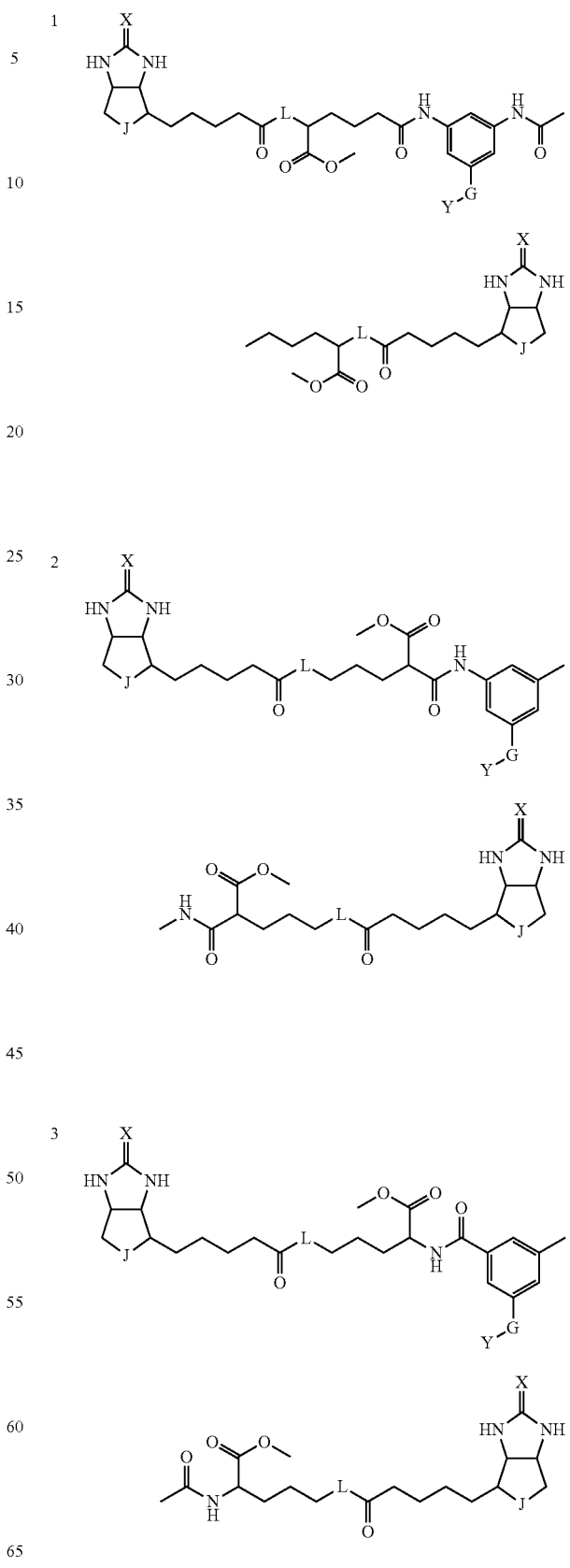

247 248
TABLE A7-continued
4
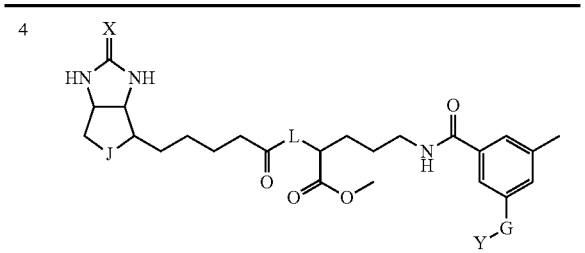
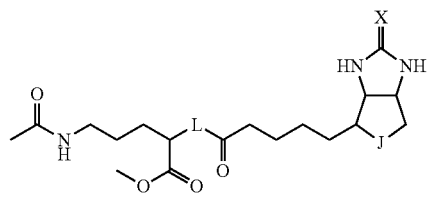
5
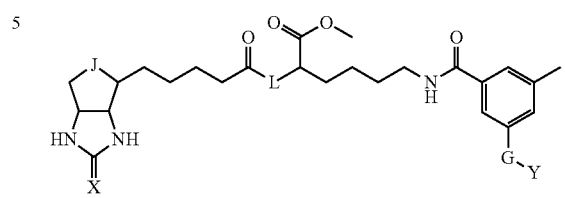
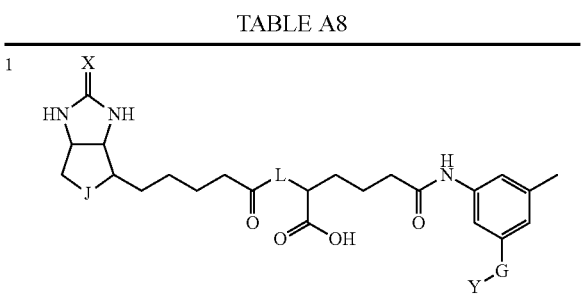
TABLE A8
1
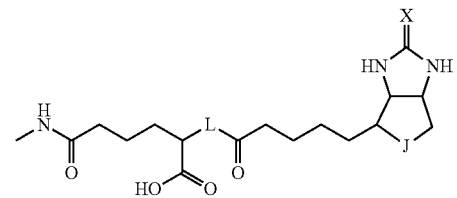
TABLE A8-continued
2
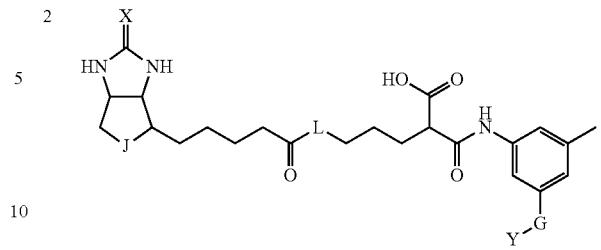
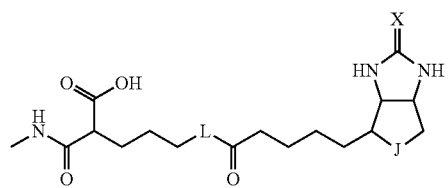
3
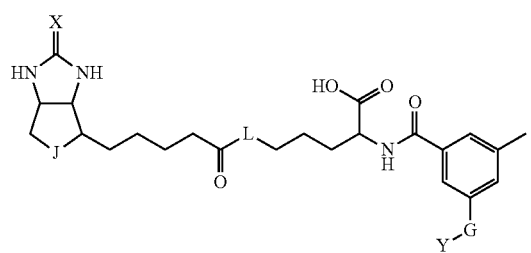
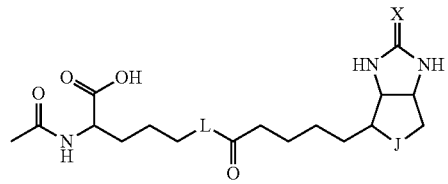
4
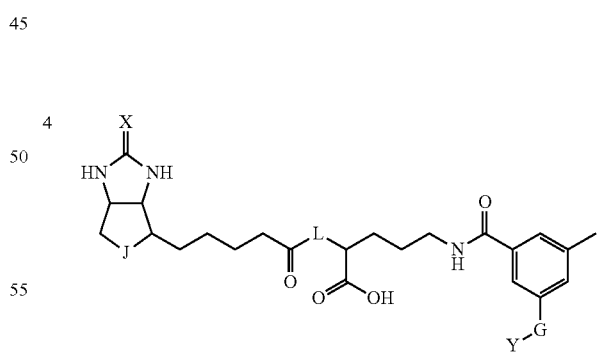
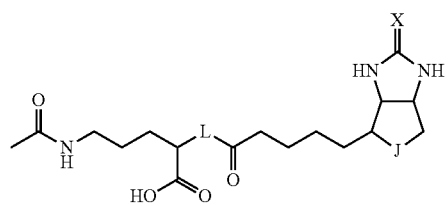

TABLE A8-continued
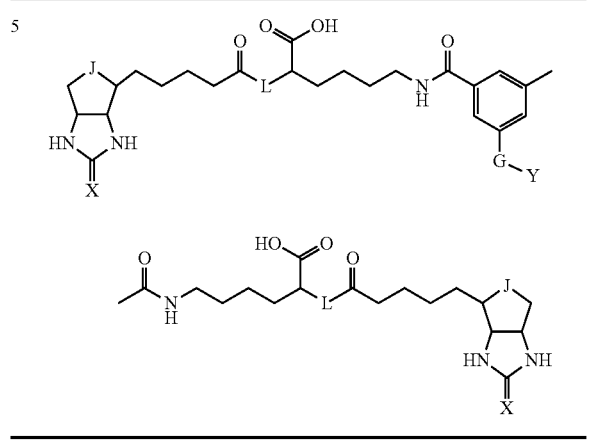
TABLE A9
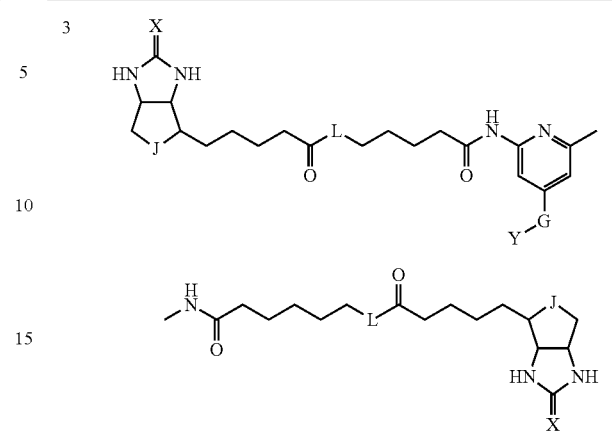
TABLE A9-continued
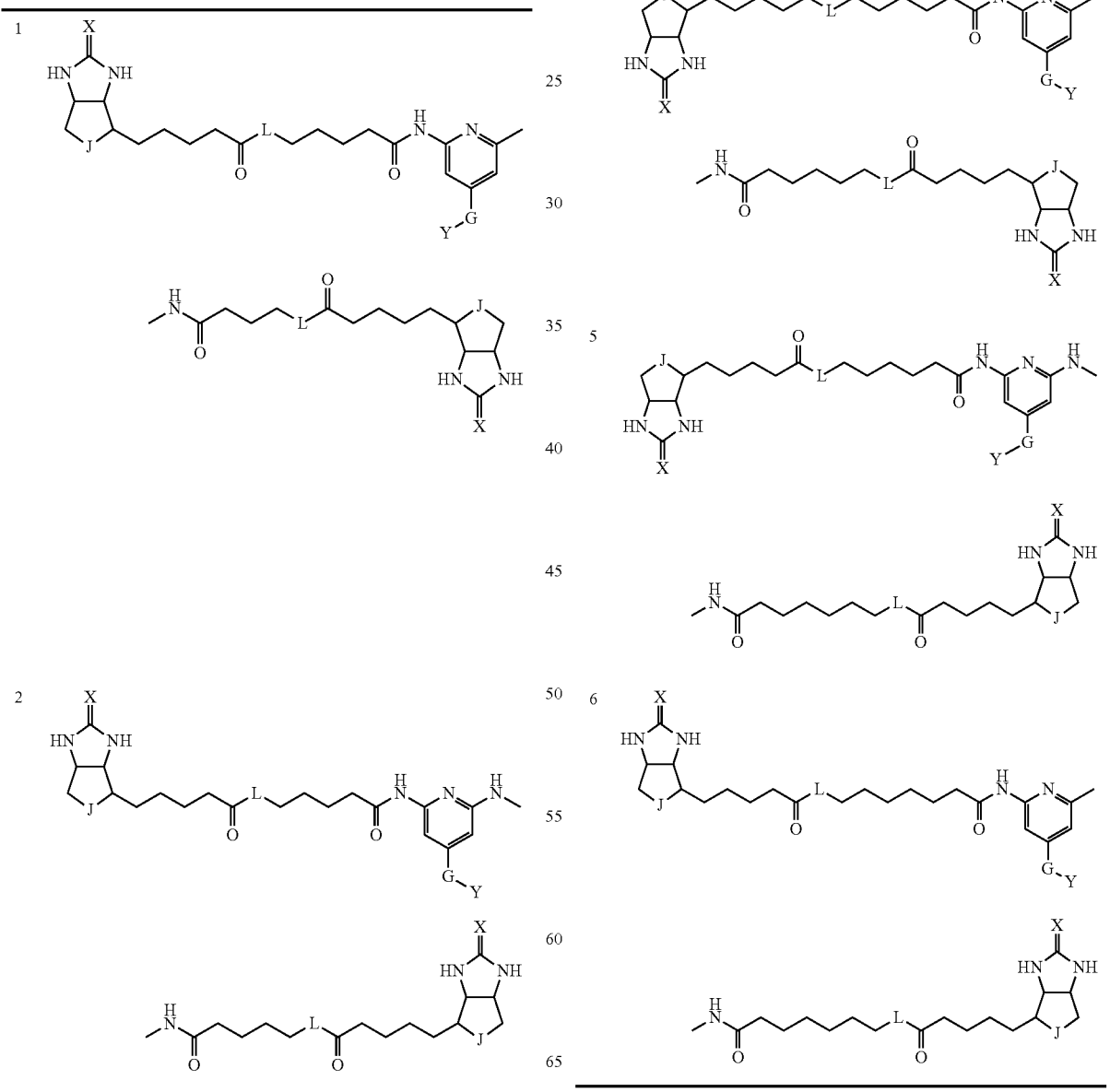

TABLE A10
1 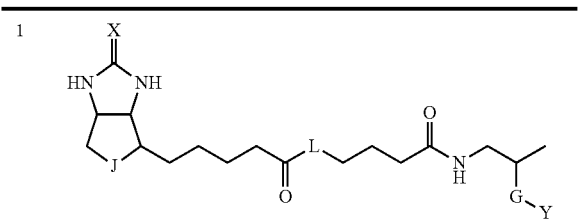
2 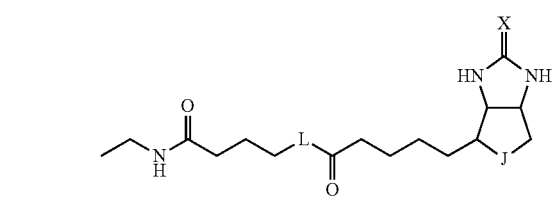
3 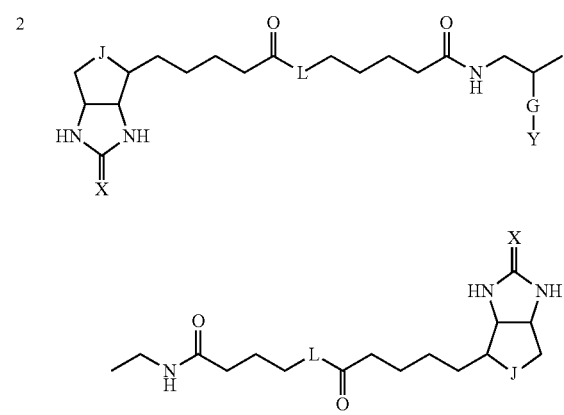
4 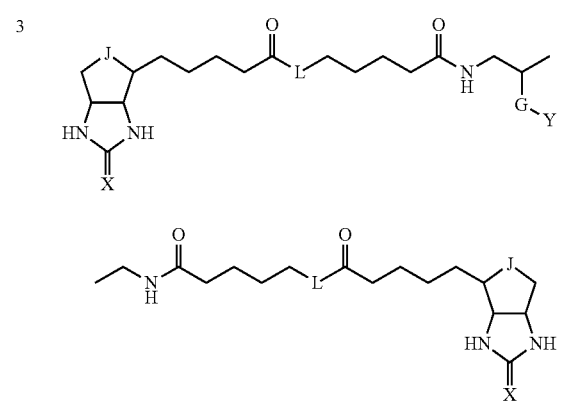
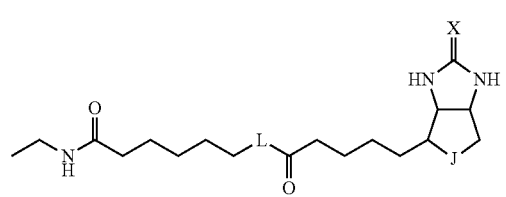
TABLE A10-continued
5 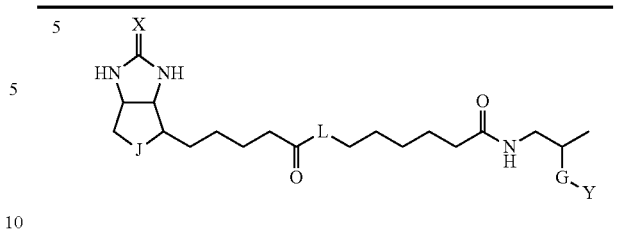
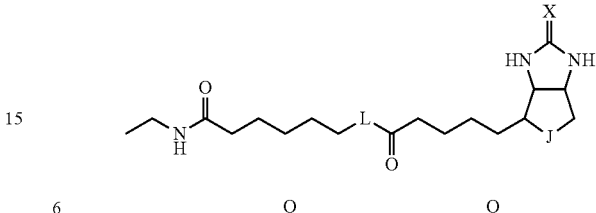
6 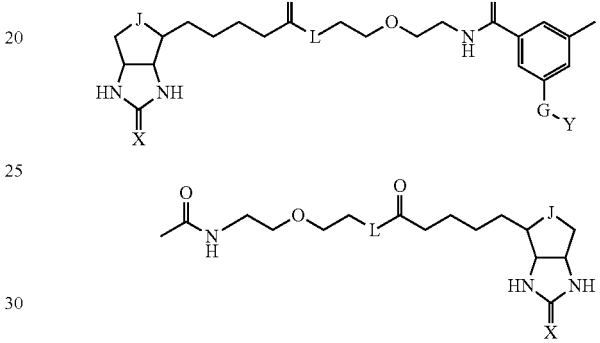
wherein X is NH, J is sulfur, L is NH, G-Y is selected from the groups shown in following Table G2, wherein E means a bond to a partial structure in each of the compounds shown in the Tables A3 to A10, and Y is an N-hydroxysuccinimide ester or an N-hydroxysulfosuccinimide ester:
TABLE G2
1 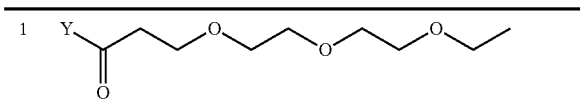
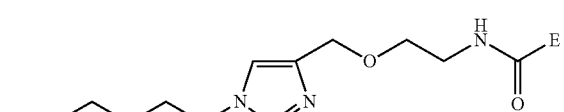
2 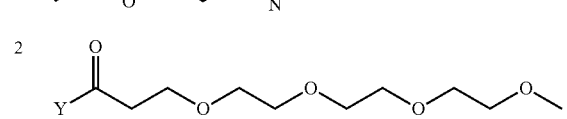
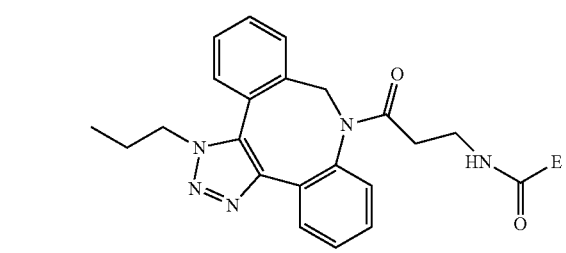

TABLE G2-continued
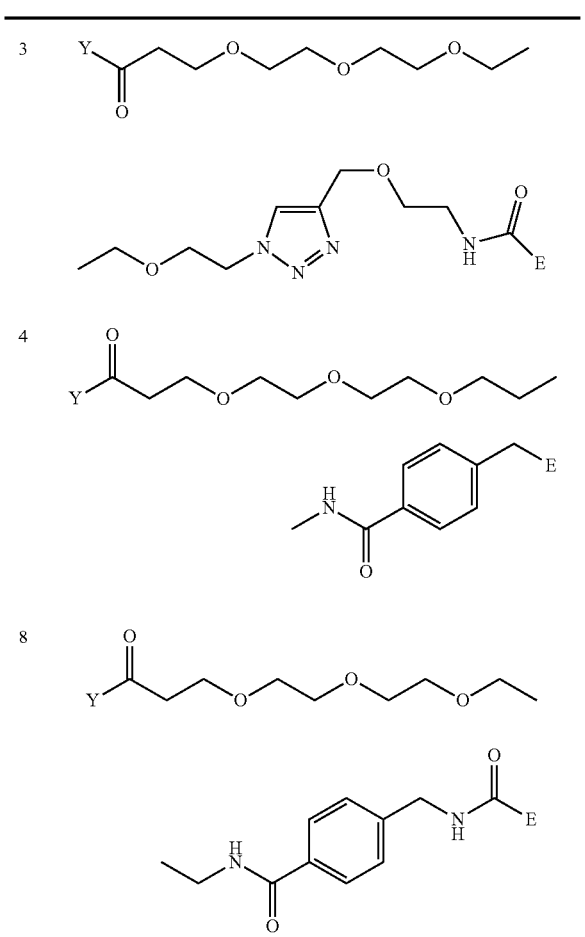
TABLE G2-continued
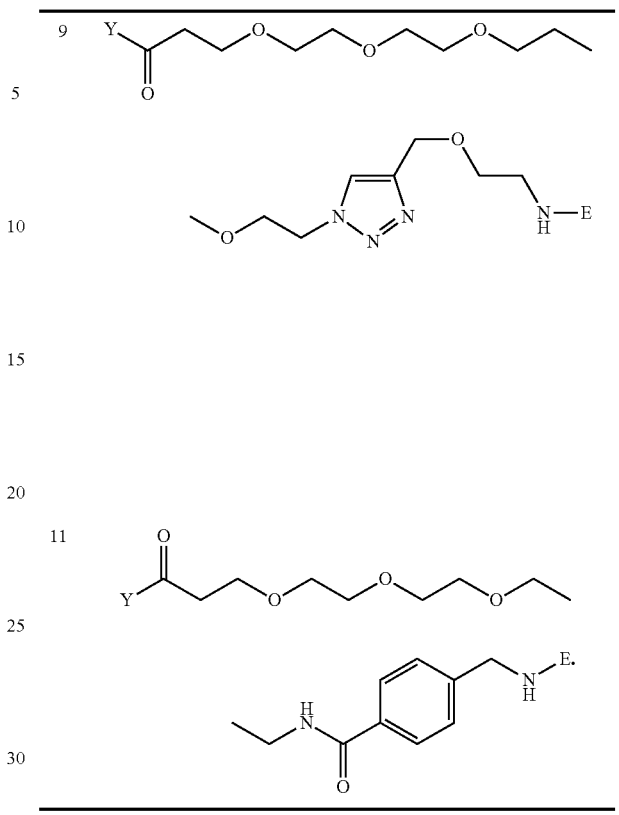
2. A labeling compound for a protein, wherein the labeling compound is at least one selected from the bis-iminobiotin compounds according to claim 1.
3. The labeling compound for a protein according to claim 2, wherein labeling of the protein is performed for identification of the protein.
\* \* \* \* \*

SEQUENCE LISTING

<160> NUMBER OF SEQ ID NOS: 36

<210> SEQ ID NO 1
<211> LENGTH: 159
<212> TYPE: PRT
<213> ORGANISM: Streptomyces avidinii
<220> FEATURE:
<223> OTHER INFORMATION: An amino acid sequence of a wild type
      streptavidin

<400> SEQUENCE: 1

Asp Pro Ser Lys Asp Ser Lys Ala Gln Val Ser Ala Ala Glu Ala Gly
1               5                   10                  15

Ile Thr Gly Thr Trp Tyr Asn Gln Leu Gly Ser Thr Phe Ile Val Thr
            20                  25                  30

Ala Gly Ala Asp Gly Ala Leu Thr Gly Thr Tyr Glu Ser Ala Val Gly
        35                  40                  45

Asn Ala Glu Ser Arg Tyr Val Leu Thr Gly Arg Tyr Asp Ser Ala Pro
    50                  55                  60

Ala Thr Asp Gly Ser Gly Thr Ala Leu Gly Trp Thr Val Ala Trp Lys
65                  70                  75                  80

Asn Asn Tyr Arg Asn Ala His Ser Ala Thr Thr Trp Ser Gly Gln Tyr
                85                  90                  95

Val Gly Gly Ala Glu Ala Arg Ile Asn Thr Gln Trp Leu Leu Thr Ser
            100                 105                 110

Gly Thr Thr Glu Ala Asn Ala Trp Lys Ser Thr Leu Val Gly His Asp
        115                 120                 125

Thr Phe Thr Lys Val Lys Pro Ser Ala Ala Ser Ile Asp Ala Ala Lys
    130                 135                 140

Lys Ala Gly Val Asn Asn Gly Asn Pro Leu Asp Ala Val Gln Gln
145                 150                 155

<210> SEQ ID NO 2
<211> LENGTH: 127
<212> TYPE: PRT
<213> ORGANISM: Streptomyces avidinii
<220> FEATURE:
<223> OTHER INFORMATION: Truncated amino acid sequence of a wild type
      streptavidin

<400> SEQUENCE: 2

Ala Glu Ala Gly Ile Thr Gly Thr Trp Tyr Asn Gln Leu Gly Ser Thr
1               5                   10                  15

Phe Ile Val Thr Ala Gly Ala Asp Gly Ala Leu Thr Gly Thr Tyr Glu
            20                  25                  30

Ser Ala Val Gly Asn Ala Glu Ser Arg Tyr Val Leu Thr Gly Arg Tyr
        35                  40                  45

Asp Ser Ala Pro Ala Thr Asp Gly Ser Gly Thr Ala Leu Gly Trp Thr
    50                  55                  60

Val Ala Trp Lys Asn Asn Tyr Arg Asn Ala His Ser Ala Thr Thr Trp
65                  70                  75                  80

Ser Gly Gln Tyr Val Gly Gly Ala Glu Ala Arg Ile Asn Thr Gln Trp
                85                  90                  95

Leu Leu Thr Ser Gly Thr Thr Glu Ala Asn Ala Trp Lys Ser Thr Leu
            100                 105                 110

Val Gly His Asp Thr Phe Thr Lys Val Lys Pro Ser Ala Ala Ser
        115                 120                 125

```
<210> SEQ ID NO 3
<211> LENGTH: 44
<212> TYPE: DNA
<213> ORGANISM: Artificial
<220> FEATURE:
<223> OTHER INFORMATION: Forward primer for mutation

<400> SEQUENCE: 3
ttaccggcac ctggtatgat cagctgggca gcacctttat tgtg            44

<210> SEQ ID NO 4
<211> LENGTH: 44
<212> TYPE: DNA
<213> ORGANISM: Artificial
<220> FEATURE:
<223> OTHER INFORMATION: Reverse primer for mutation

<400> SEQUENCE: 4
aaggtgctgc ccagctgatc ataccaggtg ccggtaatac ctgc            44

<210> SEQ ID NO 5
<211> LENGTH: 45
<212> TYPE: DNA
<213> ORGANISM: Artificial
<220> FEATURE:
<223> OTHER INFORMATION: Forward primer for mutation

<400> SEQUENCE: 5
ggtatgatca gctgggcgcg acctttattg tgaccgccgg cgcag            45

<210> SEQ ID NO 6
<211> LENGTH: 45
<212> TYPE: DNA
<213> ORGANISM: Artificial
<220> FEATURE:
<223> OTHER INFORMATION: Reverse primer for mutation

<400> SEQUENCE: 6
gcggtcacaa taaaggtcgc gcccagctga tcataccagg tgccg            45

<210> SEQ ID NO 7
<211> LENGTH: 43
<212> TYPE: DNA
<213> ORGANISM: Artificial
<220> FEATURE:
<223> OTHER INFORMATION: Forward primer for mutation

<400> SEQUENCE: 7
tgaccggcac ctatgaagcg gccgtgggta atgcggaaag ccg             43

<210> SEQ ID NO 8
<211> LENGTH: 44
<212> TYPE: DNA
<213> ORGANISM: Artificial
<220> FEATURE:
<223> OTHER INFORMATION: Reverse primer for mutation

<400> SEQUENCE: 8
tccgcattac ccacggccgc ttcataggtg ccggtcagcg cacc            44

<210> SEQ ID NO 9
<211> LENGTH: 43
<212> TYPE: DNA
<213> ORGANISM: Artificial
<220> FEATURE:
<223> OTHER INFORMATION: Forward primer for mutation
```

<400> SEQUENCE: 9
tgaccggcac ctatgaaaac gccgtgggta atgcggaaag ccg          43

<210> SEQ ID NO 10
<211> LENGTH: 44
<212> TYPE: DNA
<213> ORGANISM: Artificial
<220> FEATURE:
<223> OTHER INFORMATION: Reverse primer for mutation

<400> SEQUENCE: 10
tccgcattac ccacggcgtt ttcataggtg ccggtcagcg cacc         44

<210> SEQ ID NO 11
<211> LENGTH: 45
<212> TYPE: DNA
<213> ORGANISM: Artificial
<220> FEATURE:
<223> OTHER INFORMATION: Forward primer for mutation

<400> SEQUENCE: 11
atgaagcggc cgtgggtggc gcggaaagcc gttatgttct gaccg        45

<210> SEQ ID NO 12
<211> LENGTH: 45
<212> TYPE: DNA
<213> ORGANISM: Artificial
<220> FEATURE:
<223> OTHER INFORMATION: Reverse primer for mutation

<400> SEQUENCE: 12
acataacggc tttccgcgcc acccacggcc gcttcatagg tgccg        45

<210> SEQ ID NO 13
<211> LENGTH: 43
<212> TYPE: DNA
<213> ORGANISM: Artificial
<220> FEATURE:
<223> OTHER INFORMATION: Forward primer for mutation

<400> SEQUENCE: 13
caattatcgt aacgcccatg gcgcgaccac ctggagcggc cag          43

<210> SEQ ID NO 14
<211> LENGTH: 43
<212> TYPE: DNA
<213> ORGANISM: Artificial
<220> FEATURE:
<223> OTHER INFORMATION: Reverse primer for mutation

<400> SEQUENCE: 14
gctccaggtg gtcgcgccat gggcgttacg ataattgttt ttc          43

<210> SEQ ID NO 15
<211> LENGTH: 43
<212> TYPE: DNA
<213> ORGANISM: Artificial
<220> FEATURE:
<223> OTHER INFORMATION: Forward primer for mutation

<400> SEQUENCE: 15
caattatcgt aacgcccatc gtgcgaccac ctggagcggc cag          43

<210> SEQ ID NO 16
<211> LENGTH: 43

```
<212> TYPE: DNA
<213> ORGANISM: Artificial
<220> FEATURE:
<223> OTHER INFORMATION: Reverse primer for mutation

<400> SEQUENCE: 16
gctccaggtg gtcgcacgat gggcgttacg ataattgttt ttc          43

<210> SEQ ID NO 17
<211> LENGTH: 43
<212> TYPE: DNA
<213> ORGANISM: Artificial
<220> FEATURE:
<223> OTHER INFORMATION: Forward primer for mutation

<400> SEQUENCE: 17
cccagtggct gctgaccctg ggcaccaccg aagccaatgc gtg          43

<210> SEQ ID NO 18
<211> LENGTH: 43
<212> TYPE: DNA
<213> ORGANISM: Artificial
<220> FEATURE:
<223> OTHER INFORMATION: Reverse primer for mutation

<400> SEQUENCE: 18
ggcttcggtg gtgcccaggg tcagcagcca ctgggtgtta atg          43

<210> SEQ ID NO 19
<211> LENGTH: 43
<212> TYPE: DNA
<213> ORGANISM: Artificial
<220> FEATURE:
<223> OTHER INFORMATION: Forward primer for mutation

<400> SEQUENCE: 19
cccagtggct gctgaccatt ggcaccacca atgccaatgc gtg          43

<210> SEQ ID NO 20
<211> LENGTH: 43
<212> TYPE: DNA
<213> ORGANISM: Artificial
<220> FEATURE:
<223> OTHER INFORMATION: Reverse primer for mutation

<400> SEQUENCE: 20
ggcattggtg gtgccaatgg tcagcagcca ctgggtgtta atg          43

<210> SEQ ID NO 21
<211> LENGTH: 43
<212> TYPE: DNA
<213> ORGANISM: Artificial
<220> FEATURE:
<223> OTHER INFORMATION: Forward primer for mutation

<400> SEQUENCE: 21
cccagtggct gctgaccgtg ggcaccacca atgccaatgc gtg          43

<210> SEQ ID NO 22
<211> LENGTH: 43
<212> TYPE: DNA
<213> ORGANISM: Artificial
<220> FEATURE:
<223> OTHER INFORMATION: Reverse primer for mutation

<400> SEQUENCE: 22
```
ggcattggtg gtgcccacgg tcagcagcca ctgggtgtta atg 43

<210> SEQ ID NO 23
<211> LENGTH: 43
<212> TYPE: DNA
<213> ORGANISM: Artificial
<220> FEATURE:
<223> OTHER INFORMATION: Forward primer for mutation

<400> SEQUENCE: 23
cccagtggct gctgaccatg ggcaccacca atgccaatgc gtg 43

<210> SEQ ID NO 24
<211> LENGTH: 44
<212> TYPE: DNA
<213> ORGANISM: Artificial
<220> FEATURE:
<223> OTHER INFORMATION: Reverse primer for mutation

<400> SEQUENCE: 24
ggcattcggt ggtgcccatg gtcagcagcc actgggtgtt aatg 44

<210> SEQ ID NO 25
<211> LENGTH: 43
<212> TYPE: DNA
<213> ORGANISM: Artificial
<220> FEATURE:
<223> OTHER INFORMATION: Forward primer for mutation

<400> SEQUENCE: 25
cccagtggct gctgacccgt ggcaccaccg aagccaatgc gtg 43

<210> SEQ ID NO 26
<211> LENGTH: 43
<212> TYPE: DNA
<213> ORGANISM: Artificial
<220> FEATURE:
<223> OTHER INFORMATION: Reverse primer for mutation

<400> SEQUENCE: 26
ggcttcggtg gtgccacggg tcagcagcca ctgggtgtta atg 43

<210> SEQ ID NO 27
<211> LENGTH: 43
<212> TYPE: DNA
<213> ORGANISM: Artificial
<220> FEATURE:
<223> OTHER INFORMATION: Forward primer for mutation

<400> SEQUENCE: 27 ccgaagcca atgcgtggat gagcaccctg gtgggtcatga tac 43

<210> SEQ ID NO 28
<211> LENGTH: 43
<212> TYPE: DNA
<213> ORGANISM: Artificial
<220> FEATURE:
<223> OTHER INFORMATION: Reverse primer for mutation

<400> SEQUENCE: 28
tgacccacca gggtgctcat ccacgcattg gcttcggtgg tgc 43

<210> SEQ ID NO 29
<211> LENGTH: 43
<212> TYPE: DNA
<213> ORGANISM: Artificial
<220> FEATURE:

<223> OTHER INFORMATION: Forward primer for mutation

<400> SEQUENCE: 29
ccgaagccaa tgcgtggcgt agcaccctgg tgggtcatga tac         43

<210> SEQ ID NO 30
<211> LENGTH: 43
<212> TYPE: DNA
<213> ORGANISM: Artificial
<220> FEATURE:
<223> OTHER INFORMATION: Reverse primer for mutation

<400> SEQUENCE: 30
tgacccacca gggtgctacg ccacgcattg gcttcggtgg tgc         43

<210> SEQ ID NO 31
<211> LENGTH: 43
<212> TYPE: DNA
<213> ORGANISM: Artificial
<220> FEATURE:
<223> OTHER INFORMATION: Forward primer for mutation

<400> SEQUENCE: 31
ccgaagccaa tgcgtgggaa agcaccctgg tgggtcatga tac         43

<210> SEQ ID NO 32
<211> LENGTH: 43
<212> TYPE: DNA
<213> ORGANISM: Artificial
<220> FEATURE:
<223> OTHER INFORMATION: Reverse primer for mutation

<400> SEQUENCE: 32
tgacccacca gggtgctttc ccacgcattg gcttcggtgg tgc         43

<210> SEQ ID NO 33
<211> LENGTH: 43
<212> TYPE: DNA
<213> ORGANISM: Artificial
<220> FEATURE:
<223> OTHER INFORMATION: Forward primer for mutation

<400> SEQUENCE: 33
caatgcgtgg aaaagcacca acgtgggtca tgataccttt acc         43

<210> SEQ ID NO 34
<211> LENGTH: 43
<212> TYPE: DNA
<213> ORGANISM: Artificial
<220> FEATURE:
<223> OTHER INFORMATION: Reverse primer for mutation

<400> SEQUENCE: 34
aggtatcatg acccacgttg gtgcttttcc acgcattggc ttc         43

<210> SEQ ID NO 35
<211> LENGTH: 43
<212> TYPE: DNA
<213> ORGANISM: Artificial
<220> FEATURE:
<223> OTHER INFORMATION: Forward primer for mutation

<400> SEQUENCE: 35
caatgcgtgg aaaagcaccc aggtgggtca tgatacccttt acc         43

```
<210> SEQ ID NO 36
<211> LENGTH: 43
<212> TYPE: DNA
<213> ORGANISM: Artificial
<220> FEATURE:
<223> OTHER INFORMATION: Reverse primer for mutation
<400> SEQUENCE: 36
aggtatcatg acccacctgg gtgctttcc acgcattggc ttc          43
```